US011427867B2

(12) United States Patent
Mir

(10) Patent No.: US 11,427,867 B2
(45) Date of Patent: *Aug. 30, 2022

(54) SEQUENCING BY EMERGENCE

(71) Applicant: XGenomes Corp., Boston, MA (US)

(72) Inventor: Kalim Mir, Boston, MA (US)

(73) Assignee: XGENOMES CORP., Boston, MA (US)

(*) Notice: Subject to any disclaimer, the term of this patent is extended or adjusted under 35 U.S.C. 154(b) by 31 days.

This patent is subject to a terminal disclaimer.

(21) Appl. No.: 16/425,929

(22) Filed: May 29, 2019

(65) Prior Publication Data

US 2020/0056229 A1 Feb. 20, 2020

Related U.S. Application Data

(63) Continuation-in-part of application No. 16/205,155, filed on Nov. 29, 2018.

(60) Provisional application No. 62/591,850, filed on Nov. 29, 2017.

(51) Int. Cl.
C12Q 1/68 (2018.01)
C12Q 1/6869 (2018.01)
G01N 21/64 (2006.01)

(52) U.S. Cl.
CPC ....... C12Q 1/6869 (2013.01); G01N 21/6428 (2013.01); G01N 2021/6439 (2013.01)

(58) Field of Classification Search
USPC ........ 435/6.1, 6.11, 91.1, 91.2, 91.51, 283.1, 435/287.1, 287.2; 436/94, 501; 536/23.1, 24.3, 24.33, 25.3
See application file for complete search history.

(56) References Cited

U.S. PATENT DOCUMENTS

| 6,221,592 | B1 | 4/2001 | Schwartz |
| 10,982,260 | B2* | 4/2021 | Mir ........................ C12N 15/10 |
| 2004/0058349 | A1 | 3/2004 | Van Nes et al. |
| 2005/0214842 | A1 | 9/2005 | Palanisamy et al. |
| 2018/0327829 | A1 | 11/2018 | Mir |

FOREIGN PATENT DOCUMENTS

| WO | WO 2004/070005 A2 | 8/2004 |
| WO | WO 2012/055415 A1 | 5/2012 |
| WO | WO 2012/056192 A1 | 5/2012 |

OTHER PUBLICATIONS

"Molecular Beacon" from Wikipedia. Printed on Jul. 30, 2021.*
"FRET fluorescence quenchers". Printed on Jul. 30, 2021.*
Ansorge, W.J., "Next-Generation DNA Sequencing Techniques", New Biotechnology, v. 25, n. 4, Apr. 2009.
Babcock, Hazen P., et al., "Analyzing Single Molecule Localization Microscopy Data Using Cubic Splines", Scientific Reports, 7: 552 | DOI:10.1038/S41598-017-00622-w, recd. Dec. 6, 2016, accptd Mar. 6, 2017, pubd. Online Apr. 3, 2017.

(Continued)

*Primary Examiner* — Frank W Lu

(57) ABSTRACT

The invention is a method of sequencing polymers in which the sequence of one or more polymers is determined through an emergent property of the binding interactions of a repertoire of molecular probes to the polymer(s).

23 Claims, 29 Drawing Sheets

Specification includes a Sequence Listing.

(56) References Cited

OTHER PUBLICATIONS

Beliveau, Brian J., et al., "Single-molecule super-resolution imaging of chromosomes and in situ haplotype visualization using Oligopaint FISH probes", Nature Communications | 6:7147 | DOI: 10.1038/ncomms8147 .nature.com/naturecommunications, rec'd Jul. 30, 2014, accepted Apr. 9, 2015, pubd. May 12, 2015.
Bentley, David R. et al., "Accurate whole human genome sequencing using reversible terminator chemistry", Nature, v. 456, n. 6, p. 53-59 (Nov. 2008).
Bertone, P. et al., "Design Optimization Methods for Genomic DNA Tiling Arrays", Gen Res 16, 271-281 (2006).
Boyd, Nicholas et al. "Deep Loco: Fast 3D Localization Microscopy Using Neural Networks", bioRxiv preprint first posted online Feb. 16, 2018; doi; http://dx.doi.org/10.1101/267096.
Chen, Zitian et al., "Highly accurate fluorogenic DNA sequencing with information theorybased error correction", Nature Biotechnology, v. 35, n. 12, p. 1170.
Chou, et al. 2004 "PICKY: oligo microarray design for large genomes" Bioninform. 20(17), 2893-2902.
Colomb, et al. "Estimation of microscopy drift using fluorescent nanodiamonds as fiducial marker," J. Microscopy, vol. 266, Issue 3, 2017, pp. 298-306.
Cox, Henry, et al, "Self-Assembly of Mesoscopic Peptide Surfactant Fibrils Investigated by STORM Super-Resolution Fluorescence Microscopy", Biomacromolecules 18,11 (2017): 3481-3491.
Deiana, Marco, et al., "Photochromic switching of the DNA helicity induced by azobenzene derivative", Scientific Reports, 6:28605 | DOI: 10.1038/srep28605, Reed Mar. 5, 2016, Accptd Jun. 3, 2016, Pubd. Jun. 24, 2016.
Dertinger, T., et al. "Fast, background-free, 3D super-resolution optical fluctuation imaging (SOFI)," PNAS, Dec. 29, 2009, vol. 106, No. 52, pp. 22287-22292.
Dufour, Y.S., et al., "chipD: A Web Tool to Design Oligonucleotide Probes for High-Density Tiling Arrays", Nucleic Acids Res., v. 38, p. W321-W325 (2010).
Freitag, C., et al., "Visualizing the entire DNA from a chromosome in a single frame", Biomicrofluidics, Biomicrofluidics v. 9, issue 4, 044114 (2015); https://doi.org/10.1663/1.4923262, pubd. Aug. 5, 2015, acceptd. Jun. 2015.
Geertsema, Hylkje J. "Single-Molecule Imaging at High Fluorophore Concentrations by Local Activation of Dye", Biophysical J., v. 108, p. 949-956, Feb. 2015.
Henriques, Ricardo, et al. "PALM and STORM: Unlocking Live-Cell Super-Resolution," Biopolymers, vol. 95, No. 5, pp. 322-331.
Hollich, Volker, et al. "Creation of a minimal tiling path of genomic clones for *Drosophila*: provision of a common resource," Microarray Technologies, BioTechniques, vol. 37, No. 2, 2004, pp. 282-284.
Huang, Bo et al., "Super-Resolution Fluorescence Microscopy", Annual Review of Biochemistry, 78 (2009): 993-1016.
Karimi-Busheri, Feridoun et al., "Repair of DNA Strand Gaps and Nicks containing 3'-phosphate and 5'-hydroxyl termini by purified mammalian enzymes", Nucleic Acids Research, v. 26, n. 19, p. 4395-4400 (1998).
Kaykov, Atanas, et al., "Molecular Combing of Single DNA Molecules on the 10 Megabase Scale", Scientific Reports, Scientific Reports | 6:19636 | DOI: 10.1038/srep19636, received: Jul. 15, 2015, accepted: Dec. 14, 2015, Published: Jan. 19, 2016.
Kchouk, Mehdi, et al., "Generations of Sequencing Technologies: From First to Next Generation", Biology and Medicine, v. 9, n. 3 p. 1-8 (2017).
Kirshner, H. et al., "3-D PSF fitting for fluorescence microscopy: implementation and localization application," J. Microscopy, vol. 249(1), 2013, pp. 13-25.
Kulkarni, Pranav, et al., "Challenges in the Setup of Large-scale Next-Generation Sequencing Analysis Workflows", Comp. and Struc. Biot. J., n. 15, p. 471-477 (2017).
Kunkel, Thomas A., et al., "Deoxynucleoside [1-thio] triphosphates prevent proofreading during in vitro DNA synthesis", Proc. Natl. Acad. Sci. USA, v. 78, n. 11, p. 6734-3738, Nov. 1981.
Laver, T., et al., "Assessing the performance of the Oxford Nanopore Technologies MinION", Biomol. Det. and Quant., n. 3, p. 1-8 (2015).
Levesque, Marshall J., et al., "Visualizing SNVs to quantify allele-specific expression in single cells", Nat Methods, 10(9); 865-867, Sep. 2013.
Levy-Sakin, M. et al., "Beyond sequencing: optical mapping of DNA in the age of nanotechnology and nanoscopy", Current Opinion in Biotechnology, 24(4), p. 690-698 (Feb. 18, 2013).
Li, X., et al. "Selection of Optimal Oligonucleotide Probes for Microarrays Using Multiple Criteria, Global Alignment and Parameter Estimation", Nucleic Acids Res. v. 33, n. 19, p. 6114-6123 (2005).
Lin, Chenxiang, et al., "Sub-micrometer Geometrically Encoded Fluorescent Barcodes Self-Assembled from DNA", Nat Chem. 4(10); 832-839, Oct. 2012.
Lipson, et al., "Optimization of probe coverage for high-resolution oligonucleotide aCGH" Bioinform, v. 23, n. 2 p. e77-e83 (2006).
Lundquist, Paul M., et al., "Parallel confocal detection of single molecules in real time", Optics Letters, v. 33, n. 9, p. 1026, May 1, 2008.
Ma, Hongqiang, et al. "A Simple Marker-Assisted 3D Nanometer Drift Correction Method for Superresolution Microscopy", Biophysical Journal, 112, May 23, 2017, pp. 2196-2208.
Malkusch, S., et al., "Extracting Quantitative Information from Single-Molecule super-Resolution Imaging Data with LAMA-Localization Microscopy Analyzer", Scientific Report 6.1 (2016: 1-4).
Marie, Rodolphe, et al., "Integrated view of genome structure and sequence of a single DNA molecule in a nanofluidic device", PNAS, V. 110, N. 13, p. 4893-4898, Mar. 26, 2013.
Mertz, Jerome, et al., "Scanning light-sheet microscopy in the whole mouse brain with HiLo background rejection", J. of Biom. Optics, 15(1), 016027-1-016027-7, Jan./Feb. 2010.
Metzker, Michael, "Termination of DNA synthesis by novel 3'-modified deoxyribonucleoside 5'-triphosphates", Nucleic Acids Research, v. 22, n. 20, p. 4259-4267 (1994).
Mir, Kalim U., "Sequencing Genomes: From Individuals to Populations", Briefings in Functional Genomics and Proteomics, v. 8, n. 5, p. 367-378 (2009).
Neely, R. K., et al. "DNA Fluorocode: A single molecule, optical map of DNA with nanometre resolution", Chemical Science, 1(4), p. 453-460 (Aug. 11, 2020).
Nehme, Elias et al., "Deep-STORM: super-resolution single-molecule microscopy by deep learning", Optica, v. 5, n. 4, p. 458-464 (Apr. 2018).
Ovesný, Martin, et al., "ThunderSTORM: a comprehensive ImageJ plug-in for PALM and STORM data analysis and super-resolution imaging", Bionformatics, v. 30, n. 16, p. 2389-2390 (2014).
Pihlak, A., et al., "Rapid Genome Sequencing with Short Universal Tiling Probes", Nature Biotech., v. 26, n. 6. pg. 676-684 (Jun. 2008).
Ramesh, et al., Rapid Denaturation Improves Chromosome Morphology and Permits Multiple Hybridizations during Fluorescence in situ Hybridization, Biotech. Histochem., 72, 141-143, 1997.
Rhoads, A., et al., "PacBio sequencing and its applications", Genomics, Proteomics & Bioinformatics, 13(5), p. 278-289 (Nov. 2, 2015).
Roloff, Tim C., et al., "Comparative study of methyl-CpG-binding domain proteins", BMC Genomics, 2003, 4:I, available from: http://.biomedcentral.com/1471-2164/4/1.
Rouillard, et al., "OligoArray 2.0: design of oligonucleotide probes for DNA microarrays using a thermodynamic approach" Nuc Acids Res 31(12), 3057-3062 (2003).
Ryder et al., "MAMMOT—a set of tools for the design, management and visualization of genomic tiling arrays", Bioninform, Genome Analy. 22(7), 883-884 (2006).
Schnitzbauer, Joerg, et al. "Super-resolution microscopy with DNA-PAINT," Nat. Protocols 12, No. 6, 2017, pp. 1198-1228.
Song, Kyung-Mi, et al., "Aptamers and Their Biological Applications", Sensors, n. 12, p. 612-631 (2012).

(56) References Cited

OTHER PUBLICATIONS

Toseland, Christopher P., "Fluorescent labeling and modification of proteins", J. Chem Biol (2013) 6:85-95.

Urban, A.E., et al. "High-Resolution Mapping of DNA Copy Alterations in Human Chromosome 22 Using High-Density Tiling Oligonucleotide Arrays", PNAS, v. 103, n. 12, p. 4534-4539 (Mar. 21, 2006).

Vicidomini, Giuseppe, et al. "STED super-resolved microscopy," Nat Methods, vol. 15, Mar. 2018, pp. 173-182.

Wang et al., "Dried Gel Hybridizationin Place of Southern Hybridization for detection of Listeria Monocytogenes DNA Frangments", Lett. Appl. Microbiol, 12, 224-227, 1991.

Wei, Feifei, et al. "Wide Field Super-Resolution Surface Imaging through Plasmonic Structured Illumination Microscopy", Nano Letters, ACS Publications, 2014, 14, pp. 4634-4639.

Woo, Sungwook et al., "Self-assembly of two-dimensional DNA origami lattices using cation-controlled surface diffusion", Nature Communications | 5:4889 | DOI: 10.1038/ncomms5889.nature.com/naturecommunications, Received Feb. 26, 2014, Accepted Aug. 1, 2014, Published Sep. 10, 2014.

Zamboni, Javier Eduardo Diaz, et al. "Estimation Methods of the Point Spread Function Axial Position: A Comparative Computational Study," Journal of Imaging, 2017, 3, 7; mdpi.com/journal/jimaging, pp. 26.

\* cited by examiner (202) A method of sequencing a nucleic acid is provided in which the nucleic acid in double stranded linearized stretched form on a test substrate thereby forming a fixed stretched double stranded nucleic acid.

(206) Denature the fixed stretched double stranded nucleic acid to single stranded form on the test substrate thereby obtaining a fixed first strand and a fixed second strand of the nucleic acid, wherein respective bases of the fixed second strand lie adjacent to corresponding complementary bases of the fixed first strand.

(208) Expose the fixed first strand and the fixed second strand to a respective pool of a respective oligonucleotide probe in a set of oligonucleotide probes. Each oligonucleotide probe in the set of oligonucleotide probes is of a predetermined sequence and length. The exposing occurs under conditions that allow for individual probes of the respective pool of the respective oligonucleotide probe to bind and form a respective heteroduplex with each portion of the fixed first strand or the fixed second strand that is complementary to the respective oligonucleotide probe thereby giving rise to a respective instance of optical activity (210) The exposing occurs under conditions that allow for individual probes of the respective pool of the respective oligonucleotide probe to transiently and reversibly bind and form the respective heteroduplex with each portion of the fixed first strand or the fixed second strand that is complementary to the individual probes thereby giving rise to an instance of optical activity (212) Each oligonucleotide probe in the set of oligonucleotide probes is bound with a label

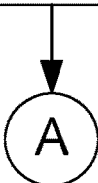

Fig. 2A

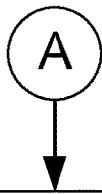

(214) Measure a location on the test substrate and a duration of each respective instance of optical activity occurring during the exposing using a two-dimensional imager.

> (216) The measuring the location on the test substrate comprises inputting a frame of data measured by the two-dimensional imager into a trained convolutional neural network. The frame of data comprises the respective instance of optical activity among a plurality of instances of optical activity. Each instance of optical activity in the plurality of instances of optical activity corresponds to an individual probe binding to a portion of the fixed first strand or the fixed second strand, and. Responsive to the inputting, the trained convolutional neural network identifies a position on the test substrate of each of one or more instances of optical activity in the plurality of instances of optical activity.

(218) Repeat the exposing and measuring for respective oligonucleotide probes in the set of oligonucleotide probes, thereby obtaining a plurality of sets of positions on the test substrate, each respective set of positions on the test substrate corresponding to an oligonucleotide probe in the set of oligonucleotide probes > (200) The set of oligonucleotide probes comprises a plurality of subsets of the oligonucleotide probes and where repeating the exposing and measuring is performed for each respective subset of oligonucleotide probes in the plurality of subsets of oligonucleotide probes (202) Determine the sequence of at least a portion of the nucleic acid from the plurality of sets of positions on the test substrate by compiling the positions on the test substrate represented by the plurality of sets of positions.

Fig. 2B (302 - 304) A method of sequencing a nucleic acid is provided in which the nucleic acid is fixed in linearized stretched form on a test substrate thereby forming a fixed stretched nucleic acid.

> (306) The nucleic acid is double stranded nucleic acid and the method further comprises denaturing the fixed double stranded nucleic acid to single stranded form on the test substrate thereby obtaining a fixed first strand and a fixed second strand of the nucleic acid, wherein the fixed second strand is complementary to the fixed first strand.

> (308) The nucleic acid is single stranded RNA (310) Expose the fixed stretched nucleic acid to a respective pool of a respective oligonucleotide probe in a set of oligonucleotide probes, wherein each oligonucleotide probe in the set of oligonucleotide probes is of a predetermined sequence and length, the exposing (b) occurring under conditions that allow for individual probes of the respective pool of the respective oligonucleotide probe to transiently and reversibly to each portion of the fixed nucleic acid that is complementary to the respective oligonucleotide probe thereby giving rise to a respective instance of optical activity (312) Measure a location on the test substrate and a duration of each respective instance of optical activity occurring during the exposing using a two-dimensional imager (314) Repeat the exposing and measuring for respective oligonucleotide probes in the set of oligonucleotide probes, thereby obtaining a plurality of sets of positions on the test substrate, each respective set of positions on the test substrate corresponding to an oligonucleotide probe in the set of oligonucleotide probes.

(316) Determine the sequence of at least a portion of the nucleic acid from the plurality of sets of positions on the test substrate by compiling the positions on the test substrate represented by the plurality of sets of positions.

Fig. 3

(402 - 404) A method of analyzing a nucleic acid is provided in which the nucleic acid is fixed in double stranded form on a test substrate thereby forming a fixed double stranded nucleic acid

(406) Denature the fixed double stranded nucleic acid to single stranded form on the test substrate thereby obtaining a fixed first strand and a fixed second strand of the nucleic acid, wherein the fixed second strand is complementary to the fixed first strand

(408) Expose the fixed first strand and the fixed second strand to one or more oligonucleotide probes and determining whether the one or more oligonucleotide probes binds to the fixed first strand or the fixed second strand.

Fig. 4 accggttgtactagaggatt cggatagctaaaatgcggattataatgtccccctcag
602        cct  cct      cct                              (SEQ ID NO. 3)
    604   604          606       604    606

Fig. 6A accggttgtactagaggatgcccaatagctggatgcgtaaaaatgcggattataatgtccccctcag
602    cctaa         cctaa           cctaa                (SEQ ID NO. 4)
    610    612-1        610   612-2     610    612-3

```
702                  704         704                706         706
 acaaattgtactagaggat cct tagctaaaatcg ttaaaatgc ggat cct tatt aatgtccccctcag
                     708         708                710                   (SEQ ID NO. 5)
```

Fig. 7B

```
         712               704         704                         704
      aac                  cct         cct                         cct
 acaaattgtactagaggat tagctaaaatcg ttaaaatgc ggat tatt aatgtccccctcag
     714            708         708                708                   (SEQ ID NO. 5)
```

Fig. 7C

```
702                     704         704          716-2      716-3     704
    ttt                 cct         cct       ttt        ttt          cct
 adaaattgtactagaggat tagctaaaatcg ttaaaatgc ggat tataatgtccccctcag
     718  716-1     708         708          720         720         708
                                                                         (SEQ ID NO. 5)
```

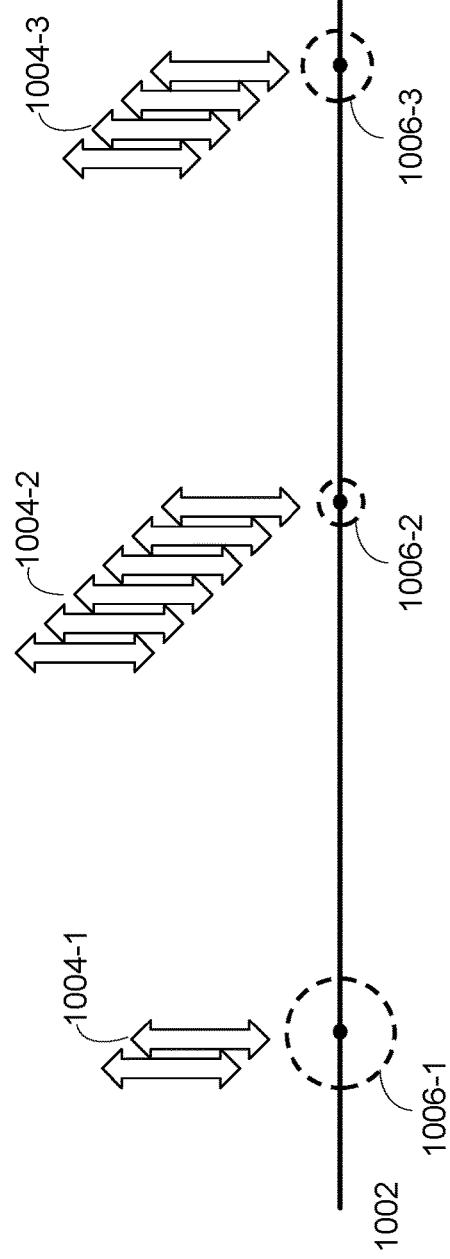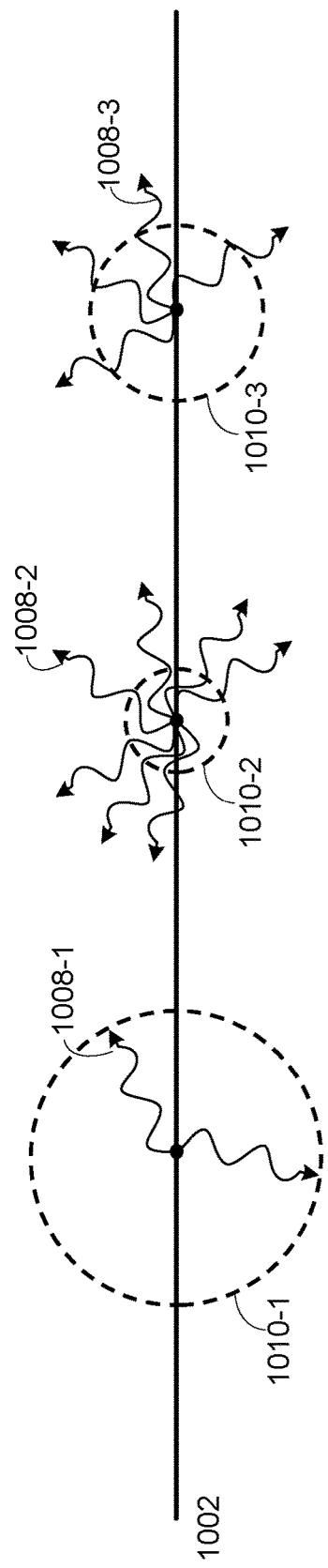

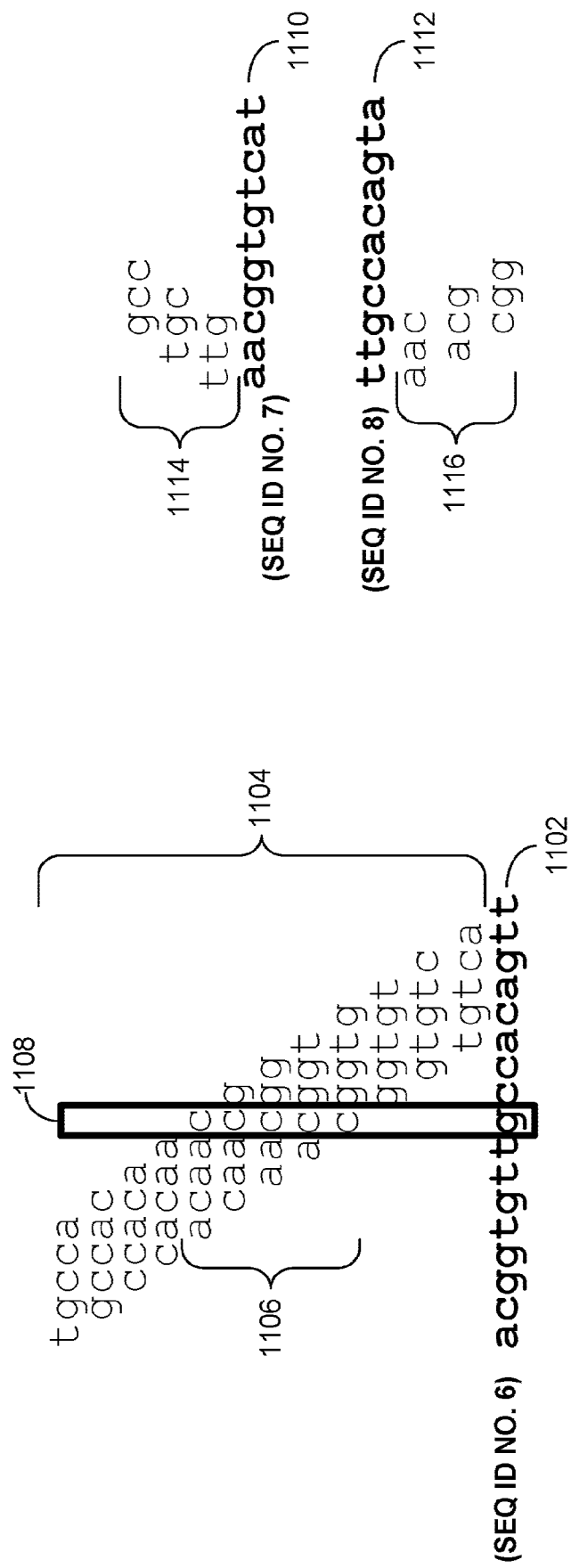

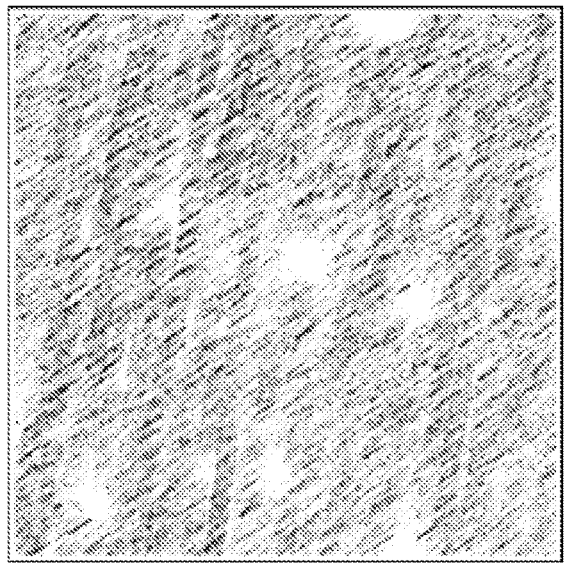 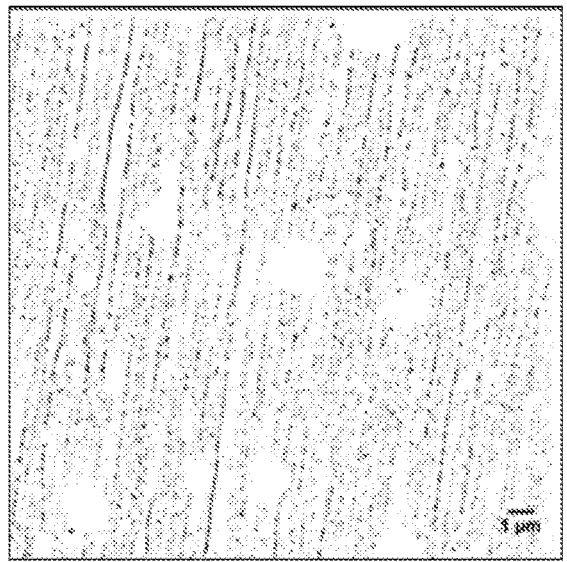
Fig. 23A        Fig. 23B
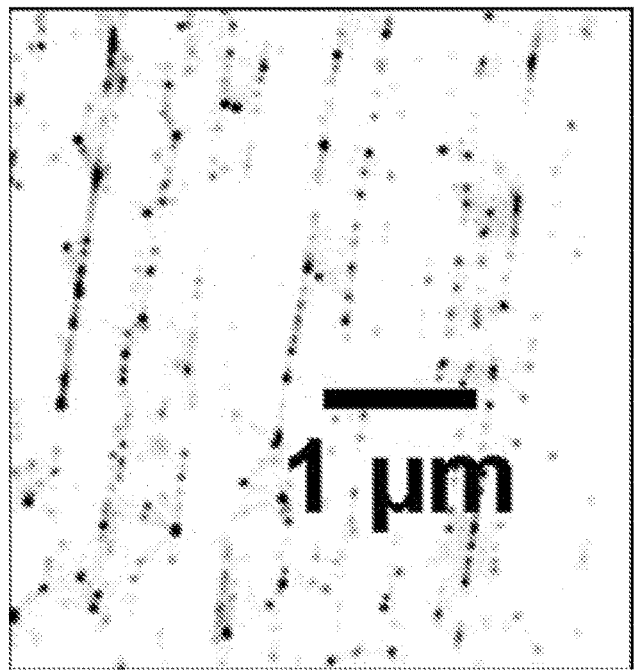
Fig. 23C

Experimental signal sites
3004 → wash → 2879 → wash → 3006 → wash → 3004
Strand 1
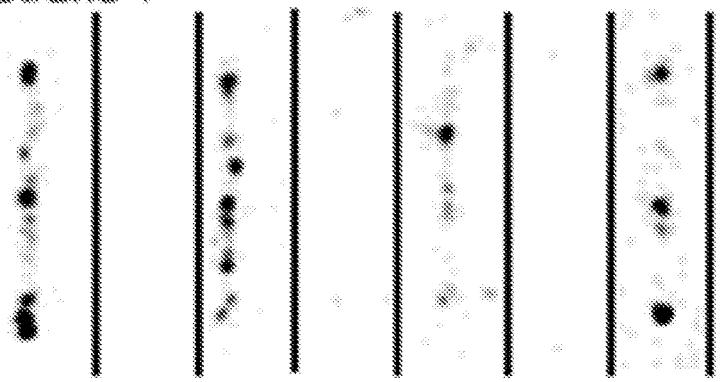
Strand 2
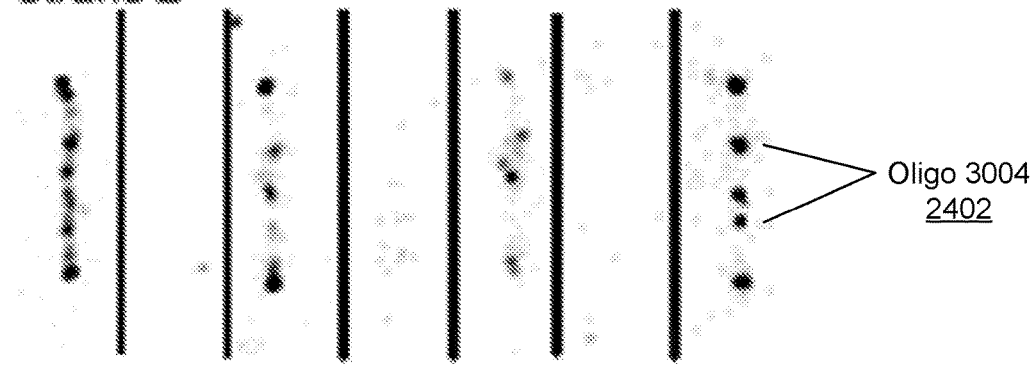
Oligo 3004
2402
Strand 3
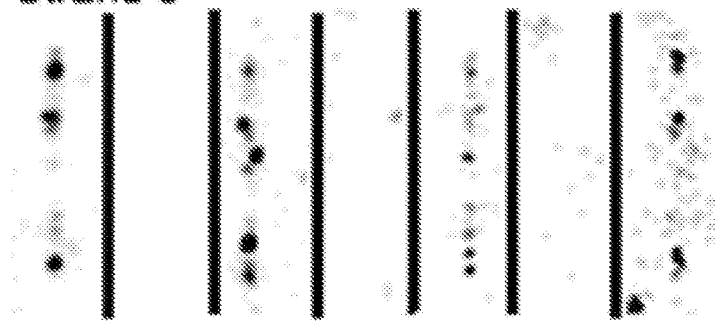
Fig. 24 a. First Cycle- XNNNN

```
        catact
           tactg
   ttgtc
      gtcat
         atact
             ctgaa
```
(SEQ ID NO. 10)
```
   aacagtatgactttt
      tgtca
         tcata
             tgaaa
           actga
         atactg
```

Fig. 25A b. Second Cycle-NXNNN

```
        catact
           tactg
   ttgtc
      gtcat
         atact
             ctgaa
```
(SEQ ID NO. 10)
```
   aacagtatgactttt
                tgaaa
           tcata
             actga
```

Fig. 25B

```
            N N t N N
              N N t N N
                N N g N N
                  N N t N N
                    N N c N N
                      N N a N N
                        N N t N N
                          N N a N N
(SEQ ID NO. 10)  a a c a g t a t g a c t t t t
                          N N c N N
                            N N t N N
                              N N g N N
                                N N a N N
                                  N N a N N
                                    N N a N N
                                      N N a N N
```

Homogeneous Sequencing with
multicolor NNXNN binding

Fig. 26 the sequencing. Chemical methods for DNA sequencing (e.g., the Illumina Inc.), is dominant.

SEQUENCING BY EMERGENCE

CROSS REFERENCE TO RELATED APPLICATIONS

This application is a continuation-in-part of U.S. Pat. No. 10,982,260 entitled "Sequencing by Emergence," filed Nov. 29, 2018 which claims priority to U.S. Provisional Patent Application No. 62/591,850 entitled "Sequencing by Emergence," filed Nov. 29, 2017, each of which are hereby incorporated by reference.

REFERENCE TO SEQUENCE LISTING

The Sequence Listing text copy submitted herewith via EFS-Web was created on Jan. 31, 2022, is entitled 1184965005US02_ST25.txt, is 7 kilobytes in size and is herein incorporated by reference in its entirety.

TECHNICAL FIELD

The present disclosure relates generally to systems and methods for sequencing nucleic acids via transitory binding of probes to one or more polynucleotides.

BACKGROUND

DNA sequencing first became a reality with gel electrophoresis-based methods: the dideoxy chain termination method (e.g., Sanger et al., Proc. Natl. Acad. Sci. 74:5463-5467, 1977), and the chemical degradation method (e.g., Maxam et al., Proc. Natl. Acad. Sci. 74:560-564, 1977). These methods of sequencing nucleotides were both time-consuming and expensive. Nevertheless, the former led to the sequencing the human genome for the first time, despite taking more than ten years and hundreds of millions of dollars.

As the dream of personalized medical care comes ever nearer to fruition, there is an increasing need for inexpensive, large-scale methods for sequencing individual human genomes (Mir, Sequencing Genomes: From Individuals to Populations, Briefings in Functional Genomics and Proteomics, 8: 367-378, 2009). Several sequencing methods that avoid gel electrophoresis (and which are subsequently less expensive) were developed as "next generation sequencing." One such method of sequencing, using reversible terminators (as practiced by Illumina Inc.), is dominant. The detection methods used in the most evolved form of Sanger sequencing and the currently dominant Illumina technology involve fluorescence. Other possible means of detecting single nucleotide insertions include detection using a proton release (e.g., via a field effect transistor, an ionic current through a nanopore and electron microscopy. Illumina's chemistry involves cyclical addition of nucleotides using reversible terminators (Canard et al., Metzker Nucleic Acids Research 22:4259-4267, 1994), which bear fluorescent labels (Bentley et al., Nature 456:53-59, 2008). Illumina sequencing starts with clonally amplifying single genomic molecules, and substantial upfront sample processing is needed to convert the target genome into a library that is then clonally amplified as clusters.

However, several methods have since reached the market that circumvents the need for amplification prior to sequencing. Both new methods conduct fluorescent Sequencing by Synthesis (SbS) on single molecules of DNA. The first method, from HelicosBio (now SeqLL), conducts stepwise SbS with reversible termination (Harris et al., Science, 320:106-9, 2008). The second method, SMRT Sequencing from Pacific Biosciences uses labels on a terminal phosphate, a natural leaving group of the reaction incorporating a nucleotide, which allows sequencing to be conducted continuously and without the need for exchanging reagents (e.g., Levene et al., Science 299:682-686, 2003 and Eid et al., Science, 323:133-8, 2009). A somewhat similar approach to Pacific Bioscience sequencing is the method being developed by Genia (now part of Roche) by detecting SbS via a nanopore, rather than via optical methods.

The most commonly used sequencing methods are limited in read length, which increases both the cost of sequencing and the difficulty of assembling the resulting reads. The read lengths obtained by Sanger sequencing are in the 1000 base range (e.g., Kchouk et al., Biol. Med. 9:395, 2017). Roche 454 sequencing and Ion Torrent both have read lengths in the hundreds of bases range. Illumina sequencing, which initially started with a read of about 25 bases, is now typically 150-300 base pair reads. However, as fresh reagents need to be supplied for each base of the read length, sequencing 250 bases rather than 25 requires 10× more time and 10× more of the costly reagents. The longest read lengths possible in commercial systems are obtained by nanopores strand sequencing from Oxford Nanopores Technology (ONT) and Pacific Bioscience (PacBio) sequencing (e.g., Kchouk et al., Biol. Med. 9:395, 2017). The latter routinely has reads that average about 10,000 bases in length, while the former on very rare occasions is able to get reads that are several hundreds of kilobases in length (e.g., Laver et al., Biomol. Det. Quant. 3:1-8, 2015).

Beside ONT and PacBio sequencing, a number of approaches exist that are not sequencing technologies per se, but are sample preparation approaches that supplement Illumina short read sequencing technology to provide a scaffold for building longer reads. Of these, one is the droplet based technology developed by 10× Genomics, which isolates 100-200 kb fragments (e.g., the average length range of fragments after extraction) within droplets and processes them into libraries of shorter length fragments each of which contains a sequence identifiers tag specific for the 100-200 kb from which they originate, which upon sequencing of the genome from a multiplicity of droplets can be deconvolved into ~50-200 Kb buckets (Goodwin et al., Nat. Rev. Genetics 17:333-351, 2016). Another approach has been developed by Bionano Genomics that stretches and induces nicks in DNA via exposure to a nicking endonuclease. The method fluorescently detects points of nicking to provide a map or scaffold of the molecule. This method at present has not been developed to have a high enough density to help assemble genomes, but it nevertheless provides a direct visualization of the genome and is able to detect large structural variations and determine long-range haplotypes.

Despite the different sequencing methods developed and the general trend in decreasing sequencing cost, the size of the human genome continues to lead to high sequencing costs for patients. An individual human genome is organized into 46 chromosomes, of which the shortest is about 50 megabases and the longest 250 megabases. NGS sequencing methods still have many issues that affect performance, including the reliance on reference genomes that can substantially increase the time required for analysis (e.g., as discussed in Kulkarni et al., Comput Struct Biotechnol J. 15:471-477, 2017).

Given the above background, what is needed in the art are devices, systems and methods for providing a stand-alone sequencing technology that is efficient in the use of reagents and time and that provides long, haplotype-resolved reads without loss of accuracy.

The information disclosed in this Background section is only for enhancement of understanding of the general background and should not be taken as an acknowledgment or any form of suggestion that this information forms the prior art already known to a person skilled in the art.

SUMMARY

The present disclosure addresses the need in the art for devices, systems and methods for providing improved nucleic acid sequencing techniques. In one broad aspect, the present disclosure comprises a method of identifying at least one unit of a multi-unit target molecule by binding molecular probes to one or more units of a double stranded target molecule. The present disclosure is based on the detection of single molecule interactions of one or more species of molecular probes with a double stranded target molecule. In some embodiments, probes bind transiently to at least one unit of a target molecule. In some embodiments, probes bind repetitively to at least one unit of a target molecule. In some embodiments, molecular entities are localized on a macromolecule, surface or matrix to nanometric accuracy.

In one aspect, a method of sequencing a nucleic acid is provided. The method comprises (a) fixing the nucleic acid in linearized elongated/stretched form on a test substrate thereby forming a fixed elongated/stretched nucleic acid. The method proceeds by (b) exposing the fixed elongated/stretched nucleic acid to respective oligonucleotide probe species in a set of oligonucleotide probe species, where each oligonucleotide probe species in the set of oligonucleotide probe species is a library of probe species of a predetermined length, comprising one defined nucleotide and one or more degenerate positions. Each defined nucleotide is selected from the set of A, C, G, T bases. Each degenerate position comprises either a mixture of A, C, G, T bases or universal base analogs. The exposing (b) occurs under conditions that allow for individual probes of the respective oligonucleotide probe species to transiently and reversibly bind to one or more portions of the fixed nucleic acid that are complementary to the respective oligonucleotide probe species, thereby giving rise to a respective instance of optical activity. The method proceeds by (c) measuring a location on the test substrate of each respective instance of optical activity occurring during or after the exposing (b) using an imaging device. The method proceeds by (d) repeating the exposing (b) and measuring (c) for respective oligonucleotide probe species in the set of oligonucleotide probe species, thereby obtaining a plurality of sets of positions on the test substrate. Each respective set of positions on the test substrate corresponds to an oligonucleotide probe species in the set of oligonucleotide probe species. The method continues by (e) determining the sequence of at least a portion of the nucleic acid from the plurality of sets of positions on the test substrate by compiling the positions on the test substrate represented by the plurality of sets of positions.

In another aspect of the present disclosure, a method of sequencing a nucleic acid is provided. This additional method comprises (a) fixing the nucleic acid in linearized elongated/stretched form on a test substrate thereby forming a fixed elongated/stretched nucleic acid. The method continues by (b) exposing the fixed elongated/stretched nucleic acid to respective oligonucleotide probe species in a set of oligonucleotide probe species. Each oligonucleotide probe species in the set of oligonucleotide probe species is a library of probe species of a predetermined length, comprising two or more defined nucleotide positions and one or more degenerate positions. Each defined nucleotide position comprises A, C, G, T bases. Each degenerate position comprises either a mixture of A, C, G, T bases or universal base analogs. The exposing (b) occurs under conditions that allow for individual probes of the respective oligonucleotide probe species to transiently and reversibly bind to one or more portions of the fixed nucleic acid that are complementary to the respective oligonucleotide probe species, thereby giving rise to a respective instance of optical activity. The method proceeds by (c) measuring a location on the test substrate of each respective instance of optical activity occurring during or after the exposing (b) using an imaging device. The method continues by (d) repeating the exposing (b) and measuring (c) for respective oligonucleotide probe species in the set of oligonucleotide probe species, thereby obtaining a plurality of sets of positions on the test substrate. Each respective set of positions on the test substrate corresponding to an oligonucleotide probe species in the set of oligonucleotide probe species. The method concludes by (e) determining the sequence of at least a portion of the nucleic acid from the plurality of sets of positions on the test substrate by compiling the positions on the test substrate represented by the plurality of sets of positions.

In another aspect of the present disclosure, a method of sequencing a nucleic acid is provided. This additional method comprises (a) fixing the nucleic acid in linearized elongated/stretched form on a test substrate thereby forming a fixed elongated/stretched nucleic acid. The method proceeds by (b) exposing the fixed elongated/stretched nucleic acid to respective oligonucleotide probe species in a set of oligonucleotide probe species. Each oligonucleotide probe species in the set of oligonucleotide probe species is a library of probe species of a predetermined length, comprising two or more defined nucleotide positions and one or more degenerate positions. Each defined nucleotide position comprises one of the set of A, C, G, T bases. Each degenerate position comprising either a mixture of A, C, G, T bases or universal base analogs. The exposing (b) occurs under conditions that allow for individual probes of the respective oligonucleotide probe species to bind stably to one or more portions of the fixed nucleic acid that are complementary to the respective oligonucleotide probe species thereby upon illumination giving rise to a respective instance of optical activity at one or more locations on the substrate corresponding to one or more portions of the fixed nucleic acid. The method proceeds by (c) allowing the instances of optical activity to bleach such that step-by-step loss of instances of optical activity is measured/recorded using an imaging device. The method continues by (d) exposing the fixed elongated/stretched nucleic acid to conditions that allow the bound oligonucleotide probes to unbind; repeating the exposing (b) and measuring (c) for respective oligonucleotide probe species in the set of oligonucleotide probe species, thereby obtaining a plurality of sets of positions on the test substrate. Each respective set of positions on the test substrate corresponding to an oligonucleotide probe species in the set of oligonucleotide probe species. The method proceeds by (d) using a single molecule localization algorithm to calculate the nanometric/fine-tuned location of each instance of optical activity, and (e) determining the sequence of at least a portion of the nucleic acid from the plurality of sets of positions on the test substrate by compiling the positions on the test substrate represented by the plurality of sets of positions.

Another aspect of the present disclosure provides a method of sequencing a nucleic acid. The method comprises (a) fixing/immobilizing the nucleic acid on a test substrate thereby forming a fixed/immobilized nucleic acid. The method proceeds with (b) exposing the fixed/immobilized nucleic acid to respective oligonucleotide probe species in a set of oligonucleotide probe species. The exposing (b) occurs under conditions that allow for individual probes of the respective oligonucleotide probe species to bind to one or more portions of the fixed/immobilized nucleic acid that are complementary to the respective oligonucleotide probe species, thereby giving rise to a respective instance of optical activity. The method proceeds by (c) measuring a location on the test substrate of each respective instance of optical activity occurring during or after the exposing (b) using an imaging device. The method continues by (d) repeating the exposing (b) and measuring (c) for respective oligonucleotide probe species in the set of oligonucleotide probe species, thereby obtaining a plurality of sets of positions on the test substrate. Each respective set of positions on the test substrate corresponding to an oligonucleotide probe species in the set of oligonucleotide probe species. The method concludes by (e) determining the sequence of at least a portion of the nucleic acid from the plurality of sets of positions on the test substrate by compiling the positions on the test substrate represented by the plurality of sets of positions.

Other embodiments are directed to systems, portable consumer devices, and computer readable media associated with methods described herein.

As disclosed herein, any embodiment disclosed herein when applicable can be applied to any aspect.

Additional aspects and advantages of the present disclosure will become readily apparent to those skilled in this art from the following detailed description, where only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

BRIEF DESCRIPTION OF THE DRAWINGS

FIGS. 2A and 2B collectively provide a flow chart of processes and features of a method for determining a sequence and/or structural characteristics of a target polymer in accordance with various embodiments of the present disclosure.

FIG. 3 provides a flow chart of processes and features of an additional method for determining a sequence and/or structural characteristics of a target polymer in accordance with various embodiments of the present disclosure.

FIG. 4 provides a flow chart of processes and features of an additional method for determining a sequence and/or structural characteristics of a target polymer in accordance with various embodiments of the present disclosure.

FIGS. 6A and 6B collectively illustrate an example of probes of different k-mers in length binding to a target polynucleotide in accordance with various embodiments of the present disclosure.

FIGS. 7A, 7B, and 7C collectively illustrate an example of using a reference oligo with successive cycles of oligonucleotide sets in accordance with various embodiments of the present disclosure.

FIGS. 10A and 10B collectively illustrate an example that a number of transient binding events collected correlates with a degree of localization of probe that can be achieved in accordance with various embodiments of the present disclosure.

FIGS. 11A and 11B collectively illustrate an example of tiling probes in accordance with various embodiments of the present disclosure.

FIGS. 23A, 23B, and 23C collectively illustrate examples of fluorescence in accordance with various embodiments of the present disclosure.

FIG. 24 illustrates transient binding on synthetic denatured double-stranded DNA in accordance with various embodiments of the present disclosure.

FIGS. 25A and 25B illustrate two cycles of "footprint" sequencing where in this case of 5-mers, 5 cycles are used in which each cycle has a different single nucleotide position defined along the 'footprint' or length of the oligonucleotide and the rest of the nucleotides are degenerate comprising either a library of all 4 nucleotides at each position or universal nucleotide analogs at each degenerate position (e.g., a nitroindole, nitropyrrole or inosine etc.). Each defined base is represented with a different color which when added in the same mix is linked to one of four distinct labels each of which can be distinguished from each other. In the figure position 1 is defined in the first cycle and position 2 is defined in the second cycle. Going through these cycles the identity of position 1, 2, 3, 4, 5 in the target (under the footprint of the oligo) are obtained in consecutive cycles. In some embodiments, the identity of the interrogated base in the target is complementary to the corresponding defined base in the oligo. In some such embodiments the localization needs to be sufficient to pinpoint the location of the oligo binding footprint, the position within the footprint is defined by a code such as color or the cycle number.

FIG. 26 schematically illustrates a case where only one nucleotide is defined and all four different defined nucleotides are indicated with a different color. The different colors in some embodiments indicate different fluorophores or different addition cycles. When it is different color the whole sequencing process can be carried out in a single homogeneous or one-pot reaction, without the need for reagent exchange. In this approach strands of DNA are elongated/stretched on a surface and short oligos are added in solution and bind to their complementary locations.

DETAILED DESCRIPTION

Figure 1A:
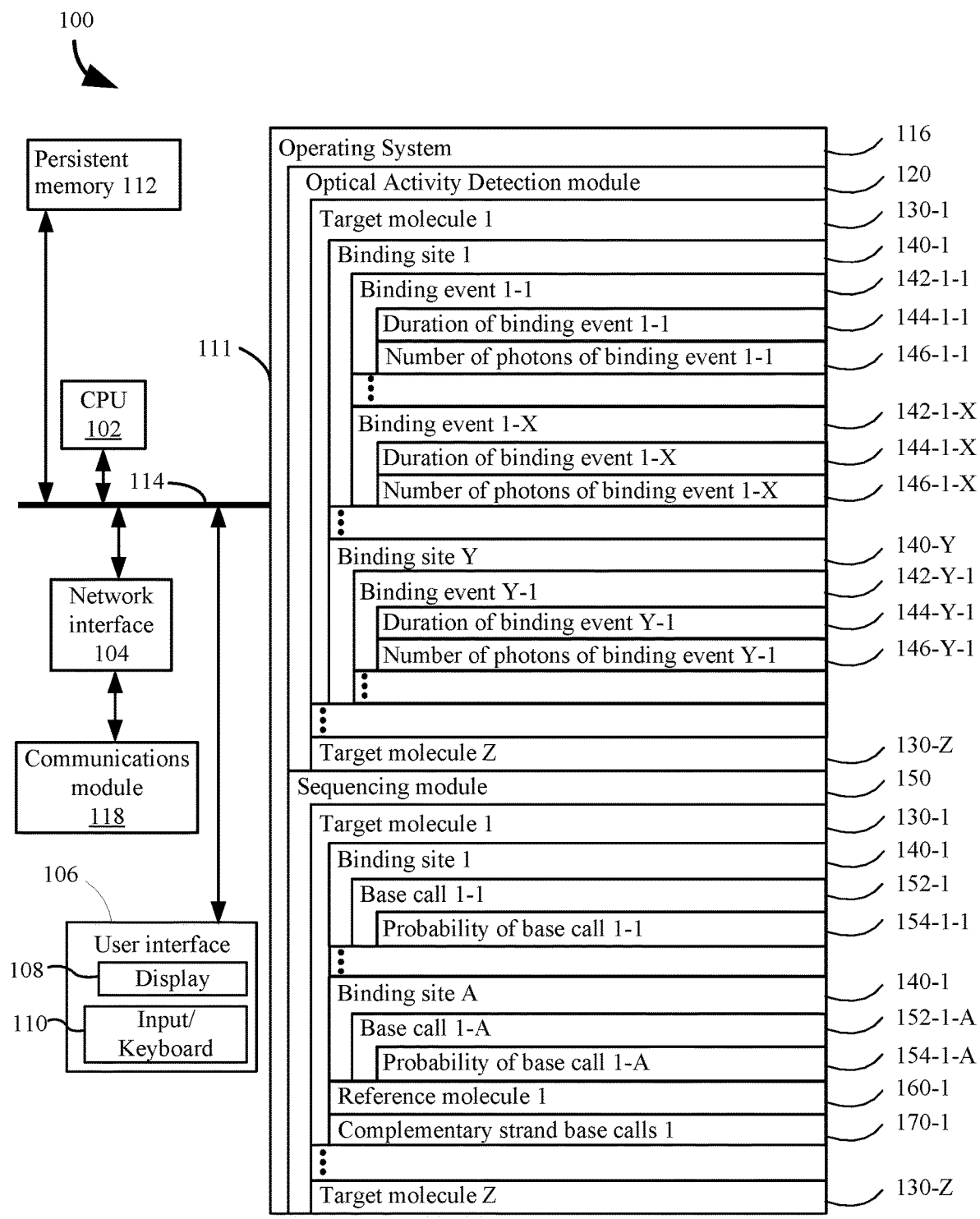
FIGS. 1A and 1B collectively illustrate an exemplary system topology that includes a polymer with multiple probes that participate in binding events, a computer storage medium to collect and store information relating to localization and sequence identification of binding events and then to further perform analysis to determine a polymer sequence in accordance with various embodiments of the present disclosure.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure is practiced without these specific details. In other instances, well-known methods, procedures, components, circuits, and networks have not been described in detail so as not to unnecessarily obscure aspects of the embodiments.

Definitions

The terminology used in the present disclosure is for the purpose of describing particular embodiments only and is not intended to be limiting of the invention. As used in the description and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is construed to mean "when" or "upon" or "in response to determining" or "in response to detecting," depending on the context. Similarly, the phrase "if it is determined" or "if [a stated condition or event] is detected" is construed to mean "upon determining" or "in response to determining" or "upon detecting [the stated condition or event]" or "in response to detecting [the stated condition or event]," depending on the context.

The term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

It will also be understood that, although the terms first, second, etc. is used herein to describe various elements, these elements should not be limited by these terms. These terms are only used to distinguish one element from another. For example, a first filter could be termed a second filter, and, similarly, a second filter could be termed a first filter, without departing from the scope of the present disclosure. The first filter and the second filter are both filters, but they are not the same filter.

As used herein, the terms "about" or "approximately" can mean within an acceptable error range for the particular value as determined by one of ordinary skill in the art, which can depend in part on how the value is measured or determined, e.g., the limitations of the measurement system. For example, "about" can mean within 1 or more than 1 standard deviation, per the practice in the art. "About" can mean a range of ±20%, ±10%, ±5%, or ±1% of a given value. The terms "about" or "approximately" can mean within an order of magnitude, within 5-fold, or within 2-fold, of a value. Where particular values are described in the application and claims, unless otherwise stated the term "about" meaning within an acceptable error range for the particular value should be assumed. The term "about" can have the meaning as commonly understood by one of ordinary skill in the art. The term "about" can refer to ±10%. The term "about" can refer to ±5%.

As used herein, the terms "nucleic acid," "nucleic acid molecule," and "polynucleotide" are used interchangeably. The terms may refer to nucleic acids of any compositional form, such as deoxyribonucleic acid (DNA, e.g., complementary DNA (cDNA), genomic DNA (gDNA) and the like), ribonucleic acid (RNA, e.g., message RNA (mRNA), short inhibitory RNA (siRNA), ribosomal RNA (rRNA), transfer RNA (tRNA), microRNA, RNA highly expressed by the fetus or placenta, and the like), and/or DNA or RNA analogs (e.g., containing synthetic base analogs and or naturally occurring (epigenetically modified) base analogs, sugar analogs and/or a non-native backbone and the like), RNA/DNA hybrids and peptide nucleic acids (PNAs), all of which can be in single- or double-stranded form. Unless otherwise limited, a nucleic acid can comprise known analogs of natural nucleotides, some of which can function in a similar manner as naturally occurring nucleotides. A nucleic acid can be in any form useful for conducting processes as described herein (e.g., linear, circular, supercoiled, single-stranded, double-stranded and the like). In some instances, a nucleic acid is, or is from, a plasmid, phage, autonomously replicating sequence (ARS), centromere, artificial chromosome, chromosome, or other nucleic acid able to replicate or be replicated in vitro or in a host cell, a cell, a cell nucleus or cytoplasm of a cell in certain embodiments. A nucleic acid In some embodiments, can be from a single chromosome or fragment thereof (e.g., a nucleic acid sample from one chromosome of a sample obtained from a diploid organism). A nucleic acid molecule can comprise a complete length of a natural polynucleotide (e.g., a long non-coding (lnc) RNA, mRNA, chromosome, mitochondrial DNA or a polynucleotide fragment). A polynucleotide fragment can be at least 200 bases in length or can be at least several thousands of nucleotides in length, or in the case of genomic DNA, polynucleotide fragments can be hundreds of kilobases to multiple megabases in length.

In certain embodiments nucleic acids comprise nucleosomes, fragments or parts of nucleosomes or nucleosome-like structures. Nucleic acids sometimes comprise protein (e.g., histones, DNA binding proteins, and the like). Nucleic acids analyzed by processes described herein sometimes are substantially isolated and are not substantially associated with protein or other molecules. Nucleic acids also include derivatives, variants and analogs of RNA or DNA synthesized, replicated or amplified from single-stranded ("sense" or "antisense", "plus" strand or "minus" strand, "forward" reading frame or "reverse" reading frame) and double-stranded polynucleotides. Deoxyribonucleotides include deoxyadenosine, deoxycytidine, deoxyguanosine and deoxythymidine. For RNA, the base cytosine is replaced with uracil and the sugar 2' position includes a hydroxyl moiety. In some embodiments, a nucleic acid is prepared using a nucleic acid obtained from a subject as a template.

As used herein the term "ending position" or "end position" (or just "end") can refer to a genomic coordinate or genomic identity or nucleotide identity of an outermost base, e.g., at the extremities, of a cell-free DNA molecule, e.g., a plasmid DNA molecule. An end position can correspond to either end of a DNA molecule. In this manner, if one refers to a start and end of a DNA molecule, both can correspond to an ending position. In some embodiments, one end position is a genomic coordinate or nucleotide identity of an outermost base on one extremity of a cell-free DNA molecule that is detected or determined by an analytical method, e.g., massively parallel sequencing or next-generation sequencing, single molecule sequencing, double- or single-stranded DNA sequencing library preparation protocols, polymerase chain reaction (PCR), or microarray. In some embodiments, such in vitro techniques can alter true in vivo physical end(s) of cell-free DNA molecules. Thus, each detectable end can represent a biologically true end or an end can be one or more nucleotides inwards or one or more nucleotides extended from an original end of a molecule e.g., 5' blunting and 3' filling of overhangs of non-blunt-ended double-stranded DNA molecules by a Klenow fragment. A genomic identity or genomic coordinate of the end position can be derived from results of alignment of sequence reads to a human reference genome, e.g., hg19. It can be derived from a catalog of indices or codes that represent original coordinates of a human genome. It can refer to a position or nucleotide identity on a cell-free DNA molecule that is read by but not limited to target-specific probes, mini-sequencing, DNA amplification. The term "genomic position" can refer to a nucleotide position in a polynucleotide (e.g., a gene, a plasmid, a nucleic acid fragment, a viral DNA fragment). The term "genomic position" is not limited to nucleotide positions within a genome (e.g., the haploid set of chromosomes in a gamete or microorganism, or in each cell of a multicellular organism).

As used herein, the terms "mutation," "single nucleotide variant," "single nucleotide polymorphism", "variant", "epigenetic modification", and "structural rearrangement" refer to one or more detectable changes of one or more differing types in genetic material of one or more cells. In a particular example, one or more mutations can be found in, and can identify, cancer cells (e.g., driver and passenger mutations). A mutation can be transmitted from a parent cell to a daughter cell. A person having skill in the art will appreciate that a genetic mutation (e.g., a driver mutation) in a parent cell can induce additional, different mutations (e.g., passenger mutations) in a daughter cell. A mutation or variant generally occurs in a nucleic acid. In a particular example, a mutation can be a detectable change in one or more deoxyribonucleic acids or fragments thereof. A mutation generally refers to nucleotides that is added, deleted, substituted for, inverted, or transposed to a new position in a nucleic acid. A mutation can be a spontaneous mutation or an experimentally induced mutation. A mutation in the sequence of a particular tissue is an example, of a "tissue-specific allele." For example, a tumor can have a mutation that results in an allele at a locus that does not occur in normal cells. Another example, of a "tissue-specific allele" is a fetal-specific allele that occurs in the fetal tissue, but not the maternal tissue. The term "allele" can be used interchangeably with mutation in some cases.

The term "transient binding" means that a binding reagent or probe binds reversibly to a binding site on a polynucleotide, and the probe does not usually remain attached to its binding site. This provides useful information regarding the location of binding sites during the course of analysis. Typically, one reagent or probe binds to an immobilized polymer and then detaches from a polymer after some dwell time. The same or another reagent or probe may then bind to a polymer at another site. In some embodiments, multiple binding sites along a polymer may also be bound by multiple reagents or probes at a same time. In some instances, different probes bind to overlapping binding sites. This process of reagents or probes reversibly binding to a polymer may repeat many times over the course of analysis. Location, frequency, dwell time, photon emission of such binding events eventually results in a map of the chemical structure of a polymer. Indeed, the transient nature of these binding events enables detection of an increased number of such binding events. For, if probes remained bound for long periods of time, then each probe would inhibit binding of other probes.

The term "repetitive binding" means that a same binding site in a polymer is bound by a same binding reagent or probe or same species of binding reagent or probe multiple times during a course of an analysis. Typically, one reagent binds to a site and then dissociates, another reagent binds on and then dissociates, etc., until a map of a polymer has been developed. Repetitive binding increases sensitivity and accuracy of information obtained from probes. More photons are accumulated and multiple independent binding events increase a probability that a real signal is being detected. Sensitivity increases in cases where a signal is too low to call over background noise when only detected once. In such cases, a signal become callable when seen persistently (e.g., a confidence that a signal is real increases when a same signal is seen multiple times). Accuracy of binding site calls increases because multiple readings of information confirm one reading with another.

As used herein, the term "probe" can comprise an oligonucleotide, with one or more optional labels, which can be fluorescent labels attached. In some embodiments, a probe is a peptide or polypeptide, optionally labeled with fluorescent dyes or fluorescent or light scattering particles. These probes can be used to determine localization of binding sites, to nucleic acids or to proteins, carbohydrates, fatty acids or other biomolecules or non-biological polymers.

As used herein, the term "oligonucleotide probe species" can comprise one or more different oligonucleotides used as probes, where a portion of a sequence of the oligonucleotide is common to all members of the oligonucleotide probe species, and other portions, particularly the bases adjacent to the common sequence is degenerate or universal, and may thus result in multiple members of an oligonucleotide probe species. In some cases the term "oligonucleotide probe species" may indicate a single member of the species, such as an individual oligonucleotide probe; in other cases the term may indicate a plurality of all members of the species. An oligonucleotide probe species will all have a common label or labels if provided with a label or labels. As used herein, the term "set of oligonucleotide species" means multiple oligonucleotide species which have different common sequences.

As used herein, the term "complete set of oligonucleotide species" means all oligonucleotide species used in a sequencing method. Different members of a complete set of oligonucleotide have a same length k-mers, or have different length k-mers. A complete set of oligonucleotide probe species may comprise all k-mer sequences of a single length of k-mer, or may comprise subsets thereof.

As used herein, the term "tiling set of sequence probes" or "tiling set" means a set of oligonucleotide probe species for which all but two oligonucleotide probe species of the set will have all but one oligonucleotide probe species common bases also in common with two other oligonucleotide probe species in the set and where the corresponding different bases are at each end of the oligonucleotide probe species common sequence. Two members of the tiling set have oligonucleotide probe species which will have all but one oligonucleotide probe species common bases also in common with one other oligonucleotide probe species, and the different bases are at a respective 3' and 5' ends to complete a set of oligos which all overlap.

As used herein, the terms "oligonucleotide" and "oligo" mean short nucleic acid sequences. In some embodiments, oligos are of defined sizes, for example, each oligo is k nucleotide bases (also referred to herein as "k-mers") in length. Typical oligo sizes are 3-mers, 4-mers, 5-mers, 6-mers, and so forth. Oligos may also be referred to herein as N-mers.

As used herein, the term "label" encompasses a single detectable entity (e.g., wavelength emitting entity) or multiple detectable entities. In some embodiments, a label transiently binds to nucleic acids or is bound, either covalently or non-covalently to a probe. Different types of labels may blink during fluorescence emission, fluctuate in photon emission, or photo-switch off and on. Different labels is used for different imaging methods. In particular, some labels is uniquely suited to different types of fluorescence microscopy. In some embodiments, fluorescent labels fluoresce at different wavelengths and also have different lifetimes. In some embodiments, background fluorescence is present in an imaging field. In some such embodiments, such background is removed from analysis by rejecting a time window of fluorescence due to scattering or background fluorescence. If a label is on one end of a probe (e.g., a 3' end of an oligo probe), accuracy in localization corresponds to that end of a probe (e.g., a 3' end of a probe sequence and 5' of a target sequence). Apparent transient, fluctuating, or blinking, or dimming behavior of a label can differentiate whether an attached probe is binding on and off from its binding site.

As used herein, the term "flap" refers to an entity that acts as a receptor for binding of a second entity. Two entities can comprise molecular binding pairs. Such binding pairs can comprise nucleic acid binding pairs. In some embodiments, a flap comprises a stretch of oligo- or polynucleotide sequence that binds to a labeled oligonucleotide. Such binding between a flap and an oligonucleotide should be substantially stable during a course of a process of imaging a transient binding of a part of a probe that binds a target.

The terms "elongated," "extended," "stretched," "linearized," and "straightened" can be used interchangeably. In particular, the term "elongated polynucleotide" (or "extended polynucleotide," etc.) indicates a nucleic acid molecule that has been adhered to a surface or matrix in some manner and then stretched into a linear form. Generally, these terms mean that binding sites along a polynucleotide is separated by a physical distance more or less correlated with a number of nucleotides between them (e.g., the polynucleotide is straight). Some imprecision in an extent to which a physical distance matches a number of bases can be tolerated.

The term "imaging," as used herein, includes both two-dimensional array and two-dimensional scanning detectors. In most cases, imaging techniques used herein will necessarily include a fluorescence excitation source (e.g., a laser of appropriate wavelength) and a fluorescence detector.

As used herein, the term "sequence bit" indicates one or a few bases of sequence (e.g., from 1 to 9 bases in length). In particular, in some embodiments, a sequence corresponds to a length of oligos (or peptides) used for transient binding. Thus, in such embodiments, a sequence refers to a region of the target polynucleotide.

As used herein, the term "haplotype" refers to a set of variations that are typically inherited in concert. This occurs because a set of variations is present in close proximity on a polynucleotide or chromosome. In some cases, a haplotype comprises one or more single nucleotide polymorphisms (SNPs). In some cases, a haplotype comprises one or more alleles.

As used herein, the term "methyl-binding proteins" refers to proteins that contain a methyl-CpG-binding domain, which comprises around 70 nucleotide residues. Such domains have low affinity for unmethylated regions of DNA, and can thus be used to identify locations in a nucleic acid that have been methylated. Some common methyl-binding proteins include MeCP2, MBD1, and MBD2. However, there are a range of different proteins that contain the methyl-CpG-binding domain (e.g., as described by Roloff et al., BMC Genomics 4:1, 2003). Similarly, other types of antibodies is used to bind to other types of epigenetic modifications, such as methyl adenine.

As used herein, the term "nanobody" refers to a set of proteins comprising heavy chain only antibody fragments. These are highly stable proteins and can be designed to have sequence homology similar to a variety of human antibodies, thus enabling specific targeting of cell type or region in the body, or to specific types of naturally occurring epigenetically modified nucleobases. A review of nanobody biology can be found in Bannas et al., Frontiers in Immu. 8:1603, 2017.

As used herein, the term "affimer" refers to non-antibody binding proteins. These are highly customizable proteins, with two peptide loops and an N-terminal sequence that, in some embodiments, are randomized to provide affinity and specificity to desired protein targets. Thus, in some embodiments, affimers are used to identify sequences or structural regions of interest in proteins. In some such embodiments, affimers are used to identify many different types of protein expression, localization and interactions (e.g., as described in Tiede et al., ELife 6:e24903, 2017).

As used herein, the term "aptamer" refers to another category of highly versatile, customizable binding molecules. Aptamers comprise nucleotide and/or peptide regions. It is typical to produce a random set of possible aptamers sequences and then select for desired sequences that bind to specific target molecules of interest. Aptamers have additional characteristics beyond their stability and flexibility that make them desirable over other categories of binding proteins (e.g., as described in Song et al., Sensors 12:612-631, 2012 and Dunn et al., Nat. Rev. Chem. 1:0076, 2017).

Several aspects are described below with reference to example applications for illustration. It should be understood that numerous specific details, relationships, and methods are set forth to provide a full understanding of the features described herein. One having ordinary skill in the relevant art, however, will appreciate that the features described herein can be practiced without one or more of the specific details or with other methods. The features described herein are not limited by the illustrated ordering of acts or events, as some acts can occur in different orders and/or concurrently with other acts or events. Furthermore, not all illustrated acts or events are required to implement a methodology in accordance with the features described herein.

Exemplary System Embodiments

In one aspect, disclosed herein is a method of sequencing a target nucleic acid. A method may comprise (a) fixing a target nucleic acid in double-stranded linearized stretched form on a test substrate thereby forming a fixed stretched double-stranded nucleic acid. A method may further comprise (b) denaturing a fixed stretched double-stranded nucleic acid to single stranded form on a test substrate thereby obtaining a fixed first strand and a fixed second strand of a target nucleic acid, where respective bases of a fixed second strand may lie adjacent, or is in close proximity to corresponding complementary bases of a fixed first strand. A method may further comprise (c) exposing a fixed first strand and a fixed second strand to a respective pool of a respective oligonucleotide probe species in a set of oligonucleotide probe species, where each oligonucleotide probe species in the set of oligonucleotide probe species is of a predetermined sequence and length. Exposing (c) may occur under conditions that allow for individual probes of respective pools of respective oligonucleotide probe species to bind and form a respective duplex with each portion of a fixed first strand or a fixed second strand that is complementary to a respective oligonucleotide probe species. And may thereby give rise to a respective instance of optical activity. A method may continue with (d) measuring a location on a test substrate and optionally with a duration of each respective instance of optical activity occurring during exposing (c) using one or more two-dimensional imagers. Then, a method may proceed by (e) repeating exposing (c) and measuring (d) for respective pools of oligonucleotide probe species in a set of oligonucleotide probes species, thereby obtaining a plurality of sets of positions on a test substrate. Each respective set of positions on a test substrate may correspond to one or more oligonucleotide probe species in a set of oligonucleotide probe species. Multiple sets of positions on a test substrate is obtained from a single step of exposing (c) if, either serially and or simultaneously as a result of the use of multiple labels associated thereto, multiple different oligonucleotide probe species is measured. A method may further include (f) determining a sequence of at least a portion of a target nucleic acid from a plurality of sets of positions on a test substrate by compiling positions on a test substrate represented by the plurality of sets of positions corresponding to different, or different sets of oligonucleotide probe species.

In some embodiments, exposing (c) occurs under conditions that allow for individual oligonucleotide probe species of a respective pool of a respective oligonucleotide probe species to transiently and reversibly bind and form a respective duplex with each portion of a fixed first strand or a fixed second strand that is complementary to individual oligonucleotide probes thereby giving rise to an instance of optical activity. In some embodiments, exposing (c) occurs under conditions that allow for individual oligonucleotide probe species of a respective pool of respective oligonucleotide probe species to repeatedly transiently and reversibly bind and form respective duplex with each portion of a fixed first strand or a fixed second strand that is complementary to individual probes thereby repeatedly giving rise to respective instances of optical activity. In some such embodiments, each oligonucleotide probe, in a pool of oligonucleotide species, in a set of oligonucleotide probe species is bound with a label (e.g., a dye, a fluorescent nanoparticle, or a light-scattering particle).

In some embodiments, in a method, exposing is conducted in the presence of a first label in the form of an intercalating dye. In some embodiments, each oligonucleotide probe, in a pool of oligonucleotide species, in a set of oligonucleotide probe species that are bound with a second label, a first label and a second label have overlapping donor emission and acceptor excitation spectra that causes one of a first label fluorescence and a second label fluorescence to increase when a first label and a second label are in close proximity to each other, and a respective instance of optical activity is from a proximity of an intercalating dye, intercalating a respective duplex between an oligonucleotide probe and a fixed first strand or a fixed second strand, to a second label which is bound to an oligonucleotide probe. In other embodiments, both a first label and a second label are bound to an oligonucleotide probe.

In some embodiments, exposing is in the presence of a first label in the form of an intercalating dye, each oligonucleotide probe species in a set of oligonucleotide probe species is bound with a second label, a first label may cause fluorescence of a second label to increase when a first label and a second label is in close proximity to each other, and a respective instance of optical activity is from a proximity of an intercalating dye, intercalating a respective duplex between an oligonucleotide probe and a fixed first strand or a fixed second strand, to a second label.

In some embodiments, exposing is in the presence of a first label in the form of an intercalating dye, each oligonucleotide probe species in a set of oligonucleotide probe species is bound with a second label, a second label causes fluorescence of a first label to increase when a first label and a second label are in close proximity to each other, and a respective instance of optical activity is from a proximity of an intercalating dye, intercalating a respective duplex between an oligonucleotide probe and a fixed first strand or a fixed second strand, to a second label.

In some embodiments, exposing is in the presence of an intercalating dye, and a respective instance of optical activity is from a fluorescence of an intercalating dye intercalating a respective duplex between an oligonucleotide probe and a fixed first strand or a fixed second strand. In such embodiments, a respective instance of optical activity is greater than a fluorescence of an intercalating dye before it intercalates a respective duplex.

In some embodiments, more than one oligonucleotide probe species in a set of oligonucleotide probe species is exposed to a fixed first strand and a fixed second strand during a single instance of the exposing (c), and each different oligonucleotide probe species in a set of oligonucleotide probe species that is exposed to a fixed first strand and a fixed second strand during a single instance of exposing (c) is associated with a different label. In some such embodiments, a first pool of a first oligonucleotide probe species in a set of oligonucleotide probe species, a first oligonucleotide probe species being associated with a first label, is exposed to a fixed first strand and a fixed second strand during a single instance of exposing (c), a second pool of a second oligonucleotide probe species in a set of oligonucleotide probe species, a second oligonucleotide probe species being associated with a second label, is exposed to a fixed first strand and a fixed second strand during a single instance of exposing (c), and a first label and a second label are different. Alternatively, a first pool of a first oligonucleotide probe species in a set of oligonucleotide probe species, a first oligonucleotide probe species being associated with a first label, are exposed to a fixed first strand and a fixed second strand during a single instance of the exposing (c), a second pool of a second oligonucleotide probe species in a set of oligonucleotide probe species, a second oligonucleotide probe species being associated with a second label, is exposed to a fixed first strand and a fixed second strand during a single instance of exposing (c), a third pool of a third oligonucleotide probe species in a set of oligonucleotide probe species, a third oligonucleotide probe species being associated with a third label, is exposed to a fixed first strand and a fixed second strand during a single instance of exposing (c), and a first label, a second label, and a third label are each different.

In other embodiments, any number of different labels which are distinguished by excitation, emission, fluorescence lifetime or the like are used with associated pools of oligonucleotide probe species.

In some embodiments, a pool of oligonucleotide probe species comprises a single oligonucleotide probe species. In other embodiments, a pool of oligonucleotide probe species comprises multiple oligonucleotide probe species. In further embodiments, a pool of multiple oligonucleotide probe species has a distinguishing label associated with (which is binding) each single oligonucleotide probe species in a pool of multiple oligonucleotide probe species. In further embodiments, some or all of a set of multiple different oligonucleotide probe species have a same type of label, which is not be directly distinguishable from other oligonucleotide probes species in a pool of multiple oligonucleotide probe species. In yet further embodiments, one or more oligonucleotide probe species in a pool of multiple oligonucleotide probe species is unlabeled.

In some embodiments, repeating (e), exposing (c), and measuring (d) is performed for each single oligonucleotide probe species in a set of oligonucleotide probes species.

In some embodiments, exposing (c) and measuring (d) and repeating are performed sequentially. In other embodiments exposing (c) and measuring (d) are concurrent, where measurement (d) begins as soon as a single frame obtained during an exposing (c) process. In further embodiments, multiple exposing (c) processes are performed, for example with different pools of oligonucleotide probes prior to performing a measuring (d) process.

In some embodiments, exposing (c) is done for a first pool of oligonucleotide probe species, which comprise a singular species or comprise multiple oligonucleotide probe species in a set of oligonucleotide probes at a first temperature and repeating (e), exposing (c), and measuring (d) include performing exposing (c) and measuring (d) for a first pool of oligonucleotide probes species at a second temperature.

In some embodiments, exposing (c) is done for a first pool of oligonucleotide probe species in a set of oligonucleotide probes species at a first temperature, instances of repeating (e), exposing (c), and measuring (d) include performing exposing (c) and measuring (d) for a first pool of oligonucleotide probe species at each of a plurality of different temperatures, and further comprise constructing a melting curve for a first pool of oligonucleotide probe species using measured locations and durations of optical activity recorded by measuring (d) for a first temperature and each temperature in a plurality of different temperatures. In other embodiments, differing salt concentrations are used instead of differing temperatures. In additional embodiments, denaturing reagents such as formamide or changes in pH are used to change binding affinity. In further embodiments, any combination of differing salt concentrations, differing temperatures, differing pH levels, or differing levels of denaturing reagents are utilized for one or more oligonucleotide probe species to effectuate a melt curve equivalent.

In some embodiments, a set of oligonucleotide probe species comprises a plurality of subsets comprising pools of multiple different types of oligonucleotide probes species and repeating (e), exposing (c), and measuring (d) are performed for each respective subset of pools comprising multiple different types of oligonucleotide probes species in a plurality of subsets of oligonucleotide probe species. In some such embodiments, each respective subset comprising pools multiple different types of oligonucleotide probes species comprise two or more different oligonucleotide probe species from a set of oligonucleotide probes species. Alternatively, each respective subset comprising pools multiple different oligonucleotide probe species comprises four or more different oligonucleotide probe species from a set of oligonucleotide probe species. In some such embodiments, a set of oligonucleotide probe species consist of four subsets comprising pools of oligonucleotide probe species. In some embodiments, a method further comprises dividing the a set of oligonucleotide probe species into a plurality of subsets comprising pools of oligonucleotide probe species based on a calculated or experimentally derived melting temperature of each oligonucleotide probe species, where oligonucleotide probe species with similar melting temperature are placed in a same subset of oligonucleotide probes by the dividing and where a temperature or a duration of an instance of exposing (c) is determined by an average melting temperature of an oligonucleotide probes species in a corresponding subset comprising pools of oligonucleotide probe species. Further still, in some embodiments, a method further comprises dividing a set of oligonucleotide probes into a plurality of subsets comprising pools of oligonucleotide probe species based on a sequence of each oligonucleotide probe species, where oligonucleotide probe species with overlapping sequences are placed in different subsets comprising pools of oligonucleotide probe species.

In some embodiments, measuring a location on a test substrate comprises identifying and fitting a respective instance of optical activity with a fitting function to identify and fit a center of a respective instance of optical activity or a portion of a respective instance of optical activity in a frame of data obtained by a two-dimensional imager, and a center of a respective instance of optical activity is deemed to be a position of a respective instance of optical activity on a test substrate. In some such embodiments, a fitting function is a Gaussian function, a first moment function, a gradient-based approach, or a Fourier Transform.

In some embodiments, a respective instance of optical activity persists across a plurality of frames measured by a two-dimensional imager, a single frame in a plurality of frames comprising a respective instance of optical activity is a portion of a respective instance of optical activity, a measuring a location on a test substrate comprises identifying and fitting a respective instance of optical activity with a fitting function across a plurality of frames to identify a center of a respective instance of optical activity across a plurality of frames, and a center of a respective instance of optical activity is deemed to be a position of a respective instance of optical activity on a test substrate across a plurality of frames. In some such embodiments, a fitting function is a Gaussian function, a first moment function, a gradient-based approach, or a Fourier Transform.

In some embodiments, a measuring a location on a test substrate comprises inputting a frame of data measured by a two-dimensional imager into a trained convolutional neural network, a frame of data comprises a respective instance of optical activity among a plurality of instances of optical activity, each instance of optical activity in a plurality of instances of optical activity corresponds to an individual oligonucleotide probe of an oligonucleotide species binding to a portion of a fixed first strand or a fixed second strand, and responsive to inputting, a trained convolutional neural network identifies a position on a test substrate of each of one or more instances of optical activity in a plurality of instances of optical activity. In some embodiments, multiple instances of optical activity are present at different positions in one or more frames of data, where the multiple different positions of optical activity, each of which have multiple instances of optical activity in an exposing step, and correspond with different binding sites on a first and or a second strand of one or more target polynucleotides. In further embodiments, respective instances of optical activity with a same position occur over different sets of frames, and are processed separately and or simultaneously with other instances of respective optical activity with different positions and over different sets of frames.

In some embodiments, a measuring resolves a center of a respective instance of optical activity to a position on a test substrate with a localization precision of at least 20 nm, at least 2 nm, at least 60 nm, or at least 6 nm.

In some embodiments, a measuring resolves a center of a respective instance of optical activity to a position on a test substrate, where a position is determined with a sub-diffraction limited accuracy and or precision.

In some embodiments, a measuring (d) a location on a test substrate and a duration of a respective instance of optical activity measures more than 5000 photons at a location, more than 50,000 photons at a location, or more than 200,000 photons at a location. In some embodiments, a number of photons used in a measuring (d) result from a single frame, or result from a combination of frames deemed to comprise a single instance of optical activity In some embodiments, a respective instance of optical activity is more than a predetermined number of standard deviations (e.g., more than 3, 4, 5, 6, 7, 8, 9, or 10 standard deviations) over background optical activity observed for a test substrate.

In some embodiments, each respective oligonucleotide probe species in a set or subset of a plurality of oligonucleotide probe species comprises unique N-mer sequence, where N is an integer in the set $\{1, 2, 3, 4, 5, 6, 7, 8, \text{and } 9\}$ and where all unique N-mer sequences of length N are resented by a set or subset comprising a plurality of oligonucleotide probe species. In some such embodiments, a unique N-mer sequence comprises one or more nucleotide positions occupied by one or more degenerate nucleotides and or one or more universal bases (e.g., 2'-Deoxyinosine, CPG 500, 5-nitroindole). In some such embodiments, a unique N-mer sequence is 5' flanked by a single degenerate or universal nucleotide position and 3' flanked by a single degenerate or universal nucleotide position. In some embodiments, a target nucleic acid is at least 140 bases in length and a determining (f) determines a percentage of a sequence of a target nucleic acid of greater than 70%. In some embodiments, a target nucleic acid is at least 140 bases in length and a determining (f) determines a percentage of a sequence of a target nucleic acid of greater than 90%. In some embodiments, a target nucleic acid is at least 140 bases in length and a determining (f) determines a percentage of a sequence of a target nucleic acid of greater than 99%. In some embodiments, a determining (f) determines a percentage of a sequence of a target nucleic acid of greater than 99%.

In some embodiments, a target nucleic acid is at least 10,000 bases in length or is at least 1,000,000 bases in length.

In some embodiments, a test substrate is washed prior to repeating exposing (c) and measuring (d), thereby removing a one or more oligonucleotide probe species from a test substrate prior to exposing a test substrate to one or more oligonucleotide probe species in the set of oligonucleotide probe species.

In some embodiments, fixing (a) comprises applying a nucleic acid to a test substrate by molecular combing (receding meniscus), flow stretching nanoconfinement, or electro-stretching.

In some embodiments, each respective instance of optical activity have an observation metric that satisfies a predetermined threshold. In some such embodiments, an observation metric comprises a duration, a signal to noise, a photon count, or an intensity. In some embodiments, a predetermined threshold distinguishes between (i) a first form of binding in which each base, or each non-degenerate and or non-universal base of a unique N-mer sequence binds to a complementary base in a fixed first strand or a fixed second strand of a target nucleic acid, and (ii) a second form of binding in which there is at least one mismatch between the bases, or each non-degenerate and or non-universal base of a unique N-mer sequence and a sequence in a fixed first strand or a fixed second strand of a target nucleic acid that a respective oligonucleotide probe has bound to form a respective instance of optical activity.

In some embodiments, each respective oligonucleotide probe species in a set of oligonucleotide probe species have its own corresponding predetermined threshold. In some such embodiments, a predetermined threshold for each respective oligonucleotide probe species in a set of oligonucleotide probe species is derived from a training dataset. In some embodiments, a predetermined threshold for each respective oligonucleotide probe species in a set of oligonucleotide probe species is derived from a training dataset, and a training set comprises, for each respective oligonucleotide probe species in a set of oligonucleotide probe species, a measure of an observation metric for a respective oligonucleotide probe upon binding to a reference sequence such that each base, or each non-degenerate and or non-universal base of a unique N-mer sequence of a respective oligonucleotide probe species binds to a complementary base in a reference sequence. In some such embodiments, a reference sequence is fixed on a reference substrate. Alternatively, a reference sequence is included with a target nucleic acid, either separate from a target nucleic acid or ligated thereto, and fixed on a test substrate. In some embodiments, a reference sequence comprises all or a portion of the genome of, PhiX174, M13, lambda phage, T7 phage, *Escherichia coli, Saccharomyces cerevisiae, Saccharomyces pombe*, or any other naturally occurring genome or transcriptome. In some embodiments, a reference sequence is a synthetic construct of known sequence. In some embodiments, a reference sequence comprises all or a portion of rabbit globin RNA.

In some embodiments, a respective oligonucleotide probe species in a set of oligonucleotide probe species yields a first instance of optical activity by binding to a complementary portion of a fixed first strand, and a second instance of optical activity by binding to a complementary portion of a fixed second strand.

In some embodiments, a respective oligonucleotide probe species in a set of oligonucleotide probe species yields two or more instances of optical activity at different positions on a test substrate by binding to two or more complementary portions of a fixed first strand, and or to two or more second instances of optical activity at different positions on a test substrate by binding to two or more complementary portions of a fixed second strand.

In some embodiments, a respective oligonucleotide probe species binds to a portion of a fixed first strand or a fixed second strand that is complementary to a respective oligonucleotide probe species two or more times at a same position during exposing (c) thereby resulting in two or more instances of optical activity, each instance of optical activity representing a binding event in a plurality of binding events.

In some embodiments, a respective oligonucleotide probe binds to a portion of a fixed first strand or a fixed second strand that is complementary to a respective oligonucleotide probe species at multiple positions, and binds at each position multiple times, potentially creating multiple instances of optical activity at each position of optical activity during exposing (c) each instance of optical activity representing a binding event in a plurality of binding events.

In some embodiments, exposing (c) occurs for five minutes or more, for five minutes or less, for two minutes or less, or for one minute or less.

In some embodiments, exposing (c) occurs across one or more frames of a two-dimensional imager, two or more frames of a two-dimensional imager, 500 or more frames of a two-dimensional imager or across 5,000 or more frames of a two-dimensional imager.

In some embodiments, multiple two-dimensional imagers is utilized, either simultaneously and or sequentially, where each of the multiple two-dimensional imagers is optimized to detect a particular type of label, thereby allowing simultaneous collection of data for multiple labels which are associated with multiple different oligonucleotide probe species.

In some embodiments, exposing (c) is done for a first oligonucleotide probe species in a set of oligonucleotide probe species for a first period of time, where repeating (e), exposing (c) and measuring (d) includes performing exposing (c) for a second oligonucleotide probe species for a second period of time, and a first period of time is different than a second period of time.

In some embodiments, exposing (c) is done for a first oligonucleotide probe species in a set of oligonucleotide probe species for a first number of frames of a two-dimensional imager, where repeating (e), exposing (c) and measuring (d) includes performing exposing (c) for a second oligonucleotide probe species for a second number of frames of a two-dimensional imager, and a first number of frames is different than a second number of frames.

In some embodiments, exposing (c) is done for a first oligonucleotide probe species in a set of oligonucleotide probe species for a first number of frames of a two-dimensional imager, where repeating (e), exposing (c) and measuring (d) includes performing exposing (c) for a second oligonucleotide probe species for a second number of frames of a two-dimensional imager, and an exposure duration for each frame in a first number of frames is different than an exposure duration for each frame in a second number of frames.

In some embodiments, each oligonucleotide probe species in a set of oligonucleotide probe species is of a same length.

In some embodiments, each oligonucleotide probe species in a set of oligonucleotide probe species is of a same length M, where M is be a positive integer of 2 or greater (e.g., M is 2, 3, 4, 5, 6, 7, 8, 9, 10, or greater than 10), and determining (f) a sequence of at least a portion of a target nucleic acid from a plurality of sets of positions on a test substrate further uses overlapping sequences of different oligonucleotide probe species represented by a plurality of sets of positions. In some such embodiments, each oligonucleotide probe species in a set of oligonucleotide probe species shares M−1 sequence homology with another oligonucleotide probe in a set of oligonucleotide probe species. In some such embodiments, determining a sequence of at least a portion of a target nucleic acid from a plurality of sets of positions on a test substrate comprises determining a first tiling path corresponding to a fixed first strand and a second tiling path corresponding to a fixed second strand. In some such embodiments, a break in a first tiling path is resolved using a corresponding portion of the second tiling path, where a second tiling path is complementary to a first tiling path. In other embodiments, a break in a first tiling path or a second tiling path is resolved using a reference sequence. In other embodiments, a break in a first tiling path or a second tiling path is resolved using corresponding portions of a third tiling path or a fourth tiling path obtained from another instance of a target nucleic acid. In some such embodiments, a confidence in sequence assignment of a target nucleic acid sequence is increased using corresponding portions of a first tiling path and a second tiling path. In other embodiments, a confidence in sequence assignment of a target nucleic acid sequence is increased using corresponding portions of a third tiling path or a fourth tiling path obtained from another instance of a target nucleic acid.

In some embodiments, a length of time of an instance of the exposing (c) is determined by an estimated melting temperature of a respective oligonucleotide probe species in the set of oligonucleotide probe species used in an instance of exposing (c).

In some embodiments, a method further comprises (f) exposing a fixed double strand or fixed first strand and fixed second strand to an antibody, affimer, nanobody, aptamer, or methyl-binding protein to thereby determine a modification to a target nucleic acid or to correlate with a sequence of a portion of a target nucleic acid from a plurality of sets of positions on a test substrate. In some embodiments, a method may allow determination of various epigenetic modifications which may comprise a portion of a target nucleic acid.

In some embodiments, a test substrate may comprise a two-dimensional surface. In some such embodiments, a two-dimensional surface is coated with a gel or a matrix.

In some embodiments, a test substrate may comprise a flow cell, a cell, a three-dimensional matrix or a gel.

In some embodiments, a test substrate is bound with sequence-specific oligonucleotide probe species prior to fixing (a) and fixing (a) may comprise capturing a target nucleic acid on a test substrate using a sequence-specific oligonucleotide probe species bound to a test substrate.

In some embodiments, sequence specific oligonucleotide probe species, which is bound to a surface of a test substrate, and may comprise bases, such as PNA and or LNA bases, which have a higher melting temperature than natural oligonucleotide bases, and may allow denaturation of target nucleic acid. In some embodiments, multiple different sequence specific oligonucleotide probe species, which is complementary and thereby allows binding of a first strand and a second strand of a target nucleic acid, which may allow determination of a higher percentage of bases of a target nucleic acid from each single target nucleic acid.

In some embodiments, a nucleic acid is in a solution that comprises an additional plurality of cellular components and fixing (a) or denaturing (b) may further comprise washing a test substrate after a target nucleic acid has been fixed to a test substrate and prior to exposing (c) thereby purifying an additional plurality of cellular components away from a target nucleic acid.

In some embodiments, a test substrate is passivated with polyethylene glycol, bovine serum albumin-biotin-streptavidin, casein, bovine serum albumin (BSA), one or more different tRNAs, one or more different deoxyribonucleotides, one or more different ribonucleotides, salmon sperm DNA, pluronic F-127, Tween-20, hydrogen silsesquioxane (HSQ), or any combination thereof prior to exposing (c).

In some embodiments, a test substrate is coated with a vinylsilane coating comprising 7-octenyltrichlorosilane or methacryloxypropyltrimethoxysilane prior to fixing (a).

Another aspect of the present disclosure provides a method of sequencing a nucleic acid, which may comprise (a) fixing a target nucleic acid in linearized stretched form on a test substrate thereby forming a fixed stretched target nucleic acid, (b) exposing a fixed stretched target nucleic acid to a respective pool of a respective oligonucleotide probe species in a set of oligonucleotide probe species, where each oligonucleotide probe species in the set of oligonucleotide probe species is of a predetermined sequence and length, exposing (b) occurring under conditions that allow for individual oligonucleotide probes of the respective pool of the respective oligonucleotide probe species to transiently and reversibly to each portion of a fixed target nucleic acid that is complementary to a respective oligonucleotide probe species thereby giving rise to a respective instance of optical activity, (c) measuring a location on a test substrate and optionally a duration of each respective instance of optical activity occurring during exposing (b) using a two-dimensional imager, (d) repeating exposing (b) and measuring (c) for respective oligonucleotide probe species in the set of oligonucleotide probe species, thereby obtaining a plurality of sets of positions on a test substrate, where each respective set of positions on a test substrate may correspond to an oligonucleotide probe species in the set of oligonucleotide probe species, and (e) determining a sequence of at least a portion of a target nucleic acid from a plurality of sets of positions on a test substrate by compiling positions on a test substrate represented by a plurality of sets of positions, where a set of positions may comprise locations of optical activity in differing and or a same location on a test substrate. In some such embodiments, a target nucleic acid is double-stranded nucleic acid and a method may further comprise denaturing a target fixed double-stranded nucleic acid to single stranded form on a test substrate thereby obtaining a fixed first strand and a fixed second strand of a target nucleic acid, where a fixed second strand is complementary to a fixed first strand. In some embodiments, a target nucleic acid is single stranded RNA.

Another aspect of the present disclosure provides a method of analyzing a nucleic acid, which may comprise (a) fixing a target nucleic acid in double-stranded form on a test substrate thereby forming a fixed double-stranded nucleic acid, (b) denaturing a target fixed double-stranded nucleic acid to single stranded form on a test substrate thereby obtaining a fixed first strand and a fixed second strand of a target nucleic acid, where a fixed second strand is complementary to a fixed first strand, and (c) exposing a fixed first strand and a fixed second strand to one or more oligonucleotide probe species and determining whether one or more oligonucleotide probe species binds to a fixed first strand or a fixed second strand.

Details of an exemplary system are now described in conjunction with FIG. 1A. FIG. 1A is a block diagram illustrating a system 100 in accordance with some implementations. Device 100 in some implementations may include one or more processing units (CPU(s)) 102 (also referred to as processors or processing core), one or more network interfaces 104, a user interface 106, a non-persistent memory 111, a persistent memory 112, and one or more communication buses 114 for interconnecting these components. One or more communication buses 114 optionally include circuitry (sometimes called a chipset) that interconnects and controls communications between system components. Non-persistent memory 111 typically includes high-speed random access memory, such as DRAM, SRAM, DDR RAM, whereas persistent memory 112 typically includes CD-ROM, digital versatile disks (DVD) or other optical storage, magnetic cassettes, magnetic tape, magnetic disk storage or other magnetic storage devices, magnetic disk storage devices, optical disk storage devices, ROM, EEPROM, flash memory devices, or other non-volatile solid state storage devices. Persistent memory 112 optionally includes one or more storage devices remotely located from CPU(s) 102. Persistent memory 112, comprises non-transitory computer readable storage medium. In some implementations, non-persistent memory 111 or alternatively the non-transitory computer readable storage medium may store the following programs, modules and data structures, or a subset thereof, sometimes in conjunction with persistent memory 112:

an optional operating system 116, which may include procedures for handling various basic system services and for performing hardware dependent tasks;

an optional network communication module (or instructions) 118 for connecting system 100 with other devices, or a communication network;

an optical activity detection module 120 for collecting information for target molecule(s) 130;

information for each respective binding site 140 in a plurality of binding sites, which may directly correlate with a set of positions of optical activity, for target molecule(s) 130;

information for each respective binding event 142 in a plurality of binding events for each binding site 140 which may include (i) a duration 144 and (ii) a number of photons emitted 146;

a sequencing module 150 for determining a sequence of target molecule(s) 130;

information for each respective binding site 140 in a plurality of binding sites for each target molecule 130 which may include (i) a base call 152 and (ii) a probability 154;

optional information regarding a reference genome 160 for each target molecule 130; and optional information regarding a complementary strand 170 for each target molecule 130.

In various implementations, one or more of the above identified elements are stored in one or more of previously mentioned memory devices, and correspond to a set of instructions for performing a function as described hereinabove. Herein, above identified modules, data, or programs (e.g., sets of instructions) need not be implemented as separate software programs, procedures, datasets, or modules, and thus various subsets of these modules and data is combined or otherwise re-arranged in various implementations. In some implementations, non-persistent memory 111 optionally stores a subset of modules and data structures identified above. Furthermore, in some embodiments, non-persistent memory 111 or persistent memory 112 store additional modules and data structures not described above. In some embodiments, one or more of the above identified elements is stored in a computer system, other than that of visualization system 100, that is addressable by visualization system 100 so that visualization system 100 may retrieve all or a portion of such data when needed.

Examples of network communication modules 118 include, but are not limited to, the World Wide Web (WWW), an intranet, a local area network (LAN), controller area network (CAN), Cameralink and/or a wireless network, such as a cellular telephone network, a wireless local area network (WLAN) and/or a metropolitan area network (MAN), and other devices by wireless communication. Wired or wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSDPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

Although FIG. 1A depicts a "system 100," the figure is intended more as functional description of the various features that is present in computer systems than as a structural schematic of the implementations described herein. In practice, and as recognized by those of ordinary skill in the art, items shown separately could be combined and some items could be separated. Moreover, although FIG. 1A depicts certain data and modules in non-persistent memory 111, some or all of these data and modules is in persistent memory 112. Furthermore, In some embodiments, the memory 111 and/or 112 stores additional modules and data structures not described above. In other embodiments, one or more different hardware modules (not shown) are included as a part of a system 100, such as one or more two-dimensional imagers, optical systems which include lasers and grating or filter wheels and associated controllers, and fluid systems which include a variety of pumps, valves, heaters and other mechanical systems.

While a system in accordance with the present disclosure has been disclosed with reference to FIG. 1A, methods in accordance with the present disclosure are now detailed with reference to FIGS. 2A, 2B, 3 and 4.

Block 202. A method of determining a chemical structure of a molecule, which is a target nucleic acid, is provided. A goal of the present disclosure is to enable single nucleotide resolution sequencing of a target nucleic acid. In some embodiments, a method of characterizing interactions between one or more probes, which comprise an oligonucleotide probe species or other molecule and a target nucleic acid or other molecule are provided. A method includes adding one or more probes, which may comprise an oligonucleotide probe species or another molecule to a target nucleic acid or other molecule under conditions that cause one or more probe species to transiently bind to a target nucleic acid or other molecule. A method may proceed by continuously monitoring individual binding events on a target nucleic acid or other molecule on a detector, which may comprise one or more two-dimensional imagers, and may comprise recording binding event(s) over a period of time or over a series of frames. Data from binding event(s) may then be analyzed to determine one or more characteristics of the interactions.

In some embodiments, a method of determining the identity, which is a sequence, of a polymer, which is a target nucleic acid, is provided. In some embodiments, a method of determining the identity of a cell or tissue is provided. In some embodiments, a method of determining the identity of an organism is provided. In some embodiments, a method of determining the identity of an individual is provided. In some embodiments, methods is applied to single cell nucleic acid and or protein sequencing.

Target Polynucleotides.

In some embodiments, a molecule is a target nucleic acid, and is a native target polynucleotide, or is a copy of a native polynucleotide. In various embodiments, a method may further comprise extracting a single target polynucleotide molecule from a single cell, a single organelle, a single chromosome, a single virus, an exosome or body fluid as an intact target polynucleotide which may also be described herein as a sample. In further embodiments, a method may comprise extracting one or more target polynucleotide molecules from a single cell, a single organelle, a single chromosome, a single virus, an exosome or body fluid as an intact target polynucleotide which may also be described herein as a sample. In yet further embodiments, a method may comprise extracting one or more target polynucleotide molecules from multiple cells, multiple organelles, multiple chromosomes, multiple viruses, multiple exosomes or body fluid as an intact target polynucleotide which may also be described herein as a sample. In some embodiments, a single target polynucleotide may comprise a single RNA, a single ssDNA, or a single dsDNA.

In some embodiments, a target nucleic acid is a short polynucleotide (e.g., <1 kilobases or <300 bases). In some embodiments, a short polynucleotide is 100-200 bases, 150-250 bases, 200-350 bases, or 100-500 bases in length, as is found for cell-free DNA in body fluids such as urine and blood.

In some embodiments, a target nucleic acid is at least 10,000 bases in length. In some embodiments, a target nucleic acid is at least 1,000,000 bases in length.

In various embodiments, a single target nucleic acid is a chromosome. In various embodiments, a single target polynucleotide is about $10^2$, $10^3$, $10^4$, $10^5$, $10^6$, $10^7$, $10^8$ or $10^9$ bases in length, or any length between $10^{\wedge}2$ and $10^{\wedge}9$ bases.

In some embodiments, a method enables analysis of an amino-acid sequence of a target protein, target polypeptide or target peptide. In some embodiments, a method for analyzing and determining an amino acid sequence of a target protein, target polypeptide, or target peptide is provided. In some embodiments, a method for analyzing peptide modifications as well as an amino-acid sequence of a target polynucleotide is provided. In some embodiments, a target molecular entity is a polymer, comprising at least 5 units. In such embodiments binding probes are molecular probes comprising oligonucleotides, antibodies, affimers, nanobodies, aptamers, binding proteins, or small molecules, etc.

In some embodiments, each, or one or more of the standard 20 amino acids, 22 proteinogenic amino acids, non-proteinogenic amino acids as found in alloproteins or as a result of post translational modification, naturally occurring D-amino acids, or naturally occurring L-amino acids, is bound by a corresponding specific probe comprising an N-recognin, nanobody, antibody, aptamer, etc. The binding of each probe is specific to each corresponding amino acid within a target protein, target polypeptide chain, or target peptide. In some embodiments, the order of sub-units in a target protein, target polypeptide chain, or target peptide is determined. In some embodiments, binding is to surrogates of binding sites. In some embodiments, surrogates are tags attached at certain amino acids or peptide sequences, and transient binding is to surrogate tags.

In some embodiments, a molecule is a heterogeneous molecule. In some embodiments, a heterogeneous molecule may comprise a portion of a supramolecular structure. In some embodiments, a method enables identifying and ordering units of chemical structure for a heterogeneous polymer or of identifying and ordering units of chemical structure of a supramolecular structure, where such units may comprise different types of polymer subunits, such as nucleic acids and amino acids. Such embodiments may comprise elongating one or more polymers and binding a plurality of probes to identify a chemical structure at a plurality of sites along an elongated polymer. Elongating a heteropolymer may permit sub-diffraction level (e.g., nanometric) localization of probe binding sites.

Figure 1B:
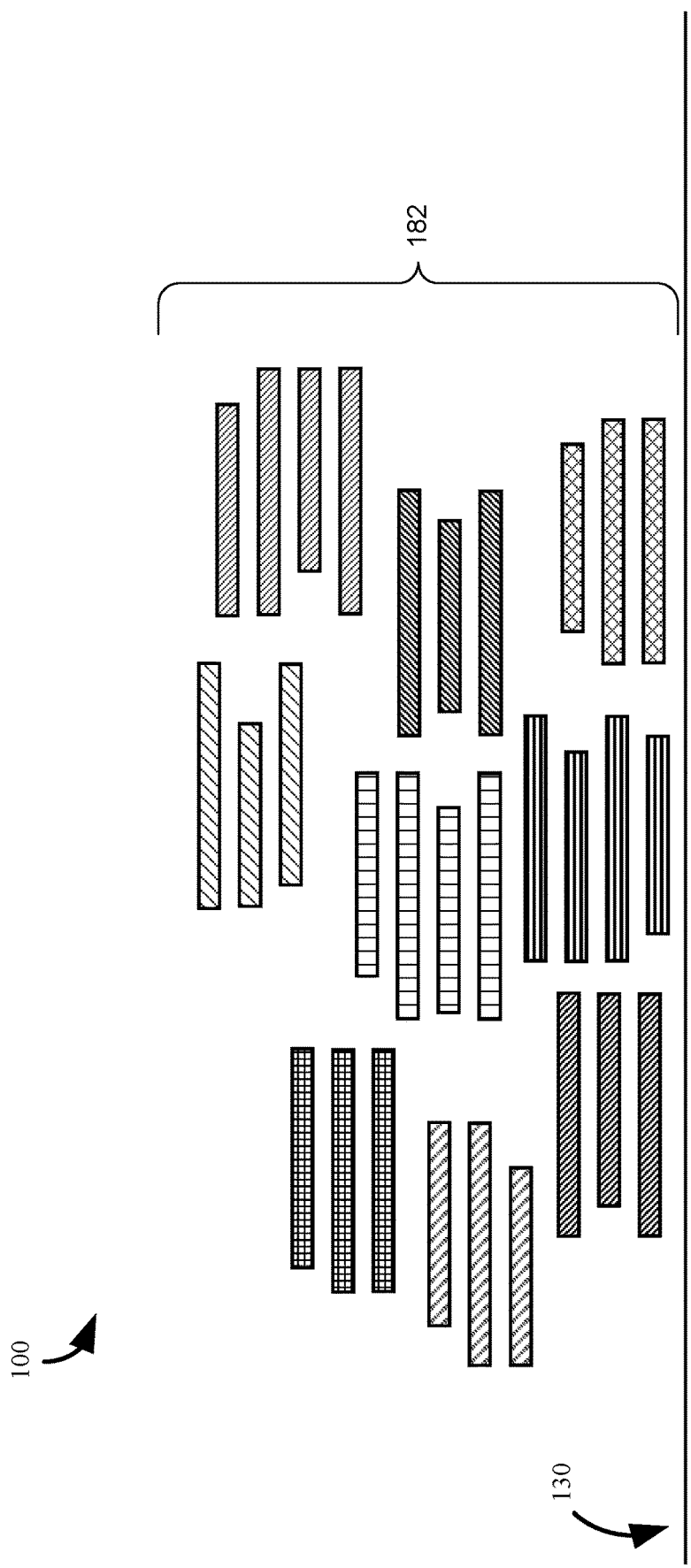

In some embodiments, methods for sequencing polymers by binding of oligonucleotide probes species that recognize subunits of a polymer are provided. Typically, binding of one oligonucleotide probe species is not sufficient to sequence a polymer. For example, in FIG. 1B an embodiment is depicted where a sequencing of a polymer 130 is based on measuring transient interactions with a complete set of probe species 182 (e.g., interaction of a denatured target nucleic acid with a complete sets of oligonucleotide probe species or interaction of a denatured target, protein, target polypeptide, or target peptide with a set of nanobodies or affimer, antibody or other amino acid specific binding agent probe species, where different probe species is labeled to allow observation of optical activity).

Extraction and/or Preparation of Target Polymers.

In some embodiments, it is desirable to separate cells that are of interest from other cells that are not of interest, or to create a library of several cells of a single type before nucleic acid extraction is conducted. In one such example, circulating tumor cells or circulating fetal cells are isolated from blood (e.g., by using cellular surface markers for affinity capture). In some embodiments, it is desirable to separate microbial cells from human cells, where an interest is to detect and analyse target nucleic acids from microbial cells. In some embodiments, Opsonins are used to affinity capture a wide-range of microbes and separate them from mammalian cells. In other embodiments, differential lysis is performed. Mammalian cells are lysed first, under relatively gentle conditions. Microbial cells are typically hardier (more difficult to lyse) than mammalian cells, and hence microbial cells may remain intact through a lysis of mammalian cells. Lysed mammalian cell fragments are washed away. Then harsher conditions are used to lyse microbial cells. Target microbial polynucleotides are then selectively sequenced.

In some embodiments, a target nucleic acid is extracted from a cell prior to sequencing. In alternate embodiments, sequencing (e.g., of chromosomal DNA) is conducted inside a cell where chromosomal DNA follows a convoluted path during interphase. Stable binding of oligonucleotide probe species in situ has been demonstrated by Beliveau et al., Nature Communications 6:7147 (2015). Such in situ binding of oligonucleotide probe species and nanometic localization of oligonucleotide probe species in three-dimensional space may enable determination of sequence and structural arrangement of a chromosomal molecule (target nucleic acid) within a cell.

Target polynucleotides are often present in native folded states. For example, genomic DNA is highly condensed in chromosomes, while RNA may form secondary structures. In some embodiments, long lengths of polynucleotide are obtained (e.g., by preserving substantially native lengths of native polynucleotides) during extraction from a biological sample. In some embodiments, a polynucleotide is linearized such that locations along its length are traced with little or no ambiguity. Ideally, a target polynucleotide is straightened, stretched or elongated, either before or after being linearized.

In some embodiments, methods are particularly suited to sequencing very long polymer lengths, where native lengths or a substantial proportion thereof are preserved (e.g., for DNA whole chromosomes or about 1 megabase or greater fragments). However, common molecular biology methods may result in unintended fragmentation of DNA. For instance, pipetting and vortexing causes shear forces that may break DNA molecules. Nuclease contamination can cause nucleic acids to be degraded or fragmented. In some embodiments, native lengths or substantial high molecular weight (HMW) fragments of native lengths are preserved before immobilization, stretching and sequencing commences.

In some embodiments, polynucleotides are intentionally fragmented to relatively homogeneous long lengths (e.g., about 1 Mb in length) before proceeding with sequencing. In some embodiments, polynucleotides are fragmented to relatively homogeneous long lengths after or during fixing or elongation. In some embodiments, fragmentation is effectuated enzymatically. In some embodiments, fragmentation is effectuated physically. In some embodiments, physical fragmentation is effectuated via sonication. In some embodiments, physical fragmentation effectuated via ionic bombardment or radiation. In some embodiments, physical fragmentation effectuated via electromagnetic radiation. In some embodiments, physical fragmentation is effectuated via UV illumination. In some embodiments, a dose of UV illumination is controlled to effectuate fragmentation to a given length. In some embodiments, physical fragmentation is effectuated via a combination of UV illumination and staining with a dye (e.g., YOYO-1). In some embodiments, a fragmentation process is halted by a physical action or addition of a reagent. In some embodiments, a reagent that may affect a halt in a fragmentation process is a reducing agent such as beta-mercaptoethanol (BME).

Fragmenting by Dose of Radiation and Sequencing

In some embodiments, where a field of view of a two-dimensional imager may allow a complete megabase length of DNA to be viewed in one dimension of a two-dimensional imager, it is efficient to produce genomic DNA in lengths of 1 Mb. In other embodiments where a larger or smaller fragment can be visualized by a fragment fitting within one dimension of a two-dimensional imager. In further embodiments, a length of a target nucleic acid is used which is larger than can be imaged in as single image by a two-dimensional imager, where images of different portions a target nucleic acid is taken at different times, and is imaged with one or more frames for one or more regions of a target nucleic acid in one imaging (c) step, or a more complete process of sequencing is performed before moving a two dimensional imager field of view to a different portion of a target nucleic acid, which may comprise utilization of a complete set of oligonucleotide probe species or any subset thereof. It should also be noted that reducing a size of chromosome length fragments may also minimizes tangling of strands, and may allow a maximum length of DNA in a stretched well-isolated form.

A method for sequencing long sub-fragments of a chromosome comprising the following steps:
i) Staining chromosomal double stranded DNA with a dye, said dye intercalating between base pairs of the double-strand DNA
ii) Exposing intercalating dye stained chromosomal DNA to a pre-determined dose of electromagnetic radiation to create sub-fragments of the chromosomal DNA within a desired size range
iii) Elongating and fixing intercalating dye stained chromosomal sub-fragments DNA on a surface
iv) Denaturing stained chromosomal fragments to disrupt base-pairs and thereby releasing any intercalating dye
v) Exposing resulting de-stained, elongated, fixed, single-stranded chromosomal fragments to one or more sets of oligonucleotide probe species of a desired length and sequence
vi) Determining a location(s) of binding along de-stained elongated single stranded chromosomal fragments for each oligonucleotide probe species in the one or more sets of oligonucleotide probe species
vii) Compiling locations of binding of oligonucleotide probe species in the one or more sets of oligonucleotide probe species to obtain full sequencing of chromosomal sub-fragments.

In some embodiments, as described hereinabove, staining may occur when a chromosome is in a cell. In some embodiments, as described hereinabove, labeled oligonucleotide is labeled as a result of adding more intercalating dye stain and subsequently intercalating into a duplex when a duplex forms. In some embodiments, as described hereinabove, optionally in addition to denaturing, a dose of electromagnetic radiation capable of bleaching the stain is applied. In some embodiments, of the above, said pre-determined dose is achieved by manipulating a strength and duration of exposing and stopping of fragmenting by chemical exposure, where said chemical exposure is a reducing agent such as beta-mercaptoethanol. In some embodiments, of the above, a dose is pre-determined to produce a Poisson distribution around 1 Mb length of fragments.

Methods of Fixation and Immobilization.

Block 204. Target nucleic acid is fixed in a double-stranded linearized stretched form on a test substrate, thereby forming a fixed stretched double-stranded nucleic acid. Optionally, a molecule is immobilized on a surface or matrix. In some embodiments, fragmented or native polymers are fixed. In some embodiments, a fixed double-stranded linearized nucleic acid may be straight or may follow a curvilinear or tortuous path.

In some embodiments, fixing may comprise applying a target nucleic acid to a test substrate by molecular combing (receding meniscus), flow stretching, nanoconfinement, or electro-stretching. In some embodiments, application or fixing of a target nucleic acid to a substrate may further comprise a UV crosslinking step, where a target nucleic acid is covalently bonded to a substrate. In some embodiments, UV crosslinking of a target nucleic acid to a substrate may not be effectuated, and a target nucleic acid is bonded to a substrate through other means (e.g., such as hydrophobic interactions, hydrogen bonding, etc.).

Immobilizing (e.g., fixing) a target nucleic acid at just one end may permit a polynucleotide to stretch and contract in uncoordinated ways. Thus, whatever method of elongation is used, a percentage of stretching along a length of a target nucleic acid may vary for any particular position in a target nucleic acid. In some embodiments, it is necessary for relative positions of multiple locations along a target nucleic acid to be fixed and not subject to fluctuation. In such embodiments, an elongated target nucleic acid is immobilized or fixed to a surface by multiple points of contact along its length (e.g., as is done in the molecular combing technique of Michalet et al, Science 277:1518-1523, 1997; see also Molecular Combing of DNA: Methods and Applications, Journal of Self-Assembly and Molecular Electronics (SAME) 1:125-148 for stretching on a surface can be used (e.g., ACS Nano. 2015 Jan. 27; 9(1):809-16)), and as described in Bensimon et al in U.S. Pat. No. 6,344,319, and Dedecker et al. in US20130130255.

In some embodiments, an array of target nucleic acids is immobilized on a surface and in some embodiments, target nucleic acids of an array are far enough apart to be individually resolved by diffraction-limited imaging. In some embodiments, target nucleic acids is fixed on a surface in an ordered manner, so that target nucleic acids are maximally packed within a given surface area and target nucleic acids may not overlap. In some embodiments, this is effectuated by making a patterned surface (e.g., an ordered arrangement of hydrophobic patches or strips at such locations to which ends of target nucleic acids may bind). In some embodiments, target nucleic acids of an array may not be far enough apart to be individually resolved by diffraction limited imaging and are individually resolved by super-resolution methods.

In some embodiments, target nucleic acids are organized utilizing DNA Curtains (Greene et al., Methods Enzymol. 472:293-315, 2010). This is particularly useful for long target nucleic acids. In such embodiments, transient binding is recorded while DNA strands, which is attached at one end and are elongated by flow or electrophoretic forces, or after both ends of the strand have been captured. In some embodiments, where many copies of a same target nucleic acid sequence, which may form a plurality, of target nucleic acids utilized in a DNA curtain method, a sequence is assembled from a binding pattern in aggregate from a plurality of target nucleic acids rather than from one target nucleic acid. In some embodiments, both ends of target nucleic acids may bind to pads (e.g., regions of a test substrate that may bind more strongly to target nucleic acid more than other sections of a test substrate), and each end may bind to a different pad. In some embodiments, two pads to which a single linear target nucleic acid may bind may hold a stretched configuration of a single linear target nucleic acid in place and may allow an ordered array of equally spaced, non-overlapping or non-interacting single linear target nucleic acids to be formed. In some embodiments, only one target nucleic acid may occupy an individual pad. In some embodiments, where pads are populated using a Poisson process, some pads are occupied by no target nucleic acids, some by one no target nucleic acids, and some by more than one no target nucleic acids.

In some embodiments, target molecules, which is target nucleic acids are captured onto an ordered supramolecular scaffold (e.g., DNA Origami structure). In some embodiments, a scaffold structure may initially be used in free solution to take advantage of solution phase kinetics for capturing target molecules, which is target nucleic acids. Once occupied, scaffolds may settle or self-assemble onto a surface and are bound to a surface. An ordered array may enable efficient sub-diffraction packing of molecules allowing a higher density of molecules (high density array) per field of view. Single molecule localization methods may allow target molecules, which is target nucleic acids within a high density array to be super-resolved (e.g., to distances 40 nm or less point to point).

In some embodiments, a hairpin is ligated (optionally after polishing the end of a target nucleic acid) onto an end of a duplex target nucleic acid. In some embodiments, a hairpin may contain a biotin which may immobilize a target nucleic acid to a surface. In alternative embodiments, a hairpin may serve to covalently link two strands of a duplex target nucleic acid. In some such embodiments, the other end of a target nucleic acid is tailed for surface capture by olio d(T), or by specific sequences as examples. After denaturation both strands of a target nucleic acid are available for interaction with oligonucleotide or other probe species.

In some embodiments, an ordered array may take the form of individual scaffolds that link together to form a large DNA lattice (e.g., as described in Woo and Rothemund, Nature Communications, 5: 4889). In some such embodiments, individual small scaffolds may lock on to one another by base-pairing. In some embodiments, small scaffolds may bind together thus presenting a highly ordered nanostructured array for sequencing steps as described herein. In some embodiments, capture sites are arranged at a 10 nm pitch in an ordered two-dimensional lattice. With full occupancy such a lattice has the capability of capturing on the order of one trillion molecules per square centimeter.

In some embodiments, capture sites in a lattice are arranged at a 5 nm pitch, a 10 nm pitch, a 15 nm pitch, a 30 nm pitch, or a 50 nm pitch in an ordered two-dimensional lattice. In some embodiments, capture sites in a lattice are arranged at between a 5 nm pitch and a 50 nm pitch in an ordered two-dimensional lattice.

In some embodiments, an ordered array of target nucleic acids or other target molecules is created using nanofluidics. In one such example, an array of nanotrenches or nanogrooves (e.g., 100 nm wide and 150 nm deep) are formed into a surface and serve to order long target nucleic acids. In such embodiments, an occurrence of one target nucleic acid in a nanotrench or nanogroove may exclude entry of another target nucleic acid. In another embodiment, a nanopit array is used, where segments of long target nucleic acids are in pits, and is bound in pits and intervening long segments of target nucleic acids are spread between pits.

In some embodiments, a high density of target nucleic acids may still permit super-resolution imaging and precise sequencing. For example, in some embodiments, where only a subset of a target nucleic acid is of interest (e.g., targeted sequencing). In such embodiments, only a subset of target nucleic acids and or regions of target nucleic acids from a complex sample (e.g., whole genome or transcriptome, multiple genomes) may need to be analyzed when targeted sequencing is performed, and target nucleic acids is fixed to a test substrate or matrix at a higher density than usual. In such embodiments, even when there are several polynucleotides present within a diffraction limited space or a SMLM resolution space, when a signal is detected, there is high probability that it is from only one of the targeted loci and that this locus is not within a diffraction limited distance or a SMLM resolution space, of another such locus that is simultaneously bound to a same oligonucleotide probe species. Required distance between each target nucleic acid undergoing targeted sequencing is correlated to a percentage of polynucleotides that is targeted. For example, if <5% of polynucleotides is targeted, then a density of polynucleotides is twenty times greater than if all target nucleic acid sequence is desired. In some embodiments, of targeted sequencing, an imaging time is shorter than in a case where a whole genome is analyzed (e.g., in the example above, targeted sequencing imaging could be 10× faster than whole genome sequencing).

In some embodiments, a test substrate is bound with a sequence-specific oligonucleotide probe species prior to a fixing step, and a fixing step may comprise capturing or fixing a target nucleic acid on a test substrate using a sequence-specific oligonucleotide probe species bound to a test substrate. In some embodiments, a target nucleic acid is fixed or bound at a 5' end. In some embodiments, a target nucleic acid is fixed or bound at a 3' end. In another embodiment, where there are two separate probes on a test substrate, one probe may fix or bind to a first end of a target nucleic acid and second probe may fix or bind to a second end of a target nucleic acid. In cases, where two probes are used, it may also be desirable to have prior information regarding a length of a target nucleic acid. In some embodiments, a target nucleic acid is cut with a predetermined endonuclease prior to fixing or binding to a test substrate. In additional embodiments, a target nucleic acid is caused to be fixed or bound at additional points along a length of a target nucleic acid after initially fixing or binding at one or both ends.

In various embodiments, prior to fixation, a target nucleic acid is extracted into or embedded in a gel or matrix (e.g., as described in to Shag et al., Nature Protocols 7:467-478, 2012). In one such non-limiting example, target nucleic acids is deposited in a flow channel containing a medium that undergoes a liquid to gel transition. Target nucleic acids is initially elongated and distributed in a liquid phase and then is fixed by changing phase to a solid/gel phase (e.g., by heating, which may cause or accelerate cross linking, or in the case of polyacrylamide by adding a co-factor or with time). In some embodiments, target nucleic acids is elongated in a solid/gel phase.

In some alternative embodiments, one or more oligonucleotide probe species is immobilized on or in a test substrate or matrix. In such embodiments, one or more target nucleic acids is suspended in solution and may bind transiently to one or more fixed oligonucleotide probe species. In some embodiments, a spatially addressable array of one or more oligonucleotide probe species is used to capture target nucleic acids. In some embodiments, where short target nucleic acids (e.g., <300 nucleotides) such as cell-free DNA or microRNA or relatively short target nucleic acids (e.g., <10,000 nucleotides) such as mRNA are immobilized randomly on a surface by capturing a modified or non-modified end of a target nucleic acid using an appropriate capture molecule, which may comprise one or more oligonucleotide probe species, or may comprise other binding mechanisms such as biotin avidin. In some embodiments, short or relatively short target nucleic acids have multiple interactions with a test substrate, and sequencing is carried out in a direction parallel to a test substrate. Thus splicing isoformic organization or structural DNA modifications is resolved. For example, in some isoforms, locations of exons that are repeated or shuffled may delineated or determined, or in cancerous cells, significant structural rearrangement may occur, and such structural rearrangements and relationships with genes or important noncoding regions of DNA is delineated or determined.

In some embodiments, immobilized probes may comprise a common sequence that may anneal to target nucleic acids. Such an embodiment is particularly useful when target nucleic acids have a common sequence, which may occur at one or both ends. In some embodiments, a target nucleic acid is single stranded and has a common sequence, such as a polyA tail. In one such example, native mRNA carrying polyadenylated tails, and which have polyadenylated tails added, for example using blunt ligation or ligation utilizing a splint oligo to a 5' end of a native mRNA, and are captured on an array or lawn of oligonucleotide polyd(T) probes on a test substrate or other surface or matrix. In some embodiments, especially those where short DNA is analyzed, ends of a target nucleic acid is adapted by for example ligating specific short oligos or by binding biotin for interaction with capture molecules, which is specific complementary oligonucleotide probe species on a test substrate or other surface or matrix.

In some embodiments, target nucleic acids may comprise double stranded DNA with sticky ends, which is generated by a restriction enzyme. In some non-limiting examples, restriction enzymes with infrequent sites (e.g., Pmme1 or NOT1) are used to generate long fragments of target nucleic acids, each fragment containing a sticky end with a common end sequence. In some embodiments, adaptation is performed using terminal transferase. In other embodiments, ligation or tagmentation is used to introduce adaptors in a similar manner to that which is utilized by users of Illumina sequencing. This enables users to use well-established Illumina protocols to prepare samples, which may then be captured and sequenced by methods described herein. In such embodiments, target nucleic acids is captured or fixed for sequencing before any amplification, which introduces error and bias, and removes any epigenetic information which may comprise a part of native target nucleic acid.

Methods of Elongation

In most embodiments, a polynucleotide or other target molecule, such as a target nucleic acid, target protein, target polypeptide, or target peptide may need to be attached, bound or fixed to a test substrate, surface or matrix for elongation to occur. In some embodiments, elongation of a target nucleic acid renders it equal to, longer or shorter than its crystallographic length (e.g., where there is a known in situ 0.34 nm separation from one base to the next for dsDNA). In some embodiments, a target nucleic acid is stretched longer than an in situ crystallographic length.

In some embodiments, a target nucleic acid is stretched via molecular combing (e.g., as described in Michalet et al., Science 277:1518-1523, 1997 and Deen et al., ACS Nano 9:809-816, 2015). This may enable stretching and unidirectional aligning of millions and billions of target nucleic acids in parallel. In some embodiments, molecular combing is performed by washing a solution containing desired target nucleic acid onto a test substrate and then retracting a meniscus of a solution. Prior to retracting a meniscus, target nucleic acids may form covalent or other interactions with a test substrate. As a solution recedes, target nucleic acids is pulled in a same direction as a meniscus (e.g., through surface retention); however, if a strength of binding or fixing interactions between target nucleic acids and a test substrate is sufficient to overcome a surface retention force, then target nucleic acids is stretched in a uniform manner in a direction of a receding meniscus. In some embodiments, molecular combing is performed as described in Kaykov et al., Sci Reports. 6:19636 (2016), which is hereby incorporated by reference in its entirety. In other embodiments, molecular combing is performed in channels (e.g., of a microfluidic device) using methods or modified versions of methods described in Petit et al. Nano Letters 3:1141-1146 (2003).

A shape of an air/water interface may determine an orientation of elongated target nucleic acids that are stretched by molecular combing. In some embodiments, a target nucleic acid is elongated perpendicularly to an air/water interface. In some embodiments, a target nucleic acid is attached, bound or fixed to a test substrate or other surface without modification of one its ends, or is bound or fixed without modification to either of its ends. In some embodiments, where ends of a double-stranded target nucleic acid are captured by hydrophobic interactions, stretching with a receding meniscus may cause parts of a double-stranded target nucleic acid to denature and form additional hydrophobic interactions with a test substrate or surface.

In some embodiments, a target nucleic acid is stretched via molecular threading (e.g., as described by Payne et al., PLoS ONE 8(7):e69058, 2013). In some embodiments, molecular threading is performed after a target nucleic acid has been denatured into single strands (e.g., by chemical denaturants, temperature or enzymes, salt concentration or pH). In some embodiments, a target nucleic acid is tethered at one end and then stretched utilizing fluid flow (e.g., as illustrated in Greene et al., Methods in Enzymology, 327: 293-315).

In various embodiments, a target nucleic acid is present within a micro-fluidic channel. In some embodiments, a target nucleic acid is flowed into a microfluidic channel or is extracted from one or more chromosome, exosomes, nuclei, or cells into a flow channel. In some embodiments, rather than inserting a target nucleic acid into a nanochannel via a micro- or nanofluidic flow cell, a target nucleic acid is inserted into open-top channels by constructing one or more channels, which is a nano-channel or a micro-channel in such a way that a surface which may form walls and or bottom of a channel, is electrically biased (e.g., see Asanov et al., Anal Chem. 1998 Mar. 15; 70(6):1156-6). In some embodiments, a positive bias is applied to the surface which may form the walls and or bottom of a channel, so that negatively charged target nucleic acids is attracted into a nanochannel. Concurrently, areas between channels may not be electrically biased, so that target nucleic acids is less likely to deposit on the areas between channels.

In some embodiments, extension is effectuated by hydrodynamic drag. In some embodiments, a target nucleic acid is stretched via a crossflow in a nanoslit (Marie et al., Proc Natl Acad Sci USA 110:4893-8, 2013). In some embodiments, extension of a target nucleic acid is effectuated by nanoconfinement in a flow channel. Flow stretching nanoconfinement may involve stretching a target nucleic acid into a linear conformation via flow gradients, generally performed within a microfluidic or nanofluidic device. A nanoconfinement portion of a microfluidic or nanofluidic device which may utilize this stretching method may refer to a narrow region of a microfluidic or nanofluidic device. Use of a narrow region or channel may help overcome the issue of molecular individualism (e.g., the tendency of an individual nucleic acid or other polymer to adopt multiple conformations during stretching). One problem with flow stretching methods is that the flow may not always be applied equally along a target nucleic acid. This can result in target nucleic acids exhibiting a range, which is a wide range, of extension lengths. In some embodiments, flow stretching methods may involve extensional flow and/or hydrodynamic drag. In some embodiments, where a target nucleic acid is attracted into a microchannel or nanochannel, one or more target nucleic acids is nanoconfined in a microchannel or nanochannel, and thereby elongated. In some embodiments, after nanoconfinement a target nucleic acid is deposited, bound or fixed on a biased surface or on a coating or matrix atop a test substrate or other surface.

In some embodiments, any of multiple methods of applying a positive or a negative bias to a surface is utilized. In some embodiments, a test substrate or other surface is made with or is coated with a material that has non-fouling characteristics, a test substrate or other surface is passivated with lipids (e.g., lipid bilayers), bovine serum albumin (BSA), casein, various PEG derivatives, etc. Passivation may serve to prevent polynucleotide sequestration, binding or fixing in any one part of a channel and thus may enable elongation and or more even elongation. In some embodiments, a test substrate or other surface may also comprise indium tin oxide (ITO) or other transparent electrically conductive surfaces such as wide spectrum transparent conductive oxides, conductive polymers, graphene, very thin metal films or the like.

In some embodiments, for creation of lipid bilayers (LBLs) on test substrates or other surfaces comprising microfluidic or nanofluidic channels, zwitterionic POPC (1-palmitoyl-2-oleoyl-sn-glycero-3-phosphocholine) lipids with 1% Lissamine™ rhodamine B 1,2-dihexadecanoyl-sn-glycero-3-phosphoethanolamine is coated onto a surface. Addition of triethylammonium salt (rhodamine-DHPE) lipids may enable observation of a LBL formation with fluorescence microscopy. Methods of lipid bilayer passivation that are used In some embodiments, of the present disclosure are described by Persson et al., Nano Lett. 12:2260-2265, 2012

In some embodiments, extension of one or more target nucleic acids is performed via electrophoresis or dielectrophoresis. In some embodiments, a target nucleic acid is tethered at one end and then stretched by an electric field (e.g., as described by Giese et al., Nature Biotechnology 26: 317-325, 2008). Electro-stretching of nucleic acid is predicated upon the fact that nucleic acids are highly negatively charged molecules. The method of electro-stretching, for example, as described by Randall et al. 2006, Lab Chip. 6, 516-522, involves nucleic acid being drawn through a microchannel or nanochannel (to induce orientation of a target nucleic acid molecule) by an electric field. In some embodiments, electro-stretching is conducted either within or without a gel or entangled polymer. One benefit of using a gel or entangled polymer is to limit the three-dimensional space available to a target nucleic acid, thus helping to overcome molecular individualism. A general advantage of electro-stretching over pressure-driven stretching methods such as nanoconfinement is a lack of shear forces that is sufficient to break nucleic acid molecules.

In some embodiments, when a plurality of polynucleotides is present on a test substrate or other surface, target nucleic acids may not be aligned in a same orientation or may not be straight (e.g., target nucleic acids may attach, bind or fix to a test substrate or other surface or have threaded through a gel or entangled polymer in a curvilinear path). In such embodiments, there is an increased likelihood that two or more of a plurality of target nucleic acids will overlap, leading to potential confusion regarding localization of probes along a length of each target nucleic acid. In some embodiments, although a same sequencing information is obtained from curved target nucleic acids as from straight well-aligned target nucleic acids, an image processing task of processing sequencing information from curved target nucleic acids may require more computational power or time than that obtained from straight well-aligned target nucleic acids.

In embodiments, where one or more target nucleic acids is elongated in a direction parallel to a planar surface, which is a surface of a test substrate, lengths of target nucleic acids are imaged across a series of adjacent pixels in a two-dimensional imager which is an array detector such as a CMOS or CCD camera. In some embodiments, the one or more target nucleic acids is elongated in a direction perpendicular to a test substrate or other surface. In some embodiments, target nucleic acids is imaged via light sheet microscopy, spinning disk confocal microscopy, three-dimensional super resolution microscopy, three-dimensional single molecule localization, or laser scanning disc confocal microscopy or its variants. In some embodiments, target nucleic acids is elongated at an oblique angle to a test substrate or other surface. In some embodiments, target nucleic acids is imaged via a two-dimensional imager or detector and resulting images or frames is processed via a Single Molecule Localization algorithm software (e.g., the Fiji/ImageJ plug-in ThunderSTORM as described in Ovesny et al., BioInform. 30:2389-2390, 2014).

Extracting and Isolating DNA from a Single Cell Prior to Fixing and Elongation.

In some embodiments, traps for single cells are designed within microfluidic structures to hold individual cells in one place while target nucleic acids in individual cells is released (e.g., by using the device designs of WO/2012/056192 or WO/2012/055415). In some embodiments, instead of extracting and stretching a target nucleic acid in nanochannels, a cover-glass or foil is used to seal micro/nanofluidic structures, which may further be coated with polyvinylsilane to enable molecular combing (e.g., by movements of fluids as described by Petit et al., Nano Letters 3:1141-1146. 2003). Gentle conditions inside a fluidic chip may enable extracted target nucleic acids to be preserved having long lengths.

A number of different approaches are available for extracting biopolymers from single cells or nuclei (e.g., some suitable methods are reviewed in Kim et al., Integr Biol 1(10), 574-86, 2009). In some non-limiting examples, cells are treated with high concentrations of KCL to burst or remove cell membranes. Cells are lysed by adding a hypotonic solution. In some embodiments, each cell is separately isolated, each cell's DNA is separately extracted, and then each set of target nucleic acids associated with a single cell is separately sequenced in a microfluidic vessel or device. In some embodiments, target nucleic acid extraction may occur by treating one or more cells with detergent and/or protease. In some embodiments, chelating agents (e.g., EDTA or EDDS) are provided in a lysis solution to capture divalent cations required by nucleases (and thus decrease nuclease activity).

In some embodiments, nuclear and extra nuclear constituents of a single cell are separately extracted by the following method. One or more cells are provided to a feeding channel of a microfluidic device. One or more cells may then be captured, where each cell is captured by one trapping structure. A first lysis buffer is flowed into a trapping structure of a microfluidic device with one or more captured cells, where a first lysis buffer may lyse cellular membranes but may preserve integrity of cell nuclei. Upon flowing of a first lysis buffer, extranuclear constituents of one or more captured cells in a trapping structure of a microfluidic device is released into a flow cell within a microfluidic device where released RNA and cytoplasmic is immobilized. One or more nuclei may then be further lysed by supplying a second lysis buffer to a trapping structure of a microfluidic device with one or more captured cells or remnants thereof. Addition of a second lysis buffer may cause release of constituents of the one or more nuclei and or mitochondria (e.g., genomic DNA or mitochondrial DNA) into a flow cell in a microfluidic device where DNA is subsequently immobilized. Extranuclear and intracellular components of one or more cells is immobilized at different locations of a same flow cell or in different flow cells within the same microfluidic device, or in different microfluidic devices.

Figure 16A:
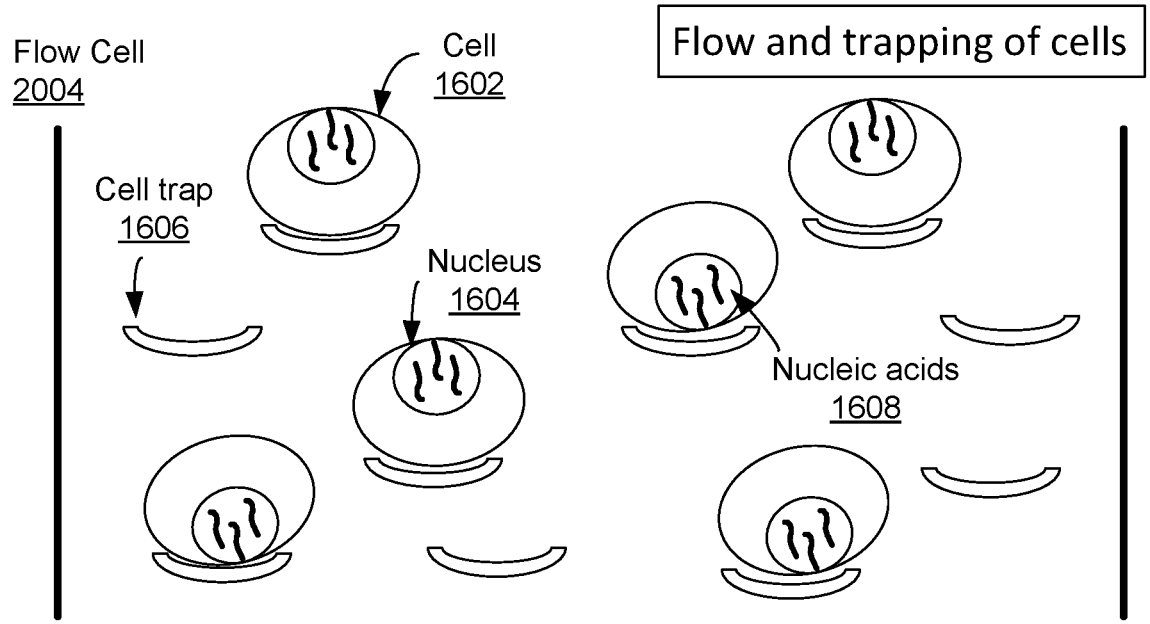
FIGS. 16A and 16B collectively illustrate an example of cell lysis and nucleic acid immobilization and elongation in accordance with various embodiments of the present disclosure.
Figure 16B:
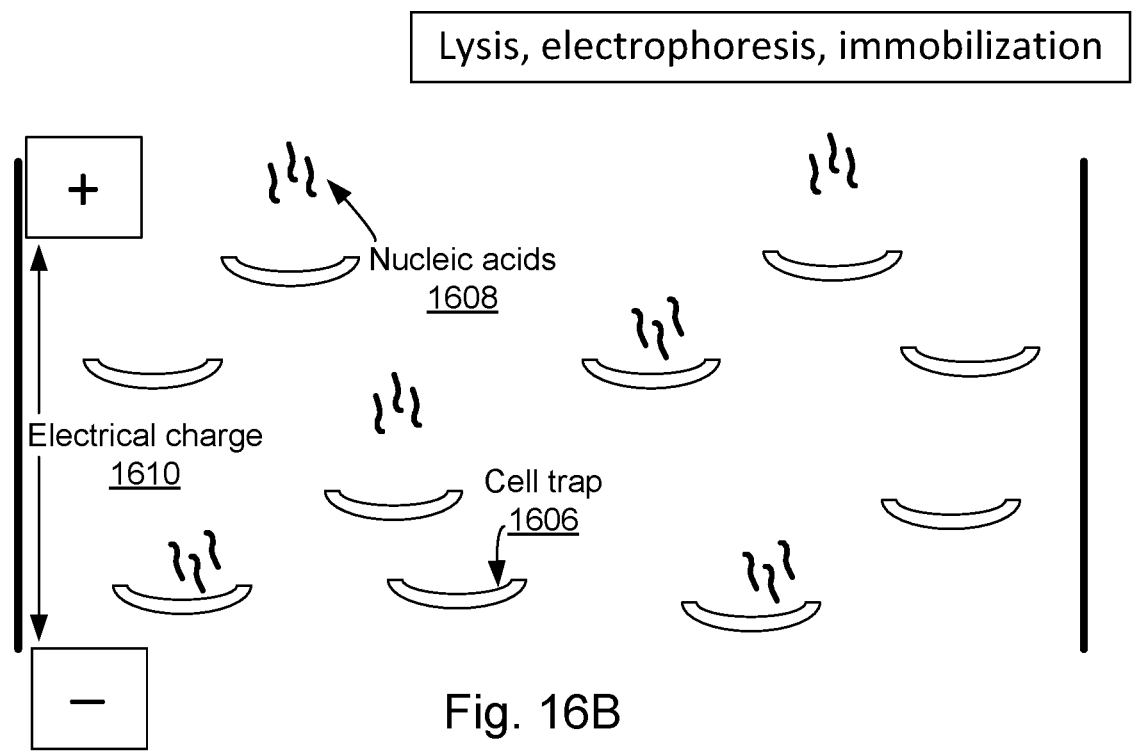

The schematics in FIGS. 16A and 16B show a microfluidic architecture that may capture and isolate multiple single cells. Cells 1602 are captured by cell traps 1606 within a flow cell 2004. In some embodiments, after cells have been captured, lysis reagents are flowed into and through an illustrated with cell traps 1606. After lysis, nucleic acids 1608 may then be distributed close to capture traps 1606, while remaining isolated from nucleic acids 1608 extracted from other cells 1602. In some embodiments, as illustrated in FIG. 16B, electrophoretic induction is performed (e.g., by using electrical charge 1610) to maneuver nucleic acids. Lysis may release nucleic acids 1608 from cells 1602 and nuclei 1604. Nucleic acids 1608 may remain in a position (e.g., relative to the cell traps 1606) in which nucleic acids 1608 were when cells 1602 were trapped. The traps are the dimension of single cells (e.g., from 2-10 μm). In some embodiments, channels bringing a sample bearing microdroplet and microfluidic device flow cell together is wider and taller than 2 μm, 10 μm or greater than 10 μm. In some embodiments, a distance between bifurcating channels and traps is from 1-1000 microns.

Extracting and Elongating High Molecular Weight DNA on a Surface.

Various methods for stretching HMW polynucleotide are used in different embodiments (e.g., ACS Nano. 9(1):809-16, 2015). In one such example, elongation on a surface is conducted in a flow cell (e.g., by using the approach described by Petit and Carbeck in Nano. Lett. 3: 1141-1146, 2003). In addition to fluidic or microfluidic approaches, In some embodiments, polynucleotides are stretched using an electric field such as disclosed in Giess et al., Nature Biotechnology 26, 317-325 (2008). Several approaches are available for elongating polynucleotides when they are not attached to a surface (e.g., Frietag et al., Biomicrofluidics, 9(4):044114 (2015); Marie et al., Proc Natl Acad Sci USA 110:4893-8, 2013).

In some embodiments, as an alternative to using DNA in a gel plug, chromosomes suitable for loading onto microfluidic device which may comprise a test substrate is prepared by a poly amine method as described by Cram et al., Methods Cell Sci., 2002, 24, 27-35, and is pipetted directly into a microfluidic device which may comprise a test substrate. In some such embodiments, proteins bound to DNA in a chromosome is digested using a protease to release substantially naked DNA, which may then be fixed and elongated as described hereinabove.

Treating Samples for Locational Preservation of Reads.

In embodiments where very long regions or polymers are to be sequenced, any degradation of a target nucleic acid has the potential to significantly decrease accuracy of overall sequencing. Methods to facilitate preservation of the entire elongated polymer are presented below.

A target nucleic acid has the potential to become damaged during extraction, storage or preparation. Nicks, gaps, oxidation of bases, delamination of cytosine, and adducts can form in a native double-stranded genomic DNA molecule. This is especially the case for when the sample polynucleotides are from FFPE material. Thus, in some embodiments, a DNA repair solution is introduced before or after DNA is immobilized. In some embodiments, DNA repair is done after DNA extraction into a gel plug. In some embodiments, a repair solution may contain DNA endonuclease, kinases and other DNA modifying enzymes. In some embodiments, a repair solution may comprise polymerases and ligases. In some embodiments, a repair solution is the pre-PCR kit form New England Biolabs. In some embodiments, such methods are performed largely as described in Karimi-Busheri et al., Nucleic Acids Res. October 1; 26(19):4395-400, 1998 and Kunkel et al., Proc. Natl Acad Sci. USA, 78, 6734-6738, 1981. In other embodiments, it is desirable to detect target nucleic acid damage. For example it is desirable to determine a number and location of one or more DNA adducts. In such embodiments, additional labeled adduct specific binding moieties is utilized as a part of a sequencing method.

In some embodiments, after a target nucleic acid is elongated, a gel overlay is applied. In some such embodiments, after elongation and denaturation on a test substrate or other surface, a target nucleic acid, which is double-stranded or denatured, is covered with a gel layer. Alternatively, a target nucleic acid is elongated while already in a gel environment (e.g., as described hereinabove). In some embodiments, after a target nucleic acid is elongated it is cast in a gel. For example, in some embodiments, when a target nucleic acid is attached to a surface at one end and stretched by a reagent flow stream or by an electrophoretic field, a surrounding region medium is cast into a gel. In some embodiments, casting into a gel may occur by including acrylamide, ammonium persulfate and TEMED in a reagent flow stream. Such compounds, when polymerized, become polyacrylamide. In alternative embodiments, a gel that responds to heat is applied. In some embodiments, an end of a target nucleic acid is modified with acrydite, which may polymerize with the acrylamide. In some such embodiments, an electric field is applied that elongates the polynucleotide towards the positive electrode, given the negative charge of the backbone of native polynucleotides.

In some embodiments, a target nucleic acid is extracted from cells in a gel plug or a gel layer to preserve integrity of target nucleic acids; and then an AC electric field is applied to dielectrophoretically stretch or elongate target nucleic acids within a gel; dielectrophoretic stretching is performed in a gel layer atop a cover glass, or in a gel associated with a test substrate or other surface, subsequently any of the methods as described herein is utilized can be applied to a stretched target nucleic acid to detect transient oligonucleotide probe species binding.

In some embodiments, a sample or target nucleic acid is cross-linked to a matrix of its environment. In one example this is a cellular milieu. For example, when a method nucleic acid sequencing as described herein is conducted in situ in a cell, a target nucleic acid is cross-linked to a cellular matrix using a heterobifunctional cross linker. This is performed as a part of a sequencing method directly inside cells using a technique such as FISSEQ (Lee et al., Science 343:1360-1363, 2014).

Much of damage to target biomolecules occurs in the process of extracting a target biomolecule from cells and tissues and subsequent handling of a target biomolecule before it is analyzed. In the case of target nucleic acids, aspects of its handling that lead to its loss of integrity may include pipetting, vortexing, freeze-thawing and excessive heating. In some embodiments, mechanical stress is minimized such as in the manner disclosed in ChemBioChem, 11:340-343 (2010). In addition, high concentrations of non-catalytic divalent cations such as calcium or zinc, EDTA, EGTA or Gallic Acid (and its analogues and derivatives) may inhibit degradation by nucleases. In some embodiments, a 2:1 ratio of sample to non-catalytic divalent cation weight is sufficient to inhibit nucleases even in samples such as stool, where there are extreme levels of nucleases.

In order to preserve the integrity of a target nucleic acid (e.g., to not induce DNA damage or breakage into smaller fragments), In some embodiments, it is desirable to keep a biomacromolecule such as DNA or RNA in its natural protective environment such as chromosomes, mitochondria, cells, nuclei, exosomes etc. In some embodiments, where a target nucleic acid is already outside its protective environment, it is desirable to encase it in a protective environment such as a gel or a microdroplet. In some embodiments, a target nucleic acid is released from its protective environment in close physical proximity to where it will be sequenced (e.g., a part of a fluidic system or flow cell where sequencing data may be acquired). Thus, in some embodiments, a biomacromolecule (e.g., nucleic acid, protein) is provided in a protective entity, said protective entity preserving a biomacromolecule close to its native state (e.g., native length), bringing a protective entity which comprises a biomacromolecule into close proximity with where biomacromolecule may be sequenced, then releasing a biomacromolecule into an area where it is sequenced or close to an area where it is sequenced. In some embodiments, the flow cell may comprise an agarose gel which may effectively encapsulate sample target genomic DNA, said agarose gel preserving a substantial fraction of genomic DNA with lengths greater than 200 Kb in length, placing an agarose gel comprising target genomic DNA in proximity of an environment (e.g., test substrate, surface, gel, matrix) where target genomic DNA is sequenced, releasing target genomic DNA from an agarose gel into a sequencing environment (or close to a sequencing environment so that a target genomic DNAs further transport and handling is minimized) and carrying out one or more sequencing methods. Release into a sequencing environment is by application of an electric field or by digestion of an agarose gel by agarase.

Polymer Denaturation.

Block 206. In some embodiments, fixed stretched double-stranded target nucleic acid is subsequently denatured to single stranded form on a test substrate, thereby obtaining a fixed first strand and a fixed second strand of a target nucleic acid. Respective bases of a fixed second strand may lie adjacent to corresponding complementary bases of a fixed first strand. In some embodiments, denaturation is performed by first elongating or stretching a double stranded target nucleic acid and then adding a denaturation solution to separate the two strands.

In some embodiments, denaturation is chemical denaturation comprising one or more reagents (e.g., 0.5M NaOH, DMSO, formamide, urea, etc.). In some embodiments, denaturation is heat denaturation (e.g., by heating the sample to 85° C. or higher). In some embodiments, denaturation is through enzymatic denaturation such as through the use of helicases, or other enzymes with helicase activity. In some embodiments, target nucleic acids is denatured through interaction with a surface or by a physical process such as stretching beyond a critical length. In some embodiments, denaturation is full or partial.

In some embodiments, binding of oligonucleotide probe species to modifications on repeating units of a target nucleic acid (e.g., epigenetically modified nucleotides in a polynucleotide, or phosphorylation of a polypeptide) are conducted before or after an optional denaturation step.

In some embodiments, the optional denaturation of a double-stranded target nucleic acid may not be performed at all. In some such embodiments, oligonucleotide probe species is utilized bind or anneal to a duplex structure of a target nucleic acid. For example, in some embodiments, oligonucleotide probe species may bind to individual strands of duplex form target nucleic acid through strand invasion (e.g., using PNA probes), by inducing excessive breathing of the duplex form target nucleic acid, by recognizing a sequence in the duplex form target nucleic acid by using a modified zing-finger protein, or by using a Cas9 or similar protein that denatures a duplex form of a target nucleic acid allowing a guide RNA to bind. In some embodiments, a guide RNA may comprise an interrogation probe sequence and a label, thus functioning as an oligonucleotide probe species as described herein, and a gRNA comprising each sequence for one or more sets of oligonucleotide probe species is provided.

In some embodiments, a double-stranded target nucleic acid may contain nicks (e.g., natural nicks or those created by DNase1 treatment). In such embodiments, under the conditions of a reaction, one strand transiently frays or peels away from the other strand of the duplex (e.g., transiently denaturing), or natural base-pair breathing occurs. This may allow an oligonucleotide probe species to transiently bind, before it is displaced by rehybridization of native strands.

In some embodiments, a single double-stranded target nucleic acid is denatured, such that each of the strands of a duplex is available for binding by an oligonucleotide probe species. In some embodiments, a single target nucleic acid is damaged, either by a denaturing process or at another step in a sequencing method, and is repaired (e.g., by the addition of a suitable DNA polymerase and or ligase).

In some embodiments, immobilization and linearization of double-stranded target genomic DNA (in preparation for fixing or binding to a test substrate or other surface) may comprise molecular combing, UV crosslinking of double-stranded target genomic DNA to a surface, optional wetting, denaturation of double-stranded target genomic DNA through exposure to chemical denaturants (e.g., alkali solutions, DMSO, etc.), optional exposure to acidic solution after washing, and exposure to optional pre-conditioning buffers.

Annealing of Probes.

Block 208. After an optional denaturation step, a method may continue by exposing a fixed first strand and a fixed second strand to a respective pool of a respective oligonucleotide probe species in a set of oligonucleotide probe species, where each oligonucleotide probe species in a set of oligonucleotide probe species is of a predetermined sequence and length. Exposing may occur under conditions that allow for individual oligonucleotide probes of the respective pool of the respective oligonucleotide probe species to bind and form a respective duplex with each portion (or portions) of a fixed first strand or a fixed second strand that is complementary to a respective oligonucleotide probe species thereby giving rise to a respective instance of optical activity.

Figure 5A:
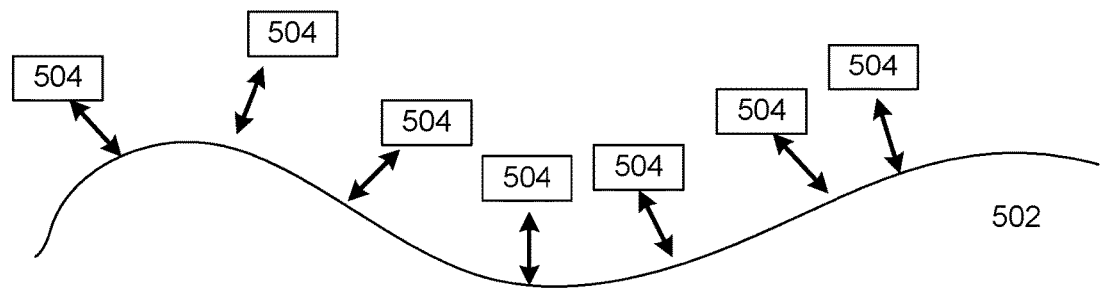
FIGS. 5A, 5B, and 5C collectively illustrate an example, of transient binding of probes to a polynucleotide in accordance with various embodiments of the present disclosure.
Figure 5B:
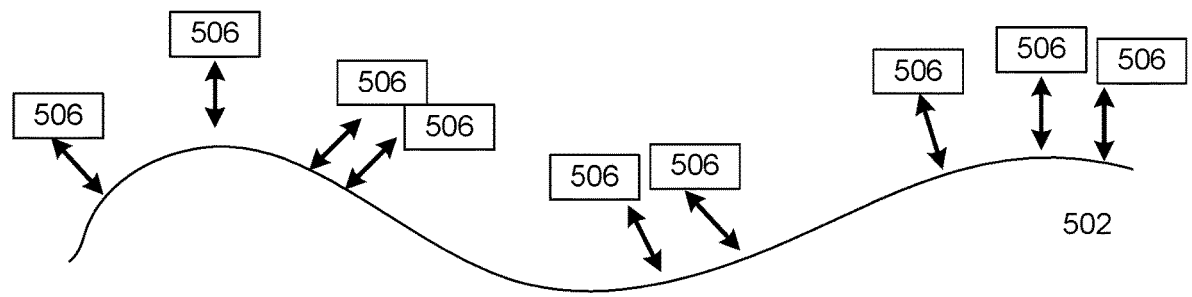
Figure 5C:
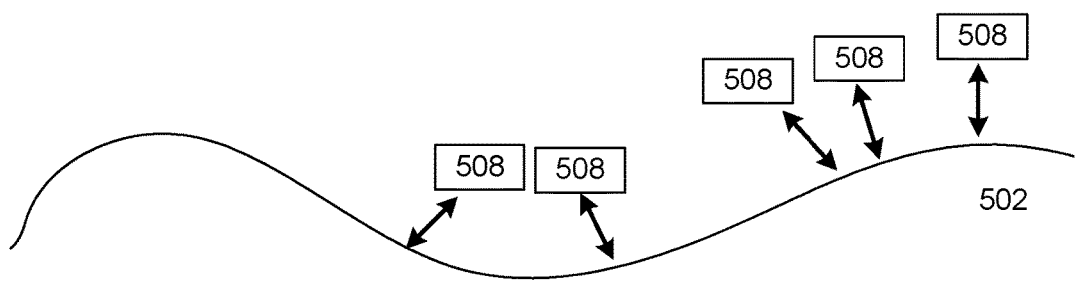

FIGS. 5A, 5B, and 5C illustrate an example of transient binding of different probe species to one polymer 502. Each probe (e.g., 504, 506, and 508) may comprise a specific interrogation sequence (e.g., an oligonucleotide or peptide sequence). After application of probe species 504 to polymer 502, probe species 504 are washed off of polymer 502 with one or more wash steps. Similar wash steps are used to subsequently remove probe species 506 and 508.

Probe Design and Targets.

In some embodiments, a solution comprising one or more pools of oligonucleotide probe species is provided to target nucleic acids in solution. When a pool comprising oligonucleotide probe species is brought into contact with target nucleic acids on a test substrate, other surface, or matrix, oligonucleotide probes are able to make contact with target nucleic acids through diffusion and molecular collisions. In some embodiments, a solution comprising one or more pools of oligonucleotide probe species is agitated to bring oligonucleotide probes in contact with the one or more target nucleic acids. In some embodiments, the oligonucleotide probe species containing solution is exchanged to bring fresh oligonucleotide probes to the one or more target nucleotides on a test substrate, other surface or matrix. In some embodiments, an electric field is used to attract oligonucleotide probes to a test substrate, or other surface, for example, a positively biased surface or AC field may attract negatively charged oligos.

In some embodiments, a target nucleic acid may comprise a particular polynucleotide sequence and a specific binding part of an oligonucleotide probe species comprises, for example, a 3-mer, a 4-mer, a 5-mer, or a 6-mer oligonucleotide sequence interrogation portion, optionally one or more degenerate or universal positions, and optionally a nucleotide spacer (e.g., one or more T nucleotides) or an abasic or non-nucleotide portion. As illustrated in FIGS. 6A and 6B, similar binding occurs along a target nucleic acid 602, regardless of the length of oligonucleotide probe species (e.g., 604 and 610) that are used. The primary difference inherent to different k-mer length oligonucleotides is that the k-mer length sets a length of binding sites that is be bound by respective oligonucleotide probe species (e.g., 3-mer probes 604 will primarily and more stably bind to 3-nucleotide long sites such as 606, and 5-mer probes 610 will primarily and more stably bind to 5-nucleotide long sites such as 610).

In FIG. 6A, illustrated 3-mer oligonucleotide probe species are unusually short for use as oligonucleotide probes. Normally such short sequences are not used as oligonucleotide probes because they cannot bind stably unless very low temperatures and long incubation times are used. However, such short oligonucleotide probe species do form transient bonds to a target nucleic acid, as required by detection methods as described herein. Further, the shorter the oligonucleotide probe species sequence, the fewer oligonucleotide probe species are present in a set of oligonucleotide probe species. For example, only 64 oligonucleotide sequences are required for a complete set of 3-mer oligonucleotide probe species, while 256 oligonucleotide sequences are required for a complete 4-mer set of oligonucleotide probe species. Further, pools of ultra-short oligonucleotide probe species are modified In some embodiments, to increase melting temperature and, in some embodiments, may include degenerate (e.g., N) or universal nucleotides as described herein. For example, four N nucleotides would increase the stability of a 3-mer oligonucleotide to the stability of a 7-mer oligonucleotide.

In FIG. 6B, the schematic illustrates binding of a 5-mer oligonucleotide probe to its perfect match position (612-3), a 1 base mismatch position (612-2) and a 2 base mismatch position (612-1).

The binding of any one oligonucleotide probe may not be sufficient to allow sequencing of a target nucleic acid. In some embodiments, a complete set of oligonucleotide probes is needed to reconstruct a sequence of a target nucleic acid. Information on locations of oligonucleotide probe species binding sites, temporally separated binding of oligonucleotide probe species to overlapping binding sites, partial binding of mismatches between the oligonucleotide probe species and a target nucleic acid, frequency of bindings, and duration of bindings may all contribute to deducing a sequence or a target nucleic acid. In the case of elongated or stretched target nucleic acids, locations of oligonucleotide probe species binding along a length of a target nucleic acid may contribute to building a sequence with high confidence. In the case of double-stranded target nucleic acids, a higher confidence sequence may emerge from sequencing of both strands of a duplex form target nucleic acid (e.g., both complementary strands) simultaneously.

In some embodiments, a common reference oligonucleotide probe species is added together with each of a one more pools of oligonucleotide probe species in one or more sets of oligonucleotide probe species. For example, in FIGS. 7A, 7B, and 7C a common reference oligonucleotide probe species 704 binds to the same binding sites 708 on target nucleic acid 702 regardless of any additional probes included in a set of oligonucleotide probe species (e.g., 706, 712, and 716). The presence of common reference oligonucleotide probe species 704 does not inhibit binding of the other oligonucleotide probe species 706, 712, and 716 to their respective binding sites (e.g., 710, 714, 718, 720, and 722).

As depicted in FIG. 7C, binding sites 718, 720, and 722 illustrate how individual oligonucleotide probes (716-1, 716-2, and 716-3) will bind to all of the possible sites, even when those sites are overlapping. In FIGS. 7A, 7B, and 7C, the probe sequences are depicted by 3-mers. However, similar methods could equally well be performed with probes that are 4-mers, 5-mers, 6-mers, etc.

In some embodiments, one or more sets of oligonucleotide probe species may comprise every oligo of a given length. For example, a complete set of the 1024 individual 5-mers is encoded and included in one or more sets of oligonucleotide probe species in accordance with one embodiment of the present disclosure. In some embodiments, one or more sets of oligonucleotide probe species may include all oligonucleotide probe species of multiple lengths. In some embodiments, a set of oligonucleotide probes is a tiling series of oligonucleotide probe species. In some embodiments, a set of oligonucleotide probe species is a panel of oligonucleotide probe species. In the case of certain applications in synthetic biology (e.g., DNA data storage) sequencing may comprise finding an order of specific blocks of sequence, where blocks are designed to encode desired data.

Figure 8A:
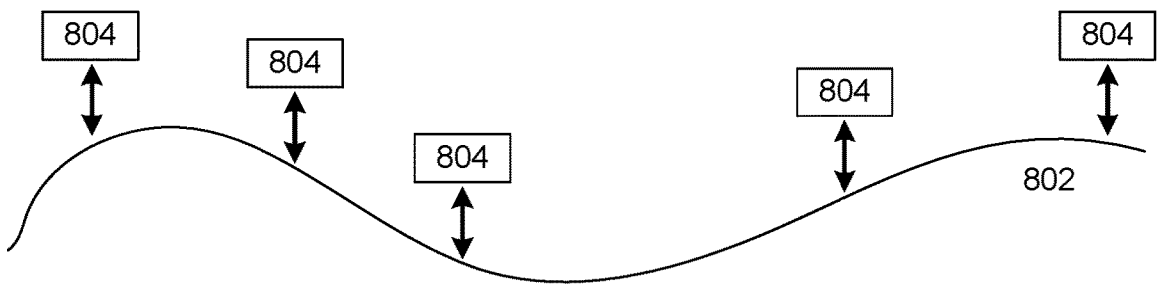
FIGS. 8A, 8B, and 8C collectively illustrate an example of applying distinct probe sets to a single reference molecule in accordance with various embodiments of the present disclosure.
Figure 8B:
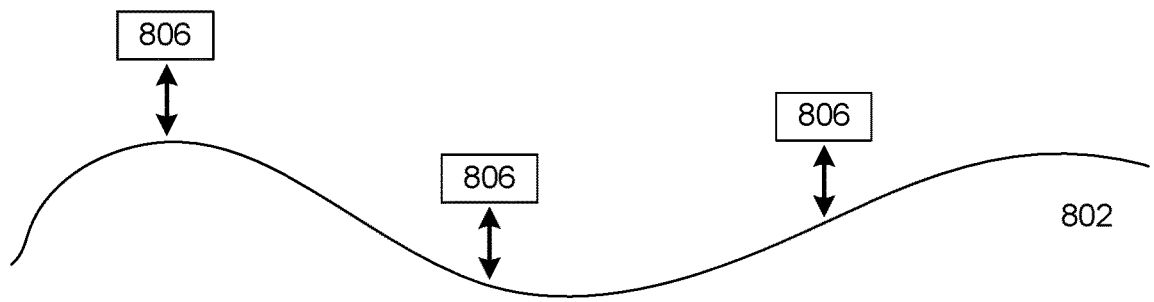
Figure 8C:
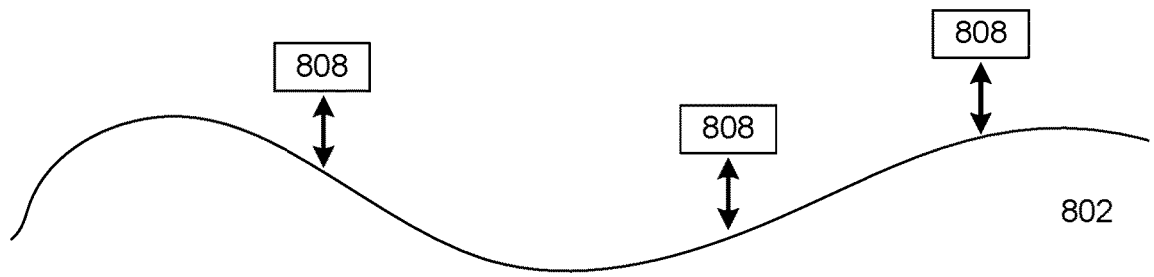

As illustrated by FIGS. 8A, 8B, and 8C, multiple sets of oligonucleotide probe species (e.g., 804, 806, and 808), are applied to any target nucleic acid 802 in some embodiments. Each oligonucleotide probe species will bind preferentially to its complementary binding sites. In some embodiments, washing with a buffer in between each exposing (c) aids removal of oligonucleotide probe species in a previous set.

Figure 9A:
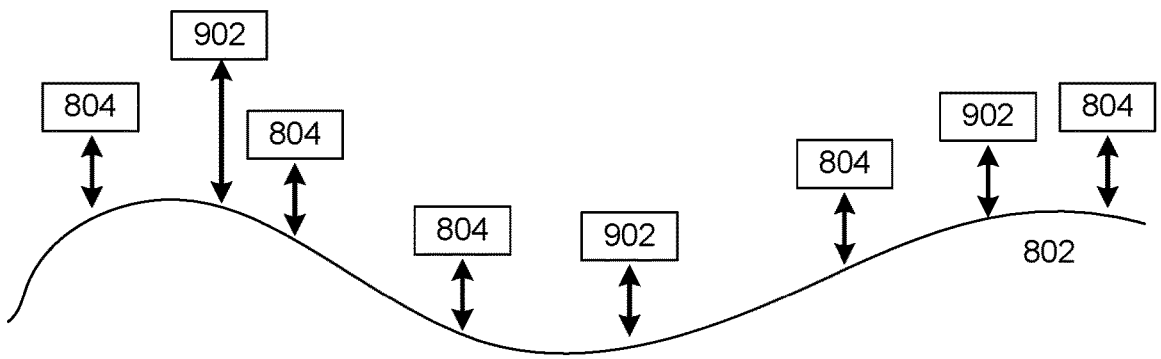
FIGS. 9A, 9B, and 9C collectively illustrate an example of transient binding in cases where multiple types of probes are used, in accordance with various embodiments of the present disclosure.
Figure 9B:
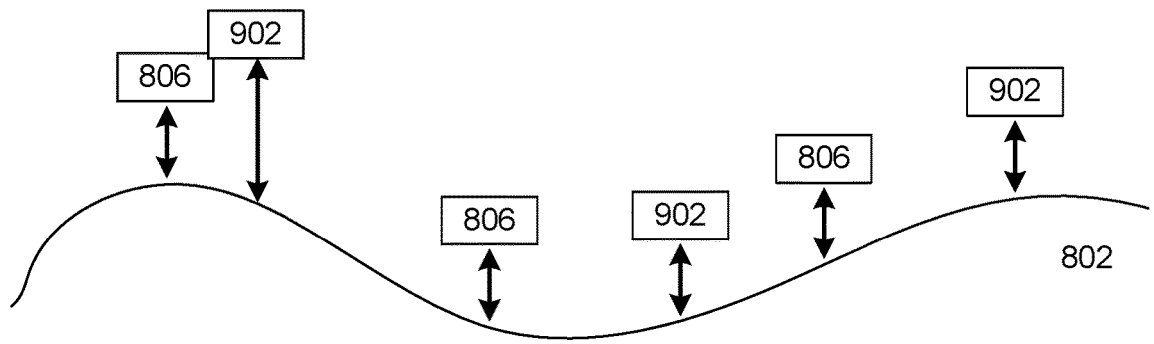
Figure 9C:
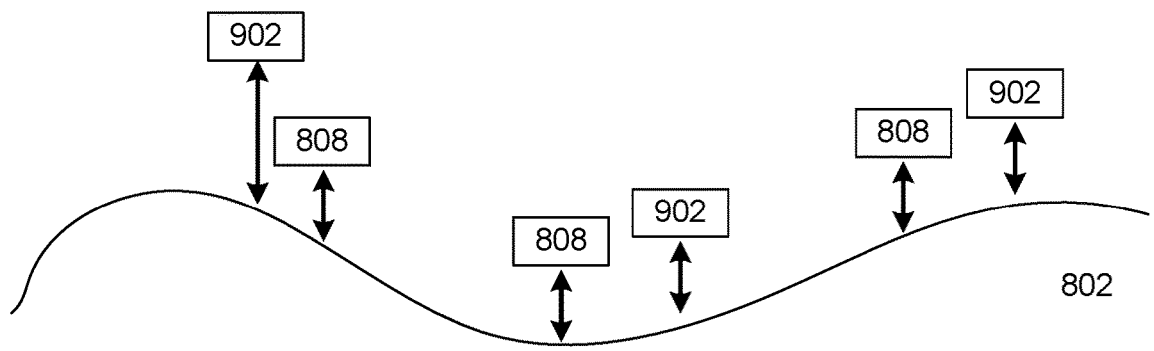

In some embodiments, probes for nucleic acid sequencing are oligonucleotides and the probes for epi-modifications are modification-binding proteins or peptides (e.g., methyl binding proteins such as MBD1) or anti-modification antibodies (e.g., anti-methyl C antibody). In some embodiments, oligonucleotide probe species may target specific sites in the genome (e.g., sites with known mutations). As illustrated in FIGS. 9A, 9B, and 9C, both oligonucleotides (e.g., 804, 806, and 808) and alternate probes (e.g., 902) are applied concurrently (and through multiple exposure steps) to a target nucleic acid 802 in some embodiments. A method of determining target sites of interest is provided by Liu et al., BMC Genomics 9: 509 (2008), which is hereby incorporated by reference.

In some embodiments, each of the probe species, which is oligonucleotide probe species of one or more sets of probes, which is an oligonucleotide probe species or a subset of one or more sets of probe species, which is one or more sets of oligonucleotide probe species is applied one after another (e.g., the binding of one probe species, which is an oligonucleotide probe species or a subset or one or more sets of oligonucleotide probe species is first detected and then may removed, before a next oligonucleotide probe species is added, detected and removed then the next, etc.). In some embodiments, all or a subset of probes in one or more sets of probes is added simultaneously in a single pool and each binding probe is linked to a label that codes completely or partially for identity of a binding probe and code for each of the binding probes is decoded by detection and analysis processes.

As illustrated by FIGS. 11A and 11B, a tiling series or tiling set of probes may used to gain information for binding sites of multiple probes in some embodiments. In FIG. 11A a first tiling set 1104 is applied to a target nucleic acid 1102.

Each tiling probe in a subset of tiling probes in a first tiling set 1104 contains one common base 1108, thereby resulting in 5× depth of coverage of that one common base 1108 in the target nucleic acid 1102. Depth of coverage will be proportional to the k-mer length of probes in a tiling series (e.g., a set of 3-mer oligos will result in about 3× coverage of every base in a target nucleic acid).

In some embodiments, when a set of oligonucleotide probe species tiles along a target base, there is a potential for a problem to arise when there is a break in a tiling path. For example, with a set of oligonucleotide probe species of 5-mers there is no oligonucleotide probe species that is capable of binding to one or more stretches of sequence in the target molecule longer than 5 bases. In this case, one or more approaches is utilized in some embodiments. First, if a target nucleic acid comprises a double-stranded nucleic acid, one or more base assignments is deferred to or may rely on sequence(s) obtained from a complementary strand of a duplex. Second, when multiple copies of a target nucleic acid are available, one or more base assignments may rely on other copies of a same sequence on other copies of a target nucleic acid. Third, in some embodiments, if a reference sequence is available, one or more base assignments may defer to or rely on a reference sequence, and one or more bases are annotated to indicate that they are artificially implanted from a reference sequence.

In some embodiments, certain oligonucleotide probe species are omitted from one or more sets of oligonucleotide probe species for various reasons. For example, some oligonucleotide probe sequences exhibit problematic interactions with themselves—such as self-complementarity or palindromic sequences, with other probes in a complete set of oligonucleotide probe species or with a target nucleic acid (e.g., known stochastic promiscuous binding). In some embodiments, a minimal number of informative oligonucleotide probe species is determined for each type of target nucleic acid. Within a complete set of k-mer oligonucleotide probe species, half of the oligonucleotides are completely complementary to other half of the oligonucleotides. In some embodiments, it is ensured that these complementary pairs (and others that are problematic due to substantial complementarity) may not be added to the polynucleotide at a same time, but may rather assigned to different subsets or pools of oligonucleotide probe species. In some embodiments, where both sense and antisense single-stranded DNA (from a single double stranded target nucleic acid) are present, sequencing is performed with just one member of each complementary oligonucleotide probe species pair. Sequencing information obtained from both sense and antisense strands is combined to generate an overall sequence.

In some embodiments, oligonucleotide probe species may comprise a library made using custom microarray synthesis. In some embodiments, a microarray library may comprise oligonucleotides that systematically bind to specific target parts of a genome. In some embodiments, a microarray library may comprise oligonucleotide probe species that systematically bind to locations a certain distance apart across a target genome. For example, a library comprising one million oligonucleotide probe species could comprise oligonucleotide probes species that are designed to bind about every 3000 bases. Similarly, a library comprising ten million oligonucleotide probe species could be designed to bind about every 300 bases, and a library comprising 30 million oligonucleotide probe species could be designed to bind about every 100 bases. In some embodiments, sequence of oligonucleotide probe species is designed computationally based on a reference genome sequence.

In some embodiments, regions of a genome that are targeted are specific genetic loci. In other embodiments, the regions of a genome that are targeted are a panel of loci (e.g., genes or other highly conserved regions linked to cancer) or genes or other highly conserved regions within a chromosomal interval identified by a genome-wide association study. In some embodiments, targeted loci may also comprise the dark matter of a genome, chromatic regions of a genome that are typically repetitive, as well the complex genetic loci that are in the vicinity of repetitive regions. Such regions include telomeres, centromeres, short arms of acrocentric chromosomes as well as other low complexity regions of a genome. Traditional sequencing methods cannot address repetitive parts of a genome (as of 2019 there is still not a complete human genome), but when nanometric precision is high methods described herein comprehensively address these regions.

In some embodiments, each respective oligonucleotide probe species in a plurality of oligonucleotide probe species comprises a unique N-mer sequence, where N is an integer in the set $\{1, 2, 3, 4, 5, 6, 7, 8, \text{and } 9\}$ and where all unique N-mer sequences of length N are represented by a plurality of oligonucleotide probe species.

The longer the oligo length used to make oligonucleotide probe species the more potential there is for palindromic or foldback sequences having an effect on the oligonucleotide probe species to function as an efficient probe. In some embodiments, binding efficiency is substantially improved by reducing a length of such oligos by removing one or more degenerate or universal bases. For this reason, the use of shorter interrogation sequences (e.g., 4-mers) for oligonucleotide probe species are advantageous. However, shorter oligonucleotide probe sequences exhibit less stable binding (e.g., lower binding temperatures). In some embodiments, binding stability of an oligonucleotide probe species is enhanced by using specific stabilizing base modifications or oligo conjugates (e.g., a stilbene cap). In some embodiments, 3-mer or 4-mers that are completely modified (e.g., locked nucleic acids (LNA) and or peptide nucleic acids (PNA)) are used.

In some embodiments, unique N-mer sequence may comprise one or more nucleotide positions occupied by one or more degenerate nucleotides. In some embodiments, a degenerate position comprises all four nucleotides and members of an oligonucleotide probe species comprising oligonucleotide probes each of the four nucleotides provided in a degenerate base location. In some embodiments, one or more nucleotide positions in an oligonucleotide probe species is occupied by a universal base. In some embodiments, a universal base is 2'-Deoxyinosine or other universal bases as described herein. In some embodiments, a unique N-mer sequence is flanked at the 5' end by a single degenerate or universal nucleotide position and flanked at the 3' end by a single degenerate or universal nucleotide position. In some embodiments, the 5' single universal nucleotide and or the 3' single universal nucleotide may each be 2'-Deoxyinosine or other universal bases as described herein.

In some embodiments, each oligonucleotide probe species in a set of oligonucleotide probe species is of a same length M. In some embodiments, M is a positive integer of 2 or greater. Determining (f) a sequence of at least a portion of a target nucleic acid from a plurality of sets of positions of optical activity on a test substrate may further use overlapping sequences of oligonucleotide probe species represented by a plurality of sets of positions of optical activity, which may comprise a combination of different locations of a single oligonucleotide probe species and different times, durations, intensities photons, or summations thereof at a same location of optical activity. In some embodiments, each oligonucleotide probe species in a set of oligonucleotide probe species shares M−1 sequence homology with another oligonucleotide probe in a set of oligonucleotide probes. In other embodiments, a subset or none of a set of oligonucleotide probes may share M−1 sequence homology with other oligonucleotide species in a set.

Probe labels.

In some embodiments, each oligonucleotide probe species in a set of oligonucleotide probes is bound with a label. FIGS. 14A-E illustrate different methods of labeling oligonucleotide probes or other probe types. In some embodiments, a label is a dye, a fluorescent nanoparticle, or a light-scattering particle. In some embodiments, a probe 1402 is bound directly to a label 1406. In some embodiments, a probe 1402 is indirectly labeled via a flap sequence 1410 which may comprise a sequence 1408-B that is complementary to a sequence on an oligonucleotide probe 1408-A.

Many types of organic dyes with favorable characteristics are available for labeling, some with high photo stability and/or high quantum efficiency and/or minimal dark-states and/or high solubility, and/or low non-specific binding. Atto 542 is a favorable dye that possesses a number of favorable qualities. Cy3B is a very bright dye and Cy3 is also effective. Some dyes allow the avoidance of wavelengths where auto fluorescence from proteins, cells or cellular material is prevalent, such as the red dyes Atto 655 and Atto 647N. Many types of nanoparticles are available for labeling. Beyond fluorescently labeled latex particles, the present disclosure makes use of gold or silver particles, semiconductor nanocrystals (Quantum dots), and nanodiamonds as nanoparticle labels. Nanodiamonds, in some embodiments, are particularly favorable as labels. Nanodiamonds emit light with high quantum efficiency (QE), have high photo stability, high chemical stability, long fluorescent lifetimes (e.g., on the order of 20 ns, which can be used to reduce observed background from light scattering and/or autofluorescence), have more than one fluorescence emission, have different emission bandwidths, and are small (e.g., around 40 nm in diameter). DNA nanostructures and nanoballs can be exceptionally bright labels, either by incorporating multiple organic dyes into their structure, which may comprise a bifurcated structure or utilizing labels such as intercalating dyes.

In some embodiments, each indirect label may specify an identity of a base being coded in a sequence interrogation part of an oligonucleotide probe species. In some embodiments, a label may comprise one or more molecules of a nucleic acid intercalating dye. In some embodiments, a label may comprise one or more types of dye molecules, fluorescent nanoparticles, or light-scattering particles. In some embodiments, a label is selected which does not photobleach quickly, to permit longer imaging times.

Figure 12A:
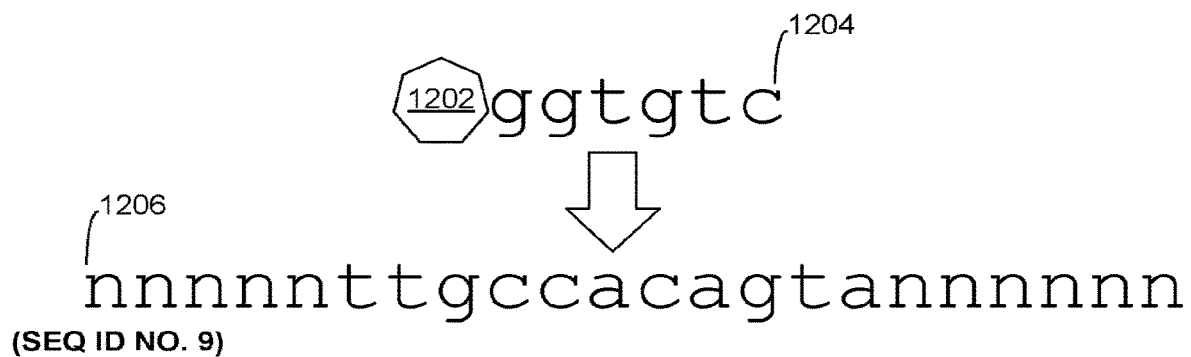
FIGS. 12A, 12B, and 12C collectively illustrate an example of transient binding of a directly labeled probe in accordance with various embodiments of the present disclosure.
Figure 12B:
Figure 12C:
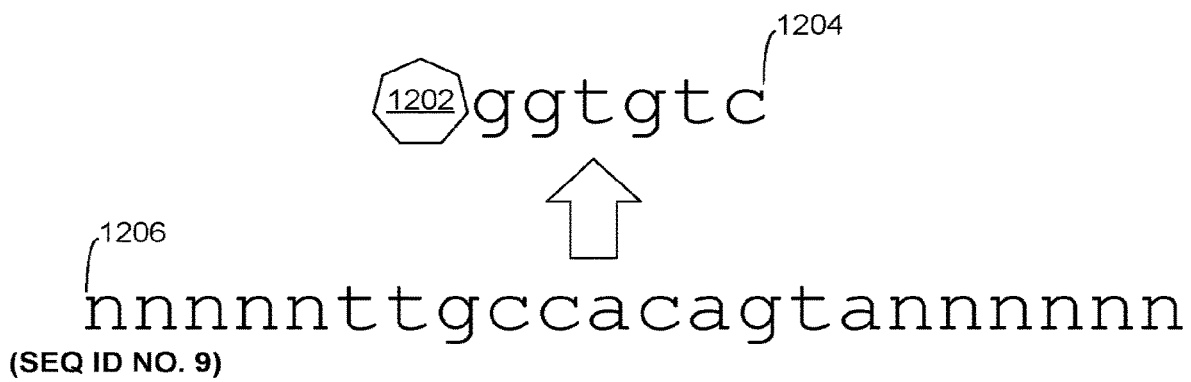
Figure 13A:
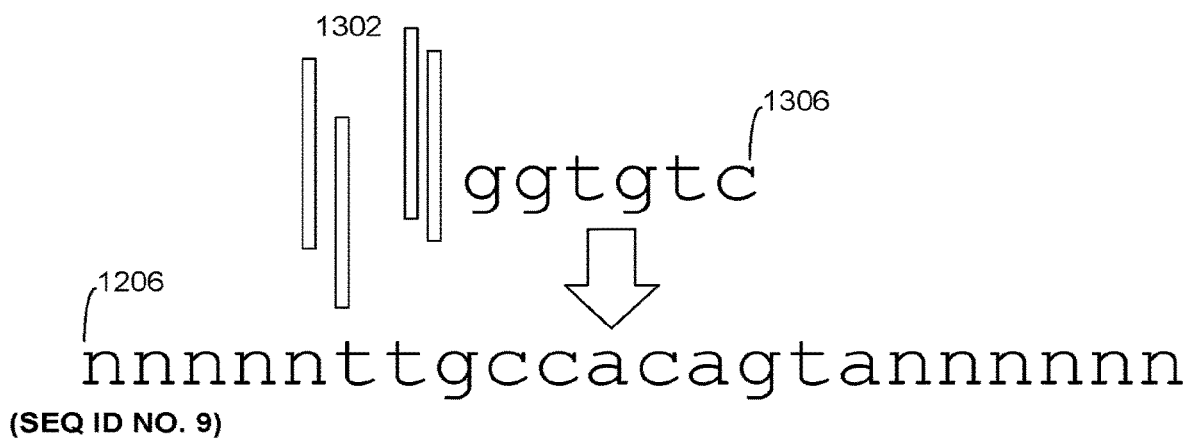
FIGS. 13A, 13B, and 13C collectively illustrate an example of transient probe binding in the presence of an intercalating dye in accordance with various embodiments of the present disclosure.
Figure 13B:
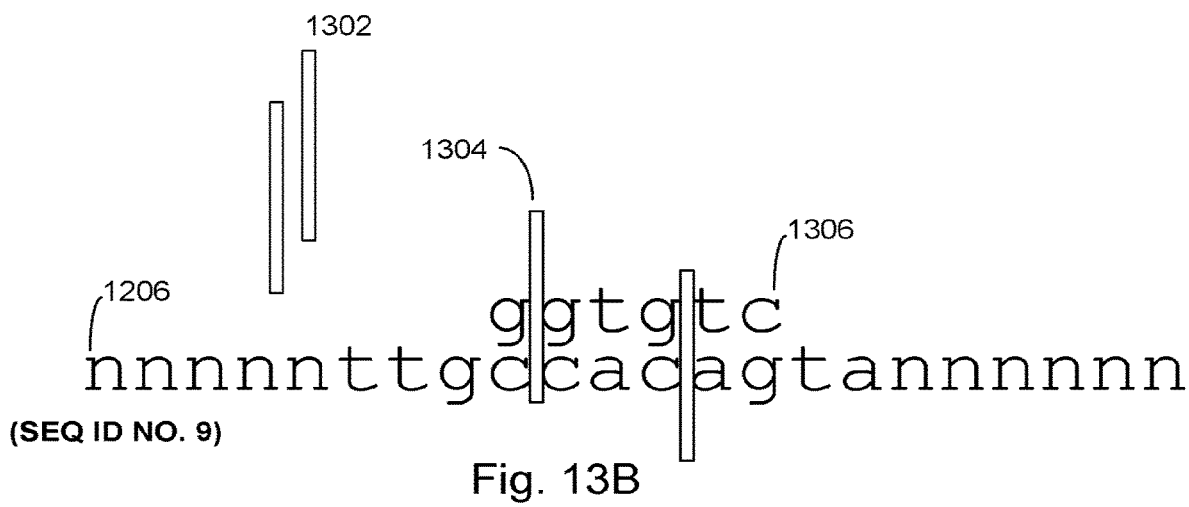
Figure 13C:
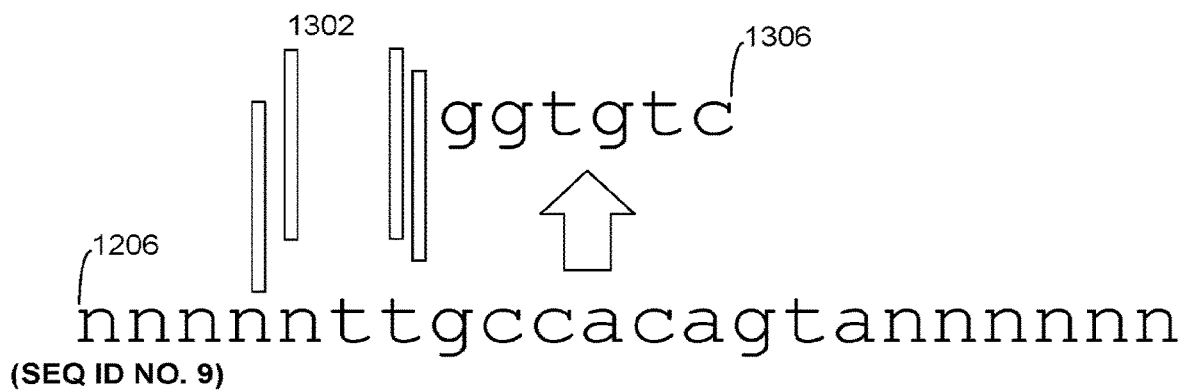

FIGS. 12A, 12B, and 12C, illustrate transient on-off binding of an oligonucleotide probe 1204 with an attached fluorescent label 1202 to a target nucleic acid 1206. Label 1202 will fluoresce regardless of whether an oligonucleotide probe 1204 binds to a binding site on the target nucleic acid 1206. Similarly, FIGS. 13A, 13B, and 13C illustrate transient on-off binding of an unlabeled oligonucleotide probe 1306. A binding event is detected by intercalation of a dye 1304 (e.g., YOYO-1) from solution 1302 into a transiently forming duplex 1304. An intercalating dye exhibits a significant increase in fluorescence when bound into a double-stranded nucleic acid as compared to floating free in solution.

In some embodiments, an oligonucleotide probe species that may bind to a target nucleic acid may not be directly labeled. In some such embodiments, an oligonucleotide probe species may contain a flap. In some embodiments, building oligonucleotide probe species (e.g., encoding them) comprises coupling specific sequence units, where a unit is of sufficient length to bind a label with an complementary (to a particular unit) encoded oligonucleotide sequence bound thereto to one end (e.g., a flap sequence) of each k-mer in one or more sets of oligonucleotide probe species. Each unit of an encoding sequence of a flap may acts as a docking or binding site for a distinct fluorescently labeled probe. In order to encode a 5 base probe sequence, a flap on a probe may contain 5 distinct units or binding locations, for example, each location is a different DNA base sequence linked tandemly to the next location. For example, a first unit or binding position on a flap is adjacent to an oligonucleotide probe species sequence (the part that may bind to a target nucleic acid), the second unit or binding position is adjacent to the first unit or binding position, and so on. In advance of using probe-flaps in sequencing, each variety of probe-flap is coupled to a set of fluorescently labeled oligos, and may comprise oligos which is unlabeled if a number of units or binding positions on a flap sequence is greater than a desired number of fluorescent label types where oligos associated with different labels have respective sequences complementary to different units or binding positions to generate a unique identifier tag for an oligonucleotide probe species sequence. In some embodiments, this may done by using four distinctly labeled oligo sequences that are complementary to each respective unit or binding position on a flap (e.g., a total of as many as sixteen distinct label combinations).

In some embodiments, probes where A, C, T and G are defined are coded in a manner that the label reports on just one defined nucleotide at a specific position in an oligonucleotide probe species (and other positions are degenerate or universal). This may require only a four color coding, one color per nucleotide.

In some embodiments, only one fluorophore color is used throughout an exposing process. In such an embodiment, each exposing process is split into 4-sub-processes, in each of which one oligonucleotide probe species of a set of four oligonucleotide probe species with different bases at a specified position (e.g., position 1) is added individually before a next oligonucleotide probe species of a set is added. In each cycle, oligonucleotide probe species may carry a same label. In this implementation for 5-mer oligonucleotide probe species sequence lengths, a complete set of one or more sets of oligonucleotides may comprise five sets of oligonucleotide probe species corresponding to interrogation at a single base position where each set may comprises four oligonucleotide probe species corresponding to varying a single base at a single position in a set of 5-mer oligonucleotide probe species, and a total number of exposing sub-processes is 20 (five sets corresponding to each base position in a complete set of 5-mer oligonucleotide probe sets, where each set has four oligonucleotide probe species), a significant saving in time.

In some embodiments, a first base in an oligonucleotide probe species sequence is encoded by a first unit in a flap sequence, a second base by a second unit, etc. An order of units in a flap may correspond to an order of an oligonucleotide probe species base sequence. Distinct fluorescent labels may then be bound or docked onto each corresponding unit comprised in a flap (through complementary base pairing). A first label associated with a first unit and thus with a first oligonucleotide probe species sequence position, in one example, may emits at wavelengths from 500 nm-530 nm, a second label associated with a second unit and thus with a second oligonucleotide probe species sequence position may emit at wavelengths from 550 nm-580 nm, a third at 600 nm-630 nm, a fourth at 650 nm-680 nm and a fifth at 700 nm-730 nm. An identity of a base at each location may then, for example, be encoded by a fluorescence lifetime of a label. In one such example, a label corresponding to A have a longer lifetime a label corresponding to C, which have a longer lifetime than a label corresponding to G, which have a longer lifetime than a label corresponding to T. In the example, above, base A at position 1 may emit at 500 nm-530 nm with a longest lifetime and base G at position 3 may emit at 600 nm-630 nm with a third longest lifetime, etc.

Figure 14A:
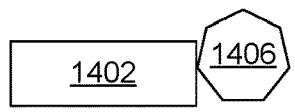
FIGS. 14A, 14B, 14C, 14D, and 14E collectively illustrate examples of different probe labeling techniques in accordance with various embodiments of the present disclosure.
Figure 14B:
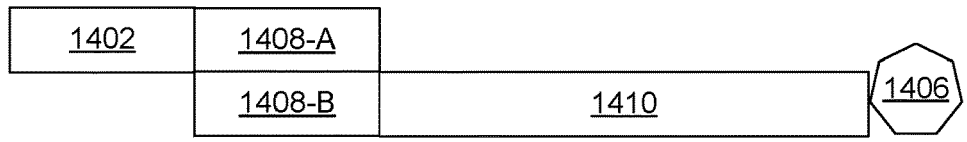
Figure 14C:
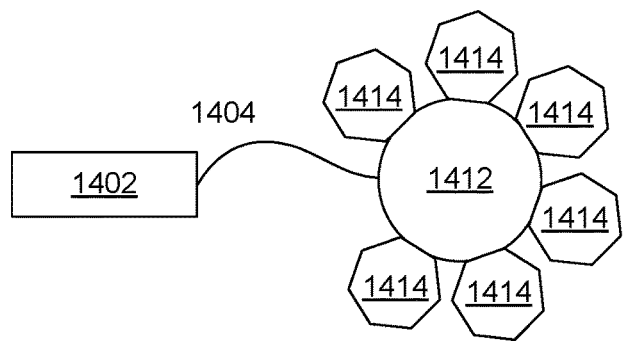
Figure 14D:
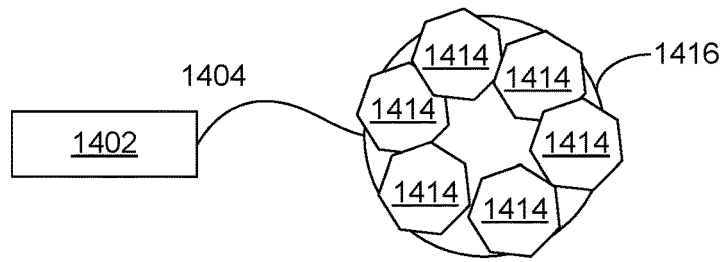
Figure 14E:
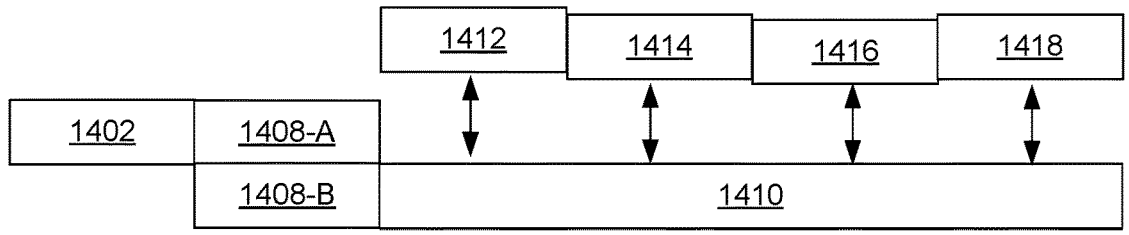

In some embodiments, as illustrated in FIG. 14E, an oligonucleotide probe species 1402 may include a sequence 1408-A that corresponds to sequence 1408-B. Sequence 1408-B is bound, attached, or linked to a flap region 1410. As an example of possible sequences that could result in a FIG. 14E overall construct, each of the four unit positions in 1410 are defined by a sequence AAAA (e.g., a region complementary to 1412), CCCC (e.g., a region complementary to 1414), GGGG (e.g., a region complementary to 1416), and TTTT (e.g., a region complementary to 1418) respectively. Thus, an overall flap sequence is (SEQ ID NO. 1) 5'-AAAACCCCGGGGTTTT-3'. Then each unit position is coded utilizing a specific emission wavelength range, and the four different bases that could be at that position are coded for by four different fluorescence lifetime-labeled oligos, where a lifetime/brightness ratio may correspond to a particular base position and base code corresponding to oligonucleotide probe species 1402 sequence itself.

An example of suitable codes is the following:

Position 1—A base code—TTTT-Emission peak 510, lifetime/brightness #1
Position 1—C base code—TTTT-Emission peak 510, lifetime/brightness #2
Position 1—G base code—TTTT-Emission peak 510, lifetime/brightness #3
Position 1—T base code—TTTT-Emission peak 510, lifetime/brightness #4
Position 2—A base code—GGGG-Emission peak 560, lifetime/brightness #1
Position 2—C base code—GGGG-Emission peak 560, lifetime/brightness #2
Position 2—G base code—GGGG-Emission peak 560, lifetime/brightness #3
Position 2—T base code—GGGG-Emission peak 560, lifetime/brightness #4
Position 3—A base code—CCCC-Emission peak 610, lifetime/brightness #1
Position 3—C base code—CCCC-Emission peak 610, lifetime/brightness #2
Position 3—G base code—CCCC-Emission peak 610, lifetime/brightness #3
Position 3—T base code—CCCC-Emission peak 610, lifetime/brightness #4
Position 4—A base code—AAAA-Emission peak 660, lifetime/brightness #1
Position 4—C base code—GGGG-Emission peak 660, lifetime/brightness #2
Position 4—G base code—GGGG-Emission peak 660, lifetime/brightness #3
Position 4—T base code—GGGG-Emission peak 660, lifetime/brightness #4

In other embodiments, different unit positions are coded by fluorescence lifetime and bases are coded by fluorescence emission wavelength. In some embodiments, other measureable physical attributes may alternatively be used for coding or if measurement thereof is compatible with measurement of wavelength and lifetime. For example, polarization or brightness of the emission may also be measured to increase a size of a number of codes available for inclusion into a flap.

In some embodiments, toe-hold probes (e.g., as described by Levesque et al., Nature Methods 10:865-867, 2013) are used. These probes are partly double-stranded, and are competitively destabilized when bound to a mismatching target (e.g., a detailed in Chen et al., Nature Chemistry 5, 782-789, 2013). In some embodiments, toe-hold probes are used alone. In some embodiments, toe-hold probes are used to ensure correct hybridization. In some embodiments, toe-hold probes are used to facilitate an off reaction rate of other probes bound to a target nucleic acid.

In some embodiments, a label is utilized which is excited by a common excitation line is a quantum dot. In some such embodiments, in accordance with this example, Qdot 525, Qdot 565, Qdot 605, and Qdot 655 are chosen to correspond to four respective nucleotides. Alternatively, four distinct laser lines are used to excite four distinct organic fluorophores and resulting emissions detected split by an image splitter. In some other embodiments, an emission wavelength is common for two or more of organic dyes but a fluorescent lifetime is different. The skilled artisan will be able to envisage a number of different encoding and detection schemes without undue effort and experimentation.

In some embodiments, different oligonucleotide probe species in one or more sets of oligonucleotide probe species may not be added individually but is encoded and pooled together. The simplest step up from one color and one oligo at a time, is two colors (or two lifetimes, two of other detectable differences between labels) and two oligonucleotide probe species at a time. It is reasonable to expect to pool up to around 5 oligonucleotide probe species at a time using direct detection of 5 distinguishable single dye encoded labels, one dye encoded label for each of the 5 oligonucleotide probe species.

In other embodiments where a higher level of complexity is needed or desired, a flavors or codes may increase. For example, to individually code for each base in a complete set of 3-mer oligonucleotide probe species, 64 distinct codes would be required. Also, by example, to individually code for each base in a complete set of 5-mer oligonucleotide probe species 1024 distinct codes is required. Such a large number of codes is achieved by having a code per oligo composed of multiple different detectable label characteristics. In some embodiments, a smaller set of codes is used to encode a smaller set or subset of a complete set of oligonucleotide probe species e.g., in some instance 64 codes is used to encode 16 subsets of a complete set of 1024 oligonucleotide probe species sequences of 5-mers.

In some embodiments, a large set of oligo codes is obtained in a number of ways. For example, in some embodiments, beads are loaded with code-specific dyes or DNA nanostructure-based codes may comprise an optimal spacing of different fluorescent wavelength emitting dyes (e.g., Lin et al., Nature Chemistry 4: 832-839, 2012). In some embodiments, as illustrated in FIGS. 14C and 14D, a bead 1412 may comprise multiple fluorescent labels 1414. In FIG. 14C, labels 1414 are depicted as being coated on bead 1412. In FIG. 14D, labels 1414 are depicted as being encapsulated in bead 1412. In some embodiments, each label 1414 is a different type of fluorescent molecule. In some embodiments, all labels 1414 are the same type of fluorescent molecule (e.g., Cy3). In further embodiments, one or more of different labels comprising different and or a same fluorescent molecules is coated on bound to, or encapsulated in a bead.

In some embodiments, a coding scheme is used in which a modular code is used to describe a position of a base in an oligonucleotide probe species and its identity. In some embodiments, this is implemented by adding a coding arm to an oligonucleotide probe species which may comprise a combination of labels that may identify an oligonucleotide probe species. For example, where it is desired for a library of every possible 5-mer oligonucleotide probe to be encoded, an arm have five sites, units or binding positions, each site, unit or binding position corresponding to each of five nucleobases in a 5-mer oligonucleotide probe species, and each of the five sites is bound to five distinguishable labels, where each of the five distinguishable labels associated with a site, unit or binding position is further distinguishable from the 15 other labels associated determination of different bases. In one such example, labels comprising fluorophores with a specific peak emission wavelength correspond to each site, unit or binding position (e.g., 500 nm for site, unit or binding position one, 550 nm for site, unit or binding position two, 600 nm for site, unit or binding position three, 650 nm for site, unit or binding position four and 700 nm for site, unit or binding position five), and four fluorophores with a same emission wavelength but different fluorescence lifetimes may code for each of the four bases at each position.

In some embodiments, different labels on, bound to, or linked to oligonucleotide probe species or other binding reagents are coded, or partly coded by wavelength of emission. In some embodiments, different labels are coded, or partly coded by fluorescence lifetime. In some embodiments, different labels are coded, or partly coded by fluorescence polarization. In some embodiments, different labels are coded, or partly coded by any combination of wavelength, fluorescence lifetime fluorescence polarization lifetime or any other optically observable mechanism.

In some embodiments, different labels are coded, or partly coded by repetitive on-off hybridization kinetics of associated probe species, which is an associated oligonucleotide probe species. Different binding probes, which is different oligonucleotide probe species with different association-dissociation constants are used. In some embodiments, probes, which is oligonucleotide probe species are coded, or partly coded by fluorescence intensity. In some embodiments, the probes, which is oligonucleotide probe species are fluorescent intensity coded by having different numbers of optionally non-self-quenching fluorophores bound, attached, or linked thereto. Individual fluorophores typically need to be well separated to prevent or reduce quenching. In some embodiments, this is accomplished using an optionally rigid linker or a DNA nanostructure to hold the labels in place at a suitable distance from each other.

In some embodiments, coding by fluorescence intensity is effectuated by using dye variants that have similar emission spectra but differ in quantum yield or other measureable optical character. For example, Cy3B, with an excitation/emission 558/572, is substantially brighter (e.g., a quantum yield of 0.67) than Cy3, with an excitation/emission 550/570 and a quantum yield of 0.15) but have similar absorption/emission spectra. In some such embodiments, a 532 nm laser is used to excite both dyes. Other suitable dyes may include Cy3.5 (with an excitation/emission 591/604 nm) that has an up shifted excitation and emission spectra but will nonetheless be excited by a 532 nm laser. However, an excitation at that wavelength is sub-optimal for Cy3.5 and emission of Cy3.5 will appear less bright in a bandpass filter optimized for Cy3. Atto 532, with an excitation/emission 532/553, has a quantum yield of 0.9 and would be expected to be bright as the 532 nm laser may excite Atto 532 at its maximal excitation.

In other embodiments, multiple codes is effectuated using a single excitation wavelength to measure emission lifetimes of dyes. In one example in accordance with such an embodiment, a set comprising Alexa Fluor 546, Cy3B, Alexa Fluor 555 and Alexa Fluor 555 is used. In some instances, other dyes sets are more useful. In some embodiments, a set of codes is expanded by using FRET pairs and/or also by measuring polarization of emitted light. Another method for increasing a number of coded labels is by coding with multiple colors.

Figure 15:
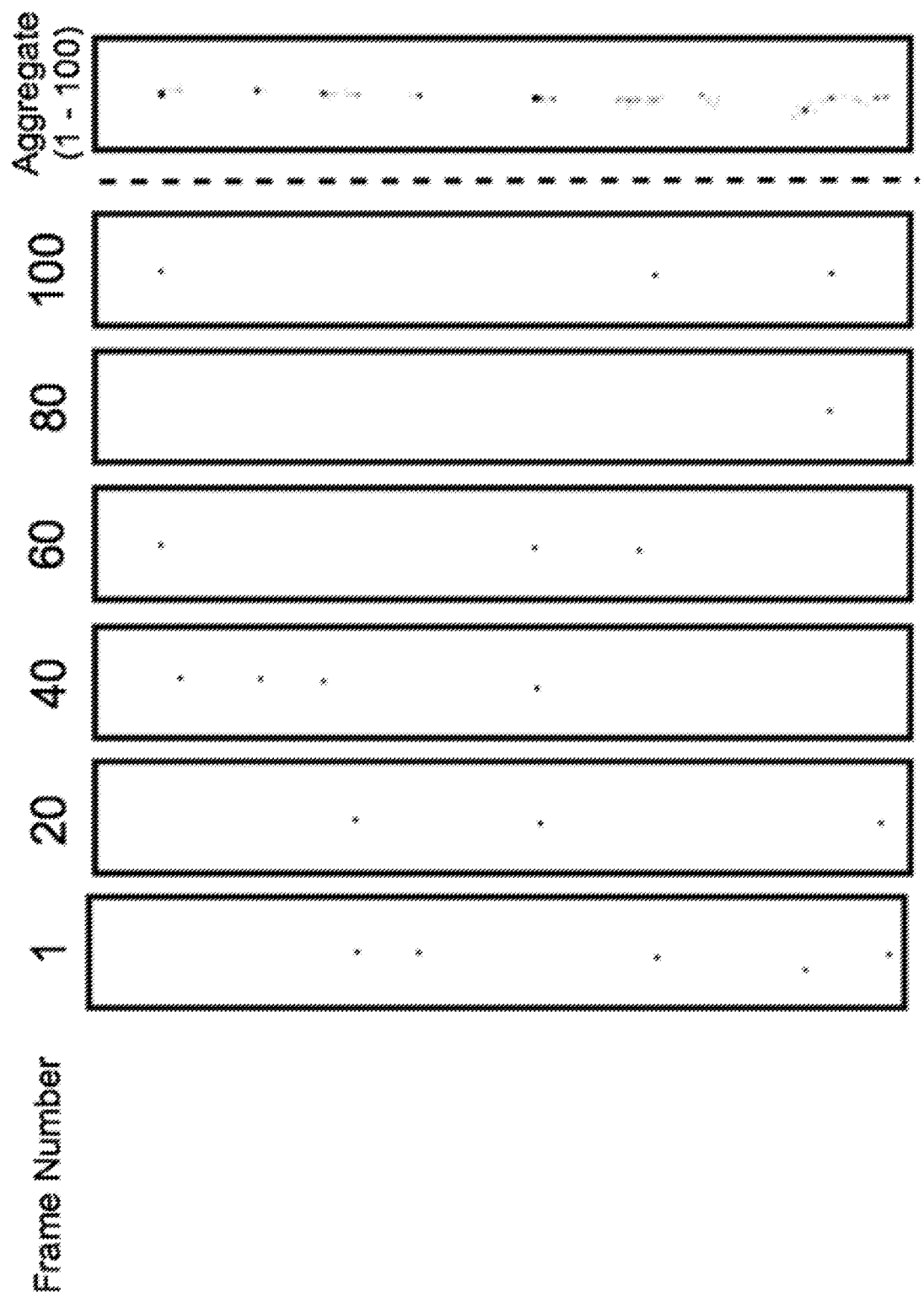
FIG. 15 illustrates an example of transient binding of probes on denatured, combed, double-stranded DNA in accordance with various embodiments of the present disclosure.

FIG. 15 illustrates an example of fluorescence from transient binding of oligonucleotide probe species to a target nucleic acid. Selected frames from the time series (e.g., Frame Numbers 1, 20, 40, 60, 80, 100) show presence (e.g., dark spots) and absence of signal (e.g., white regions) at specific sites, indicative of on-off binding. Each respective frame shows the fluorescence resulting from multiple bound oligonucleotide probe species along a target nucleic acid. The Aggregate image shows aggregation or summation of fluorescence of all previous frames, indicating all sites where oligonucleotide probe species have bound and been detected during 100 frames.

Transient Binding of Probes to Target Polynucleotides.

Binding of probes, which is oligonucleotide probe species, is a dynamic process, and a probe that is bound constantly has some probability of becoming coming unbound (e.g., as determined by various factors including temperature, salt concentration, competition between probes, and a number of other factors). Hence, there is always an opportunity for displacement of one probe with another. For example, in one embodiment, pools of oligonucleotide probe species comprising oligonucleotide probe species which is complementary are used and may cause a continuous competition between annealing to a stretched target nucleic acid on a test substrate or other surface and with a complementary oligonucleotide probe species in solution. In another embodiment, a probe have three parts, where a first part is fully complementary to a target nucleic acid, a second part is partially complementary to a target nucleic acid and partially complementary to one or more other oligonucleotide probe species in a common pool exposed to a target nucleic acid, and a third part is fully complementary to one or more other oligonucleotide probe species in a common pool exposed to a target nucleic. In some embodiments, collecting information on precise spatial location of units of chemical structure, such as base positions of a target nucleic acid, may aid in determining a structure and/or sequence of a macromolecule. In some embodiments, locations of oligonucleotide probe species binding sites are determined with nanometric or even sub-nanometric precision (e.g., by using a single molecule localization algorithm). In some embodiments, a plurality of observed oligonucleotide probe species binding sites are resolvable by diffraction limited optical imaging methods, and are resolved because binding events are temporally separated. A sequence of a target nucleic acid is determined based on identity of oligonucleotide probe species that may bind to each location.

In some embodiments, an exposing process may occur using conditions that allow for individual probes of a respective pool of respective oligonucleotide probe species to transiently and reversibly bind and form respective duplexes with each portion of a fixed first strand or a fixed second strand or a target nucleic acid that is complementary to individual oligonucleotide probe species, thereby giving rise to an instance of optical activity. In some embodiments, dwell time (e.g., a duration and/or persistence of binding by a particular oligonucleotide probe species), is used in determining whether a binding event is a perfect match, mismatch, or spurious.

In some embodiments, an exposing process may occur using conditions that allow for individual probes of a respective pool of a respective oligonucleotide probe species to repeatedly transiently and reversibly bind and form respective duplexes with each portion of a fixed first strand or a fixed second strand of a target nucleic acid that is complementary to individual oligonucleotide probe species thereby repeatedly giving rise to respective instances of optical activity.

In some embodiments, a sequencing process or method may comprise subjecting an elongated target nucleic acid to transient interactions from each of a complete set of one or more sets of oligonucleotide probe species provided sequentially (where a solution carrying one oligonucleotide probe species is removed, and a solution carrying a next oligonucleotide probe species is added). In some embodiments, binding of each oligonucleotide probe species is carried out using conditions that would allow an oligonucleotide probe species to bind transiently. So for example, a binding is conducted at 25° C. for one oligonucleotide probe species and 30° C. for the next oligonucleotide probe species. In some embodiments, oligonucleotide probe species is utilized in sets, which is in a common pool of oligonucleotide probe species. For example, all oligonucleotide probe species that may bind transiently using similar conditions, such as similar temperatures, similar salt concentrations or other factors which may influence hybridization binding, can be gathered into sets and used together, optionally in a common pool of oligonucleotide probe species. In some such embodiments, each oligonucleotide probe species of the set is differentially labeled or differentially encoded.

In some embodiments, oligonucleotide probe species transient binding is conducted in a buffer with a small amount of divalent cation, but with no monovalent cation. In some embodiments, a buffer may comprise 5 mM Tris-HCl, 10 mM magnesium chloride, mm EDTA, 0.05% Tween-20, and pH 8. In some embodiments, a buffer may include less than 1 nM, less than 5 nM, less than 10 nM, or less than 15 nM of magnesium chloride, calcium chloride, manganese chloride, or other appropriate divalent cations. In other embodiments, a concentration of divalent cation is provided which is slightly more than half of a concentration of negatively charged nucleobases in a solution, which solution may comprise oligonucleotide probe species and target nucleic acids.

In some embodiments, multiple conditions that promote transient binding are used. In some embodiments, one condition is used for one oligonucleotide probe species depending on its Tm and another condition is used for another oligonucleotide probe species depending on its Tm and so on for a complete set of nucleotide probe species, for example, each 5-mer oligonucleotide probe species from a complete set of 1024 possible 5-mers. In some embodiments, only 512 non-complementary 5-mers are provided (e.g., because a target nucleic acid is in duplex form, and thus both complementary strands are present in a sample). In some embodiments, each oligonucleotide probe species addition may comprises a mixture of oligonucleotide probes comprising a same 5 specific bases in a same sequence order and 2 degenerate or universal bases, (hence 16 heptamers) all labeled with a same label that may function as a single pentamer oligonucleotide probe with respect to system throughput and number of different reagents sets used to interrogate target nucleic acid sequences. Degenerate or universal bases may add stability without increasing complexity of a set of oligonucleotide probe species.

In some embodiments, a same conditions are provided for a plurality of oligonucleotide probe species that may share a same or similar Tms. In some such embodiments, each oligonucleotide probe species in a set of oligonucleotide probe species may comprise different encoding labels (which may prove different moieties such that each label species is uniquely identified). In such instances, temperature is held through several oligonucleotide probe species, which is pools of oligonucleotide probe species exchanges, before being changed for a next set of oligonucleotide probe species that may share a same or similar Tms.

In some embodiments, during an oligonucleotide probe species binding period, which is a part of an exposure process, a temperature is altered so that binding behavior of oligonucleotide probe species at more than one temperature is measured. In some embodiments, an analogue of a melting curve is conducted, where binding behavior or binding pattern of oligonucleotide probe species to a target nucleic acid is correlated with a step-wise set of temperatures through a selected range (e.g., from 10° C. to 65° C. or 1° C. to 35° C.). In other embodiments, changes is made to other parameters which may affect oligonucleotide probe binding to target nucleic acids in a manner similar to changes of temperature, such as changes of salt, addition of denaturing agents such as formamide, and changes of other parameters known to affect oligonucleotide probe binding. In other embodiments, a single temperature is utilized, and observation of binding kinetics is used as another measurable parameter which may correlate with oligonucleotide probe binding Tm.

In some embodiments, oligonucleotide probe species Tms are calculated, for example, by nearest neighbor parameters. In other embodiments, oligonucleotide probe species Tms are empirically derived. For example, an optimal melting temperature range is derived by carrying out a melting curve (measuring extent of melting by absorption for example, over a range of temperatures). In some embodiments, composition of sets oligonucleotide probe species is designed according to associated theoretically matching Tms that are validated by empirical testing. In some embodiments, binding of oligonucleotide probe species as a part of an exposure process is done at a temperature that is substantially below Tm (e.g., up to 33° C. below the calculated Tm). In some embodiments, an empirically defined optimal temperature for each individual oligonucleotide probe species in a set of oligonucleotide probe species is used for the binding of each individual oligonucleotide probe species as a part of an exposing process in a sequencing method.

In some embodiments, as an alternative or in addition to modifying a temperature for oligonucleotide probe species with different Tms, concentration of probes and/or salt is altered and/or the pH is altered. In some embodiments, an electrical bias on a test substrate of other surface is repeatedly switched between positive and negative to actively facilitate transient binding between oligonucleotide probe species and one or more target nucleic acids.

In some embodiments, a concentration of oligonucleotide probe species used is adjusted according to AT versus GC content of an oligonucleotide probe species sequence. In some embodiments, a higher concentration of oligonucleotide probe species is provided for oligos with a higher GC content. In some embodiments, buffers that may compensate for an affect of base composition (e.g., buffers containing, CTAB, Betaine or chaotropic reagents such as Tetramethyl Ammonium Chloride (TMACl)) are used at concentrations between 2.5 M and 4 M, and may thus equalize effective Tm for different oligonucleotide probe species with differing AT versus GC sequence content and different Tms as measured using a same set of conditions.

In some embodiments, oligonucleotide probe species are distributed unevenly across a sample (e.g., a test substrate, a flow chamber, a slide, a length of target nucleic acid(s) and/or an ordered array of target nucleic acids) due to stochastic effects or to aspects of the design of a sequencing chamber (e.g., eddies in a flow cell that may trap probes in a corner or against a wall of a nanochannel). Local depletion of probes is addressed by ensuring there is efficient mixing or agitation of an oligonucleotide probe species solution. In some instances, this is effectuated using acoustic waves, by including particles in solution that may produce turbulence and/or by structuring a flow cell (e.g., herringbone pattern on one or more surfaces) to produce turbulent flows. In addition, due to laminar flow present in flow cells, there is typically little mixing and solution close to a surfaces mixes very little with bulk solution. This may creates a problem in removing reagents/binding probes that are close to a surface and to bring fresh reagents/probes to surfaces. Turbulence creating approaches as described hereinabove can be implemented to mitigate this, and/or extensive fluid flow/exchange over surface(s) can be conducted. In some embodiments, before or after target nucleic acids have been arrayed, non-fluorescent beads or spheres are attached to a surface, which is a surface to which target nucleic acids is bound, giving the surface landscape a rough texture. This may create eddies and currents to more effectively mix and/or exchange fluids close to the surface. In other embodiments, an electrical field is utilized to concentrate and or to remove bound oligonucleotide probe species, where a field is impressed between a surface to which one or more target nucleic acids is bound and a bulk solution.

In some embodiments, a complete set or subsets of oligonucleotide species are added together. In some such embodiments, a buffer that equalizes base composition effects (e.g., TMACl or Guanidinium thiocyanate and others, as described in U.S. Pat. Appl. No. 2004/0058349) is used. In some embodiments, probe species with a same or similar Tms are added together. In some embodiments, oligonucleotide probe species added together may not be differentially labeled. In some embodiments, oligonucleotide probe species added together are differentially labeled. In some embodiments, differential labels are labels with emissions that have different brightness, lifetime, excitation maxima, emission maxima, or other observable optical properties, for example, and/or combinations of such physical properties.

In some embodiments, where two or more oligonucleotide probe species are used together, and their location of binding determined without provision to distinguish between signals resulting from the different oligonucleotide species (e.g., the oligos are labeled with a same emission wavelength). When both strands of a duplex target nucleic acid are available, obtaining binding site data from both strands may permit differentiation between two or more oligonucleotides as part of an assembly algorithm. In some embodiments, one or more reference oligonucleotide probe species are added together with each oligonucleotide probe species of a set or subset an assembly algorithm can then use locations of optical activity and resulting binding locations of such reference probes to scaffold or anchor target nucleic acid sequence assembly. In other embodiments, where two or more oligonucleotide probe species is used together, and their location of binding determined without provision to distinguish between signals resulting from the different oligonucleotide species (e.g., the oligos is labeled with a same emission wavelength), by creating multiple sets of oligonucleotide probe species, where each oligonucleotide probe species in a complete set of oligonucleotide probe species is represented in more than one subset of oligonucleotide probe species, and identification of oligonucleotide probe species is effectuated using a combination of different subsets, determining common locations of optical activity and thus oligonucleotide probe species binding locations.

In one alternative embodiment, oligonucleotide probe species may bind stably using favorable binding conditions, but a change in binding conditions to unfavorable binding conditions is utilized to control binding and enforce transient binding. In non-limiting embodiments, a conditional change is heat, pH, electric field or reagent exchange which may cause oligonucleotide probe species to unbind. Then conditions is changed back to favorable binding conditions, allowing oligonucleotide probe species to bind again. In some embodiments, when a first favorable binding condition time interval may not saturate all target nucleic acid sites, oligonucleotide probe species, which is a same set of oligonucleotide probe species as used in a first favorable binding conditions time interval in a second favorable binding conditions time interval oligonucleotide robe species may bind to a different set of target nucleic acid sites than a first favorable binding conditions time interval. In some embodiments, these cycles are carried out multiple times at a controllable rate.

In some embodiments, transient binding persists for less than or equal to 1 millisecond, less than or equal to 50 milliseconds, less than or equal to 500 milliseconds, less than or equal to 1 microsecond, less than or equal to 10 microseconds, less than or equal to 50 microseconds, less than or equal to 500 microseconds, less than or equal to 1 second, less than or equal to 2 seconds, less than or equal to 5 seconds, or less than or equal to 10 seconds.

In some embodiments, when using a transient binding method and ensuring a continuous supply of fresh oligonucleotide probe species, photo bleaching of fluorophores may not cause significant issues, and sophisticated field stops or Powell lenses may not be needed to limit illumination. Therefore, a choice of fluorophore (or the provision of an antifade, redox system) may not be important, and In some such embodiments, a relatively simple optical system is constructed; e.g., an f-stop, which may prevent illumination of target nucleic acids not in a field of view of a two-dimensional imager.

In some embodiments, another advantage of transient binding is that multiple measurements can be made at every binding site along a polynucleotide, thus increasing confidence in the accuracy of an optical activity instance or detection. For example, in some cases, due to the typical stochastic nature of molecular processes, an oligonucleotide probe species may bind to an incorrect location. With transiently bound probes, such an outlier, which will likely be much shorter than a correct binding, isolated binding events can be discarded, and only those binding events that are corroborated by multiple detected interactions are accepted as valid detection events for the purpose of target nucleic acid sequence determination.

Detection of Transient Binding and Localization of Binding Sites.

Transient binding is an integral component enabling sub-diffraction levels of localization. There is a probability at any time that each oligonucleotide probe in a set of transiently binding oligonucleotide probe species will either be bound to a target nucleic acid or be present in solution. Thus, not all of target nucleic acid binding sites will be bound by an oligonucleotide probe at any one time. This may allows detection of binding events at sites that are closer than the diffraction limit of light (e.g., two sites that are only 10 nm apart on a target nucleic acid). For example, if a sequence AAGCTT is repeated after 60 bases, repeated sequences will be about 20 nm apart (when a target nucleic acid is elongated and straightened to Watson-Crick base lengths of about 0.34 nm). Twenty nanometers would not normally be distinguishable by optical imaging. However, if probes bind to the two sites at different times during imaging, they are individually detected. This permits super-resolution imaging of binding events. Nanometric precision is particularly important for resolving sequence repeats, which is homopolymer repeats, or may two base repeats, three base repeats, or more than three base repeats and determining their number.

In some embodiments, multiple binding events associated with multiple instances of optical activity and correlated to a location in a target nucleic acid may not be from a single oligonucleotide probe species sequence, but are determined by analyzing the data from a complete set of oligonucleotide probe species, and taking into account binding events or instances of optical activity that may result from partially overlapping sequences. In one example, a same (actually a sub-nanometically close) location is bound by probe ATTAAG and TTAAGC, which are 6-mers that share a common 5 base sequence and each would validate the other, as well as extending a sequence one base on either side of a common 5 base sequence. In some cases, a base on each side of a 5 base sequence is a mismatch (mismatches at the ends are typically expected to be tolerated more than mismatches that are internal) and only the 5 base sequence is that is present in both binding events is validated.

In some alternative embodiments, transient single molecule binding is detected by non-optical method. In some embodiments, a non-optical method is an electrical method. In some embodiments, a transient single molecule binding is detected by non-fluorescence methods where there is no direct excitation method; rather a bioluminescence or chemiluminescence mechanism is used.

In some embodiments, each base in a target nucleic acid is interrogated by multiple oligonucleotide probe species whose sequences may overlap. This repeated sampling of each base permits detection of rare single nucleotide variants or mutations in a target nucleic acid.

In some embodiments, all instances of optical activity or binding interactions (which have a duration longer than a threshold binding duration) that each oligonucleotide probe species has had with a target nucleic acid under analysis is utilized in such an analysis. In some embodiments, sequencing may not only comprise stitching or reconstructing sequence from perfect matches but may in a first software sequence determination process obtain a sequence by first analyzing the valid instances of optical activity or binding events associated with each oligonucleotide probe species. In some embodiments, transient binding is recorded as a means of detection but may not be used for improving localization of oligonucleotide probe species binding.

Imaging Techniques to Detect Optical Activity and Determine Localization of Binding Sites.

Block 214. In some embodiments, locations on a test substrate and optionally a duration of each respective instance of optical activity occurring during an exposing process using a two-dimensional imager are measured.

In some embodiments, measuring a location on a test substrate may comprise inputting a frame of data measured by a two-dimensional imager into a trained convolutional neural network. A frame of data may comprise respective instances of optical activity in different locations among a plurality of instances of optical activity in different locations and in a same location. Each instance of optical activity in plurality of instances of optical activity may correspond to an individual nucleotide probe species binding to a portion of a fixed first strand or a fixed second strand of a target nucleic acid. Responsive to the inputting, a trained convolutional neural network may identify a position on a test substrate of each of one or more instances of optical activity in a plurality of instances of optical activity.

In some embodiments, a detector is a two-dimensional detector, and binding events are localized to a nanometer accuracy (e.g., by using a single molecule localization algorithm). In some embodiments, interaction characteristics may comprise duration of each instance of optical activity or binding event, which may correspond to a binding affinity of oligonucleotide probe species with a target nucleic acid. In some embodiments, a characteristic is a location on a test substrate, surface or matrix, which may corresponds to a location within an array of a particular target nucleic acids (e.g., polynucleotides corresponding to a specific gene sequence).

In some embodiments, each respective instance of optical activity have an observation metric that may satisfy a predetermined threshold. In some embodiments, an observation metric comprises a duration, a signal to noise, a photon count, or an intensity, or a combination thereof. In some embodiments, a predetermined threshold is satisfied when a respective instance of optical activity is observed for one frame. In some embodiments, an intensity of a respective instance of optical activity is comparatively low, and a predetermined threshold is satisfied when a respective instance of optical activity is observed for a tenth of one frame.

In some embodiments, a predetermined threshold may distinguished between (i) a first form of binding in which each residue of a unique N-mer sequence of an oligonucleotide probe species binds to a complementary base in a fixed first strand or a fixed second strand of a target nucleic acid, and (ii) a second form of binding in which there is at least one mismatch between the unique N-mer sequence of an oligonucleotide probe species and a sequence in a fixed first strand or a fixed second strand of a target nucleic acid to which a respective oligonucleotide probe species has bound to form a respective instance of optical activity or binding event.

In some embodiments, each respective oligonucleotide probe species in a set of oligonucleotide probe species have its own corresponding predetermined threshold.

In some embodiments, a predetermined threshold is determined based on observing 1 or more, 2 or more, 3 or more, 4 or more, 5 or more, or 6 or more binding events between an oligonucleotide probe species and a target nucleic acid at a particular location along a target nucleic acid.

In some embodiments, a predetermined threshold for each respective oligonucleotide probe species a the set of oligonucleotide probe species is derived from a training dataset (e.g., a dataset derived from information obtained by applying a transient binding method to sequencing lambda phage, or any known synthetic target nucleic acid). In some embodiments, different thresholds is determined for different base variants, such as epigenetically modified bases or RNA bases such as uridine relative to DNA bases, and such different thresholds is used corresponding to one of an anticipated sample target nucleic acid type, or a potentially modified base region, such as a CpG island.

In some embodiments, a predetermined threshold for each respective oligonucleotide probe species in a set of oligonucleotide probe species is derived from a training dataset. A training set comprises, for each respective oligonucleotide probe species in the set of oligonucleotide probe species, a measure of an observation metric for each respective oligonucleotide probe species upon binding to a reference nucleic acid sequence such that each residue of the unique N-mer sequence of the respective oligonucleotide probe species binds to a complementary base in a reference nucleic acid sequence.

In some embodiments, a reference nucleic acid is fixed on a reference substrate. In some embodiments, a reference nucleic acid is included with and fixed on a test substrate. In some embodiments, a reference nucleic acid sequence may comprise all or a portion of the genome of, PhiX174, M13, lambda phage, T7 phage, *Escherichia coli, Saccharomyces cerevisiae*, or *Saccharomyces pombe*. In some embodiments, a reference nucleic acid sequence is a synthetic construct of known sequence. In some embodiments, a reference nucleic acid sequence may comprises all or a portion of rabbit globin RNA (e.g., which is utilized when a target nucleic acid comprises RNA or when only one strand of a target nucleic acid is sequenced).

In some embodiments, an exposing process may utilize a first label in the form of an intercalating dye. Each oligonucleotide probe species in the set of oligonucleotide probe species is bound with a second label. A first label and a second label have overlapping donor emission and acceptor excitation spectra that may cause one of a first label and a second label to increase a fluorescence level when a first label and a second label are in close proximity to each other. A respective instance of optical activity may result from proximity of an intercalating dye, intercalating a respective duplex between an oligonucleotide probe species and a fixed first strand or a fixed second strand of a target nucleic acid, to a second label. In some embodiments, an exposing process and associated fluorescence may comprise a Förster resonance energy transfer (FRET) method. In such embodiments, an intercalating dye may comprise a FRET donor, and a second label may comprise a FRET acceptor.

In some embodiments, an instance of optical activity is detected utilizing FRET between an intercalating dye to a label bound, linked, or associated with an oligonucleotide probe species or a target nucleic acid sequence. In some embodiments, after target nucleic acids is immobilized, ends of all target nucleic acids is labeled, for example, by terminal transferase adding fluorescently labeled nucleotides that may act as FRET partners. In some such embodiments, an oligonucleotide probe species is labeled at one of its ends with a Cy3B or Atto 542 label.

In some embodiments, FRET is replaced by photo activation. In such embodiments, a donor (e.g., a label on a target nucleic acid) may comprise a photo activator, and an acceptor (e.g., a label on an oligonucleotide probe species)

iscome a fluorophore in an inactivated or darkened state (e.g., Cy5 label can be darkened by caging with 1 mg/mL NaBH4 in 20 mM Tris at pH 7.5, 2 mM EDTA, and 50 mM NaCl before fluorescent imaging experiments). In such embodiments, fluorescence of a darkened fluorophore, which is bound to an oligonucleotide probe species, and is switched on when in close proximity to an activator, which activator is bound to a target nucleic acid.

In some embodiments, an exposing process may utilize a first label in the form of an intercalating dye (e.g., a photo activator). Each oligonucleotide probe species in a set of oligonucleotide probe species is bound with a second label (e.g., a darkened fluorophore). A first label may cause a second label to fluoresce when a first label and a second label are in close proximity to each other. A respective instance of optical activity may result from proximity of an intercalating dye, intercalating a respective duplex between an oligonucleotide probe species and a fixed first strand or a fixed second strand of a target nucleic acid, to a second label, which is bound to an oligonucleotide probe species.

In some embodiments, an exposing process may utilize a first label in the form of an intercalating dye (e.g., a darkened fluorophore). Each oligonucleotide probe species in a set of oligonucleotide probe species is bound with a second label (e.g., a photo activator). A second label may cause a first label to fluoresce when a first label and a second label are in close proximity to each other. A respective instance of optical activity may result from proximity of an intercalating dye, intercalating a respective duplex between an oligonucleotide probe species and a fixed first strand or a fixed second strand of a target nucleic acid, to a second label, which is bound to an oligonucleotide probe species.

In some embodiments, an exposing process may utilize an intercalating dye. A respective instance of optical activity may result from a fluorescence of an intercalating dye intercalating a respective duplex between an oligonucleotide probe species and a fixed first strand or a fixed second strand of a target nucleic acid, where a respective instance of optical activity is greater than a fluorescence of an intercalating dye before it intercalates a respective duplex. Increased fluorescence (100× or more) of one or more intercalating dyes intercalating into a duplex between a target nucleic acid and an oligonucleotide probe species, may provide a point source-like signal for a single molecule localization algorithm and may allow precise determination of a location of a binding site. Intercalating dyes may intercalate into a duplex, producing a significant number of duplex caused instances of optical activity associated with binding events for each oligonucleotide probe species binding site that are robustly detected and precisely localized.

In some embodiments, a respective oligonucleotide probe species in a set of oligonucleotide probe species may yield a first instance of optical activity by binding to a complementary portion of a fixed first strand of a target nucleic acid, and a second instance of optical activity by binding to a complementary portion of a fixed second strand of a target nucleic acid. In some embodiments, a portion of a fixed first strand of a target nucleic acid may yield an instance of optical activity by binding of its complementary oligonucleotide probe species, and a portion of a fixed second strand of a target nucleic acid complementary to a portion of a fixed first strand of a target nucleic acid may yield another instance of optical activity by binding of its complementary oligonucleotide probe species.

In some embodiments, a respective oligonucleotide probe species in a set of oligonucleotide probe species may yield two or more first instances of optical activity by binding to two or more complementary regions of a fixed first strand of a target nucleic acid and two or more second instances of optical activity by binding two or more complementary regions of the fixed second strand of a target nucleic acid.

In some embodiments, a respective oligonucleotide probe species may bind to a portion of a fixed first strand or a fixed second strand of a target nucleic acid, which is complementary to a respective oligonucleotide probe species three or more times during an exposing process, thereby resulting in three or more instances of optical activity, where each instance of optical activity may represent a binding event in a plurality of binding events.

In some embodiments, a respective oligonucleotide probe species may bind to a portion of a fixed first strand or a fixed second strand of a target nucleic acid, which is complementary to a respective oligonucleotide probe five or more times during an exposing process, thereby resulting in five or more instances of optical activity, where each instance of optical activity may represent a binding event in a plurality of binding events.

In some embodiments, a respective oligonucleotide probe species may bind to a portion of a fixed first strand or a fixed second strand that is complementary to a respective oligonucleotide probe species ten or more times during an exposing process, thereby resulting in ten or more instances of optical activity, where each instance of optical activity may represent a binding event in a plurality of binding events.

In some embodiments, an exposing process may occur for five minutes or less, four minutes or less, three minutes or less, two minutes or less, or one minute or less.

In some embodiments, an exposing process may occur for 1 or more frames of a two-dimensional imager. In some embodiments, an exposing process may occur for 2 or more frames of a two-dimensional imager. In some embodiments, an exposing process may occur for 500 or more frames of a two-dimensional imager. In some embodiments, an exposing process may occur for 5,000 or more frames of a two-dimensional imager. In some embodiments, when optical activity is sparse (e.g., there are spatially few instances of probe binding), one frame of transient binding is sufficient to localize a signal associated with an oligonucleotide probe species binding site.

In some embodiments, an expected length of time of an average instance of optical activity during an exposing process is determined by an estimated melting temperature of a respective oligonucleotide probe species in a set of oligonucleotide probe species used in an exposing process.

In some embodiments, optical activity may comprise detection of fluorescence emissions from a label. A respective label is excited and corresponding emission wavelengths is detected separately using distinct filters in a filter wheel. In some embodiments, label emission lifetimes are measured using a fluorescence lifetime imaging (FLIM) system. Alternatively, emission wavelengths are split and projected to different quadrants of a single sensor or onto four separate sensors. In some embodiments, a method using a prism to split an emission spectrum over pixels of a CCD is sued as described by Lundquit et al., Opt Lett., 33:1026-8, 2008. In some embodiments, a spectrograph may also used. Alternatively, in some embodiments, an emission wavelength may combined with brightness levels to provide information on a probe's dwell time in a binding site when an expected oligonucleotide probe species binding time is significantly shorter than a frame exposure time.

Several detection methods, such as scanning probe microscopy (including high speed atomic force microscopy) and electron microscopy, are capable of resolving nanometric distances when a polynucleotide molecule is elongated in a plane of detection. However, these methods do not provide information regarding optical activity of fluorophores. There are multiple optical imaging techniques to detect fluorescent molecules at super-resolution precision. These include stimulated emission depletion (STED), stochastic optical reconstruction microscopy (STORM), super-resolution optical fluctuation imaging (SOFI), single molecule localization microscopy (SMLM) and total internal reflection fluorescence (TIRF) microscopy. In some embodiments, an SMLM approach most similar to points accumulation in nanoscale topography (PAINT) is used. These systems typically require one or more lasers to excite fluorophores, a focus detection/hold mechanism, one or more CCD or CMOS cameras, an appropriate objective, relay lenses and mirrors. In some embodiments, an exposing step may occur for a number of image frames (e.g., a movie or video) to record binding-on and -off of oligonucleotide probe species.

SMLM methods rely on high photon counts. High photon counts improve precision with which a centroid of a fluorophore emission generated Gaussian pattern is determined, but a need for high photon counts is also associated with long image acquisitions and dependence upon bright and photo stable fluorophores. High solution concentrations of probe is utilized without causing detrimental background by using quenched probes, molecular beacons, or having two or more labels associated with complementary oligonucleotide probe species e.g., one on each side of a duplex form target nucleic acid. In such embodiments, labels are quenched in solution via-dye-dye interactions. However, when bound to their target labels become separated and are able to fluoresce brightly (e.g., twice as brightly as a single dye) making them easier to detect.

In some embodiments, an on-rate of a probe species, which is an oligonucleotide probe species is changed (e.g., increased) by for example, increasing probe concentration, increasing temperature, or increasing molecular crowding (e.g., by including PEG 400, PEG 800, etc. in the solution). In other embodiments, an off rate of a probe species, which is an oligonucleotide probe species is changed, by for example, decreasing thermal stability of a probe species which is an oligonucleotide probe species by engineering its chemical components, adding de-stabilizing appendages, or in the case specifically of oligonucleotide probe species, decreasing their lengths, using epigenetically modified or synthetically modified bases instead of natural bases, modifying an oligonucleotide probe species backbone by for example changing a spacing between nucleobases, or sugar, by for example adding charge, can increase the off-rate. In some embodiments, an off-rate is increased by increasing temperature, reducing salt concentration (e.g., increasing stringency), or altering pH.

In some embodiments, a concentration of oligonucleotide probe species used is increased without significantly raising a background level by making probe labels, which is oligonucleotide probe species labels, essentially non-fluorescent until they bind. One way to do this is that binding induces a photo activation event. Another is that labels are quenched until binding occurs (e.g., Molecular Beacons). Another is that a signal is detected as a result of an energy transfer event (e.g., FRET, CRET, BRET). In some embodiments, a biopolymer, which is a target nucleic acid, is bound to a donor, and is on a surface, which is a test substrate, and a probe, which is an oligonucleotide probe species, is bound to an acceptor) or vice versa. In another embodiment an intercalating dye is provided in solution and upon binding of a labeled probe there is a FRET interaction between an intercalating dye and a labeled probe. An example of an intercalating dye is YOYO-1 and an example of a label on a probe is ATTO 655. In another embodiment, intercalating is dye is used without a FRET mechanism—both a single stranded target nucleic acid on a test substrate or other surface and an oligonucleotide probe species is unlabeled and signal may only detected when binding creates a complementary double strand into which an intercalating dye may intercalate. An intercalating dye, depending on its identity, is 100× or 1000× less bright when it is not intercalated into a duplex nucleic acid and is instead free in solution. In some embodiments, either TIRF or highly inclined and laminated optical (HILO) (e.g., as described in Mertz et al., J. of Biomedical Optics, 15(1): 016027, 2010) microscopy is used to eliminate any background signals from an intercalating dye in solution.

In some embodiments, reduction of high background fluorescence which may obscures detection of the signals on a test substrate or other surface which obscuration may result from high concentrations of labeled probes. In some embodiments, this is addressed by utilizing a DNA stain or intercalating dye to label the duplex that is formed on a test substrate or other surface. Dyes may not intercalate when a target nucleic acid is single stranded nor with the single stranded probe, but intercalating dyes will intercalate when a duplex is formed between an oligonucleotide probe species and a target nucleic acid. In some embodiments, an oligonucleotide probe species is unlabeled, and a signal that is detected may result only from an intercalating dye. In some embodiments, an oligonucleotide probe species is labeled with a label that may acts as a FRET partner to an intercalating dye or DNA stain. In some embodiments, an intercalating dye is a donor and may couple with acceptors of different wavelengths, hence allowing oligonucleotide probe species to be encoded with multiple fluorophores.

In some embodiments, an exposing process may detect multiple instances of optical activity or binding events associated with each target nucleic acid site complementary to an oligonucleotide probe species. In some embodiments, multiple events are from a single oligonucleotide probe molecule binding on and off, from a subspecies of an oligonucleotide probe species binding on and off, or from an oligonucleotide probe species binding on and off and any combination of the aforementioned binding events (single, subspecies, or species of oligonucleotide probes) may occur multiple times. In some embodiments, binding on- or off-rate may not be affected by altering conditions. For example, both binding-on and binding-off occurs under the same conditions (e.g., salt concentration, temperature, etc.) and is due to the probe-target interaction being weak.

In some embodiments, sequencing is conducted by imaging multiple instances of optical activity or on-off binding events at multiple locations on a single target nucleic acid that is shorter, a same length or within an order of magnitude of an oligonucleotide probe species length. In such embodiments, a longer target nucleic acid is fragmented or a panel of fragments have been pre-selected and arrayed on a test substrate or other surface so that each target nucleic acid molecule is individually resolvable. In these cases, a frequency or duration of instances of optical activity or oligonucleotide probe species binding to a specific location is used to determine whether an oligonucleotide probe species is fully complementary to a target nucleic acid sequence. A frequency or duration of oligonucleotide probe species binding may determine whether an oligonucleotide probe species is complementary to all or part of the target nucleic acid sequence (with remaining bases mismatched or overhanging).

In some embodiments, an occurrence of side-by-side overlap between target nucleic acids is detected In some embodiments, by an increase in fluorescence from a DNA stain. In some embodiments, where stain may not be used, overlap is detected by an increase in frequency of apparent binding sites within a region of a nominally single but actually overlapped pair of target nucleic acids. For example, in some instances where diffraction-limited molecules optically appear to be overlapping but may not be actually physically overlapping, they are super-resolved using single molecule localization as described elsewhere in the present disclosure. Where end-on-end overlap does occur, in some embodiments, labels marking ends of target nucleic acids are used to distinguish juxtaposed target nucleic acids from true contiguous lengths of a single target nucleic acid. In some embodiments, such optical chimeras are dismissed as artifacts if many copies of a genome or targeted sequences are expected and only one occurrence of an apparent chimera is found. In some embodiments, where the ends of target nucleic acids (diffraction-limited) optically appear to overlap, but are not physically overlapping, they are resolved by the methods of the present disclosure. In some embodiments, location determination is so precise that signals emanating from very close labels are resolved.

In some embodiments, sequencing is conducted by imaging multiple instances of optical activity or on-off binding events at multiple locations on a single target nucleic acid that is longer than an oligonucleotide probe species. In some embodiments, a location of instances of optical activity or probe binding events over a single target nucleic acid are determined. In some embodiments, a location of oligonucleotide probe species instances of optical activity or binding events over a single target nucleic acid is determined by elongating a target nucleic acid, so that different locations of instances of optical activity or binding events along a length of a target nucleic acid is detected and resolved.

In some embodiments, differentiating optical activity of unbound oligonucleotide probe species from oligonucleotide probe species that have bound to a target nucleic acid may requires rejection or removal of signal from oligonucleotide probe species that have not bound. In some such embodiments, this is effectuated, for example, utilizing an evanescent field or waveguide for illumination, or by utilizing FRET pair labels or by utilizing photo activation to detect oligonucleotide probe species in specific locations (e.g., as described in Hylkje et al., Biophys J. 2015; 108(4): 949-956).

In some embodiments, as illustrated in FIGS. 13A-13C, oligonucleotide probe species may not be labeled, but an interaction with a target is detected using a DNA stain such as unbound intercalating dye 1302, which may intercalates into a duplex and isgins fluorescing as an intercalated dye 1304 as binding occurs or has occurred (e.g., as illustrated in FIGS. 13A-13C). In some embodiments, one or more intercalating dyes may intercalate into a single duplex between a target nucleic acid and an oligonucleotide probe species at any one time. In some embodiments, fluorescence emitted by an intercalating dye once it is intercalated is orders of magnitude greater than fluorescence from unbound intercalating dye floating free in solution. For example, a signal from intercalated YOYO-1 dyes is about 100× greater than a signal from YOYO-1 dye in free solution. In some embodiments, when a lightly stained (or partially photo bleached) double-stranded polynucleotide is imaged, individual signals along a polynucleotide that are observed may correspond to single intercalating dye molecules. To facilitate exchange of YOYO-1 dye in a duplex and to obtain a bright signal Redox-Oxidation system (ROX) comprising Methyl Viologen and ascorbic acid are provided in the binding buffer in some embodiments.

In some embodiments, sequencing on single target nucleic acids by detecting incorporation of individual nucleotides labeled with a single dye molecule (e.g., as is effectuated by Helicos and PacBio sequencing) may introduce errors when a dye is not detected. In some instances, this is because a nucleotide may no longer be bound to a dye, a single nucleotide binding event is too short to detect, a dye has photo bleached, a cumulative signal detected is weak due to dye blinking, a dye emits too weakly or a dye enters into a long dark photophysical state. In some embodiments, this is overcome in a number of alternative ways. The first is to label the nucleotide with robust individual dyes that have favorable photophysical properties (e.g., Cy3B). Another is to provide buffer conditions and additives that reduce photo bleaching and dark photophysical states (e.g., beta-mercaptoethanol, Trolox, Vitamin C and its derivatives, redox systems). Another is to minimize exposure to light (e.g., having more sensitive detectors requiring shorter exposures or providing stroboscopic illumination). The second is to label nucleotides with nanoparticles such as quantum dots (e.g., Qdot 655), fluorospheres, nanodiamond, plasmon resonant particles, light scattering particles, etc., instead of single dyes.

Another is to have many dyes per nucleotide rather than a single dye (e.g., as illustrated in FIGS. 14C and 14D). In this case the multiple dyes 1414 are organized in a way that minimizes their self-quenching (e.g., using rigid nanostructures 1412 such as DNA origami that spaces them far enough apart) or a linear spacing via rigid linker.

In some embodiments, a detection error rate is further reduced (and signal longevity increased) in the presence in the solution of one or more compound(s) selected from urea, ascorbic acid or salt thereof, isoascorbic acid or salt thereof, beta-mercaptoethanol (BME), DTT, a redox system, or Trolox.

In some embodiments, transient binding of probes to target nucleic acids alone is sufficient to reduce errors due to dye photophysics. Information obtained during an exposing process is an aggregate of many on/off interactions of different labeled oligonucleotide probe species. Thus, even if a label is missing, a single binding event is too short to properly detect, a label is photo bleached or is in a dark state, labels on other oligonucleotide probe species that bind to a target nucleic acid may not all be missing a label, have binding events too short to detect, have a photo bleached or in a dark state label and will thus provide information on the location of their binding sites in some embodiments.

In some embodiments, an instance of optical activity signal from a label in each transient binding event is projected through an optical path (typically, providing a magnification factor) to cover more than one pixel of a two-dimensional imager. A point spread function (PSF) of for an instance of optical activity signal is determined and a centroid of a PSF is used as a precise location of an instance of optical activity signal. In some embodiments, localization is determined to sub-diffraction (e.g., super resolution) and even sub-nanometer accuracy. Localization accuracy is inversely proportional to a number of photons collected. Therefore, the more photons emitted per second by a fluorescent label or the longer photons are collected, the higher the accuracy.

In one example, as illustrated in FIGS. 10A and 10B, both a number of instances of optical activity or binding events at each oligonucleotide probe species binding site and a number of photons collected is correlated with a degree of localization that is achieved. For a target nucleic acid 1002, a smallest number of binding events 1004-1 and a fewest number of photons 1008-1 recorded for a binding site are correlated with the least precise localizations 1006-1 and 1010-1, respectively. As either a number of binding events 1004-2, 1004-3 or a number of photons recorded 1008-2, 1008-3 increases for a binding site, a degree of localization increases 1006-2, 1006-3 and 1010-2, 1010-3, respectively. In FIG. 10A, a differing number of detected stochastic instances of optical activity or binding events (e.g., 1004-1, 1004-2, 1004-4) of labeled oligonucleotide probe species with a target nucleic acid 1002 results in differing degrees of localization of the probes (1006-1, 1006-2, 1006-3), where a larger number of binding events (e.g., 1004-2) is correlated with a higher degree of localization (e.g., 1006-2), and a smaller number of binding events (e.g., 1004-1) is correlated with a lower degree of localization (e.g., 1006-1). In FIG. 10B, a differing number of photons (e.g., 1008-1, 1008-2, and 1008-3) that are detected similarly results in differing degrees of localization (1010-1, 1010-2, and 1010-3 respectively).

In an alternative embodiment, signal from a label in each transient binding event may not be projected through an optical magnification path. Instead, substrate (typically an optically transparent surface upon which target nucleic acid molecules may reside) is directly coupled to a two-dimensional detector array. When the pixels of a detector array are small (e.g., one micron square or less), a one-to-one projection of signals on a surface of a detector may allow a binding signal to be localized with at least one-micron accuracy. In some embodiments, where a target nucleic acid has been stretched sufficiently (e.g., where two kilobases of a target nucleic acid has been stretched to 1 micron in length), signals that are two kilobases apart are resolved. For example, in the case of 6-mer probes where signals would be expected to occur every 4096 bases or every 2 microns, the aforementioned resolution is sufficient to unequivocally localize individual binding sites. A signal may originate partially between two pixels, and intermediate locations (e.g., a resolution could be 500 nm or better for a pixel one micron square if a signal falls between two pixels). In some embodiments, super resolution methods is utilized for systems which have target nucleic acids in appropriate locations relative to a two dimensional imager. Such a location may vary depending upon a type of sensor used for a two dimensional imager. For example, a backside thinned CCD have an actual sensor region further from a detection surface of a sensor than a front side illuminated CCD, and both is significantly different than a CCD or CMOS imager that may utilize nano-lens associated with each pixel. In some embodiments, a substrate is physically translated in an X and or Y dimension in relation to the two-dimensional array detector (e.g., in increments of 100 nm) to provide higher resolution. In such embodiments, a device or system is smaller (or thinner), as it does not need lenses or space in between lenses. In some embodiments, translation of the substrate also provides a direct conversion of molecular storage readout into electronic readout more compatible with existing computers and databases. In some embodiments, time resolved fluorescence is utilized, and is utilized to capture fluoresce lifetime, or is used simply to eliminate excitation background.

In some embodiments, to capture high speed transient incidents of optical activity or binding events, a capture frame rate is increased and a data transfer rate is increased over standard microscopy techniques. In some embodiments, a speed of an exposing process is increased by coupling high frame rates with an increased concentration of probes. However, a maximum frame rate is appropriate to reduce electronic noise relative to acquired signal associated with each frame. Electronic noise of a 200 millisecond exposure is the same as a single 100 millisecond exposures, but is as much as the square root of two higher when comparing a single 200 millisecond exposure with two 100 millisecond exposures.

Faster CMOS cameras are becoming available that will enable faster imaging. For example, the Andor Zyla Plus allows up to 398 frames per second over 512×1024 pixels squared with just a USB 3.0 connection and is even faster over restricted regions of interest (ROI) (smaller numbers of pixels) or when using a CameraLink connection.

In some embodiments, a system which may effectuate fast imaging may use a galvo mirror or digital micromirror to send temporally incremented images to different sensors. A correct order for frames of a movie is reconstructed by interleaving frames from different sensors according to their time of acquisition.

In some embodiments, a transient binding process can be sped up by tuning various biochemical parameters, such as salt concentration. There are a number of cameras with high frame rates that can be used to match the speed of binding, often with a restricted field of view to obtain a faster readout from a subset of pixels. In some embodiments, a galvanometer mirror is utilized to temporally distribute consecutive signals to different regions of a single sensor or to separate sensors. The latter allows the utilization of a full field of view of a sensor but increases overall temporal resolution when the distributed signals are compiled.

Building a Dataset of Multiple Binding Events.

Block 218. In some embodiments, exposing and measuring processes is repeated for individual oligonucleotide probe species in a set of oligonucleotide probe species, thereby obtaining a plurality of sets of positions of optical activity or binding events on a test substrate, each respective set of positions of optical activity or binding events on a test substrate corresponding to a single oligonucleotide probe species in a set of oligonucleotide probe species.

In some embodiments, a set of oligonucleotide probes may comprise a plurality of subsets of oligonucleotide probes and repeating exposing and measuring processes is performed for each respective subset of oligonucleotide probes species in a plurality of subsets of oligonucleotide probes species.

In some embodiments, each respective subset of oligonucleotide probe species may comprises two or more different oligonucleotide probe species from a set of oligonucleotide probe species. In some embodiments, each respective subset of oligonucleotide probe species may comprise four or more different oligonucleotide probe species from a set of oligonucleotide probe species. In some embodiments, a set of oligonucleotide probes may comprise of four subsets of oligonucleotide probe species.

In some embodiments, a method may further comprise dividing a set of oligonucleotide probe species into a plurality of subsets of oligonucleotide probe species based on a calculated or experimentally derived melting temperature of each oligonucleotide probe species. Oligonucleotide probe species with similar melting temperatures are placed in a same subset of oligonucleotide probes by a dividing. Further, a temperature or a duration of an exposing process is determined by an average melting temperature of oligonucleotide probe species in a corresponding subset of oligonucleotide probe species.

In some embodiments, a method may further comprise dividing a set of oligonucleotide probes into a plurality of subsets of oligonucleotide probes based on a sequence of each oligonucleotide probe species, where oligonucleotide probe species with overlapping sequences are placed in different subsets.

In some embodiments, repeating exposing and measuring processes is performed for each single oligonucleotide probe species in a set of oligonucleotide probe species.

In some embodiments, an exposing process is done for a first oligonucleotide probe species in a set of oligonucleotide probe species at a first temperature and repeating exposing and measuring processes may include performing exposing and measuring processes for a first oligonucleotide probe species at a second temperature.

In some embodiments, an exposing process may is done for a first oligonucleotide probe species in a set of oligonucleotide probe species at a first temperature. Instances of repeating exposing and measuring processes may include performing the exposing and the measuring processes for a first oligonucleotide probe species at each of a plurality of different temperatures. A method may further comprise constructing a melting curve for a first oligonucleotide probe species using measured locations and optionally durations of instances of optical activity determined by exposing and measuring processes for a first temperature and each temperature in a plurality of different temperatures.

In some embodiments, a test substrate is washed prior to repeating exposing and measuring processes, thereby removing one or more respective oligonucleotide probe species from a test substrate prior to exposing a test substrate to a different one or more oligonucleotide probe species. Optionally, first oligonucleotide probe species are replaced with one or more wash solutions, then a different one or more oligonucleotide probe species are added.

In some embodiments, measuring a binding event location on a test substrate may comprises identifying and fitting a respective instance of optical activity with a fitting function to identify and fit a center of a respective instance of optical activity in a frame of data obtained by a two-dimensional imager. A center of a respective instance of optical activity is deemed to be a location of a respective instance of optical activity or binding event on a test substrate.

In some embodiments, a fitting function is a Gaussian function, a first moment function, a gradient-based approach, or a Fourier transform. A Gaussian fit will only be an approximation of a PSF of a microscope system, but addition of a spline (e.g., a cubic spline) or a Fourier transform approach, in some embodiments, mayo improve accuracy of determining a center of a PSF (e.g., as described in Babcock et al., Sci Rep. 7:552, 2017 and Zhang et al., 46:1819-1829, 2007).

In some embodiments, after completing measuring processes, sets of positions of optical activity for a single nominal binding locations of an oligonucleotide probe species have a position determined and an oligonucleotide probe species identified (e.g., due to a detected emission wavelength) and a process may determine which of oligonucleotide probe species from a set, have overlapping nominal binding locations to a target nucleic acid (e.g., which bind to a same nanometric location within a determined tolerance, which is different for different oligonucleotide probe species, for example due to different numbers of photons being detected). In one example, a nanometric location is defined with precision of 1 nm center (+/−0.5 nm), and all oligonucleotide probe species whose respective precision or tolerance about respective a PSF centroid overlap, would thus be binned together. Each single defined oligonucleotide probe species may bind multiple times (e.g., depending on number of photons emitted and collected) to enable accurate localization to a nanometer (or sub-nanometer) centroid with an appropriate precision or tolerance (nanometer or sub-nanometer).

In some embodiments, nanometric or sub-nanometric localization may determine, for example, that a first base is an A, a second base is a G, a third base is a T, a fourth base is a C and a fifth base is a G for an oligonucleotide probe species sequence of 5'-AGTCG-3'. Such a pattern suggests a target sequence of 5'-CGACT-3'. Thus, all single-base defined 1024 5-mer oligonucleotide probe species are applied or tested using five cycles using probe coding systems as described hereinabove, where each cycle may comprise exposing, determining, and repeating processes and may further comprise both an oligonucleotide probe species pool addition and washing step. In some embodiments, a concentration of each specific oligonucleotide probe species in the pool of oligonucleotide [probe species is lower than it would be when used alone. In some embodiments, acquisition of data is taken for a longer time or more frames is acquired during an exposure process in order to reach a threshold number of binding events, potentially as a result of competition between different oligonucleotide probe species. In some embodiments, higher concentrations of oligonucleotide probe species which may utilize degenerate or universal bases are used an oligonucleotide probe species of a same k-mer species length without degenerate bases or universal bases. In some embodiments, a coding scheme is effectuated by direct labeling of oligonucleotide probe species, for example, by synthesizing or conjugating a label at a 3' or 5' position of oligonucleotide probe species. However, in some alterative embodiments, this is done by indirect labeling (e.g., by attaching a flap sequence to each labeled oligo as described herein).

In some embodiments, a location of each oligonucleotide probe species is precisely defined by determining PSFs for multiple binding events for that location and may then be corroborated by partial sequence overlap from offset binding events (and where, available, data from complementary strands of a duplex form target nucleic acid). Some embodiments as described herein is highly reliant on the single molecule localization of probe binding to one or a few nanometers.

In some embodiments, respective instances of optical activity may persist across a plurality of frames as measured by a two-dimensional imager. Measuring a location on a test substrate comprises identifying and fitting respective instances of optical activity with a fitting function across a plurality of frames to identify a center of a respective instance of optical activity across a plurality of frames. A center of a respective instance of optical activity is deemed to be a position of a respective instance of optical activity on a test substrate across a plurality of frames. In some embodiments, a fitting function may determine the center on each frame in the plurality of frames individually. In other embodiments, a fitting function may determine a center for an instance of optical activity collectively across a plurality of frames.

In some embodiments, fitting may utilize a tracking step where if a localization immediately adjacent (e.g., within half a pixel) is present in a next frame, it may average them together, weighted by how bright they are; it may assumes this is single instance of optical activity or binding event. However, if there instances of optical activity is separated by multiple frames (e.g., at least a 5 frame gap, at least a 10 frame gap, at least a 25 frame gap, at least a 50 frame gap, or at least a 100 frame gap between binding events), then a fitting function may assumes they are distinct binding events. Tracking distinct instances of optical activity or binding events may help to increase confidence in sequence assignment.

In some embodiments, measuring process may resolves a center of a respective instance of optical activity to a position on a test substrate with a localization precision of at least 20 nm. In some embodiments, a measuring process may resolves a center of a respective instance of optical activity to a position on a test substrate with a localization precision of at least 2 nm, at least 60 nm, at least 6 nm. In some embodiments, measuring may resolve a center of a respective instance of optical activity to a position on a test substrate with a localization precision of between 2 nm and 100 nm. In some embodiments, a measuring process may resolve a center of a respective instance of optical activity to a position on a test substrate, where a position is a sub-diffraction limited position and have a precision which may also be sub-diffraction limited. In some embodiments, a resolution is more limiting than precision.

In some embodiments, a measuring process may determine a location on a test substrate and optionally a duration of a respective instance of optical activity, and a measuring process may determine that one or more instances of optical activity have comprised more than 5000 photons at a location. In some embodiments, a measuring process may determine a location on a test substrate and optionally a duration of a respective instance of optical activity, and a measuring process may determine that one or more instances of optical activity have comprised more than 50,000 photons at a location or more than 200,000 photons at a location.

Each dye has a maximum rate at which it may generate photons (e.g., 1 KHz-1 MHz). For example, some dyes it is only possible to measure 200,000 photons in one second. A typical lifetime for a dye is 10 nanoseconds, thus emitting 100,000,000 photons per second, which when combined with collection efficiency, detector quantum efficiency filtration losses may result in orders of magnitude fewer photons per second being detected. Thus, in some embodiments, measuring a location on a test substrate and optionally a duration of a respective instance of optical activity may measure more than 1,000,000 photons at an associated location.

In some instances, certain outlier sequences may bind in a non-Watson Crick manner or a short motif may result in inordinately high on-rate or low off-rate. For example, some purine-polypryrimidine interactions between RNA and DNA are very strong (e.g., RNA motifs such as AGG). These not only have lower off rates, but also higher on rates due to a more stable nucleation sequence. In some cases, binding occurs from outliers that do not necessarily conform to certain known rules. In some embodiments, algorithms are used to identify such outliers or take the expectation of such outliers into account.

In some embodiments, a respective instance of optical activity is more than a predetermined number of standard deviations (e.g., more than 3, 4, 5, 6, 7, 8, 9, or 10 standard deviations) over a background observed for a test substrate.

In some embodiments, an exposing process is done for a first oligonucleotide probe species in a set of oligonucleotide probe species for a first period of time. In some such embodiments, repeating exposing and measuring processes may include performing an exposing process for a second oligonucleotide probe species for a second period of time. A first period of time is greater than a second period of time.

In some embodiments, an exposing process is done for a first oligonucleotide probe species in a set of oligonucleotide probe species for a first number of frames using a two-dimensional imager. In some such embodiments, repeating exposing and measuring processes may includes performing an exposing process for a second oligonucleotide probe species for a second number of frames using a two-dimensional imager. A first number of frames is greater than a second number of frames.

In some embodiments, complementary oligonucleotide probe species in one or more tiling sets are used to bind to each of the strands of a denatured duplex target nucleic acid. As illustrated by FIG. 11B, it is possible to determine a sequence of at least a portion of a target nucleic acid using a plurality of sets of positions on a test substrate, which may comprise determining a first tiling path 1114 corresponding to a fixed first strand of a target nucleic acid 1110 and a second tiling path 1116 corresponding to a fixed second strand of a target nucleic acid 1112.

In some embodiments, a break in a first tiling path is resolved using a corresponding portion of a second tiling path, where a break in a tiling path is an inability to determine a base sequence with a desired confidence, and resolving a break is determining a base sequence with a desired confidence. In some embodiments, a break in a first tiling path or a second tiling path is resolved using a reference sequence. In some embodiments, a break in a first tiling path or a second tiling path is resolved using corresponding portions of a third tiling path or a fourth tiling path obtained from another instance of a target nucleic acid.

In some embodiments, a confidence in sequence assignment of a target nucleic acid sequence for each binding site is increased using corresponding portions of a first tiling path and a second tiling path. In some embodiments, a confidence in sequence assignment of a target nucleic acid sequence is increased using corresponding portions of a third tiling path or a fourth tiling path obtained from another instance of a target nucleic acid.

Alignment or Assembly of the Sequence.

Block 222. In some embodiments, a sequence of at least a portion of a target nucleic acid is determined using a plurality of sets of positions on a test substrate by compiling positions on a test substrate represented by a plurality of sets of positions.

In some embodiments, a contiguous sequence is obtained via de novo assembly. In other embodiments a reference sequence is used to facilitate assembly. When complete genome sequencing requires a synthesis of information from multiple target nucleic acid molecules spanning a same region of a genome (ideally molecules that are derived from a same chromosome), algorithms may need to process information obtained from multiple target nucleic acid molecules. In some embodiments, an algorithm is utilized which may aligns target nucleic acid sequences based on sequences that are common between multiple target nucleic acid molecules, and may fill in any gaps in each target nucleic acid molecule by imputing from co-aligned molecules where the region is covered (e.g., a gap in one target nucleic acid molecule is covered by a sequence read determined for another, co-aligned target nucleic acid molecule).

In some embodiments, shotgun assembly methods (e.g., as described in Schuler et al., Science 274:540-546, 1996)

are adapted to carry out assembly using sequence assignments obtained as described herein. An advantage of the current method over Sanger or Illumina shotgun sequencing is that a multitude of reads are pre-assembled as they is sequenced from full-length, intact target nucleic acid molecules, or very large fragments thereof (e.g., a location of reads or contigs with respect to each other, and a length of gaps between reads or contigs may already be known). In various embodiments, a reference genome is used to facilitate assembly, either of long-range genome structure or of short-range polynucleotide sequence or both. In some embodiments, reads are partially de-novo assembled and then aligned to a reference and then reference-assisted assemblies is de novo assembled further. In some embodiments, various reference assemblies are used to provide some guidance for a genome assembly. In other embodiments, information obtained from actual molecules (especially if it is corroborated by two or more molecules) is weighted greater than any information from reference sequences.

In some embodiments, target nucleic acids from which sequence bits are obtained are aligned based on segments of sequence overlap between target nucleic acids, and a longer in silico contig and ultimately sequence of an entire chromosome is generated.

In some embodiments, an identity of a target nucleic acid is determined by a pattern of oligonucleotide probe species binding along its length. In some embodiments, an identity is an identity of a RNA species or an RNA isoform. In some embodiments, an identity is a location in a reference sequence to which a target nucleic acid may correspond.

In some embodiments, localization accuracy or precision may not be sufficient to stitch sequence bits together. In some embodiments, a subset of probes is found to bind within a specific locality, but strictly from localization data a sequence order is hard to determine with a desired confidence. In some embodiments, resolution is diffraction limited. In some embodiments, short-range sequence within a locality or diffraction-limited spot is assembled by sequence overlap of oligonucleotide probe species that locate within a locality or spot. Short-range sequence may thus be assembled for example, by using information about how individual sequences of a subset of oligonucleotide probe species overlap. In some embodiments, short range sequences constructed in this way may then be stitched together, based on their order on a target nucleic acid, into a long-range sequence. Long-range-sequence may thus be obtained by conjoining short-range sequence obtained from adjacent or overlapping spots.

In some embodiments, (e.g., for a target nucleic acid that is natively double-stranded), a reference sequence and sequence information obtained for a complementary strand are used to facilitate sequence assignment.

In some embodiments, a target nucleic acid is at least 140 bases in length and a determining process may determine a coverage of a sequence of a target nucleic acid sequence of greater than 70%. In some embodiments, a target nucleic acid is at least 140 bases in length and a determining process may determine a coverage of sequence of a target nucleic acid sequence of greater than 90%. In some embodiments, a target nucleic acid is at least 140 bases in length and a determining process may determine a coverage of a sequence of a target nucleic acid sequence of greater than 99%. In some embodiments, a determining process may determine a coverage of a sequence of a target nucleic acid sequence of greater than 99%.

Non-Specific or Mismatching Binding Events.

In general, sequencing assumes that a target nucleic acid contains nucleotides that are complementary to the ones bound. However, this may not always be the case. A binding mismatch error is an example of a case where this assumption does not hold. Nevertheless, mismatching, when it occurs according to known rules or behavior, is useful in determining a sequence of a target nucleic acid. Use of short oligonucleotide probe species (e.g., 5-mers) means that the effect of a single mismatch have a large effect on stability, as one base is 20% of the 5-mer length. Hence, using appropriate conditions, exquisite specificity is obtained by short oligonucleotide probe species. Even so, mismatches can occur and because of the stochastic nature of molecular interactions, some of their binding durations may not be distinguishable from binding where all 5 bases are specific. In some embodiments, algorithms is used to perform base (or sequence) calling and assembly often take occurrence of mismatches into account. Many types of mismatches are predictable and conform to certain rules. Some of these rules are derived by theoretical considerations while others are derived experimentally (e.g., as described by Maskos and Southern, Nucleic Acids Res 21(20): 4663-4669, 2013; Williams et al., Nucleic Acids Res 22:1365-1367, 1994).

In some embodiments, the effects of non-specific binding to a surface are mitigated by such non-persistence of probe binding to non-specific sites is not persistent and once one imager has occupied a non-specific (e.g., not on the complementary target sequence) binding site it can get bleached but in some cases remains in place, blocking further binding to that location (e.g., an interaction due to a G-Quartet formation). Typically, the majority of the non-specific binding sites, which prevent resolution of the imager binding to the target polynucleotide, are occupied and bleached within the early phase of imaging, leaving the on/off binding of the imager to the polynucleotide site to be easily observed thereafter. Hence in one embodiment, high laser power is used to bleach probes that initially take up non-specific binding sites, optionally images are not taken during this phase, and then the laser power is optionally reduced and imaging is started to capture the on-off binding to the polynucleotide. After the initial non-specific binding, further non-specific binding is less frequent (because probes that have bleached often remain stuck to the non-specific binding sites) and, in some embodiments, are computationally filtered out by applying a threshold, for example, to be considered as specific binding to the docking site, the binding to the same location must be persistent, e.g., should occur at the same site at least 5 times or at least 10 times. Typically, around 20 specific binding events to the docking site are detected.

In other embodiments, binding that is non-specific, is that the fluorophore signals must correlate with the position of the linear strand of the target molecule that is stretched on the surface, and other signals is removed algorithmically. In some embodiments, it is possible to determine a target nucleic acid strand's position either by staining a linear duplex form target nucleic acid strand directly or by interpolating a line through persistent binding sites. In general, signals that do not fall along a line, whether they are persistent or not, are discarded in some embodiments. Similarly, when a supramolecular lattice is used, binding events that do not correlate with a known structure of the lattice are discarded in some embodiments.

In some embodiments, multiple binding events may also increase specificity. For instance, rather than establishing identity of a moiety or sequence being detected from single "call," a consensus is obtained from multiple calls. Also multiple binding events to a target moiety or target nucleic acid may allow binding to actual locations to be differentiated from non-specific binding events, where binding (of a threshold duration) is less likely to occur multiple times at a same location. Also it is observed that measurement of multiple binding events over time allows accumulation of non-specific binding events to the surface to be bleached, after which little non-specific binding may detected again. This is likely to be because although the signals from nonspecific binding is bleached, the non-specific binding sites may remain occupied or blocked.

In some embodiments, sequencing is complicated by mismatches and non-specific binding on a target nucleic acid. In order to circumvent the effects of non-specific binding or outlier events, in some embodiments, a method may weight signals based on their location and persistence. Weighting due to location is predicated upon whether probes co-localize for example, on a stretched target nucleic acid or supramolecular lattice (e.g., a DNA origami grid), including location within lattice structure. Weighting due to persistence of binding concerns duration of binding and frequency of binding and may use a weighting associated with different nominal binding events or binding locations to determine likelihood of a full match, partial match or non-specific binding. Weighting that is established for each oligonucleotide probe species in a complete set of oligonucleotide probe species is used to determine correctness of a signal.

In some embodiments, priority is used to facilitate signal verification and base calling by determining whether a signal persistence duration is greater than a predefined threshold, whether a signal repetition or frequency is greater than a predetermined threshold, whether a signal correlates with a location of a target molecule, and/or whether a number of photons collected is greater than a predefined threshold. In some embodiments, when the answer to any of these determinations is true, a signal is accepted as real (e.g., as not a mismatch or a non-specific binding event). In other embodiments, more than one of these determinations may need to be true for a signal to be accepted as true.

In some embodiments, mismatches are distinguished by their temporal binding pattern and hence are considered as a secondary layer of sequence information. In such embodiments, when a binding signal is judged to be a mismatch due to its temporal binding characteristics, an associated sequence bit is bioinformatically trimmed to remove putative mismatching bases and remaining sequence bit is utilized for to sequence determination. As mismatches are most likely to occur at ends of hybridizing oligonucleotide probe species, use of temporal binding characteristics to determine a mismatch may result in one or more bases being trimmed from an end of an oligonucleotide probe species sequence in some embodiments. A determination as to which base is appropriately trimmed is informed by information from other oligos tiling over a same target nucleic acid region, in some embodiments.

In some embodiments, a signal that does not appear to be reversible is negatively weighted as it has a chance or degree of likelihood of corresponding to a non-specific signal (e.g., due to attachment of fluorescent contaminant to the surface).

Blocks 302-304. In some embodiments, a method of sequencing a target nucleic acid may comprise a fixing process where a target nucleic acid is bound in a linearized stretched form on a test substrate, thereby forming a fixed stretched nucleic acid. A target nucleic acid is affixed to a test substrate according to any one of the methods described hereinabove.

Isolating Single Cells on a Surface and Extracting Both DNA and RNA.

In some embodiments, either or both RNA and DNA can be isolated from a single cell and sequenced. In some embodiments, when a goal is to sequence DNA, RNase is reacted with a sample before sequencing commences. In some embodiments, when the aim is to sequence RNA, DNase is reacted with a sample before sequencing commences. In some embodiments, where both cytoplasmic nucleic acids and nuclear nucleic acids are to be analyzed, they are extracted differentially or sequentially. In some embodiments, first a cell membrane (and not the nuclear membrane) is disrupted to release and collect cytoplasmic nucleic acids. Then an associated nuclear membrane is disrupted to release nuclear nucleic acids. In some embodiments, proteins and polypeptides are collected as part of a cytoplasmic fraction. In some embodiments, RNA is collected as part of a cytoplasmic fraction. In some embodiments, DNA is collected as part of a nuclear fraction. In some embodiments, cytoplasmic and nuclear fractions are extracted together. In some embodiments, after extraction mRNA and genomic DNA are differentially captured. For example, the mRNA is captured by oligo dT probes attached to a surface. This can occur in a first part of a flow cell and DNA is captured in a second part of a flow cell that have a hydrophobic vinylsilane coating on which ends of DNA can be captured (e.g., presumably due to hydrophobic interactions).

In some embodiments, surfaces with positive charges such as poly(L)lysine (PLL) (e.g., as available from Microsurfaces Inc. or coated in house) is utilized and are known to be able to bind to cell membranes. In some embodiments, a low height and or width flow channel (e.g., <30 microns) is used so that there is increased chance for the cells to collide with a surface. The number of collisions is increased In some embodiments, by using a herringbone or serpentine pattern in a flow cell ceiling to introduce turbulent flow. In some embodiments, cell attachment may not need to be efficient as it is desirable for cells to be dispersed at low density onto a surface in such embodiments (e.g., to ensure that there is sufficient space between cells so that the RNA and DNA extracted from each individual cell may remain spatially separated). In some embodiments, cells are lysed using proteinase treatment so that both cell and nuclear membranes are disrupted (e.g., so that the cellular contents are released into a medium and are captured at a surface in the vicinity of an isolated cell). Once immobilized, DNA and RNA is stretched in some embodiments. In some embodiments, a stretching buffer is flowed unidirectionally across a cover glass surface (e.g., causing DNA and RNA polynucleotides to stretch out and align in a direction of fluid flow). In some embodiments, modulations of conditions (e.g., such as temperature, composition of the stretching buffer and physical force of a flow) may cause most RNA secondary/tertiary structure to denature so that RNA is available for binding to antibodies or for sequencing. Once RNA is stretched in a denatured form, it is possible to switch from denaturation buffer to binding buffer.

Alternatively, RNA is extracted and immobilized first by disrupting a cell membrane and inducing flow in one direction. Nuclear membrane is disrupted next using proteinase, and flow is induced in an opposite direction. In some embodiments, DNA is fragmented before or after release, by using rare-cutting restriction enzymes for example, (e.g., NOT1, PMME1). This fragmentation may aid in disentangling DNA and may allow individual strands to be isolated and combed. A system is configured such that immobilized cells are far enough apart that RNA and DNA extracted from each cell do not co-mingle. In some embodiments, this is aided by inducing a liquid to gel transition before, after or during bursting or disrupting of a cell.

In some embodiments, target nucleic acid is double-stranded nucleic acid. In such embodiments, a method may further comprise denaturing a fixed double-stranded target nucleic acid to single stranded form on a test substrate. In some embodiments, a nucleic acid must be in a single stranded form for sequencing to proceed, or is in a partially denatured form, or is double stranded when utilizing strand invasion or triplex forming oligonucleotide probe species. Once the fixed double-stranded nucleic acid has been denatured, both a fixed first strand and a fixed second strand of the nucleic acid is directly accessible. A fixed second strand is complementary to a fixed first strand of a native duplex target nucleotide.

In some embodiments, target nucleic acid is single stranded (e.g., mRNA, lncRNA microRNA). In some embodiments, where target nucleic acid is single stranded RNA, no denaturing is required before a sequencing method proceeds.

In some embodiments, a sample may comprise a single-stranded DNA polynucleotide without a native complementary strand in close proximity. In some embodiments, where binding locations for each oligonucleotide probe species of a complete set of oligonucleotide probe species along a target nucleic acid are compiled, a sequence is assembled by aggregating all sequence bits according to their location and stitching them together.

Stretching RNA.

In some embodiments, stretching of nucleic acids on a charged surface is affected by solution cationic concentration. At low salt concentrations, RNA which is single stranded and negative charges along its backbone may bind to a surface randomly along its length.

There are multiple possible methods to denature and stretch RNA into a linear form. In some embodiments, tRNA is initially encouraged to enter a globular form (e.g., by using high salt concentrations). In some such embodiments, ends of each RNA molecule (e.g., in particular, the poly A tail) become more accessible to interaction. Once the RNA has been bound in a globular form, a different buffer (e.g., a denaturing buffer) is flowed into a flow cell in some embodiments.

In alternative embodiments, a surface is pre-coated with oligo d(T) to capture poly A tails of mRNA (e.g., as described by Ozsolak et al., Cell 143:1018-1029, 2010). PolyA tails are typically regions that should be relatively free from secondary structure (e.g., as they are homopolymers). As poly A tails are relatively long (250-3000 nucleotides) in higher eukaryotes, in some embodiments, long oligo d(T) capture probes are designed so that hybridization is performed at a relatively high stringency (e.g., high temperature and/or salt conditions), sufficient to melt a significant fraction of intramolecular base pairing in RNA. After binding, in some embodiments, transitioning remaining RNA structure from a globular to a linear state is effectuated by using denaturing conditions that are not sufficient to detach from capture probes, but may disrupt intramolecular base-pairing in RNA, potentially in combination with fluid flow or electrophoretic forces.

Block 310. In some embodiments, a fixed stretched target nucleic acid is exposed to a respective pool of respective oligonucleotide probe species in a set of oligonucleotide probes. Each oligonucleotide probe species in a set of oligonucleotide probe species is of a predetermined sequence and length, and exposing may occur under conditions that allow for individual probes of a respective pool of respective oligonucleotide probe species to transiently and reversibly bind to each portion of a fixed nucleic acid that is complementary to a respective oligonucleotide probe species, thereby giving rise to a respective instance of optical activity.

Block 312. In some embodiments, a location on a test substrate and optionally a duration of each respective instance of optical activity occurring during an exposing process which may utilize a two-dimensional imager is determined in a measuring process.

Block 314. In some embodiments, exposing and measuring processes are repeated for respective oligonucleotide probe species in a set of oligonucleotide probe species, thereby obtaining a plurality of sets of positions on a test substrate, each respective set of positions on a test substrate corresponding to an oligonucleotide probe species in a set of oligonucleotide probe species.

Block 316. In some embodiments, a sequence of at least a portion of a target nucleic acid is determined from a plurality of sets of positions on a test substrate by compiling positions on a test substrate represented by a plurality of sets of positions.

RNA Sequencing.

Lengths of RNA are typically shorter than genomic DNA, but it is challenging to sequence RNA from one end to the other using current technologies. Nevertheless, because of alternative splicing and gene isoforms it is vitally important to determine the full sequence organization of mRNA. In some embodiments, mRNA is captured by binding of its Poly A tail to immobilized oligo d(T) and its secondary structure is removed by application of a stretching force (e.g., >400 pN) and denaturation conditions (e.g., comprising Formamide and or 7 M or 8 M Urea) so that it is elongated on a surface. This then allows binding oligonucleotide probe species (e.g., exon-specific) to be transiently bound. Because of the short length of RNA, it is beneficial to employ single molecule localization methods as described herein to resolve, differentiate, and locate exons. In some embodiments, just a few binding events scattered across mRNA is sufficient to determine an order and identity of exons in mRNA for a particular mRNA isoform.

Double-Strand Consensus

A method for obtaining sequence information from a sample molecule follows:

i) Provide a first oligonucleotide probe species with a first emission maxima wavelength label. Provide a second oligonucleotide probe species with a second emission maxima wavelength label where the second oligonucleotide probe species sequence is complementary in sequence to the first oligonucleotide probe species sequence ii) Elongate, fix and denature native double-stranded target-nucleic acid molecules on a substrate iii) Expose both first and second oligo to the denatured nucleic acid of ii. while creating imaging data comprising instances of optical activity iv) Determining locations of binding of first and second oligonucleotide probe species v) Where the positions of binding co-localise, locations are deemed as correct vi) Multiple locations along an elongated target nucleic acid are bound.

In some embodiments, oligonucleotide probe species may bind transiently and reversibly. In some embodiments, a first and second oligonucleotide probe species are part of complete set of first and second oligonucleotide probe species of a given length and steps ii-iii are repeated for each first and second oligo pair of the complete set of oligonucleotide probe species to sequence the entire nucleic acid.

In some embodiments, a number of corrections may need to be made to ensure that the two emission maxima wavelengths optically co-localize where they should. This may includes correcting for chromic aberrations, either optically or utilizing a software process. In some such embodiments, two complementary oligonucleotide probe species is exposed at a same time, but to prevent them from annealing to each other and thus interfering with simultaneous binding to a target nucleic acid, modified oligonucleotide chemistry is used, where non-self-pairing analogue bases where modified G cannot pair with modified C in the complementary oligonucleotides but can pair with unmodified C on a target nucleic acid, and modified A cannot pair with modified T in the complementary oligonucleotide probe species but can pair with unmodified T. Thus in such embodiments first and second oligonucleotide probe species are modified such that a first oligonucleotide probe species cannot form base pairs with a second oligonucleotide probe species, thus allowing uninterfered access to target nucleic acids, and allowing for spectral calibration of chromatic aberrations, which may vary across a field of view. In some embodiments, utilizing a same process that is used to calibrate and remove chromatic aberrations, spectral and spatial PSF variations may similarly be calibrated and compensated.

In some embodiments, a first and second oligonucleotide probe species are not added together but one is added after another.

In such embodiments, where oligonucleotide probe species is added one after another, wash steps are conducted in between; in this case complementary oligonucleotide probe species are labeled with a same emission maxima wavelength and there is no need to correct for chromic aberrations. Also, there is no possibility of the two oligos binding with each other.

In some embodiments, a target nucleic acid is exposed to further first and second oligonucleotide probe species until the entire set of oligonucleotide probe species has been exposed.

In some embodiments, a second oligonucleotide probe species is added as a next oligonucleotide probe species after a first oligo nucleotide probe species, before other pairs of complementary oligonucleotide probe species in the complete set of oligonucleotide probe species are added. In some embodiments, a second oligonucleotide probe species is not added as a next oligonucleotide probe species before other oligonucleotide probe species of the complete set of oligonucleotide probe species is added.

An example of such an embodiment comprises a method for obtaining sequence information from a sample target nucleic acid molecule follows:
i) Elongating, fixing and denaturing double-stranded target nucleic acid molecules on a substrate
ii) Exposing a first labeled oligo to denatured target nucleic acid of i) and detecting and recording its location of oligonucleotide probe species binding
iii) Removing the first labeled oligonucleotide probe species by washing
iv) Exposing a second labeled oligonucleotide probe species to the denatured target nucleic acid of i) and detecting and recording its location of oligonucleotide probe species binding
v) Optionally correcting for drift between the recordings in ii) and iv)
vi) Where the recorded positions of binding obtained in ii-iv co-localize, sequence information thus obtained about the sequence of the location is deemed as correct In some embodiments, first and second oligonucleotide probe species are part of a complete set of oligonucleotide probe species e and steps ii-iii are repeated for each first and second oligonucleotide probe species pair of a complete set of oligonucleotide probe species to sequence an entire target nucleic acid.

Co-localization may tell us we are looking at the same sequence loci. Further, oligonucleotide probe species targeting a sense strand could be looking to discriminate a central base using 4 differentially labeled oligos and oligonucleotide probe species targeting an antisense strand could be looking to discriminate a central base using 4 differentially labeled oligo nucleotide probe species with complementary sequence to oligonucleotide probe species for a sense strand. To obtain a validated base call for a central position, data for a sense strand should corroborate the data for an antisense strand. So if an oligonucleotide probe species with central A base binds to a sense strand, a complementary oligonucleotide probe species with central T base should bind to an antisense strand.

In some embodiments, obtaining such corroboration or consensus for sense and antisense strand may help to overcome the ambiguity resulting from a G:T or G:U wobble base pairing. Where this occurs on a sense strand, it is unlikely to yield signal on the antisense strand because C:A is less likely to form a base-pair.

In some embodiments, a modified G base or T/U can be used in oligonucleotide probe species to prevent formation of a wobble base-pair. In some other embodiments an assembly algorithm may takes account of the possibility of formation of a wobble base-pair, especially when corroboration with a C:G base-pair is absent on a complementary target nucleic acid strand and a location correlates with an oligonucleotide probe species binding to a complementary target nucleic acid strand that forms an A:T base pair. In some embodiments, 7-deazaguanisine with the ability to form only two hydrogen bonds rather than 3 is used as a G modification to reduce stability of base pairings it may form and formation of G-quadruplex and its very strong(and hence promiscuous binding).

Concurrent Duplex Consensus Assembly.

In some embodiments, both strands of a double helix target nucleic acid is present and are exposed to oligonucleotides probe species as described hereinabove while in close proximity between target strands. In some embodiments, it may not be possible to distinguish, from the transient optical signals that are detected, which of the two complementary strands each oligonucleotides probe species in a respective set of oligonucleotide probe species has bound. For example, when binding locations along each target nucleic acid strand for each of the oligonucleotides probe species of a respective set of oligonucleotide probe species along a target nucleic acid are compiled, it may appear as though two probes of different sequences have bound to the same location. These oligonucleotides probe species should have complementary sequences, and the difficulty then becomes determining which strand each of the two oligonucleotides probe species bound, which is a prerequisite for accurately compiling a sequence for a target nucleic acid.

In some embodiment, determination as to whether a single oligonucleotides probe species binding event is to a first or a second target nucleic acid strand, a complete set of obtained optical activity data must be considered. For example, if two tiling series of oligonucleotides probe species cover the locality in question, which of two tiling series a signal belongs to will be assigned based on which series the oligonucleotides probe species sequence generating a signal overlaps with. In some embodiments, a sequence may then be assembled by first using location of binding and sequence overlap to construct each tiling series. Then the two tiling series are aligned as reverse complements and base assignment at each location is accepted only if two strand sequence data are perfect reverse complements at each of those locations (e.g., thus providing duplex consensus sequence).

In some embodiments, a sequencing mismatch is flagged as being an ambiguous base call where one of the two possibilities needs to be corroborated by additional layers of information, such as from independent mismatch binding events. In some embodiments, once duplex consensus has been obtained, a conventional (multi-molecule) consensus is determined by comparing data from other target nucleic acids that cover the same region of a genome (e.g., when binding site information from multiple cells are available). One issue with such an approach is the possibility of different target nucleic acids containing haplotype sequences.

Alternatively, in some embodiments, individual strand consensus is obtained before duplex consensus of individual strand consensus is obtained. In such embodiments, sequence of each strand of the duplex target nucleic acid is obtained concurrently. This is effectuated In some embodiments, without requiring additional sample preparation steps, such differentially tagging strands of a duplex target nucleic acid with molecular barcodes, unlike current NGS methods (e.g., as described by Salk et al., Proc. Natl. Acad. Sci. 109(36), 2012).

Simultaneous sequence acquisition of both sense and antisense strands compares favorably with 2D or $1D^2$ consensus sequencing that is utilized for nanopore sequencing. These alternate methods require sequence to be obtained for one strand of a duplex before sequence of a second strand is obtained. In some embodiments, duplex consensus sequencing may provides accuracy in the $10^6$ range e.g., one error in a million bases (compared to the $10^2$-$10^3$ raw accuracy of other NGS approaches). This makes the method highly compatible with the need to resolve rare variants that indicate a cancer condition (e.g., such as those present in cell-free DNA) or that are present at low frequency in a tumor cell population.

Single-Cell Resolved Sequencing.

In various embodiments, a method may further comprise sequencing the genome of a single cell. In some embodiments, the single cells are free from attachment from other cells. In some embodiments, the single cells are attached to other cells in clusters or in tissue. In some embodiments, such cells are disaggregated into individual non-attached cells.

In some embodiments, the cells are disaggregated before they are fluidically transferred (e.g., by using a pipette) to the inlet of the structure (e.g., flow cell, or microwell) in which the polynucleotides are elongated. In some embodiments, disaggregation is done by pipetting the cells, by applying proteases, sonication or physical agitation. In some embodiments, the cells are disaggregated after they are fluidically transferred into the structure where they elongated.

In some embodiments, the single cell is isolated and the target nucleic acid is released from single cell, such that all target nucleic acids originating from the same cell remain disposed close to one another and at a location that is distinct from the locations where the contents of other cells are disposed. In some embodiments, the trap structures are as described by Di Carlo et al., Lab Chip 6:1445-1449, 2006 are used.

In some embodiments, it is possible to use a microfluidic architecture that either captures and isolates multiple single cells (e.g., in a case where the traps are separate, such as that shown in FIGS. 16A and 16B), or an architecture that captures multiple non-isolated cells (e.g., in a case where the trap is continuous). In some embodiments, the traps are the dimension of single cells (e.g., from 2 μM-10 μM. In some embodiments, the flow cell is several hundreds of microns to millimeters in length, with a depth of ~30 microns.

Figure 17:
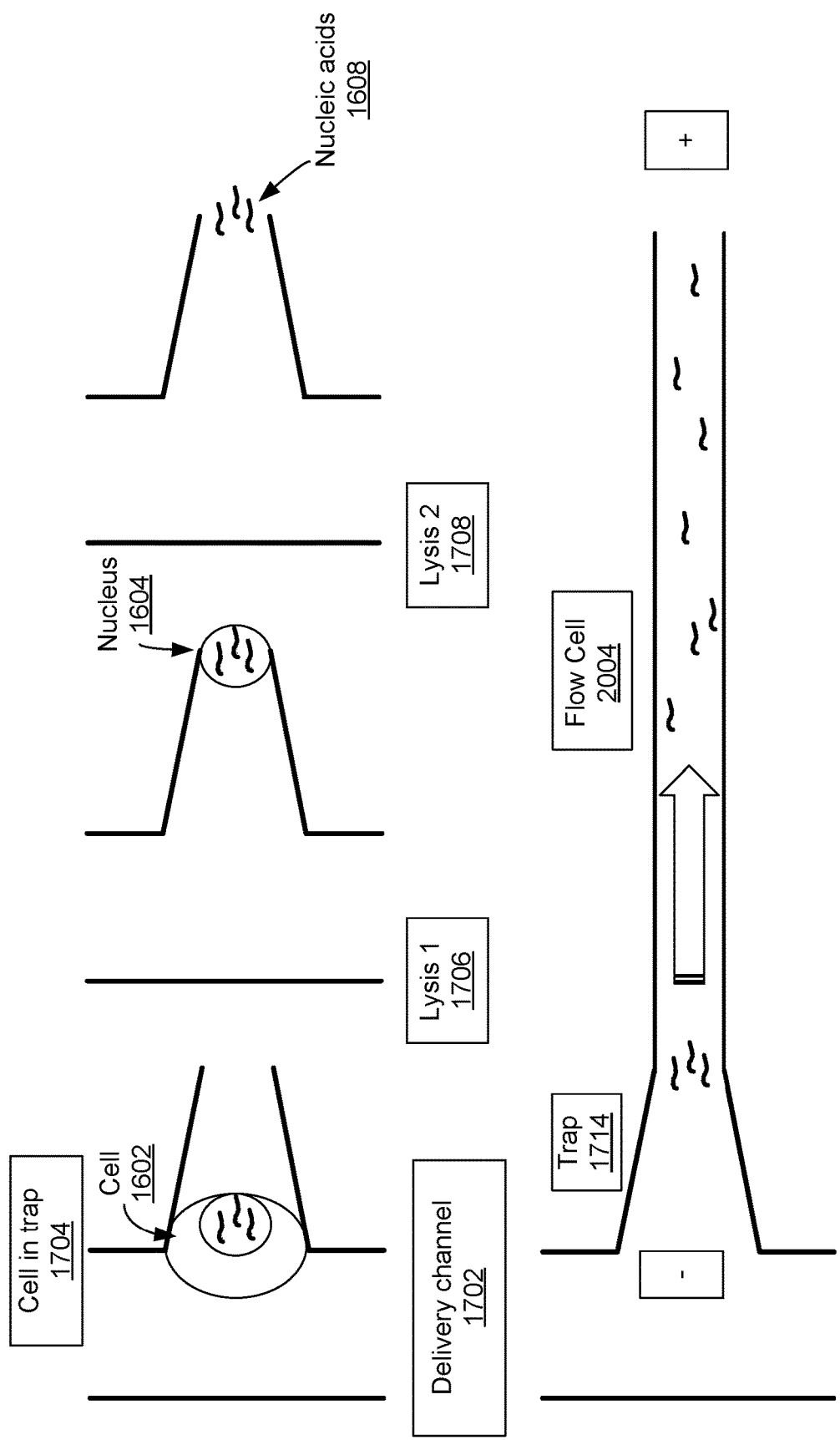
FIG. 17 illustrates an example microfluidic architecture which captures a single cell and optionally provides for extraction, elongation, and sequencing of the nucleic acids from the cell in accordance with various embodiments of the present disclosure.
Figure 18:
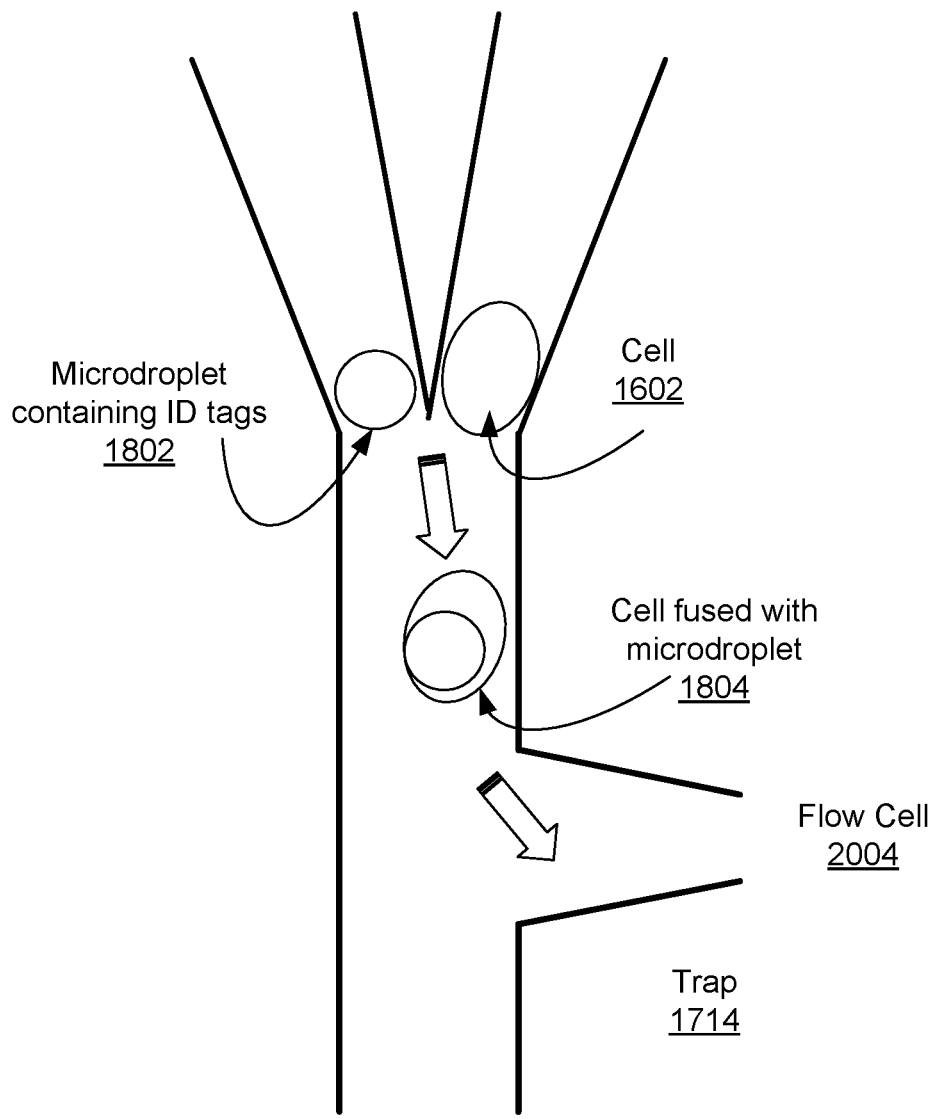
FIG. 18 illustrates an example microfluidic architecture that provides distinct ID tags to individual cells in accordance with various embodiments of the present disclosure.

In some embodiments, for example as shown in FIG. 17, the single cell is flowed into a delivery channel 1702, trapped 1704, and the polynucleotides are released and then elongated. In some embodiments, the cell 1602 is lysed 1706, and then the cell nucleus is lysed through a second lysis step 1708, thus releasing the extracellular and intracellular polynucleotides 1608 sequentially. Optionally, both extra nuclear and intranuclear polynucleotides are released using a single lysis step. After release, the polynucleotides 1608 are immobilized along the length of a flow cell 2004 and elongated. In some embodiments, the traps are the dimension of single cells (e.g., 2 μM-10 μM wide). In one embodiment, the trap dimensions are 4.3 μM-wide at the bottom, 6 μm at middle depth and 8 μm at the top with a depth of 33 μm and the device is made from cyclic olefin (COC) using injection molding.

In some embodiments, the single cell is lysed into an individual channel and each individual cell is reacted with a unique tag sequence via transposase mediated integration, before the polynucleotides are combined and sequenced in the same mixture. In some embodiments, the transposase complex is transfected into cells or is in a droplet merged into a droplet containing the cells.

In some embodiments, the aggregates are small clusters of cells and in some embodiments, the entire cluster is tagged with the same sequencing tag. In some embodiments, the cells are not aggregating and are free floating cells such as circulating tumor cells (CTCs) or circulating fetal cells.

In single cell sequencing there is a problem of cytosine-to-thymine single nucleotide variants caused by spontaneous cytosine deamination after cell lysis. This is overcome by pretreating samples with uracil N-glycosylase (UNG) prior to sequencing (e.g., as described by Chen et al., Mol Diagn Ther. 18(5): 587-593, 2014)

Identifying Haplotypes.

In various embodiments, the methods described above are used for sequencing haplotypes. Sequencing haplotypes includes sequencing a first target nucleic acid spanning a haplotype of a diploid genome using the methods described herein. A second target nucleic acid that spans a second haplotype region of the diploid genome must also be sequenced. The first and second target nucleic acids will be from different copies of a homologous chromosome. The sequences of the first and second target polynucleotides are compared, thereby determining the haplotypes on the first and second target nucleic acids.

Hence, single molecule reads and assemblies that are obtained from the embodiments, are classed as being haplotype-specific. The only case where haplotype-specific information is not necessarily easily obtained over a long range is when assembly is intermittent. In such embodiments, the location of the reads is provided nonetheless.

Even in such a situation, if multiple polynucleotides are analysed that cover the same segment of the genome, the haplotype is determined computationally.

In some embodiments, homologous molecules are separated, according to haplotype or parental chromosome specificity. The visual nature of the information obtained by the methods of the present disclosure, actually physically or visually, is capable of showing a particular haplotype. In some embodiments, the resolution of haplotypes enables improved genetic or ancestry studies to be conducted. In other embodiments, the resolution of haplotypes enables better tissue typing to be done. In some embodiments, the resolution of haplotypes or the detection of a particular haplotype enables a diagnosis to be made.

Sequencing Polynucleotides from Multiple Cells Concurrently.

In various embodiments, the methods described above are used to sequence polynucleotides from a plurality of cells (or nuclei) where each polynucleotide retains information of its cell of origin.

In certain embodiments, transposon mediated sequence insertion is mediated inside the cell, and each insertion comprises a unique ID sequence tag as a label for the cell of origin. In other embodiments, the transposon mediated insertion occurs inside a container in which a single cell has been isolated, such containers comprising, agarose beads, oil-water droplets etc. The unique tag indicates that all the polynucleotides bearing the tag must originate from the same cell. All DNA and or RNA is then extracted, allowed to mix, and elongated. Then when sequencing according to embodiments as described herein (or any other sequencing method) is conducted on a target nucleic acid, the reading of the ID sequence tag indicates which cell a target nucleic acid originates from. In some embodiments, the cell identifying tag is short. For 10,000 cells (e.g., from a tumor microbiopsy), ~65,000 unique sequences are provided by an identifier sequence of eight nucleotides in length and around a million unique sequences are provided by an identifier sequence of ten nucleotides in length.

Figure 19:
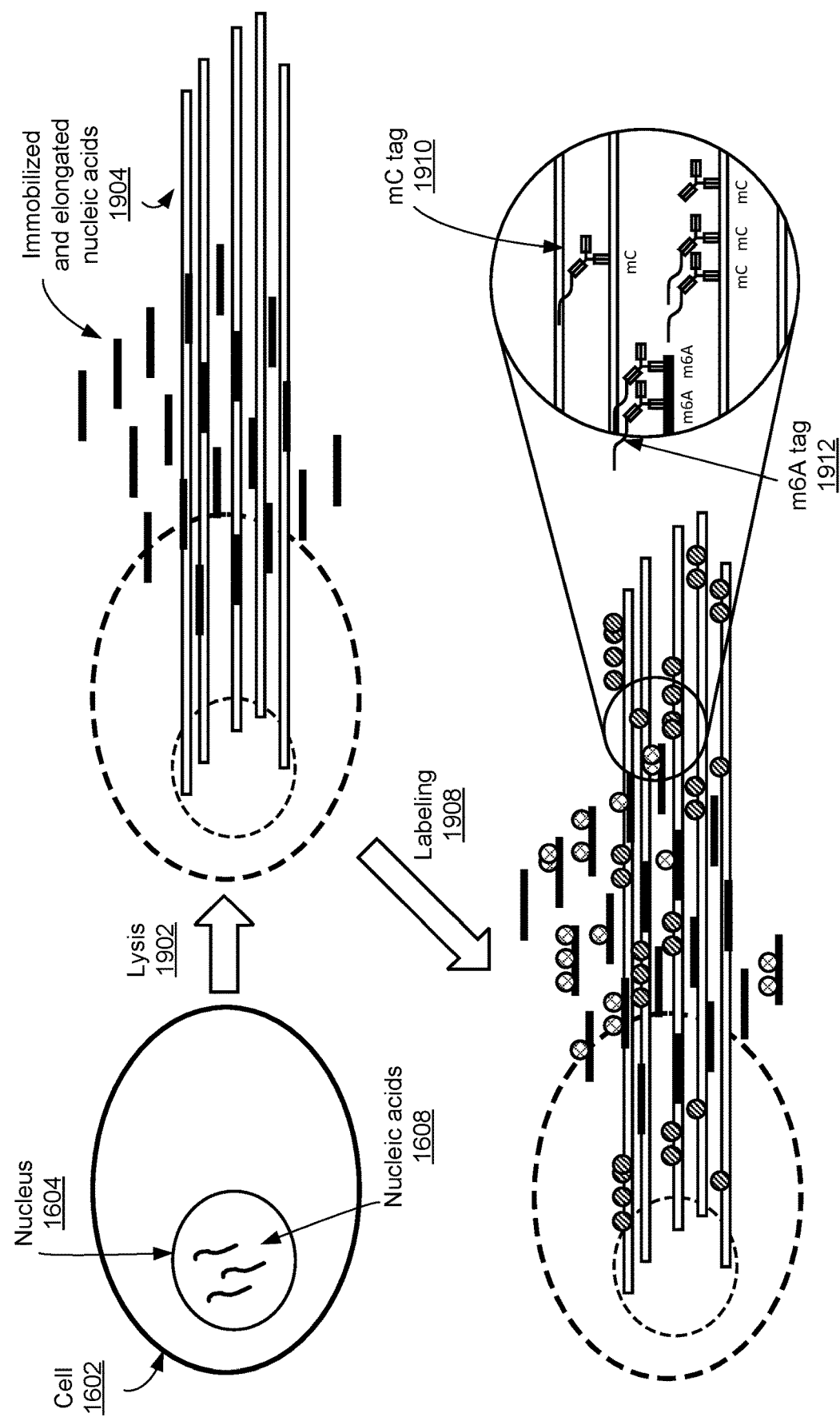
FIG. 19 illustrates an example of sequencing polynucleotides from an individual cell in accordance with various embodiments of the present disclosure.

In some embodiments, individual cells are tagged with identity (ID) tags. As shown in FIG. 19, In some embodiments, the identity tags integrate into the polynucleotides by tagmentation, for which reagents are provided directly to the single cell or in a microdroplet that merges with or engulfs the cell 1802. Each cell receives a different ID tag (from a large set e.g., greater than a million possible tags). After the microdroplet and the cell have fused 1804, the ID tags are integrated into the polynucleotides within individual cells. The contents of the individual cells are mixed within the flow cell 2004. Sequencing (e.g., by methods disclosed herein) then reveals which cell a particular target nucleic acid originates from. In alternative embodiments, the microdroplet engulfs the cell and delivers the tagging reagents to the cell (e.g., by diffusing into the cell or bursting the cell contents into the microdroplet).

This same indexing principle is applied to samples other than cells (e.g., from different individuals) when the aim is to mix the samples, sequence them together, but to recover the sequence information pertaining to each individual sample.

Further, when multiple cells are sequenced, it is possible to determine the haplotype diversity and frequency in the cell population. In some embodiments, the heterogeneity of genomes in a population is analyzed without the need to keep the content of single cells together because, if molecules are long enough, the different chromosomes, long chromosomes segments or haplotypes that are present in the population of cells is determined. Although this does not indicate which two haplotypes are present in a cell together, it does report on the diversity of genomic structural types (or haplotypes) and their frequency and which aberrant structural variants are present.

In some embodiments, when the target nucleic acid is RNA and a cDNA copy is sequenced, addition of the tag comprises cDNA synthesis with a primer containing the tag sequence. Where RNA is sequenced directly, a tag is added by ligation of the tag to the 3' RNA termini using T4 RNA Ligase. An alternative method of generating the tag is to extend the RNA or DNA with terminal transferase with more than one nucleotide of the four A, C, G and T bases, so that each individual polynucleotide, stochastically, gets a unique sequence of nucleotides tailed thereon.

In some embodiments, in order to keep the amount of tag sequence to be kept short, so that more of the sequence read is devoted to sequencing the polynucleotide sequence itself, the tag sequence is distributed over a number of sites. Here multiple short identifier sequences, say three, are introduced into each cell or container. Then the origin of the polynucleotide is determined from the bits of the tag that are distributed along the polynucleotide. So in this case the bit of the tag read from one location is not sufficient to determine the cell of origin, but multiple tag bits are sufficient to make the determination.

Detection of Structural Variants.

In some embodiments, the differences between the detected sequence and the reference genome comprise substitutions, indels and structural variations. In particular, when the reference sequence has not been assembled by the methods of the present disclosure, repeats are typically compressed, and the assembly will decompress repeats.

In some embodiments, the orientation of a series of sequence reads along the polynucleotide will report on whether an inversion event has occurred. One or more reads in the opposite orientation to other reads compared to the reference, indicates an inversion.

In some embodiments, the presence of one or more reads that is not expected in the context of other reads in its vicinity indicates a rearrangement or translocation compared to reference. The location of the read in the reference indicates which part of the genome has shifted to another. In some cases, the read in its new location is a duplication rather than a translocation.

In some embodiments, it is also possible to detect repetitive regions or copy number variations. The repeated occurrence of a read or related read carrying paralogous variation is observed as multiple or very similar reads occurring at multiple locations in the genome. These multiple locations are packed close together in some instances (e.g., as in satellite DNA) or they are dispersed across the genome in other cases (e.g., as in pseudogenes). The methods of the present disclosure are applied to the Short Tandem Repeats (STRS), variable number of tandem repeats (VNTR), trinucleotide repeats, etc. The absence or repetition of specific reads indicates that a deletion or amplification, respectively has occurred. In some embodiments, methods as described herein are particularly applied in cases where there are multiple and/or complex rearrangements in a polynucleotide. Because methods as described herein are based on analysing single polynucleotides, in some embodiments, the structural variants described above are resolved down to a rare occurrence in small numbers of cells for example, just 1% of cells from a population.

Similarly, in some embodiments, segmental duplications or duplicons are correctly localized in the genome. Segmental duplicons are typically long regions in a DNA sequence (e.g., greater than 1 kilobase in length) of nearly identical sequence. These segmental duplications cause a lot of the structural variation in individual genomes, including somatic mutations. Segmental duplicons may exist in distal parts of the genome. In current next generation sequencing, it is difficult to determine which segmental duplicon a read arises from (thus complicating assembly). In some embodiments, of the present disclosure, sequence reads are obtained over long molecules (e.g., 0.1-10 Megabase length range), and it is usually possible to determine the genomic context of a duplicon by using the reads to determine which segments of the genome are flanking the particular segment of the genome corresponding to the duplicon.

Breakpoints of structural variants are localized precisely In some embodiments, of the present disclosure. In some embodiments, it is possible to detect that two parts of the genome have fused, and the precise individual read at which the breakpoint has occurred is determined. Sequence reads, collected as described herein, comprise a chimera of the two fused regions, all the sequences on one side of the breakpoint will correspond to one of the fused segments and the other side is the other of the fused segments. This gives high confidence in determining a breakpoint, even in cases where the structure is complex around breakpoint. In some embodiments, the precise chromosomal breakpoint information is used in understanding a disease mechanism, in detecting the occurrence of a specific translocation, or in diagnosing a disease.

Localization of Epigenomic Modifications.

In some embodiments, the method further comprises exposing the fixed double strand target nucleic acid or fixed first strand and the fixed second strand of a native duplex target nucleic acid to an antibody, affimer, nanobody, aptamer, or methyl-binding protein to thereby determine a modification to the nucleic acid or to correlate with the sequence of the portion of the nucleic acid from the plurality of sets of positions on the test substrate. Some antibodies bind to double strand or single strand. Methyl binding proteins would be expected to bind double stranded polynucleotides, as they do in chromatins.

In some embodiments, the native polynucleotides require no processing before they are displayed for sequencing. This allows the method to integrate epigenomic information with sequence information, as the chemical modifications of DNA will stay in place. In some embodiments, the polynucleotides are directionally well aligned and therefore relatively easy to image, image process, base call and assemble; the sequence error rate is low and coverage is high. A number of embodiments for carrying out the present disclosure are described but each is done so that the burden of sample preparation is wholly or almost wholly eliminated.

Because these methods are performed on genomic DNA without amplification, in some embodiments, they do not suffer from amplification bias and error, and epigenomic marks are preserved and are detected (e.g., orthogonally to the acquisition of sequence). In some cases, it is useful to determine in a sequence-specific manner if the nucleic acid is methylated. For example, one way of differentiating fetal from maternal DNA is the former is methylated in loci of interest. This is useful for non-invasive prenatal testing (NIPT).

Multiple types of methylation are possible, such as alkylation of carbon-5 (C5), which yields several cytosine variants in mammals, C5-methylcytosine (5-mC), C5-hydroxymethylcytosine (5-hmC), C5-formylcytosine, and C5-carboxylcytosine. Eukaryotic and prokaryotic organisms also methylate adenine to N6-methyladenine (6-mA). In prokaryotes, N4-methylcytosine is also prevalent.

Antibodies are available or are raised against each of these modifications as well as any others that are construed as of interest. Affimers, Nanobodies or Aptamers that target the modifications are particularly relevant due to the possibility of a smaller footprint. Any reference to antibody in this invention should be construed as including Affimers, Nanobodies, Aptamers and any similar reagents. In addition, other, naturally occurring DNA binding proteins, e.g., methyl proteins (MBD1, MBD2, etc.) are used in some embodiments.

Methylation analysis is carried out orthogonally to the sequencing in some embodiments. In some embodiments, this is done before sequencing. As an example, anti-methyl C antibodies or methyl binding proteins (Methyl binding domain (MBD) protein family comprise MeCP2, MBD1, MBD2 and MBD4) or peptides (based on MBD1) are bound to the polynucleotides in some embodiments, and their location detected via labels before they are removed (e.g., by adding high salt buffer, chaotrophic reagents, SDS, protease, urea and/or Heparin). In some embodiments, the reagents may bind transiently, due to use of a transient binding buffer that promotes on-off binding or the reagents are engineered to bind transiently. Similar approaches are used for other polynucleotide modifications, such as hydroxymethylation or sites of DNA damage, for which antibodies are available or are raised. After the locations of the modifications have been detected and the modification binding reagents are removed, sequencing commences. In some embodiments, the anti-methyl and anti-hydroxymethyl antibodies etc. are added after the target polynucleotide is denatured to be single stranded. The method is highly sensitive and is capable of detecting a single modification on a long polynucleotide.

FIG. 19 illustrates the extraction and stretching of DNA and RNA from a single cell and differential labeling of DNA and RNA (e.g., with antibodies to mC and m6A, respectively). The cell 1602 is immobilized on a surface and then lysed 1902. The nucleic acids 1608, which are released from the nucleus 1604 by the lysis, are immobilized and elongated 1904. The nucleic acids are then exposed to and bound by antibodies with appended DNA tags 1910 and 1912. In some embodiments, the tags are fluorescent dyes or oligonucleotide docking sequences for DNA PAINT-based single molecule localization. In some embodiments, instead of using tags and DNA PAINT, the antibodies or other binding proteins are directly fluorescently labeled, either with a single fluorescent label or multiple fluorescent labels. In the case where the antibodies are encoded, one example of the labelling is as shown in FIGS. 14A, 14C and 14D. The epi-modification analysis of both DNA and RNA is coupled with their sequence using the sequencing methods described herein in some embodiments.

In some embodiments, in addition to detecting methylation by binding proteins, the presence of methylation in a binding site is detected by the differential oligonucleotide binding behavior when a modification is present in the target nucleic acid site compared to when it is not.

In some embodiments, bisulfite treatment is used to detect methylation. Here, after running through a complete set of oligonucleotide probe species, bisulfite treatment is used to convert unmethylated cytosine to uracil and then a complete set of oligonucleotide probe is applied again. When a nucleotide position that before bisulfite treatment is read as a C, is read as a U after bisulfite treatment it can be deemed to be unmethylated.

There are no reference epigenomes for DNA modifications such as methylations. In order to be useful, the methylation map of an unknown polynucleotide needs to be linked to a sequence based map. Thus the epi-mapping methods are correlated to sequence bits obtained by oligo binding, in order to provide context to the epi-map, in some embodiments. In addition to sequence reads, other kinds of methylation information are also coupled in some embodiments. This includes, as non-limiting examples, nicking endonuclease based maps, oligonucleotide probe species-binding based maps, and denaturation and denaturation-renaturation maps. In some embodiments, transient binding of one or more oligonucleotide probe species is used to map the polynucleotides. In addition to functional modifications to the genome, the same approach is applied to other features that map on to the genome, in some embodiments, such as sites of DNA damage and protein or ligand binding.

In the present disclosure, either the base sequencing or the epigenomic sequencing is performed first. In some embodiments, both are done at the same time. For example, antibodies against specific epi-modification are differentially coded from oligos in some embodiments. In such embodiment, conditions are used (e.g., low salt concentrations) that facilitate transitory binding of both types of probes.

In some embodiments, when the polynucleotide comprises chromosome or chromatin, antibodies are used on chromosomes or chromatin to detect modifications on DNA and also modifications on histones (e.g., histone acetylation and methylation). The location of these modifications is determined by the transient binding of the antibodies to locations on the chromosome or chromatin. In some embodiments, the antibodies are labeled with oligo tags and do not bind transiently but rather are fixed permanently or semi-permanently to their binding site. In such embodiments, the antibody will include an oligo tag, and the locations of these antibody binding sites are detected by using transient binding of complementary oligos to oligos on the antibody tags.

Isolation and Analysis of Cell-Free Nucleic Acid.

Some of the most accessible DNA or RNA for diagnostics is found outside of cells in body fluids or stool. Such nucleic acids have often been shed by cells in the body. Cell-free DNA circulating in blood is used for pre-natal testing for trisomy 21 and other chromosomal and genomic disorders. It is also a means to detect tumor-derived DNA and other DNA or RNA that are markers for certain pathological conditions. However, the molecules are typically present in small segments (e.g., in the ~200 base pair length range in blood and even shorter in urine). The copy number of a genomic region are determined by comparison to the number of reads that align to particular regions of the reference compared to other parts of the genome.

In some embodiments, the methods of the present disclosure are applied to the enumeration or analysis of cell free DNA sequences by two approaches. The first involves immobilizing the short nucleic acid before or after denaturation. Transiently binding reagents are used to interrogate the nucleic acid in order to determine the identity of the nucleic acid, its copy number, whether mutations or certain SNP alleles are present, and whether the sequence detected is methylated or bears other modifications (biomarkers).

The second approach involves concatenating the small nucleic acid fragments (e.g., after the cell-free nucleic acid has been isolated from a biological sample). Concatenation enables stretching out the combined nucleic acid. Catenation is done by polishing the ends of the DNA and performing blunt end-ligation. Alternatively, the blood or the cell free DNA is split into two aliquots and one aliquot is tailed with poly A (using Terminal Transferase) and the other aliquot is tailed by poly T.

The resulting concatamers are then subjected to sequencing. The resulting "super" sequence read is then compared to reference to extract individual reads. The individual reads are computationally extracted and then processed in the same manner as other short reads.

In some embodiments, the biological sample comprises stool, a medium that contains a high number of exonucleases that degrade nucleic acids. In such embodiments, high concentrations of chelators of divalent cations (e.g., EDTA), which are needed by exonucleases to function, is employed to keep the DNA sufficiently intact and enable sequencing. In some embodiments, the cell-free nucleic acid is shed from cells via encapsulation in exosomes. Exosomes are isolated by ultracentrifugation or by using spin columns (Qiagen), and the DNA or RNA contained therein is collected and sequenced.

In some embodiments, methylation information is obtained from cell-free nucleic acid, according to methods described above.

Combining Sequencing Technologies.

In some embodiments, the methods described herein are combined with other sequencing techniques. In some embodiments, following sequencing by transient binding, sequencing by a second method is initiated on the same molecules. For example, longer more stable oligonucleotides are bound to initiate sequencing by synthesis. In some embodiments, the methods stop short of being a complete genome sequencing and are used to provide a scaffold for short read sequencing such as that from Illumina. In this case it is advantageous to conduct Illumina library prep by excluding the PCR amplification step to obtain a more even coverage of the genome. One advantage of some of these embodiments, that fold coverage of sequencing required is halved from about 40× to 20× for example. In some embodiments, this is due to the addition of sequencing done by the methods and the locational information that methods described herein provide. In some embodiments, longer more stable oligos, which are optionally optically labeled, can be bound to the target to mark out specific regions of interest in the genome (e.g., the BRCA1 loci) before or concurrently (which is differently labeled) with the short sequencing oligos through part or whole of the sequencing process.

Machine Learning Methods.

In some embodiments, artificial intelligence or machine learning is used to learn the behavior of the members of a complete set of oligonucleotide probes species when tested against polymers (e.g., polynucleotides) of known sequence and/or when the sequence of the polynucleotide is cross-validated with data from another method. In some embodiments, the learning algorithm takes into account the full behavior of a particular oligonucleotide probe species against one or more polynucleotide targets containing binding sites for the oligonucleotide probe species in one or more conditions or contexts. As more sequencing is done on the same or different samples, the more robust the knowledge from machine learning becomes. What is learned from machine learning is applied to various other assays, in particularly those involving interactions of oligos with oligos/polynucleotides (e.g., sequencing by hybridization), in addition to the transient binding-based emergent sequencing.

In some embodiments, artificial intelligence or machine learning is trained by providing data of the binding patterns experimentally obtained for binding of a complete set of short oligos (e.g., 3-mer, 4-mer, 5-mer, or 6-mer) to one or more polynucleotides of known sequence. The training data for each oligo comprises, binding locations, duration of binding and the number of binding events over given period. After this training, the machine learning algorithm is applied to a polynucleotide of sequence to be determined and based on its learning can assemble the sequence of the polynucleotide. In some embodiments, the machine learning algorithm is also provided a reference sequence.

In some embodiments, the sequence assembly algorithm comprises both a machine learning element and a non-machine learning element.

In some embodiments, instead of the computer algorithm learning from the experimentally obtained binding patterns, the binding patterns are obtained via simulations. For example, in some embodiments, simulations are done of the transient binding of oligonucleotide probe species of a complete set of oligonucleotide probe species to the polynucleotide of known sequence. The simulations are based on a model of the behavior of each oligonucleotide probe species sequence obtained from experimental or published data. For example, the prediction of binding stability is available according to the nearest neighbor method (e.g., as described in SantaLucia et al., Biochemistry 35, 3555-3562 (1996) and Breslauer et al., Proc. Natl. Acad. Sci. 83: 3746-3750, 1986). In some embodiments, the mismatching behavior is known (e.g., G mismatch binding to A can be as strong or stronger interaction than T to A) or experimentally derived. Further, in some embodiments, the inordinately high binding strength of some short sub-sequence of oligos (e.g., GGA or ACC) are known. In some embodiments, the machine learning algorithm is trained on the simulated data and then used to determine the sequence of an unknown sequence when it is interrogated by a complete set of short oligos.

In some embodiments, the data (location, binding duration, signal intensity, etc.) of oligos of a complete set of oligonucleotide probe species or panel are plugged into a machine learning algorithm, that has been trained on one or tens, or hundreds or thousands of known sequences. The machine learning algorithm is then applied to generate a data-set from a sequence in question and the machine learning algorithm generates the sequence of the unknown sequence in question. The training of the algorithm for sequencing of organisms will relatively smaller or less complex genomes (e.g., for bacteria, bacteriophage etc.) should be performed on organisms of that type. For organisms with larger or more complex genomes (e.g., S. pombe or humans), particularly those with repetitive DNA regions, the training should be performed on organisms of that type. For long-range assembly of megabase fragments to whole chromosome lengths, the training is performed on similar organisms in some embodiments, so that particular aspects of the genomes are represented during the training. For example, human genomes are diploid and exhibit large sequence regions with segmental duplication. Other genomes of interest, in particular many agriculturally important plant species have highly complex genomes. For example, wheat and other grains have highly polyploidal genomes.

In some embodiments, a machine learning based sequence assembly approach comprises: (a) providing information on the binding behavior of each oligonucleotide probe species in a complete set of oligonucleotide probe species gleaned from one or more training data-sets and (b) providing for physical binding each oligonucleotide probe species of a complete set of oligonucleotide probe species to a target nucleic acid whose sequence is to be determined and (c) providing information on binding location, and/or binding duration and/or the number of times binding occurs at each location for each oligonucleotide probe species (e.g., persistence of binding repetition).

In some embodiments, the sequence of a particular experiment is first processed by a non-machine learning algorithm. Then the output sequence of the first algorithm is used to train the machine learning algorithm, so that the training occurs on actual experimentally derived sequence of the same exact molecules. In some embodiments, the sequence assembly algorithm comprises a Bayesian approach. In some embodiments, data derived from the methods of the present disclosure are furnished to an algorithm of the type described in WO2010075570 and are optionally combined with other types of genomic or sequencing data.

In some embodiments, the sequence is extracted from the data in a number of ways. At one end of the spectrum of sequence assembly methods the localization of a monomer or a string of monomers is so precise (nanometric or sub-nanometric) that the sequence is obtained by just ordering the monomers or strings. At the other end of the spectrum the data is used to rule out various hypotheses about the sequence. For example, one hypothesis is that the sequence corresponds to a known individual genome sequence. The algorithm determines where the data diverges from the individual genome. In another case the hypothesis is that the sequence corresponds to a known genome sequence for a "normal" somatic cell. The algorithm determines where the data from a putative tumor cell diverges from the sequence of the "normal" somatic cell.

In one embodiment of the present disclosure, a training set comprising one or more known target nucleic acids (e.g., lambda phage DNA or a synthetic construct comprising a super sequence comprising complements to each oligonucleotide probe species in a complete set of oligonucleotide probe species) are used for tested iterative binding of each oligonucleotide probe species from a complete set of oligonucleotide probe species. Machine learning algorithms are used In some embodiments, to determine the binding and mismatching characteristics of the oligonucleotide probe species. Thus counter-intuitively, mismatch binding is seen as a way of providing further data that is used to assemble and/or add confidence to the sequence.

Sequencing Instrumentation and Device.

The sequencing methods have common instrumentation requirements. Basically the instrument must be capable of imaging and exchanging reagents. The imaging requirement includes: one or more from the group: objective lens, relay lens, beam-splitter, mirror, filters and a camera or point detector. The camera or imager includes a CCD, array CMOS, or avalanche photodiode array detector. The point detector includes a Photomultiplier Tube (PMT) or Avalanche Photodiode (APD). In some cases, a high speed camera is used. Other optional aspects are adjusted depending on the format of the method. For example, the illumination source (e.g., lamp, LED or laser), the coupling of the illumination to the substrate (e.g., a prism, waveguide, photonic nanostructure, grating, sol-gel, lens, translatable stage or translatable objective), the mechanism for moving the sample in relation to the imager, sample mixing/agitation, temperature control and electrical controls are each independently adjusted for different embodiments disclosed herein.

For the single molecule implementations, the illumination may utilize evanescent waves, via e.g., prism-based total internal reflection, objective-based total internal reflection, plasmonic waveguide, grating-based waveguide, hydrogel based waveguide or an evanescent waveguide created by bringing laser light into the edge of the substrate at a suitable angle. In some embodiments, the waveguide includes a core layer and a first cladding layer. The illumination alternatively comprises HILO illumination or a light sheet. In some single molecule instruments, the effects of light scatter are mitigated by using synchronization of pulsed illumination and time-gated detection; here light scattering is gated out. In some embodiments, dark field illumination is used. Some instruments are set up for fluorescence lifetime measurements.

In some embodiments, the instrument also contains means for extraction of the polynucleotide from cells, nuclei, organelles, chromosome etc.

A suitable instrument for most embodiments is the Genome Analyzer IIx from Illumina. This instruments comprises Prism-based TIR, a 20× Dry Objective, a light scrambler, a 532 nm and 660 nm laser, an infrared laser based focusing system, an emission filter wheel, a Photometrix CoolSnap CCD camera, temperature control and a syringe pump-based system for reagent exchange. Modification of this instrument with an alternative camera combination enables better single molecule sequencing in some embodiments. For example, the sensor have low electron noise, <2 e. Also the sensor has a large number of pixels. The syringe-pump based reagent exchange system is replaced by one based on pressure-driven flow in some embodiments. The system is used with a compatible Illumina flow cell or with a custom-flow cell adapted to fit the actual or modified plumbing of the instrument in some embodiments.

Alternatively, a motorized Nikon Ti-E microscope coupled with a laser bed (lasers dependent on choice of labels) or the laser system and light scrambler from the genome analyzer, a EM CCD camera (e.g., Hamamatsu ImageEM) or a scientific CMOS (e.g., Hamamatsu Orca FLASH) and optionally temperature control is used. In some embodiments, a consumer rather than scientific sensor is used. This has the potential to reduce the cost of sequencing dramatically. This is coupled with a pressure driven or syringe pump system and a specifically designed flow cell. In some embodiments, the flow cell is fabricated in glass or plastic, each having advantages and disadvantages. In some embodiments, the flow cell is fabricated using cyclic olefin copolymer (COC), e.g., TOPAS, other plastics, or PDMS or in silicon or glass using microfabrication methods. In some embodiments, injection molding of thermoplastics provides a low-cost router to industrial scale manufacture. In some optical configurations, the thermoplastic needs to have good optical properties with minimal intrinsic fluorescence. Polymers containing aromatic or conjugated systems should ideally be excluded since they are expected to have a significant intrinsic fluorescence. Zeonor 1060R, Topas 5013, and PMMA-VSUVT (e.g., as described in U.S. Pat. No. 8,057,852) have been reported to have reasonable optical properties in the green and red wavelength range (e.g., for Cy3 and Cy5), with Zeonar 1060R having the most favorable properties. In some embodiments, it's possible to bond thermoplastics over a large area in a microfluidic device (e.g., as reported by Sun et al., Microfluidics and Nanofluidics, 19(4), 913-922, 2015). In some embodiments, the glass cover glass onto which the biopolymers are attached is bonded to a thermoplastic fluidic architecture.

Alternatively, a manually operated flow cell is used atop the microscope. This is constructed In some embodiments, by making a flow cell using a double-sided sticky sheet, laser cut to have channels of the appropriate dimensions and sandwiched between a coverslip and a glass slide. From one reagent exchange cycle to another the flow cell can remain on the instrument/microscope, to registration from frames to frame. A motorized stage with linear encoders is used to ensure when the stage is translated during imaging of a large area, in some embodiments. The same locations are correctly revisited. Fiduciary markers are used to endure correct registration. In some embodiments, fiduciary markings such as etchings in the flow cell or surface immobilized beads is provided within the flow cell that are optically detected. If the polynucleotide backbone is stained (for example, by YOYO-1) those fixed, known positions are used to align images from one frame to the next.

In one embodiment, the illumination mechanism (e.g., such as that described in U.S. Pat. No. 7,175,811 and by Ramachandran et al., Scientific Reports 3:2133, 2013) that uses laser or LED illumination is coupled with an optional heating mechanism and reagent exchange system to carry out the methods described herein. In some embodiments, a smartphone based imaging set up (ACS Nano 7:9147) is coupled with an optional temperature control module and a reagent exchange system. In such embodiments, it is principally the camera on the phone that is used, but other aspects such as illumination and vibration capabilities of an iPhone or other smartphone device can also be used.

Figure 20A:
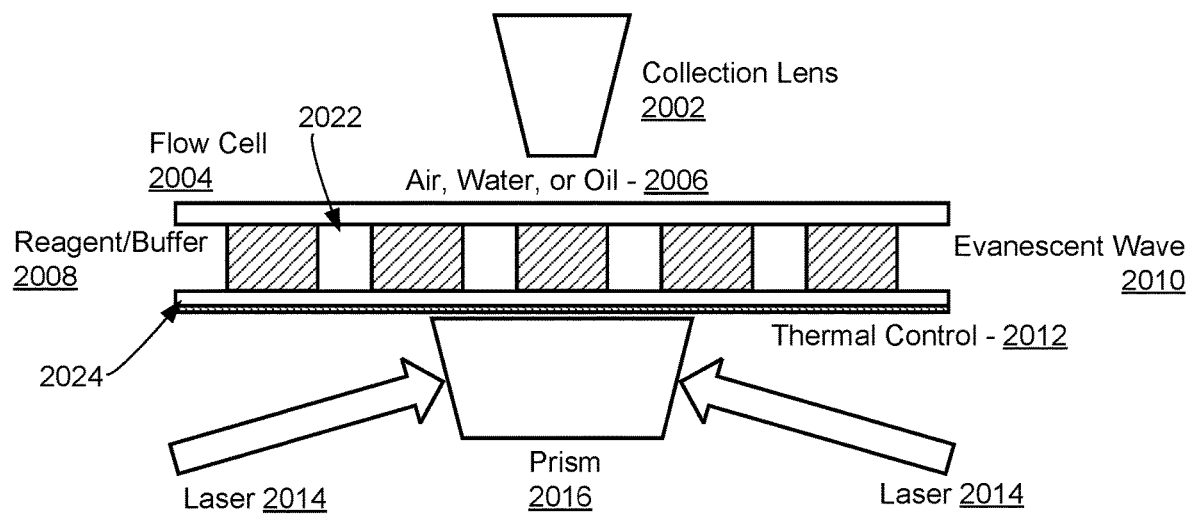
FIGS. 20A and 20B collectively illustrate example device layouts for performing imaging of transient probe binding in accordance with various embodiments of the present disclosure.
Figure 20B:
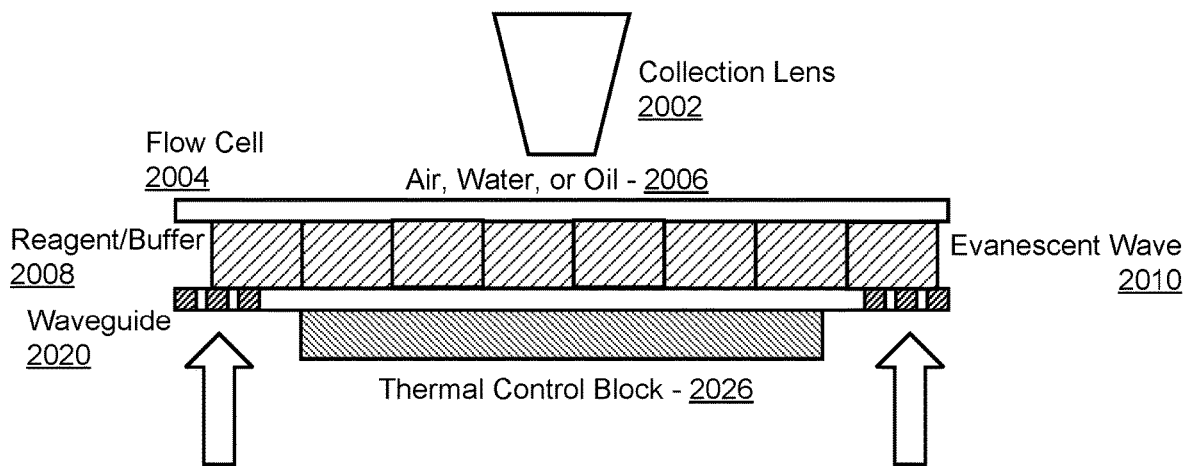

FIGS. 20A and 20B illustrate a possible device for performing imaging of transient probe binding as described herein, using a flow cell 2004 and an integrated optical layout. Reagents are delivered as packets of reagents/buffers 2008 separated by air gaps 2022. FIG. 20A illustrates an example layout where an evanescent wave 2010 is created via coupling laser light 2014 that is transmitted through a prism 2016 (e.g., a TIRF setup). In some embodiments, the temperature of the reaction is controlled by an integrated thermal control 2012 (e.g., in one example the transparent substrate 2024 comprises indium tin oxide electrically coupled and thus altering the temperature of the overall substrate 2024). Reagents are delivered as a continuous flow of reagents/buffers 2008. A grating, waveguide 2020 or photonic structure is used to couple laser light 2014 to create an evanescent field 2010. In some embodiments, thermal control is from a block 2026 that covers the space.

Figure 21:
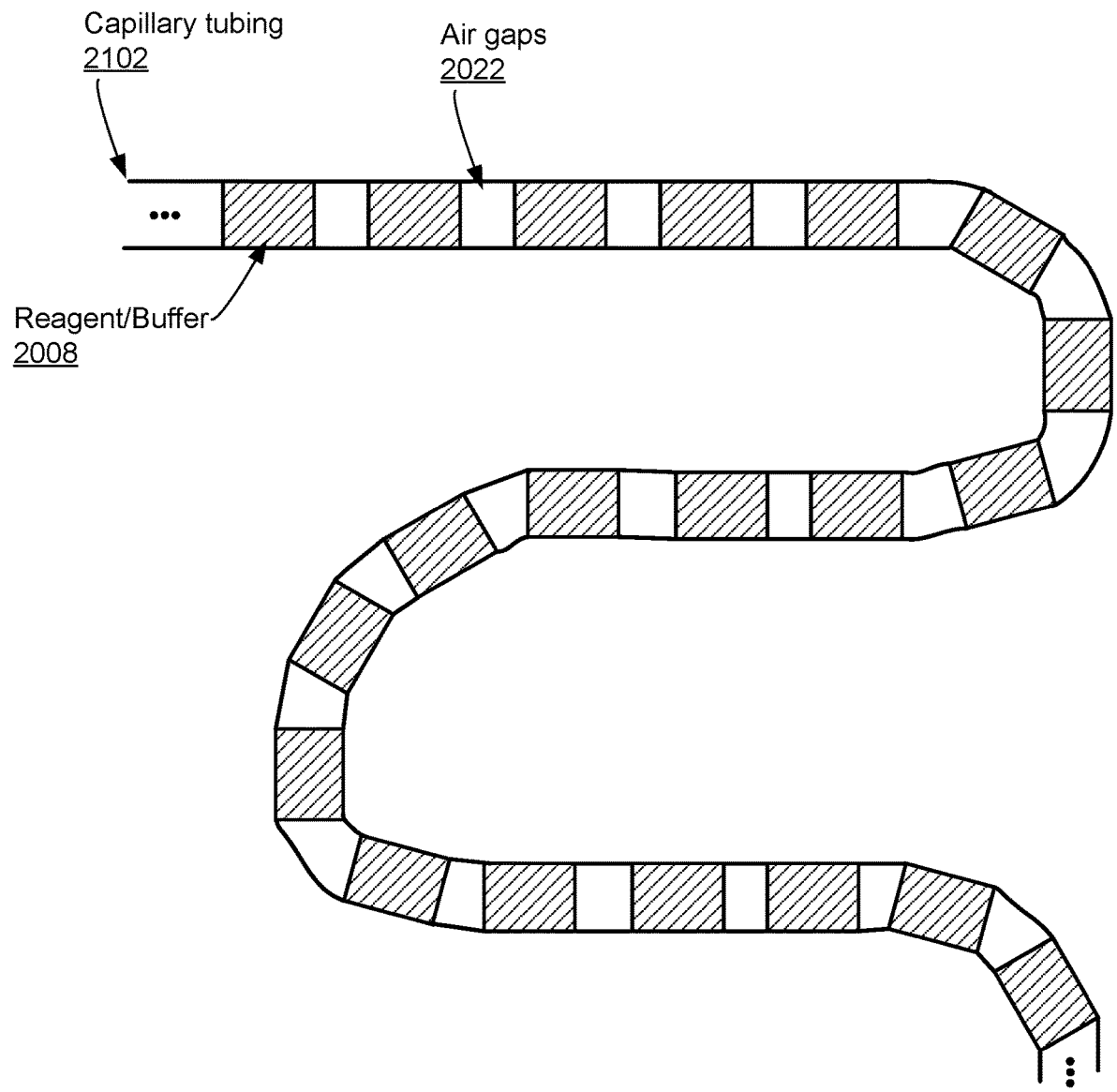
FIG. 21 illustrates an example capillary tubing containing reagents separated by air gaps in accordance with various embodiments of the present disclosure.
Figure 22B:
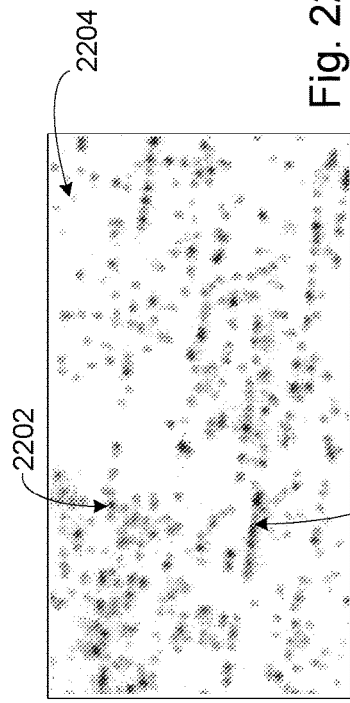
FIGS. 22A, 22B, 22C, 22D, and 22E collectively illustrate examples of fluorescence in accordance with various embodiments of the present disclosure.
Figure 22C:
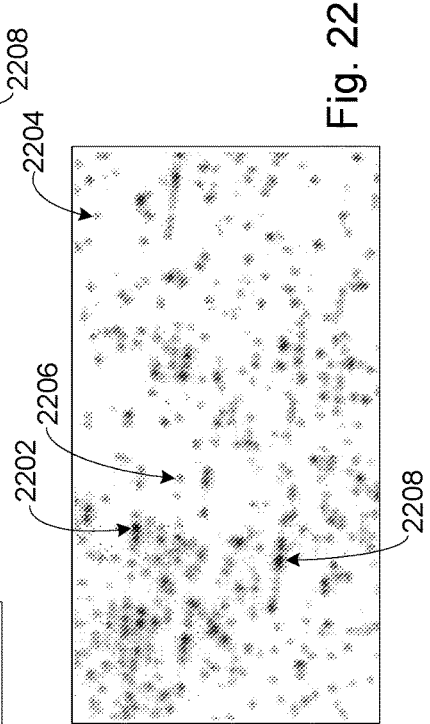
Figure 22E:
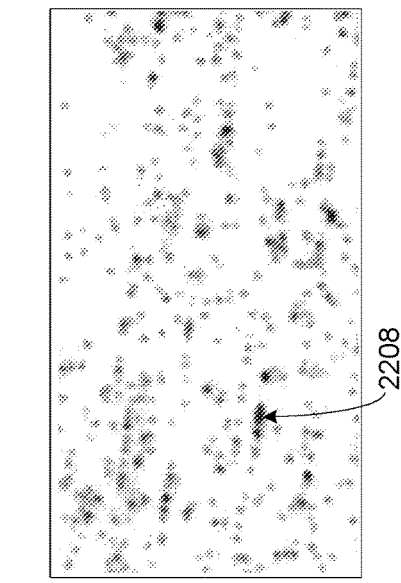
Figure 22A:
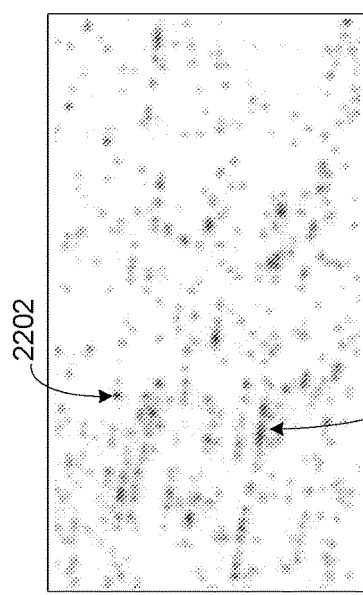
Figure 22D:
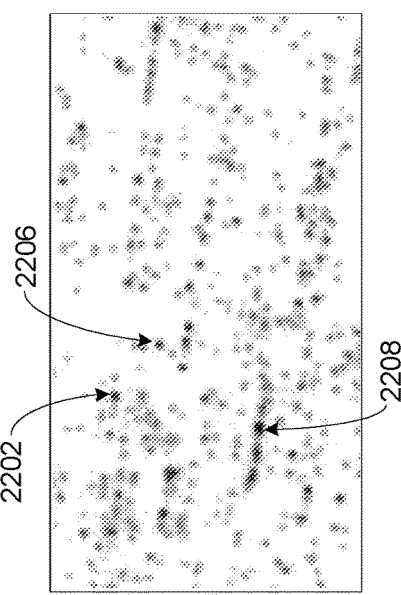
Figure 27:
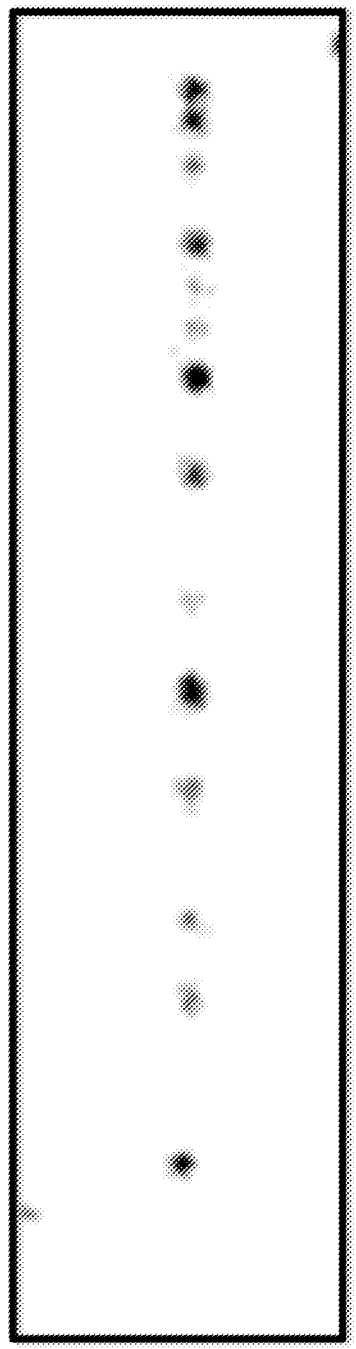
FIG. 27 illustrates binding of an oligo with three defined bases flanked by four degenerate positions on each side, 5' cy3 NNgGcNN (oligo name: 3004-3mer). The stretched DNA is lambdaphage which has been denatured by 0.5M NaOH for 20 minutes. The binding buffer is 4×SSC and 0.1% Tween 20; binding was done at 4 degrees C. and imaging was done at room temperature.

Aspects of the layout described in FIG. 20A are interchangeable with aspects of the layout described in FIG. 20B. For example, objective style TIRF, light guide TIRF, condenser TIRF can alternatively be used. The continuous or air-gapped reagent delivery is controlled by a syringe pump or a pressure driven flow in some embodiments. The air-gapped method allows all the reagents 2008 to be pre-loaded in capillary/tubing 2102 (e.g., as illustrated in FIG. 21) or channels and delivered by a push or pull from syringe pump or pressure control system. The air-gapped method allows all the reagents to be pre-loaded in capillary/tubing or channels and delivered by a push or pull from syringe pump or pressure control system. The air gap 2022 comprises air or a gas such as nitrogen or a liquid that is immiscible with the aqueous solution. The air gaps 2022 can also be used to conduct molecular combing as well as reagent delivery. A fluidic device (e.g., a fluidic vessel, cartridge, or chip) comprises the flow cell area where polynucleotide immobilization and optionally elongation is conducted, reagent storing, inlet, outlets and polynucleotide extraction as well as optional structures to shape the evanescent field. In some embodiments, the device is made of glass, plastic or a hybrid of glass and plastic. In some embodiments, thermal and electrical conductivity elements (e.g., metallic) are integrated into the glass and/or plastic components. In some embodiments, the fluidic vessel is a well. In some embodiments, the fluidic vessel is a flow cell. In some embodiments, the surface is coated with one or more chemical layers, biochemical layers (e.g., BSA-biotin, streptavidin), a lipid layer, a hydrogel, or a gel layer. Then a 22×22 mm cover glass coated in vinylsilane (BioTechniques 45:649-658, 2008 or available from Genomic Vision) or cover glass spin-coated with 1.5% Zeonex in chlorobenzene solution. The substrate can also be coated with 2% 3-aminopropyl-triethoxysilane (APTES) or Poly Lysine, and stretching occurs via electorstatic interactions at pH 7.5-8 in HEPES buffer. Alternatively, silanated coverglass spin- or dip-coated in 1-8% polyacrylamide solution containing bis-acrylamide and temed. For this as well as using vinylsilane coated coverglass, cove glass can be coated with 10% 3-methacryloxypropyltrimethoxysilane (Bind Silane; Pharmacia Biotech) in acetone (v/v) for 1 h. Polyacrylamide coating can also be obtained as described (Liu Q et al. Biomacromolecules, 2012, 13 (4), pp 1086-1092). A number of hydrogel coatings that can be used are described and referenced in Mateescu et al. Membranes 2012, 2, 40-69.

A target nucleic acid can also be elongated in an agarose gel by applying alternating current (AC) (dielectrophoretic) electric fields. The DNA molecules can be electrophoresed into the gel or the DNA can be mixed with molten agarose and then allowed to set with the agarose. Then an AC field with a frequency of about 10 Hz is applied and a field strength of 200 to 400 V/cm is used. Stretching can be done at a range of agarose gel concentrations from 0.5 to 3%. In some case the surface is coated with BSA-Biotin in flow channel or well, then streptavidin or neutravidin is added. This coated coverglass can be used to stretch double strand genomic DNA by first binding the DNA at pH 7.5 buffer and then stretching the DNA in pH 8.5 buffer. In some cases, the streptavidin coated coverglass is used to capture and immobilize the nucleic acid strands, but no stretching is carried out. Hence, the nucleic acid attached at one end, while the other end is dangling in solution.

Rather than using the various microscope-like components of an optical sequencing system such as the GAIIx, in some embodiments, a more integrated, monolithic device is constructed for sequencing. In such embodiments, the polynucleotide is attached and optionally elongated directly on the sensor array or on a substrate that is adjacent to the sensor array. Direct detection on a sensor array has been demonstrated for DNA hybridization to an array (e.g., as described by Lamture et al., Nucleic Acid Research 22:2121-2125, 1994). In some embodiments, the sensor is time gated to reduce background fluorescence due to Rayleigh scattering which is short lived compared to the emissions from fluorescent dyes.

In one embodiment, the sensor is a CMOS detector. In some embodiments, multiple emission maxima wavelengths are detected (e.g., as described in U.S. Pat. Appl. No. 2009/0194799). In some embodiments, the detector is a Foveon detector (e.g., as described in U.S. Pat. No. 6,727,521). In some embodiments, the sensor array is an array of triple-junction diodes (e.g., as described in U.S. Pat. No. 9,105,537).

In some embodiments, the reagents/buffer are delivered to the flow cell in single dosages (e.g., via a blister pack). Each blister in the pack contains a different oligonucleotide probe species from a set of oligonucleotide probe species of oligonucleotides. Without any mixing or contamination between oligonucleotide probe species, a first blister is pierced, and the target nucleic acid is exposed to its contents. In some embodiments, wash steps are applied before moving to the next blister in the series. This serves to physically separate the different sets of oligonucleotide probe species, and thus decrease background noise where oligonucleotide probe species from a previous set remain in the imaging view.

In some embodiments, the sequencing occurs in the same device or monolithic structure in which the cells were disposed and/or the polynucleotides were extracted. In some embodiments, all reagents needed for conducting the method are pre-loaded on the fluidic device before analysis commences. In some embodiments, the reagents (e.g., probes) are and present in a dry state in the device and are wetted and dissolved before reaction proceeds.

Additional Embodiments

In one broad aspect the invention is a method of obtaining supervenient information by analyzing a repertoire of subvenient events.

In one broad aspect the scope of the invention comprises a method of identifying at least one unit of a multi-unit molecule by binding molecular probes to one or more units of the molecule. The invention is based on the detection of single molecule interactions of one or more species of molecular probe with the molecule. In some embodiments, the probes bind transiently to at least one unit of the molecule. In some embodiments, the probes bind repetitively to at least one unit of the molecule. In some embodiments, the molecular entities are localized on a surface or matrix to a nanometric accuracy (typically <250 nm, preferably <50 nm, more preferably, <2 nm).

In some embodiments, the invention comprises a method of characterizing interactions between one or more probes and a molecule comprising:

Adding one or more probe species to the molecule under conditions that the probe(s) can bind(s) transiently to the molecule Continuously monitoring individual binding events on the molecule on a detector and recording for a period of time Analyzing data from step b to determine one or more characteristics of the interactions Optionally the molecule is immobilized on a surface or matrix before step a. In some embodiments, the detector of c is a 2D or detector and the binding events are localized to a nanometer accuracy on the surface or matrix, e.g., using a single molecule localization algorithm. In some embodiments, the characteristic is duration of each event which corresponds to the affinity of the probe(s) with the molecule. In some embodiments, the characteristic is the location on a surface or matrix.

In some embodiments, the invention comprises a method of identifying or characterizing the units of chemical structures in a heterogeneous macromolecule comprising binding a plurality of probes to identify the chemical structures at a plurality of sites in the macromolecule, comprising:

a) Adding one or more probe species to the macromolecule under conditions that the probe(s) can bind(s) to the macromolecule;

b) Continuously monitoring the binding events on the macromolecule on a detector and recording for a period of time; and c) Analyzing data from step b to identify the chemical structures at a plurality of sites in the macromolecule.

Optionally the macromolecule is immobilized on a surface or matrix before step a. In some embodiments, the macromolecule comprises a supramolecular structure. In some embodiments, each of the one or more probes bind transiently to the macromolecule. In some embodiments, each of a plurality of probes bind repetitively to the polymer.

In some embodiments, the molecular entity is a polymer, comprising at least 5 units. In some embodiments, the binding probes are molecular probes comprising oligonucleotides, antibodies, binding proteins, small molecules etc. Typically, the polymers comprise polynucleotides or polypeptides.

In some embodiments, the invention comprises a method of identifying or characterizing the units of chemical structures in a heterogeneous polymer comprising binding a plurality of probes to identify the chemical structures at a plurality of sites along the polymer, comprising:

a) Adding one or more probe species to a polymer under conditions that the probe(s) can bind(s) to the polymer;

b) Continuously monitoring the binding events on the polymer on a detector and recording for a period of time; and c) Analyzing data from step b to identify the chemical structures at a plurality of sites along the polymer.

In some embodiments, the polymer is immobilized on a surface or matrix before step a. In some embodiments, the polymer is denatured before step a. In some embodiments, each of the one or more probes bind transiently to the polymer. In some embodiments, each of a plurality of probes bind repetitively to the polymer. In some embodiments, the location of probe binding that identify a unit of the chemical structure is determined with nanometric (and if warranted even sub-nanometeric) accuracy/precision (e.g., using a single molecule localization algorithm) and thereby the "sequence" is determined based on the identity of probes that bind to each location.

In some embodiments, where the accuracy and precision of localization is high (sub nanometer or a few nanometers) the location and order of each sequence bit is determined unequivocally. The sequence read however emerges non-contiguously, in a punctuated manner. Where most sequencing methods read the sequence serially from start to end, in the present invention the acquisition of sequence information is stochastically distributed. When all the sequence data has been collected the sequence is put together by ordering the bits of sequence information obtained according to their spatial location, each sequence bit should overlap with the previous and next localized sequence bit of information obtained, e.g., for a 5mer each sequence bit should overlap in sequence at one end with four bases to the previous sequence bit and with four bases to the other end with the next sequence bit. Where this does not hold exactly, (e.g., only 3 not 4 overlap) the sequence bit is likely to have been obtained due to a mismatch or the localization might by slightly off. A novel aspect of the invention is that this internal checking mechanism should be able to resolve the right order of sequence bits and hence the sequence with high confidence.

In some embodiments, the duration of each cycle of probe addition is configured so that a certain number of binding events can be collected for each complementary binding site. The number of binding events is on average be 5, 10, 20 etc. In some embodiments, the duration of each cycle of probe addition is configured so that a certain number of photons can be collected for each complementary binding site. The larger the number of photons collected for each binding the better the degree (accuracy) and precision of localization that can be achieved. In some embodiments, the duration for different probes or probe sets are different. Hence, some probes can be localized to a high degree of precision, whereas others are localized to lower degree of precision. In some embodiments, the highly localized positions can be used to anchor sequence assembly, where the less well localized positions are computationally assembled by overlap in sequence. In some embodiments, localized positions (including those that are the less well localized) can be used in assembly algorithms such as those that use de Bruijn graphs.

In some embodiments, the probe is labeled. The term label encompasses a single detectable entity (e.g., wavelength emitting entity) or multiple detectable entities. In some embodiments, the multiple detectable entities may comprise a code by which the probe species can be identified. In some embodiments, the probes are labelled with fluorophores or particles. Fluorescent labels may emit fluorescence at different wavelengths and also have different lifetimes. In some embodiments, background fluorescence is removed by rejecting the early time window of fluorescence due to scattering. If the label is on one end of the probe, e.g., 3' end of oligo probe, the 1 nm accuracy corresponds to the 3' end of the probe sequence and 5' of the target sequence.

In some embodiments, the sequencing of the polymer is based on measuring its transient interactions with a repertoire of probes, e.g., the interaction of a polynucleotide with a repertoire of oligonucleotides. In some embodiments, the repertoire comprised every oligonucleotide of a given length or a given set of lengths.

In some embodiments, the invention comprises a method of sequencing nucleotide bases and/or modifications on a single target polynucleotide comprising:

a) Immobilizing the polynucleotide on a surface or matrix, optionally stretching the polynucleotide;

b) Optionally denaturing the polynucleotide to the extent that at least some of the polynucleotide becomes available to bind to probes;

c) Adding one or more probe species under conditions that the probe(s) can bind(s) transiently to the polynucleotide;

d) Continuously monitoring the binding events on the polynucleotide on a detector and recording for a period of time;

e) Removing the probes of b;

f) Repeating steps b-d each time with a different one or more probe species until the binding of a complete repertoire of probes has been monitored; and g) Compiling data from each iteration of step c to reconstruct sequence of modifications and/or bases.

In some embodiments, the sequencing of the polymer is a result of an emergent property of the transient binding interactions of a repertoire of probe species. The binding of one probe is not sufficient to sequence the polymer a complete repertoire of oligomers (e.g., for a polynucleotide, a repertoire of oligonucleotides) is needed. Information on the location of binding of oligos, the temporally separated binding to overlapping sites, the partial binding of mismatches, the frequency of binding, the duration of binding, all contribute to building a robust sequence. In the case of elongated or stretched polynucleotides the location of probe binding along the length of the polynucleotide contributes to building a robust sequence. Also in the case of double-stranded DNA, the sequence emerges from the sequencing of both strands of the duplex simultaneously.

In some embodiments, of the above, the binding of probes to modifications on the repeating units of the polymer (the nucleotides in a polynucleotide) are conducted before the optional denaturation step of b. In some embodiments, the optional denaturation of step b is not done and the probes address a duplex structure. In some cases the probes bind to the individual strands of the duplex through strand invasion (e.g., using PNA probes), inducing excessive breathing of the duplex, by recognizing the sequence in the duplex through a modified zing-finger protein or by using a Cas9 or similar protein which melts the duplex allowing for example a guide RNA sequence to bind; the guide RNA can comprise an interrogation probe sequence and a gRNA comprising each sequence of the repertoire is provided.

A caveat to the above is that In some embodiments, certain probes can be omitted from the repertoire e.g., due to their problematic interactions with themselves (e.g., self complementarity, palindromic sequences which allow binding with other copies of itself), with other probes in the repertoire or with the polynucleotide (e.g., known stochastic promiscuous binding) but sufficient probes remain to carry out the sequencing of the invention. In fact a minimal number of informative probes can be determined for each type of sequence under analysis. Another caveat relates to the fact that half of the complete repertoire is completely complementary to other oligos in the repertoire; In some embodiments, it is ensured that these complementary pairs (and others that are problematic due to substantial complementarity) are not added to the polynucleotide at the same time; in some embodiments, where both sense and antisense strands of double stranded DNA are present, sequencing is performed with just one member of the complementary pair and sequence information obtained from both sense and antisense strands are combined to generate the sequence.

In some embodiments, the reference sequence and sequence information obtained for the complementary strand (of a target that is natively double stranded) can be used to facilitate assignment of sequence at a particular location.

In some embodiments of the invention sequencing comprises the following steps (illustrated for 5 base sequencing):

a) Stretching/elongating duplex DNA on a surface;

b) Denaturing the duplex DNA to leave a pair of complementary strands remaining in situ on the surface;

c) Binding a complete repertoire of short oligos (e.g., 3, 4, 5, 6-mers) to the pair of DNA strands and recording the binding locations of each oligo along the linear length of the pair of strands;

d) Using the location of binding and the sequence overlap between oligos to construct two tiling paths of oligos representing complements to each of the two strands; and e) Comparing the reverse complement sequence of the two strands and making 'duplex consensus' derived base assignments in which the assignment is corroborated by both strands and ambiguity in the base call is indicated when corroboration is not found.

A problem can arise when there is a break in the tiling path, for example there is no oligo binding to a stretch of sequence longer than 5 base in length for 5 base sequencing. In this case, one or more approaches can be taken: the base assignment defers to the sequence obtained from the complementary strand of the duplex, when available; relies on other copies of the same segment of sequence if available; or defers to a reference sequence (in this case the bases can be annotated to indicate that the are artificially implanted from a reference).

In some embodiments, artificial intelligence or machine learning is used to learn the behavior of the members of the repertoire when tested against polymers (e.g., polynucleotides) of known sequence and/or when the sequence of the polynucleotide is cross-validated with data from another method. The learning algorithm takes into account the full behavior of a particular probe against one or more polynucleotide targets containing binding sites for the probe in one or more conditions or contexts. As more sequencing is done on the same or different samples, the more robust the knowledge from machine learning becomes. What is learnt from machine learning can be applied to various other assays, in particularly those involving interactions of oligos with oligos/polynucleotides, e.g., sequencing by hybridization, in addition to the transient binding-based emergent sequencing and other embodiments of this invention.

In some embodiments, artificial intelligence or machine learning is trained by providing data of the binding patterns experimentally obtained for binding of a complete repertoire of short oligos (e.g., 3mer, 4mer, 5mer, or 6mer) to one or more polynucleotides of known sequence. The training data for each oligo comprises, binding locations, duration of binding and the number of binding events over given period. After this training the machine learning algorithm is applied to a polynucleotide of sequence to be determined and based on its learning can assemble the sequence of the polynucleotide. The machine learning algorithm can also be provided a reference sequence.

In some embodiments, the sequence assembly algorithm comprises both a machine learning element and a non-machine learning element.

In some embodiments, the sequence assembly algorithm comprises a Bayesian approach. In some embodiments, data derived from the methods of the invention can be furnished to an algorithm of the type described in (WO2010075570) and can optionally be combined with other types of genomic or sequencing data.

In some embodiments, instead of the computer algorithm learning from the experimentally obtained binding patterns, the binding patterns are obtained via simulations. For example simulations can be done of the transient binding of oligos of the repertoire to the polynucleotide of known sequence; the simulations can be based on a model of the behavior of each oligo obtained from experimental or published data. For example the prediction of binding stability is available according to the nearest neighbor method [SantaLucia et al. Biochemistry 35, 3555-3562 (1996); Breslauer et al. Proc. Natl. Acad. Sci. USA, 83: 3746-3750 (1986)] and the mismatching behavior is known or can be experimentally derived, the inordinately high binding strength of some short sub-sequence of oligos, such as GGA to ACC are known. The machine learning algorithm can be trained on the simulated data and then used to determine the sequence of an unknown sequence when it is interrogated by a complete repertoire of short oligos.

In some embodiments, the data (location, binding duration, signal intensity etc) of oligos of the repertoire or panel are plugged into a machine learning algorithm, that has been trained on one or more preferably (tens, hundreds or thousands) of known sequences.

The machine learning algorithm is then applied to a generate a data-set from a sequence in question and the machine learning algorithm generates the sequence of the unknown sequence in question. The training of the algorithm for sequencing of lower organisms, e.g., bacteria, bacteriophage etc needs to be done on organisms of that type. For higher organisms starting from Yeast such as *S. pombe* all the way to Human or Wheat which have repetitive DNA need to also be trained on higher organisms. For long-range assembly of megabase fragments to whole chromosome lengths, the training may need to be done on similar organisms, so that particular aspects of the genomes are represented during the training. For example human genomes are diploid and have a lot of segmental duplication. Wheat is polyploid.

In some embodiments, a machine learning based sequence reconstruction approach comprises:

a) Providing information on the binding behavior of each oligo in the repertoire gleaned from one or more training data-sets and, an assembly algorithm that can use such information;

b) Physically binding each oligo of the repertoire to the polynucleotide whose sequence is to be determined and providing information on binding location, and/or binding duration and/or the number of times binding occurs to each location for each oligo (persistence of binding repetition); and c) Using the assembly algorithm that uses training data-set, to reconstruct the sequence of the polynucleotide.

For human genomes a good ground rules genome would be NA12878, which has been extensively characterized by various sequencing, haplotyping and structural mapping methods and for which the assembly is the most reliable of any human genome. Nevertheless, because thus far there is no perfect technology that we can be sure gives us a true representation of a complex genome, ground truth data sets available for such genomes may not be perfect, and the machine learning algorithm may need to take account of alternative "ground truths" or an "average" or "consensus" ground truth is pre-constructed from assemblies that have used different technologies (e.g., 10× Genomics, Bionanogenomics, PacBio, ONT) in combination with Illumina sequencing.

In some embodiments, the sequence of a particular experiment is first processed by a non-machine learning algorithm. Then the output sequence of the first algorithm is used to train the machine learning algorithm, so that the training occurs on actual experimentally derived sequence of the same exact molecules. An advantage of the machine learning algorithm is that it can be implemented faster than other algorithms.

In some embodiments, the invention comprises a method of identifying and ordering the units of chemical structures in a heterogeneous polymer comprising binding a plurality of probes to identify the chemical structures at a plurality of sites along the polymer. A plurality of said sites are closer than would be resolvable by diffraction limited optical imaging but are resolved because their detection is separated in time. The binding of the probes that identify the chemical structure is determined with nanometric/sub-nanometric localization accuracy/precision, as needed, and thereby the spatial order of the chemical structure, "the sequence" is determined.

In further embodiments a plurality of polymers that are characterized or sequenced are closer than would be resolvable by diffraction limited optical imaging but are resolved because the location of probe binding along their length are nanometrically localized.

In some embodiments, the invention comprises a method of identifying and ordering the units of chemical structures in a heterogeneous polymer comprising, elongating the polymer and binding a plurality of probes to identify the chemical structures at a plurality of sites along the elongated polymer. A plurality of said sites are closer than would be resolvable by diffraction limited optical imaging but are resolved because the polymer is elongated and/or their labelling is temporally separated. The location of binding of the probes that identify each chemical structure is determined with nanometric accuracy and thereby the spatial order of the chemical structures, "the sequence" is determined.

In some embodiments, the invention comprises a method for analyzing base sequence on a target polynucleotide. In some embodiments, the invention comprises a method for analyzing nucleotide modifications or DNA damage as well as base sequence on a target polynucleotide. In some embodiments, the invention comprises a method for analyzing the organization of sequences on a target polynucleotide.

The term "transient binding" means that the binding reagent or probe does not usually remain attached to its binding site, during the course of analysis, and typically one reagent binds on and off, then the same or another reagent binds on and off, and so on. Repetitive binding means that the same binding site is bound by the same binding reagent or probe or same species of binding reagent or probe multiple times during the course of an analysis, and typically one reagent binds on and off, then another reagent binds on and off, etc. In some embodiments, the binding interactions are continuously observed over a period of time.

In some embodiments, the repetitive binding increases the sensitivity and accuracy of the information obtained. The sensitivity increases because where a signal might be too low to call over background when detected once, is callable when seen persistently—the confidence that the signal is real, increases. The accuracy increases because multiple readings of the information confirms one reading with another (similarly reading of both strands allows confirmation of one reading with another).

In some embodiments, the mechanism of the method comprises binding of a probe molecule to a target molecule, such binding event being short-lived or transient, and many such binding events occurring repeatedly at the same location and/or partially overlapping locations. The location, frequency, dwell time and photon emission of such binding events are recorded and computationally processed.

In some embodiments, the transient binding is conducted in a buffer with a small amount of divalent cation but with no monovalent cation e.g., 5 mM Tris-HCl, 10 mM MgCl2, 1 mM EDTA, 0.05% Tween-20, pH 8.

Hence the polynucleotide sequencing comprises the steps:

a) immobilizing a polynucleotide;

b) binding a repertoire or sub-repertoire of oligos to the polynucleotide in a reaction buffer that contain <1, <5, 10 or 15 nM of magnesium chloride;

c) detecting transient binding d) repeating b-c as necessary.

Assembling the Polynucleotide Sequence

In some embodiments, the solid substrate on which the molecules are immobilized comprises glass, silicon, silicon dioxide, silicon nitride, metal (e.g., Gold), Polydimethoxysilane (PDMS), a polymer (e.g., cyclic olefin, Zeonex, poly methyl methacrylate, polystyrene). In some embodiments, the solid surface is coated, for example with polyvinylsilane. In some embodiments, the polymers are stretched on a polyvinyl coated surface by molecular combing and then crosslinked to the surface by exposure to ultra-violet light or high temperature In some embodiments, the invention comprises determining the binding locations of each member of a repertoire to an elongated polymer that forms multiple interactions with a surface or a matrix. In some embodiments, the binding locations are determined by detecting repetitive transient on-off probe binding events whose sites of binding may overlap but do not appreciably interfere with each other's binding because their binding tends to be temporally separated. If the probes were bound for longer periods the binding of one would block the binding of another.

In some embodiments, the repertoire is a complete repertoire, e.g., every oligo of a given length. In some embodiments, it is a tiling series of oligo probes. In some embodiments, it is a panel of oligo probes. In the case of certain applications in synthetic biology, e.g., DNA data storage, sequencing may comprise finding the order of specific blocks of sequence, designed to encode the data.

In some embodiments, the mechanism of the method comprises binding of a probe molecule to a target molecule, such binding being detectable due to a label, said label being transiently binding, blinking or fluctuating in its emission or photo-switching off and/or on, and many such binding events can occur repeatedly at the same location and/or at one or more partially overlapping locations. The location and duration of such binding events are recorded and processed. In some embodiments, the apparent transient, fluctuating, or blinking behavior of the label is because the label is attached to the probe which is binding on and off from the target.

In some embodiments, the probe that binds the target is not directly labeled. In some such embodiments, the probe contains a "flap", an entity that acts as a receptor for the binding of a second entity. The two entities can comprise molecular binding pairs. Such binding pairs can comprise nucleic acid binding pairs. In some embodiments, the flap comprises a stretch of oligo- or poly-nucleotide sequence that binds to a labeled oligonucleotide (oligo) and such binding is substantially stable during the course of the process of imaging the transient binding of the part of the probe that binds the target. In some embodiments, the target comprises a polynucleotide sequence and the binding part of the probe comprises, for example a 3mer or a 4mer, or a 5mer or a timer sequence interrogation portion, optionally one or more degenerate or universal positions, optionally a nucleotide spacer (e.g., one on more T nucleotides) or abasic or non-nucleotide portion and a flap portion. Such flap portion is non-modified in sequence and to retain stability during the course of the imaging, is for example 20 bases or longer in length with a sequence designed to be stable and one that is preferably screened to be infrequent in the target polynucleotide.

In some embodiments, a repertoire of probes is applied to the target. In some embodiments, each of the probes of the repertoire or a sub-set of the probes of the repertoire are applied one after the other; i.e. the binding of one or a sub-set is first detected and then it is removed, before the next added, detected and removed then the next and so on. The data is then processed to give nanometric or subnanometric localization of each probe binding event of probes of each specificity. In some embodiments, the binding order and/or locations of each probe specificity is used to put together the sequence.

In some embodiments, all or a sub-set of binding probes in the repertoire are added simultaneously and each binding probe is tethered to a label that codes completely or partially for its identity and the code for each of the binding probes is decoded by detection.

In some embodiments, the flap on the probe is modular, and may contain binding sites for different oligos, such oligos isar different labels, and is used for coding the identity of the probe part of the oligo.

In some embodiments, the nucleic acid targets are attached to a surface or matrix. In some such embodiments, one terminus of the target is attached to the surface or matrix while the rest of the target is free for interaction. In some embodiments, the targets are captured onto an ordered supramolecular scaffold (e.g., DNA Origami structure). In some embodiments, the scaffold structure starts free in solution to take advantage of solution phase kinetics for capturing target molecules. Once they are occupied, the scaffolds settle or self-assemble onto the surface and are locked down to form a large DNA lattice, individual small scaffolds locking in to one another. They then present a highly ordered nanostructured array for sequencing steps of the invention.

In some embodiments, in order to circumvent the effects of non-specific binding or outlier events, the method prioritizes signals based on their location and persistence. Priority due to location predicated upon whether the probes co-localize for example on a stretched polymer or supramolecular lattice (e.g., DNA origami grid), including location within the lattice structure. Priority due to persistence of binding concerns duration of binding and the frequency of binding and uses the priority list to determine the likelihood of a full match a partial match or non-specific binding. This priority that is established for each binding probe in a panel or repertoire is used to determine the correctness of a signal. Priority is used by an algorithm of the invention to facilitate signal verification and base calling. In some embodiments, the algorithm comprises the queries:

1. Is signal persistence duration >threshold. If yes accept as real.
2. Is signal repetition/frequency >threshold. If yes accept as real
3. Does signal correlate with pattern (grid or line). If yes accept as real.

Otherwise discard data for this signal. As an alternative to 1 and 2 the algorithm can ask if the number of photons collected are >threshold.

Also a signal that does not appear to be reversible can be discarded or weighted against in the assembly algorithm because it may correspond to a non-specific signal (e.g., attachment of fluorescent contaminant to the surface).

In some embodiments, the invention comprises a method of sequencing nucleotide modifications and/or bases on a single target polynucleotide comprising:

Immobilizing and linearizing the polynucleotide on a surface

Adding one or more labeled probe species under conditions that the probe(s) bind(s) transiently and probe binding to the target site can be differentiated from probe binding to non-target sites Continuously imaging the polynucleotide on a 2D detector and recording the pixel coordinates of probe binding, until a threshold number (depending the precision in localization required) of binding events at each location have been accumulated Removing the probes of b.

Repeating steps b-d each time with a different one or more probe species

Compiling data from each iteration of step c using a single molecule localization algorithm to provide the nanometric coordinates of each of the binding sites to which probes bind persistently (e.g., 4 or more binding events to the binding sites) and correlating the nanometrically localized site with the identity of the probe species (e.g., a specific oligonucleotide sequence or a specific antibody).

Determining the order (sequence) of the binding species to determine the sequence identity (and modification status) associated with each of the sub-nanometric or nanometric locations to compile the nucleotide modification and/or base sequence over the length of the polynucleotide and detecting any gaps over the length of the polynucleotide.

In some embodiments, an additional step is implemented before step g, in which step the duration and/or the persistence of a particular probe species to each of its binding locations as well as which probes have bound to adjacent locations and to the complementary strand if the target is a denatured double-strand, is taken into account in determining whether the binding event is a perfect match, mismatch or spurious binding.

In some embodiments, a step h can be added to determining the correlation of one type of target of binding (e.g., antigen) with another (e.g., sequence).

In some embodiments, the probes of step b are removed by reagent exchange. Optionally, first the probes are replaced with one or more wash solutions, then the next set of probes are added.

In some embodiments, in step c the imaging (of on-off binding events) is run for a period long enough that a threshold number of binding events are likely to have been accumulated.

In some embodiments, the methods comprises continuously imaging the polynucleotide on a 2D detector and recording the pixel coordinates of probe binding, until a threshold number of binding events at each location are likely to have been accumulated.

In some embodiments, the period the imaging duration depends on the localization accuracy required (e.g., nanometric or sub-nanometric). The imaging may need to be run for longer to get sub-10 nM or sub-nanometric localization. In some embodiments, the imaging duration depends on the degree of confidence needed regarding which short stretch of sequence (sequence bit) is bound by which probe. Running for longer will increase the confidence in correct matches, and allow spurious or mismatch binding to be computationally filtered out.

In some embodiments, the target polynucleotide of the invention is immobilized. In some embodiments, the immobilization is on a structural support (e.g., a planar surface, cell matrix). In some embodiments, the target polynucleotide is disposed in a fluidic vessel such as a well or a flow cell.

In some embodiments, the immobilizing and linearizing double stranded genomic DNA and preparation for transient binding on a surface comprises:
a) Molecular combing;
b) UV Crosslinking;
c) Optional wetting;
d) Denaturation comprising exposure to chemical denaturants, Alkali solution, DMSO, etc.;
e) Optional exposure to acidic solution after washing;
f) Optional pre-conditioning buffers;

In some embodiments, the polymer is a short polynucleotide, <1 Kbp or <300 bp. In some embodiments, the short polynucleotide is in the 100-200 base range, as is found for cell-free DNA in body fluids such as urine and blood. In some embodiments, the polynucleotides are attached to or captured on a surface, preferably by one of the two ends. In some embodiments, the polynucleotides are captured in an ordered way in a nanostructured lattice. The lattice is comprised of a supramolecular structure such as can be formed with DNA origami. Capture sites can be arranged at a 10 nm pitch in an ordered 2D lattice; with full occupancy such a lattice could capture one trillion molecules per cm2.

In some embodiments, the polymer is linearized. In some embodiments, the linearization renders the polymer along a wavy or meandering path on the surface. In other embodiments the polymer is elongated and straight. In some embodiments, the straight polymers are aligned in a single direction. In some embodiments, the polymer is not elongated and may form a tortuous path through 2D or 3D space. The latter is the case when the method is applied to a biopolymer inside a cell.

In some embodiments, polynucleotides are randomly arrayed on a surface or matrix. In some embodiments, the polynucleotides are arrayed in an ordered manner. In some embodiments, the polynucleotides are displayed as DNA Curtains [Greene and co-workers; US20080274905A1]. In such embodiments, the transient binding is recorded while the DNA strands, attached at one end are elongated by flow or electrophoretic forces or after both ends of the strand have been captured. In some embodiments, the capture at one or both ends is due to binding or ligation to spatially addressable oligos on the surface or at the interface from which the curtain extends. In some embodiments, the lipid surface coating used in DNA curtains minimizes surface binding and background. In some embodiments, where many copies of the same sequence form the plurality of polynucleotides in the DNA curtain, the sequence is assembled from the binding pattern in aggregate from the plurality of polynucleotides rather than from one polynucleotide.

In the case of long polynucleotides, the ordered way can be by individually attaching one end of each long polynucleotide to a pad within an ordered array of pads, where the end of a different polynucleotide occupies each pad, such as has been demonstrated for DNA Curtains (Greene and Co-workers). In some embodiments, both ends of the polynucleotide bind to pads, each end to a different pad. The two pads that a single linear polynucleotide binds can serve to hold the stretched configuration of the polynucleotide in place and allow an ordered array of equally spaced, non-overlapping or non-interacting polynucleotides to be formed. In some embodiments, only one polynucleotide can occupy an individual pad. In some embodiments, where the pads are occupied by a poissonian process, some pads is occupied by no polynucleotides, some by one and some by more than one.

In some embodiments of the invention where sequencing of DNA extracted from multiple cells, in which a substantial number are the same cell type (and expected to contain substantially the same sequence), the sequence is assembled from the binding pattern in aggregate from the plurality of polynucleotides rather than from one polynucleotide.

In some embodiments, the polynucleotides are removed from their natural context (e.g., cells, tissue, biofluids) and immobilized on a surface. In some embodiments, the polynucleotides remain in their cellular or tissue context. In some embodiments, the cells or tissue are fixed. In some embodiments, the polynucleotides are cross-linked inside the cell.

In some embodiments, the polynucleotides are single-stranded (e.g., mRNA, lncRNA microRNA). In some embodiments, the polynucleotides are double-stranded. In some embodiments, the polynucleotides are denatured. In some embodiments, the denaturation is chemical denaturation comprising one or more reagents from 0.5M or 1M NaOH, DMSO (e.g., 60%), Formamide (10-90%), Urea (7-8M) etc. In some embodiments, the denaturation is heat denaturation, 85° C. and higher. In some embodiments, the denaturation is through enzymatic denaturation such as through the use of helicases or other enzymes with helicase activity. In some embodiments, the polynucleotides are denatured through interaction with a surface or by a physical process such as stretching beyond a critical length. In some embodiments, the denaturation is full or partial.

In some embodiments, an array of polynucleotides are immobilized on the surface and In some embodiments, the polynucleotides of the array are far enough apart to be individually resolved. In some embodiments, the polynucleotides of the array are not far enough apart to be individually resolved. In some embodiments, the polynucleotides of the array are individually resolved by super-resolution methods. In some embodiments, the polynucleotide is elongated parallel to the surface. In some embodiments, the polynucleotide is elongated at an oblique angle to the surface. In some embodiments, the detection via a 2D detector is processed via a Single Molecule Localization algorithm software (e.g., Thunderstorm which is plug-in to Fiji/ImageJ or, Picasso which is available for download at https://github.com/jungmannlab/picasso). In some embodiments, the polynucleotide is elongated perpendicular to the surface. The detection of the coordinates of the labels is via spinning disc confocal microscopy, light-sheet microscopy, 3D super-resolution microscopy or 3D Single Molecule Localization microscopy or other 3D imaging approach.

In the methods of the invention a probe (from a multitude of copies of a particular species) is bound transiently to the target site in the polynucleotide in a specific manner (e.g., Watson-Crick base pairing, antibody-antigen binding) and the Cartesian coordinates and duration of transient binding is recorded. In some embodiments, probes of the same species transiently bind repeatedly to the target site. In some embodiments, one probe species is removed and another added. In some embodiments, this is repeated until a repertoire (e.g., a complete repertoire), tiling series or panel of probes has been tested. In some embodiments, the location of binding of each probe species is recorded. In some embodiments, the recordings are processed to give nanometric localization accuracy i.e. the x-y and in some embodiments, z coordinates of the binding to within a few tens of nanometers, a few nanometers and even a few sub-nanometers (angstroms) depending on the precision required or one that is useable according to the aims of the application. In some embodiments, one oligo probe species or a repertoire or panel of oligo probe sequences is provided and one or a repertoire of binding agents (e.g., proteins) that can bind to sites of nucleic acid modification or damage can also be provided.

In some embodiments, one or more physical property of the label on the probe is also recorded and different probe species are labeled with labels comprising different physical properties, such physical properties comprising, brightness (absorption, quantum yield), wavelength, lifetime, polarization. In some embodiments, the physical property is any other physical property that can be measured at the single molecule or single particle level. In some embodiments, multiple label entities comprise the label.

In some embodiments, the transient binding is for a few or several seconds. In some embodiments, the transient binding can span between 10 microseconds and several tens of seconds. In some embodiments, the transient binding is between 1 millisecond and 1 second in duration. In some embodiments, the transient binding is between 10 microseconds and 1 millisecond.

The invention is practiced on single (individual) molecules (e.g., polymers) such that the method has the potential for exquisite sensitivity and can resolve the diversity in a heterogeneous population of molecules. The sensitivity is also positively affected by the fact the invention does not require the sample molecules to be processed with its attendant losses (e.g., ligation is highly inefficient so those molecules which are not adapted by ligation are effectively lost) and introduction of artifacts (e.g., a replication error during PCR).

The multiple binding events increase sensitivity, more photons are accumulated and the multiple independent binding events increase the probability that a real signal is being detected. The multiple binding events also increase specificity, as rather than establishing the identity of a moiety or sequence being detected on a single "call" a consensus can be obtained from multiple calls. Also the multiple binding events to a target moiety or sequence allow binding to actual locations to be differentiated from non-specific binding events, where binding (of a threshold duration) is less likely to occur multiple times at the same location. Also it is observed that the measurement of multiple binding events over time allows the accumulation of non-specific binding events to the surface to be bleached out, after which little non-specific binding is detected again. This is likely to be because although the signals from the nonspecific binding is bleached out, the non-specific binding sites remain occupied or blocked. Thus an extensive effort to passivize the surface to minimize non-specific binding is not necessary, as the early frames of the movie can be sliced out.

In some embodiments, the signal from the label in each transient binding event is projected through an optical path (typically, providing a magnification factor) to cover more than one pixel of the 2D detector. The point spread function (PSF) of the signal is plotted and the centroid of the PSF taken as the precise location of the signal. This localization can be done to sub-nm accuracy. The localization accuracy is inversely proportional to the number of photons collected, so the more photons emitted per second, or the longer the photons are collected the higher the accuracy. To achieve high accuracy and precision, the drift of the sample in relation to the 2D detector has to be minimized or an effective means for drift correction needs to be implemented. In some embodiments, the drift correction approach comprises including fiduciary markers on the surface which can be used as a reference to correct drift; DNA origami with multiple specified binding locations are a very effective fiduciary markers when a precision needs to be down to a few nanometers or sub-nanometer.

In an alternative embodiment of the invention, the signal from the label in each transient binding event is not projected through an optical magnification path, rather the substrate, typically an optically transparent surface upon which the target molecules reside is directly coupled to the 2D detector array. When the pixels of the detector array are small, e.g., 1 micron or smaller then with a 1:1 projection of the signals on the surface allows the binding signal to be localized with at least one micron accuracy. In the case of stretched DNA, where say 2 kbp in length is equivalent to 1 micron, signals that fall two kilobases apart can be resolved. In the case of 6 mer probes where signals would be expected to occur every 4096 bases or every 2 microns, this resolution is sufficient. Also signal that falls partially between two pixels, provides intermediate locations, so the resolution is 500 nm for a one micron pixel. Of course in real natural polynucleotide sequences, signals would be expected to occur at locations closer than and further than every 4096 bases. However, in some exotic applications such as DNA storage, the polynucleotide constructs can be designed in such a way that the signals fall every 2 Kb for example. An advantage of this approach is that the device is simpler and more stable. Also the substrate can be translated in relation to the 2D array detector, say in increments of 100 nm, to give higher resolution. One advantage of this embodiment is that the device can be smaller (or thinner), as it does not need lenses, and space in between lenses. It can also provide a direct conversion of molecular storage readout into electronic readout more compatible with existing computers and databases.

In some embodiments, multiple conditions that promote transient binding are used. In some embodiments, one condition is used for one probe species depending on its Tm and another condition is used for another probe species depending on its Tm and so on for a whole repertoire of probes species, for example, each 5mer species from a repertoire of 1024 possible 5mers. In some embodiments, because both target polynucleotide strands are present in the sample only 512 non-complementary 5mers are provided. In some embodiments, each probe addition comprises a mixture of probes comprising 5 specific bases and 2 degenerate bases, (hence 16 heptamers) all labeled with the same label that function as one pentamer in terms of capacity to interrogate sequence; the degenerate bases add stability without increasing the complexity of the probe set.

In some embodiments, the same conditions are provided for a plurality of probes that share the same or similar Tms. Each probe in the repertoire may comprise a different encoding label (or label according to which it is identified). In such case, the temperature is held through several probe exchanges, before being raised for the next series of probes that share the same or similar Tms.

In some embodiments, the Tms are calculated, for example by nearest neighbor parameters. In other embodiments the Tms are empirically derived. For example, the optimal TM or TM range is derived by carrying out a melting curve (measuring extent of melting by absorption for example over a range of temperatures). In some embodiments, the composition of probe sets is designed according to their theoretically matching Tms which are validated by empirical testing. In some embodiments, the binding is done at a temperature that is substantially below Tm, e.g., 33 degree below Tm. In some embodiments, the optimal temperature to discriminate mismatch from perfect match is determined empirically conducting melting curves using short synthetic targets comprising the perfect match and mismatches at various locations. In some embodiments, the empirically determined optimal temperature for each oligo is used for the binding of each oligo in sequencing.

In some embodiments, the concentration of oligo used is adjusted according to the AT versus GC content of the oligo sequence. A higher concentration of oligo is provided for oligos with a higher GC content. In some embodiments, buffers that equalize the effect of base composition, containing, CTAB, Betaine or Chaotropic reagents such as Tetramethyl Ammonium Chloride (TMACl) at between 2.5 and 4M concentration are used.

The longer the oligo length used the more potential there is for palindromic or foldback sequences having an effect on the oligo to function as an efficient probe. Efficiency can be substantially improved by reducing the length of such oligos by removing one or more degenerate bases. In this case the binding stability of the oligo can be enhanced by using specific stabilizing base modifications or olio conjugates. For this reason, the use of shorter interrogation sequences, e.g., 4mers have an advantage. In some embodiments, 3mer or 4mers that are completely modified (e.g., LNA) can be used.

In some embodiments, the entire repertoire is added together. In some such embodiments, a buffer which equalizes base composition effects (e.g., TMACl or Guanidinium thiocyanate) is used. In some embodiments, probe species with the same or similar Tms are added together. In some embodiments, the probe species added together are not differentially labeled. In some embodiments, the probe species added together are differentially labeled. In some embodiments, the differential labels, is labels with emissions that have different brightness, lifetime or wavelength, for example, and combinations of such physical properties.

In some embodiments, the differential labels, is encoded, for example they is DNA Origami or DNA nanostructure-based codes. In some embodiments, a coding arm is added to the probe comprising a combination of labels that identify the probe. For example, where a library of every possible 5mer oligonucleotide probe is to be encoded, the arm has five sites each site corresponding to each of the five nucleobases in the 5mer and each of the five sites can be bound to 5 distinguishable species. For example, fluorophores with a specific peak emission wavelength may correspond to each of the positions (e.g., 500 nm for position 1, 550 for position 2, 600 nm for position 3, 650 nm for position 4 and 700 nm for position 5), and four fluorophores with the same wavelength but different fluorescence lifetime may code for each of the four bases at each position.

In some embodiments, the probes are coded in a manner that the label reports on just one nucleotide at a specific position in the oligonucleotide. A sub-set of the repertoire (sub-repertoire) can be added at the same time. A four color coding scheme can be used where at each cycle, one of the base positions in the oligo are defined and the other positions are degenerate.

All oligos where A, C, T and G are defined are each labeled with particular fluorophores that are specific for that defined base. After, binding, detection and removal, of a sub-repertoire of oligos where the first base is defined and the rest are degenerate, a sub-repertoire of probes of similar composition are added, but with the second position encoded by the label (and the others degenerate), then the third, fourth and fifth, each one after the other.

1st cycle, set 1: 4 colors represent the 4 bases at position one.

2nd cycle, set 2: 4 colors represent the 4 bases at position two.

3rd cycle, set 3: 4 colors represent the 4 bases at position three.

4th cycle, set 4: 4 colors represent the 4 bases at position four.

5th cycle, set 5: 4 colors represent the 4 bases at position five.

The whole repertoire can be exhausted in 5 cycles.

In some embodiments, less than 4, e.g., only one color is used throughout the process. In this case, each cycle is split into 4-sub-cycles, in each of which one of the 4 bases at the position (e.g., position 1) is added individually before the next one is added; each time the probes carry the same label. In this implementation the whole repertoire can be exhausted in 20 cycles.

After data processing, the single molecule localization can identify (due to color detected) which of the probes from set 1-5, have the same footprint on the polynucleotide, i.e. bind to the same nanometric location. For example, the nanometric location is defined with precision of 1 nm center (+/−0.5 nm). So all probes whose centroid of PSF falls within the same 1 nm, are binned together. Each single base defined oligo species can bind multiple times (depending on number of photons emitted and collected) to enable accurate localization to a nanometer (or sub-nanometer) centroid. So the nano- or sub-nano-metric localization may determine for example, that the 1st base is A, the second G, the third T, the fourth C and the fifth T for an oligo sequence of 5'AGTCG 3'; this would suggest a target sequence of 5'CGACT3'. Thus all single-base defined 1024 oligo probes can be gone through or tested in just 5 cycles (comprising oligo addition and washes); this covers the whole sequence space of a 5mer. In some embodiments, the concentration of each oligo in the set is lower than would be used when it is used alone, in this case acquisition of data is taken for a longer time in order to reach a threshold number of binding events; also higher concentrations of the degenerate oligo can be used than a specific oligo. This coding scheme can be carried out by direct labeling of the probe, for example, by synthesizing or conjugating the label at the 3' or 5' of the oligos. However it can also be done by indirect labeling, for example, the probe sequence can be attached to a 'flap' (a sequence not intended for the binding interaction) sequence to which a labeled oligo is bound specifying the identity of the base being coded in the sequence interrogation part of the probe. In this scheme only 4 bases need to be distinguished and so only 4 different types of labels are needed. The synthesis of the oligo libraries where just one base is encoded are inexpensive, as only 20 different oligos need to be synthesized each with one base defined and the other 4 degenerate. It is preferable to use hand-mixing during the automated synthesis of the degenerate positions, so that concentrations can be adjusted for reactivity during synthesis.

The location of each oligo is precisely defined by determining PSFs for multiple events for that location and then is corroborated by partial sequence overlap from offset events. This embodiment is highly reliant on the single molecule localization of probe binding to nanometer or sub-nanometer precision.

In some embodiments, the contribution from all four bases is equalized. This can be done by using reagents that suppress the stability of G-C pairs, or increase the stability of AT. Such reagents including, Betaine, TMA and a range of other reagents. Alternatively, nucleotide analogues, modifications and N positions can be used to equalize the Tm of N probes. So to obtain an equivalent Tm to G, a T analogue with increased stability is used.

In some embodiments, the concentration of the four partially degenerate oligo pools are each adjusted to compensate for the difference in stability of the single encoded base according to its Tm; this can only be a fractional compensation as adjustment of concentrations by Tms does not apply to degenerate positions.

In some embodiments, the probes of the probes of the repertoire are encoded. In some embodiment the entire set of 1024 5 mers, for example are encoded. In some embodiments, encoding comprises coupling specific sequence units to one end (e.g., a flap sequence) of the 5mer that is used for interrogation of sequence. Each unit of the encoding sequence acts as a docking site for a distinct fluorescently labelled probe. with fluorescent labelled oligos hybridized onto flap. In order to encode a 5 base probe sequence, the flap on the probe contains 5 distinct binding locations, for example each location is a different DNA base sequence linked tandemly to the next location. For example the first position on the flap is adjacent to the probe sequence (the part that will bind to the polynucleotide target), the second is adjacent to the first, and so on. In advance of using the probe-flap in sequencing, the each variety of probe-flap is coupled to a set fluorescently labelled oligos to generate a unique ID tag for the probe sequence. This can be done by using 4 distinctly labelled oligo sequences that are complementary to each position on the flap, in total 16 distinct labels are needed.

In some embodiments, the first base in the sequence is encoded by the first unit in the flap, the second base by the second unit and so on; the order of the units corresponding to the order of the base sequence. Distinct fluorescent labels are then docked onto each of the units (through complementary base pairing). The first position for example may emit at wavelength 500-530 nm, the second at wavelength 550-580 nm, the third at 600-630 nm, the fourth at 650-680 nm and the fifth at 700-730 nm. The identity of the base at each location may then, for example is encoded by the fluorescence lifetime of the label. For example the label corresponding to A have longer lifetime the C, which has a longer lifetime than G, which has a longer lifetime than T.

So A at position 1 would emit at 500-530 nm with the longest lifetime. G at position 3 would emit at 600-630 nm with the third longest lifetime etc.

In some such embodiments, of sequencing a polynucleotide, the method comprises:

a) Providing an encoded set of oligos such encoding comprising a modular multi-unit sequence to which labelled probes distinct for each unit are pre-bound;

b) Transiently and repetitively binding the repertoire to the polynucleotide and localizing the distinct signal of each type; and c) Reconstructing the sequence of the polynucleotide using the recorded binding locations and decoding the identity of each probe.

In some embodiments, only 4 different oligonucleotide sub-repertoires are used, where only the central base. e.g., of a 5 mer is defined and the rest are degenerate. A mismatch at the central position of an oligonucleotide would be expected to be the most destabilizing and conditions can be set-up so that there is an absolute requirement for the central base to bind and not form mismatch. The transient binding will ensure that more or less all sites are covered by oligonucleotide binding, then if the localization is done to a high level, e.g., sub-nm then the sequence of the polynucleotide can be assembled by just stitching together the base-by-base information provided by the centrally coded oligo. Each of the central bases, A, C, G, T could be coded by 4 different distinguishable fluors, e.g., Atto 488, Cy3B, Atto 655, Alexa 700.

In practice, the optimal concentrations (as well as reaction conditions and temperature) are preferably determined by iteratively adjusting the concentration of each of the pools, reaction conditions and temperature in the sequencing of polynucleotides of known sequence; concentrations/conditions that yield the most accurate sequence for a variety of representative polynucleotides can be deemed to be optimal.

In some embodiments, the invention is a method for sequencing polynucleotides comprising:

a) Immobilizing a polynucleotide;

b) Adding a library/repertoire of oligonucleotides in which one position in the oligo the base A, C, G, T is specified (X) and encoded by a label and the remaining bases are degenerate (N);

c) Imaging the repetitive binding of each labeled oligo to the polynucleotide and nanometrically localizing the binding location and identity of the specified base;

d) Adding the library/repertoire of oligonucleotides labeled for a second position and nanometrically localizing the binding location and identity of the specified base and so on for the third, 4th and 5th position;

e) Assembling the sequence at each location according to which of the base labels persistently transiently binds to the location for each position in the oligonucleotide repertoire; and f) Assembling the sequence of the polynucleotide by taking into account the binding locations and the overlap in sequence between adjacent locations.

This embodiment of the invention benefits from the nanometric localization precision being <2.5 nm or <1 nm, or =<0.34 nm such that location of the specified base in the probe oligonucleotide can be distinguished from the location of the specified base in another probe oligonucleotide binding in the same vicinity.

In some embodiments, some of the probes of the repertoire are encoded. In some embodiment the entire set of 1024 5 mers, for example are encoded. In some embodiments, encoding comprises coupling specific sequence units to one end (e.g., a flap sequence) of the 5mer that is used for interrogation of sequence. Each unit of the encoding sequence acts as a docking site for a distinct fluorescently labelled probe species with fluorescent labelled oligos hybridized onto flap. In order to encode a 5 base probe sequence, the flap on the probe contains 5 distinct binding locations, for example each location is a different DNA base sequence linked tandemly to the next location. For example the first position on the flap is adjacent to the probe sequence (the part that will bind to the polynucleotide target), the second is adjacent to the first, and so on. In advance of using the probe-flap in sequencing, the each variety of probe-flap is coupled to a set fluorescently labelled oligos to generate a unique ID tag for the probe sequence. This can be done by using 4 distinctly labelled oligo sequences that are complementary to each position on the flap, in total 16 distinct labels are needed.

In some embodiments, the first base in the sequence is encoded by the first unit in the flap, the second base by the second unit and so on; the order of the units corresponding to the order of the base sequence. Distinct fluorescent labels are then docked onto each of the units (through complementary base pairing). The first position for example may emit at wavelength 500-530 nm, the second at wavelength 550-580 nm, the third at 600-630 nm, the fourth at 650-680 nm and the fifth at 700-730 nm. The identity of the base at each location may then, for example be encoded by the fluorescence lifetime of the label. For example the label corresponding to A have longer lifetime the C, which has a longer lifetime than G, which has a longer lifetime than T.

So A at position 1 would emit at 500-530 nm with the longest lifetime. G at position 3 would emit at 600-630 nm with the third longest lifetime etc.

In some such embodiments, of sequencing a polynucleotide, the method comprises:

a) Providing an encoded set of oligos such encoding comprising a modular multi-unit sequence to which labelled probes distinct for each unit are pre-bound;

b) Transiently and repetitively binding the repertoire to the polynucleotide and localizing the distinct signal of each type; and c) Reconstructing the sequence of the polynucleotide using the recorded binding locations and decoding the identity of each probe.

The advantage of this approach is that all the individual oligos don't need to be synthesized individually, but are made simply by adding a mixture of nucleotides in a synthesis cycle.

The degree of discrimination a particular nucleotide in the oligo is able to provide is dependent on its position in the oligo. It is expected that a mismatch is tolerated worst at the center of a 5mer and is better tolerated as you move away from the center. Thus, it may sometimes be challenging to assign the correct sequence identity from the data from a single binding event, but multiple events to the site and at adjacent (overlapping, offset) sites can corroborate the sequence.

In some cases the duration of binding may not be precise, reproducible or may not correspond to what is expected. However, in some embodiments, the sequence can be assigned by selecting the probe with the longest average binding duration to the location by looking at the binding durations of all probes from the complete repertoire that bind to that location. Unless there is knowledge of abnormally high binding of mismatch or binding of a probe that forms non-Watson-Crick base-pairs is applied to the dataset, In some embodiments, the oligo with the longest binding duration is taken as the one corresponding to the sequence in the polynucleotide.

In some embodiments, more than 5 cycles are conducted, because the oligos are split up into sets according to their melting temperature. A set of approximately 20 is sufficient to represent the Tm repertoire of 5mers (apart from outliers). In some embodiments, the Tm contribution of A or T=2 and G or C=4 are used to calculate Tm. In other cases nearest neighbor parameters (e.g., according to Breslauer) are used to calculate Tm. In other cases, the Tm of each oligo is determined empirically. The empirical determination is via obtaining a melting curve or is determined by analyzing the binding of oligo complements, when of the complements is bound to a surface and the other is labeled in solution at each given temperature.

In some embodiments, the same temperature is used for all oligo binding and Tm is adjusted by adjusting the concentration of the oligos. Higher concentrations are used for the less stable oligos and lower concentration are used for the more stable oligos. The concentration of each oligo is determined empirically or theoretically. In some embodiments, a single temperature is used but the length or chemical composition of the oligonucleotide is altered.

In some embodiments, conditions are first found for short oligo probes to efficiently discriminate between match and mismatch. Short probes have very fast kinetics and therefore a large number of transient binding events can be accumulated in a short space of time (e.g., less than a second, a few seconds or one or two minutes). The rate limiting steps can be reagent exchange and temperature adjustment. The binding is imaged without drying, thereby optimal equilibrium reaction conditions for each probe can be used.

In general, sequencing assumes that the target polynucleotide contains nucleotides that are complementary to the ones bound; a binding mismatch error is an example of a case where this assumption does not hold. Nevertheless, mismatching when it occurs according to known rules or behavior can be useful in determining the sequence of the target. The use of short oligonucleotides, e.g., 5mers, means that the effect of a single mismatch has a large effect on stability, as one base is 20% of the 5mer length. Hence, at the appropriate conditions, exquisite specificity can be obtained by short oligo probes. Even so, mismatches may occur and because of the stochastic nature of molecular interactions, their binding duration might in some cases not be distinguishable from binding where all 5 bases are specific. However, algorithms that are used to perform base (or sequence) calling and assembly can take the occurrence of mismatches into account. Many types of mismatches are predictable and conform to certain rules. Some of these rules can be derived by theoretical considerations; others are derived experimentally (e.g., Maskos and Southern Nucleic Acids Res, Williams et al Nucleic Acids Res 22:13651367 (1994)

In one embodiment of the invention, a training set comprising one or more known target polynucleotide(s) (e.g., lambda phage DNA or a synthetic construct comprising a supersequence comprising complements to each oligo in the repertoire) is used for testing iterative binding of each oligonucleotide from the repertoire. Machine learning algorithms can be used to determine the binding and mismatching characteristics of the oligo probes. Thus counter-intuitively, mismatch binding can be seen as a way of providing further data which can be used to assemble and/or add confidence to the sequence.

Certain outlier sequences can bind in a non-Watson Crick manner or a short motif can lead to inordinately high on-rate or low off-rate. For example purine-polypryrimidine interactions between RNA and DNA can be very strong (e.g., RNA motifs such as agg). These not only have lower off rates, but also higher on rate, by providing more stable nucleation sequence. In some cases binding occurs from outliers that do not necessarily conform to certain known rules. Algorithms can be designed to identify such outliers or take the expectation of such outliers into account.

In the case where double stranded DNA (e.g., native human genomic DNA) is immobilized, one oligo (antisense) from the set of 1024 will bind to one strand (sense) while the other oligo (sense) binds to the other strand (anti-sense). Even following denaturation it may not be immediately possible to distinguish which strand, sense or antisense, a particular oligo has bound.

Which of the denatured strands one of the probes binds to may not be immediately distinguishable. However, the full sequencing data-set can reveal this, as oligos binding overlapping sequences are found to nanometrically locate to one side or the other (see FIG. 7).

A surprising benefit of the two strands remaining co-located is that it allows for extremely high accuracy, with the base sequence assignment based on the complementary target sites being independently interrogated. The verity of a binding of one specific oligo to one strand can be established by the binding of its complement to the other strand, which is co-located within a few or several nanometers on the surface.

In some embodiments, oligonucleotide probes with 6 defined bases are used; a complete repertoire comprises 4096 sequences. In some embodiments, oligonucleotide probes with 5 defined bases are used; a complete repertoire comprises 1024 sequences. In some embodiments, 5 or 6 bases are defined and additional universal bases or degenerate positions are included in the oligonucleotide length.

The non-specific binding typically binds for a shorter period of time than the specific probes and can thus be distinguished computationally during data processing. For example, under certain conditions binding events shorter than, 10 ms is deemed as non-specific.

The on-rate of the probes can be manipulated (increased) by increasing probe concentration, increasing temperature, increasing molecular crowding (by including PEG 400, PEG 800 etc). Decreasing thermal stability of the probe by engineering its chemical components, adding de-stabilizing appendages, or in the case of oligonucleotides, decreasing their lengths, can increase the off-rate. The off-rate can also be accelerated by increasing temperature, reducing salt concentration (increasing stringency), moving pH towards the extremes of the scale.

Increasing the on-rate by increasing the concentration of probes can become problematic, as the background fluorescence due to probes in solution can become appreciable. Single molecule detection on a surface relies on the background signal to be low so that the signals binding to surface can be detected over background.

In some embodiments, the concentration of probes that are used can be increased by making the probes essentially non-fluorescent until they bind. One way to do this is that binding induces a photoactivation event. Another is that the probes are fluorogenic. Another is that the labels are quenched until binding occurs (e.g., Molecular Beacons). Another is that the signal is detected as a result of an energy transfer event (e.g., FRET, CRET, BRET). In one embodiment the biopolymer on the surface bears a donor and the probe bears the acceptor) or vice versa. In another embodiment an intercalating dye is provided in solution and upon binding of a labelled probe there is a FRET interaction between the intercalating dye and probe. The intercalating dye can be the donor and the label on the probe the acceptor or vice versa. For example, the intercalating dye can be YOYO-1 1000-10,000× dilution or Evagreen at 100-10,000× dilution from stock and the label on the probe can be ATTO 655. In another embodiment, intercalating is dye is used without a FRET mechanism—both the single stranded target sequence on the surface and the probe sequence are unlabelled and signal is only detected when binding creates a double strand into which the intercalating dye intercalates. The intercalating dye depending on its identity can be 100 or 1000× less bright when it is not intercalated into DNA and is free in solution; coupling this with TIRF or HILO microscopy eliminates any background signals from the intercalating dye in solution.

In some embodiments, the invention comprises a method of sequencing nucleotide modifications and/or bases on a single target polynucleotide comprising:

i) Immobilizing the polynucleotide on a surface or matrix;

ii) Adding one or more probe species under conditions that the probe(s) can bind(s) transiently to the polynucleotide to effect a change in one or more fluorescence (or other detectable) signals detected from the polynucleotide;

iii) Continuously monitoring the one or more signals from the polynucleotide on a detector and recording the binding events for a period of time;

iv) Removing the probes of b;

v) Repeating steps ii-iv each time with a different one or more probe species; and vi) Compiling data from each iteration of step iii to reconstruct sequence of modifications and/or bases.

In certain embodiments the methods of the invention can be operated on an array of polynucleotides. In some embodiments, an array of target polynucleotides is immobilized so that a plurality of polynucleotides can be viewed in a single field of view.

In some embodiments, the target polynucleotides are elongated or stretched so that chemical features (base sequence, damage, modification) can be viewed along their length. In some embodiments, a single extraordinarily long target polynucleotide is immobilized so that substantially the whole of its length can be viewed in a single field of view (Frietag et al).

In some embodiments, the fluidic vessel is a well. In some embodiments, the fluidic vessel is a flow cell. In some embodiments, the surface is coated with one or more chemical layers, biochemical layers (e.g., BSA-biotin, streptavidin), a lipid layer, a hydrogel or gel layer.

In some embodiments, the native polynucleotides require no processing before they are displayed for sequencing. This allows the method to integrate epigenomic information with sequence information, as the chemical modifications of DNA will stay in place. Preferably the polynucleotides are directionally well aligned and therefore relatively easy to image, image process, base call and assemble; the sequence error rate is low and coverage is high. A number of means for carrying out the invention are described but each is done so that the burden of sample preparation is wholly or almost wholly eliminated.

The invention is surprising and counter-intuitive because it allows a million or more substantially contiguous bases of genomic DNA to be sequenced by carrying out orders of magnitude fewer reagent addition cycles than the number of bases in the genomic DNA. The methods of the invention are based, in part, on the discovery that single, target polynucleotide molecules can be sequenced by detecting the transient binding of probes to them. Accordingly, the invention, in various aspects and embodiments includes: obtaining long lengths of polynucleotides; disposing the polynucleotide in a linear state such that locations along its length can be traced.

In some embodiments, the entire or close to the entire length of the polynucleotide comprises a contiguous read with a negligible number of gaps. This provides long-range genome structure, even through repetitive regions of the genome and also allows individual haplotypes to be resolved. This method can provide highly complete sequences from one or just a few cells.

In some embodiments, the contiguous sequence is obtained via de novo assembly, using algorithms. In some cases the task of the algorithm is relatively simple as the location of a high proportion of overlapping sequence bits are experimentally obtained. However, where there are difficulties or to increase confidence, reference sequences can also be used to facilitate assembly. Some of the algorithms that process information from multiple polynucleotides are used to resolve individual haplotypes covering very long distances.

The sequence can be extracted from the data in a number of ways. At one end of the spectrum of sequence reconstruction methods the localization of a monomer or a string of monomers is so precise (nanometric or sub-nanometric) that the sequence is obtained by just ordering the monomers or strings. At the other end of the spectrum the data is used to rule out various hypotheses about the sequence. For example one hypothesis is that the sequence corresponds to a known individual genome sequence. The algorithm determines where the data diverges from the individual genome. In another case the hypothesis is that the sequence corresponds to a known genome sequence for a "normal" somatic cell. The algorithm determines where the data from a putative tumor cell diverges from the sequence of the "normal" somatic cell. Variations across the spectrum of these approaches can be implemented.

Hence In some embodiments, the assembly of an unknown sequence comprises:

a) Providing a reference genome
b) Determining in silico a theoretical binding pattern of the reference genome to a repertoire of oligos
c) Comparing the real data to the in silico theoretical reference;
d) Determining the differences between the real data and in silico theoretical reference; and
e) Modify/reconstruct the sequence of the reference according to the differences found in d to generate an assembly of the previously unknown sequence.

In some embodiments, the differences comprise substitutions, indels and structural variation. In particular, when the reference sequence has not been assembled by the methods of the invention, the repeats is compressed, and the reconstruction will decompress.

In some embodiments, where the genomic DNA is obtained from multiple cells, data can be integrated between a plurality of molecules. Each of the multiple molecules partially overlaps with at least another molecule out of the multiple molecules and they are aligned by matching common probe binding patterns. Each of the partially overlapping molecules share a stretch of sequence with the other molecule. Once alignment has been computationally done, the sequences that are unique to each of the molecules are used to fill the gaps, resulting in a completely or substantially contiguous assembled sequence.

The method can be implemented on multiple individual (non-clonal) polynucleotides in parallel and the multiple polynucleotides are disposed in such a manner that to a large extent they are individually resolvable over their entire (or substantial part) of their length and overlap between individual polynucleotides is minimal or does not occur at all. Where side-by-side overlap does occur this can be detected by the increase fluorescence from the DNA stain or where stain is not used, by the increased frequency of binding events; where molecules (diffraction-limited) optically appear to be overlapping but are not physically overlapping, they can be resolved by the super-resolution provided by single molecule localization provided by the invention. Where end-on-end overlap does occur, in some embodiments, labels marking the ends of polynucleotides can be used to distinguish juxtaposed polynucleotides from true contiguous lengths. Such optical chimeras can also be dismissed as artifacts, if many copies of the genome are expected and only one occurrence of the apparent chimera is found. Again, where the ends of molecules (diffraction-limited) optically appear to overlap, but are not physically overlapping they can be resolved by the methods of the invention. In some embodiments, the location determination is so precise that signals emanating from very close labels can be resolved.

High solution concentrations of probe can be achieved without causing detrimental background by using quenched probes molecular beacons, or having two or more labels of the same type, e.g., one on each side of the oligo. When in solution they are quenched via-dye-dye interactions. But when bound to their target they become separated and are able to fluoresce brightly, twice as brightly as a single dye, which makes them easier to detect. Such dye-dye interactions are known for Cy3.

In one aspect the invention comprises a device for sequencing a polymer by transient binding of a repertoire of probes such device comprising a light source, fluidic conduit, optical components, a detector, electronic circuitry, optionally a computer processor and computer memory. The DNA is disposed in a fluidic vessel and is in fluidic contact with the binding probes, the light source emits light which causes the label associated with the binding probes to be detected by the detector. In some embodiments, the detector is a 2D detector. In some embodiments, the polynucleotides is held in one part of the fluidic conduit and the binding probes are in another part. Optionally one part of the fluidic conduit is separated from others via valves. In some embodiments, oligos or sets of oligos are delivered as droplets or packets. In some embodiments, the droplets are pre-loaded on the flow-cell in which sequencing is conducted.

In some embodiments, a sub-set of polynucleotides to be sequenced are first selected from the first set of polynucleotides. In some such embodiments, capture oligonucleotides are used in solution to hybridize to the sub-set of polynucleotides and pull them out of solution. For example, Agilent's SureSelect or similar approach can be used. In some embodiments, the selection involves a CRISPR type of approach, where nucleic acid binding is facilitated by protein binding. Similarly, proteins or polypeptides to be sequenced can be selected from solution, by capture antibodies, nanobodies, affibodies, aptamers etc. Similarly, antibodies, affibodies or nanobodies to be sequenced can be selected from solution, by capture antigens. The isolated biopolymers are the arrayed on a surface and subjected to the sequencing methods of this invention.

In some embodiments, the binding probes, comprise a CRISPR system comprising a protein (e.g., cas9) and a guide RNA. In some embodiments, the purpose of the sequencing is to determine the locations of binding of the guide RNA to detect target and off-target effects.

In some embodiments, the target polynucleotides are those present in body fluids, e.g., circulating DNA or RNA in blood. Such polynucleotides are short in length—around 200 bases in blood and shorter in urine. These polynucleotides can be immobilized on a surface and subjected to the sequencing methods of the invention. Some such polynucleotides bear single stranded ends by which they are immobilized. For example they can be immobilized on a vinyl silane surface (Genomic Vision, France). In some embodiments, the circulating DNA or RNA are circularized and the circle is used for a rolling circle reaction. In some embodiments, the circulization is done by an enzyme such as circligase. In some embodiments, the long length of tandem copies, which are the product of a rolling circle amplification reaction are stretched out on a surface or in a matrix and are then subjected to the sequencing methods of the invention; such an approach allows a consensus sequence of the circulating polynucleotide to be obtained. In some embodiments, where the circulating DNA to be detected is rare, for example in the case of early detection of cancer, the consensus obtained by sequencing of the tandem copies enables an accuracy level to be obtained that is above the error rate of the sequencing method. For example if the raw accuracy of the method is 99.9%, the consensus read may enable an accuracy of 99.999%, enabling very rare variants to be detected. The advantage of the rolling circle amplification in this context is that it does not perpetuate errors from the first or early copying rounds (as would be PCR) as each amplicon is copied directly from the circularized polynucleotide.

In some embodiments, the method is applied in situ along stretched molecules. In some embodiments, the method is applied in situ on chromatin. In some embodiments, the method can be applied in situ on mitotic/metaphase chromosomes. In some embodiments, the method can be applied in situ on interphase chromosomes. In some embodiments, the method can be applied in situ on chromosomal DNA inside cells. In some embodiments, the method can be applied in situ along tandem copies.

In some embodiments, when the aim is to sequence DNA, RNAse is applied to the sample before sequencing commences. In some embodiments, when the aim is to sequence RNA, DNAse is applied to the sample before sequencing commences. In some embodiments, where both cytoplasmic nucleic acids and nuclear nucleic acids are to be analyzed they are extracted differentially or sequentially. First the cell membrane (and not the nuclear membrane) is disrupted to release and collect the cytoplasmic nucleic acids. Then the nuclear membrane is disrupted to release the nuclear nucleic acids. In some embodiments, proteins and polypeptides are collected as part of the cytoplasmic fraction. In some embodiments, RNA is collected as part of the cytoplasmic fraction. In some embodiments, DNA is collected as part of the nuclear fraction. In some embodiments, the cytoplasmic and nuclear fractions are extracted together. In some embodiments, after extraction the mRNA and genomic DNA are differentially captured. For example the mRNA is captured by oligo dT probes attached to the surface. This can occur in a first part of a flow cell and the DNA is captured in a second part of a flow cell which has a hydrophobic vinyl silane coating on which the ends of the DNA can be captured (presumably due to hydrophobic interactions).

The mechanism of transient binding described thus far are passive and are such because the probe binding is unstable. The following describes an alternative embodiment of the invention in which the transient binding is an active mechanism. Here the probe binding is stable and must be removed by a physical or a molecular means.

Hence, the active transient binding loop comprises:
1) Stably binding oligo or oligo set to target;
2) Actively remove oligo or oligo set from target; and
3) Repeat 1 and 2.

In some embodiments, the loop is carried out at least twice. In some embodiments, the on-off binding is continuously monitored. In some embodiments, only the on binding is monitored. Binding oligos to target in step 1 comprises binding many oligos of the same sequence. In some embodiments, multiple oligo sequences are bound to target in step 1 to different sites on the target.

In some embodiments, the sequencing method comprises:
1) Add oligo 1 or oligo set 1;
2) Allow stable binding oligos to a sub-set of target sites while imaging;
3) Actively remove oligos from target;
4) Repeat 2 and 3 until sufficient photos collected from sufficient locations;
5) Wash away oligos;
6) Add oligo 2 or oligo set 2;
7) Repeat steps 2-5;
8) Add oligo 3 or oligo set 3;
9) Repeat steps 2-5; and
10) Continue above process until the repertoire has been exhausted.

In some embodiments, step 2 and 3 is carried out multiple times for each oligo or oligo set. This is done for a number of reasons. Because binding is a stochastic process, if the binding is done for the appropriate time, so the reaction is stopped pre-equilibrium or at early stages, only a fraction of binding sites will be occupied. Thus if the binding sites of the oligos or oligo sets used are too close together in totality to be resolved individually, a subset will be statistically further apart allowing them to be individually detected, if the concentration of the oligos and the time of reaction is appropriately set. The appropriate time and concentration can be determined empirically. It allows a different sub-set of sites to be bound and interrogated at each iteration. Another reason for conducting the binding multiple times is to allow all or almost all most sites to be interrogated and substantially all or most sites to be each interrogated multiple times hence enhancing sensitivity and accuracy.

In some embodiments, the active binding and removing are effected by temperature changes. In some embodiments, the active binding and removing are effected by reagent changes. In some embodiments, the active binding and removing are effected by electrical changes.

In some embodiments of the invention, during the course of a probe binding period the temperature can be altered so that the binding behavior of the probe at more than one temperature can be determined. In some embodiments, an analogue of a melting curve is conducted, where the binding behavior or binding pattern to the target polymer is correlated with a ramp of temperature through a selected range, for example from 10 degrees to 65 degrees.

In some embodiments, as an alternative or in addition to modifying the temperature for oligonucleotide probes with different Tms, their concentration can be altered and/or the salt conditions and/or the pH can be altered. In some embodiments, an electrical bias on the surface is repeatedly switched between positive and negative to actively facilitate transient binding.

In some alternative embodiments the transient single molecule binding is detected by non-optical method. In some embodiments, the non-optical method is an electrical method. In some embodiments, the transient single molecule binding is detected by non-fluorescence methods where there is no direct excitation method rather a bioluminescence or chemiluminesence mechanism is used.

In some embodiments, the invention comprises a method for sequencing a target polynucleotide comprising:
1) Immobilizing a target polynucleotide by one or more interactions (e.g., multiple interactions) along its length with a surface/matrix;
2) Flooding the immobilized target polynucleotide with oligonucleotides of a given sequence and length or chemical composition under conditions (oligo concentration, salt concentration, temperature), that if a match is found in the target, transient binding can occur for a duration or persistence that is distinguishable above non-specific binding;
3) Detecting the transient binding events and recording their 2D coordinates;
4) Removing the oligonucleotides;
5) Adding a next set of oligonucleotides and repeating 3 and 4 until an entire repertoire of sequences of a given length are tested and removed; and
6) Using an algorithm to compile the sequence of the immobilized target polynucleotide based on the locations of the transiently binding oligonucleotides.

The methods of this invention are particularly suited to sequence very long polymer lengths, where native lengths or a substantial proportion thereof are preserved (e.g., for DNA whole chromosomes or ~1 Mbp fractions). However, common molecular biology methods result in fragmentation of DNA. Any pipetting, vortexing causes shear forces that can break DNA molecules; nuclease contamination can cause nucleic acids to be degraded. In some embodiments of the invention native lengths or substantial high molecular weight (HMW) fragments of native lengths are preserved before immobilization, stretching and sequencing commences.

Hence, In some embodiments, the invention comprises a method for sequencing a target polynucleotide comprising:
1) Disposing cells in microfluidic vessel or device;
2) Extracting polynucleotides from the cells into a microfluidic environment;
3) Immobilizing and elongating a target polynucleotide by one or more (e.g., multiple interactions) along its length with a surface/matrix;
4) Flooding the immobilized target polynucleotide with oligos of a given sequence and length or chemical composition under conditions (oligo concentration, salt concentration, temperature), that if match is found in the target, transient binding can occur for a duration or persistence that is distinguishable above non-specific binding;
5) Detecting the transient binding events and recording their 2D coordinates;
6) Removing the oligos;
7) Repeat 4-6 each time with different oligos, until an entire repertoire of sequences of a given length have been tested;
8) Using an a single molecule localization algorithm to localize each binding site nanometically; and
9) Using an algorithm to compile the sequence of the immobilized target polynucleotide based on the locations of the transiently binding oligonucleotides.

In some embodiments, a single straightened linear polymer is analysed or considered at a time. In this case rather than recording 2D coordinates, only 1D coordinates are needed.

In some embodiments, the polynucleotides are fragmented to relatively homogeneous long lengths (e.g., ~1 Mb) after, during or prior to step 1. In some embodiments, the polynucleotides are fragmented to relatively homogeneous long lengths after or during step 2. In some embodiments, the fragmentation is effected enzymatically. In some embodiments, the fragmentation is effected physically. In some embodiments, the physical fragmentation is via sonication. In some embodiments, the physical fragmentation is via ionic bombardment or radiation. In some embodiments, the physical fragmentation is via electromagnetic radiation. In some embodiments, the physical fragmentation is via UV illumination. In some embodiments, the dose of the UV illumination is controlled to effect fragmentation to a given length. In some embodiments, the physical fragmentation is via the combination of UV illumination and staining with a dye (e.g., YOYO-1). In some embodiments, the fragmentation process is halted by a physical action or addition of a reagent. In some embodiments, the reagent that effects a halt in the fragmentation process is a reducing agent such as beta-mercaptoethanol (BME).

In some embodiments, the invention includes:
1) Disposing cells in microfluidic vessel or device;
2) Staining the cells with an intercalating dye;
3) Providing a pre-determined dose of UV light to effect intercalating dye mediated fragmentation;
4) Optionally halting the fragmentation;
5) Extracting polynucleotides from the cells into a microfluidic environment;
6) Immobilizing and elongating the polynucleotides; and
7) Sequencing in situ on the immobilized and elongated polynucleotides.

These steps can be added to various embodiments of the invention including those that act on isolated single cells.

In some embodiments, each cell is separately isolated, its DNA separately extracted and separately sequenced in the microfluidic vessel or device. In some embodiments, the extraction occurs by treating with detergent and or protease. In some embodiments, chelating agents (e.g., EDTA) are provided in solution to mop up divalent cations required by nucleases. In some embodiments, and with specific sample sources the concentrations of divalent cations are higher than normally used in molecular biology.

In some favorable embodiments the present invention is faster than prevailing sequencing technologies. In some favorable embodiments the present invention is lower-cost than the prevailing sequencing technologies. In some favorable embodiments the present invention provides a longer read than the prevailing sequencing technologies. In some favorable embodiments the present invention provides higher accuracy than the prevailing sequencing technologies. In some favorable embodiments the present invention provides higher sensitivity than the prevailing sequencing technologies. In the most favorable embodiments the present invention provides all the aforesaid advantages. Moreover, in some favorable embodiments, a whole genome can be sequenced within an hour or so using small amounts of biochemical reagents costing just a few dollars or less nothwistanding that the cost of flow cell, instrumentation, and computer power adds to the cost. For example, a 5mer with a 20 base labeling site can be purchased for about $1 and a complete repertoire would cost $1000. A fluorescent labeled oligo that can bind stably to the labeling site for about $50. About one millionth of such oligos synthesized at the micromolar scale would be used, resulting in a cost less than a dollar per run.

The methods of the invention are remarkable in that they do not require enzymes and they consume only dilute solutions of the probes (oligos). Hence the methods are low cost. The sequencing chemistry consumes only simple probes and buffer, and as a consequence, costs are dominated by equipment and plastic-ware.

A surprising feature of the invention is that the single molecule elongated targets remain stable over hundreds of reagent exchange and wash cycles.

A remarkable aspect of the invention enabled by single molecule localization is that an ordered array of 10 nm pitch when fully occupied will give a trillion target molecules per Another remarkable aspect of the invention is that a single base substitution in the target would cause ten 5mer probes (for example) to change relative to the reference sequence: Five probes that previously would not bind would now bind and five probes that previously bound would now not bind. This change would be seen on the other strand too.

In its preferred embodiments the present invention is distinguished from the prior art, by comprising two or more of the following elements: no prior library preparation before polynucleotides are immobilized; in some embodiments, alignment of polynucleotides in one orientation; transient binding; repetitive binding; the contiguous sequences in the polynucleotide are constructed by stitching together bits of sequence information.

In some embodiments of the invention substantially all reagents needed for conducting the method are pre-loaded on the fluidic device before analysis commences. In some embodiments, the reagents (e.g., probes) are and present in a dry state in the device and are wetted and dissolved before reaction proceeds.

In some embodiments, the method comprises a means of sequencing a target biopolymer comprising multiple binding events to a single polymer during the course of imaging without reagent exchange. In some embodiments, the multiple binding events occur singly or multiply to each of a plurality of locations on a single biopolymer.

In some embodiments, the sequencing method comprises the transient binding of sequence probes to a single polynucleotide where said probes are substantially complementary to each of multiple overlapping sites on a single polynucleotide. In some embodiments, each of the overlapping sites are resolved by the locational accuracy and precision of the method.

In some embodiments, the sequencing method comprises the transient binding of a repertoire of sequence probes to a single polynucleotide where a plurality of probes in the repertoire are each substantially complementary to sequence bits on a single polynucleotide, where the binding of two or more probes bind to overlapping sites is temporally separated.

In some embodiments, the sequencing method comprises the transient binding of a tiling set of sequence probes to a single polynucleotide where a plurality of probes in the set are each substantially complementary to sequence bits on a single polynucleotide, where the binding of two or more probes to overlapping sites/bits is temporally separated.

In some embodiments, the sequencing method comprises the binding of a panel of sequence probes to a single polynucleotide where a plurality of probes in the panel are each substantially complementary to sequence bits on a single polynucleotide. In some such embodiments, the sequence bit is interrogated multiple times by the same or a different probe.

In some embodiments, the invention comprises a method for analyzing amino-acid sequence on a target protein. In some embodiments, the invention comprises a method for analyzing amino acid sequence on a target polypeptide. In some embodiments, the invention comprises a method for analyzing peptide modifications as well amino-acid sequence on a target polynucleotide.

In some embodiments, the methods of the invention are applied to the sequencing of polypeptides. Each of the 20 amino acids are bound by a corresponding specific probe comprising N-recognin, nanobody, antibody, aptamer etc. The binding of each probe is specific to each corresponding amino acid within the polypeptide chain.

In some embodiments, the order of sub-units in a polypeptide is determined. In some embodiments, the binding is to surrogates of the binding sites. In some embodiments, the surrogates are tags attached at certain amino acids or peptide sequences. The transient binding is to the surrogate tags.

In some embodiments, the invention comprises determining the identity of a polymer. In some embodiments, the invention comprises determining the identity of a cell or tissue. In some embodiments, the invention comprises determining the identity of an organism. In some embodiments, the invention comprises determining the identity of an individual. In some embodiments, the methods of this invention are applied to single cell sequencing.

In some embodiments, sequencing is conducted in situ inside a cell. The contents of the cell can be referred to as a matrix, and is fixed, denatured before transient binding commences. In some embodiments, the cells may form a monolayer or in others they is part of 3D architecture such as a tissue or an organoid. An imaging method that can detect events in 3D structures such as multi-photon microscopy and light sheet microscopy can be used. Fixing the molecules in a matrix or a gel and interrogation therein provides the ability to capture all the molecules, including those that are rare. In some embodiments, cells are (e.g., circulating tumour cells CTCs) are dispersed on a surface and sequenced. In some embodiments, cells are dispersed on a surface such that each cell is well isolated away from other cells. The cells can then be lysed and their molecular inventory can be captured on the surface and subjected to the sequencing methods of the invention.

In some such embodiments, the method comprises:

I) Fixing the location of polynucleotides inside cells;

II) Adding oligos of a given specificity and using single molecule localization to determine the location of all binding events;

III) Adding oligos of a different specificity and using single molecule localization to determine the location of all binding events;

IV) Repeating steps and

V) Reconstructing sequence of the linear path or territorial location of the polynucleotides within the cells by compiling the location of binding of the oligonucleotides.

In some embodiment of the above a mechanism (FRET, Fluorgenitic labels, quenched labels etc) is used to minimize background fluorescence/light scattering that would make the detection of individual point sources of difficult. In some embodiments, of the above RNAse is used to remove RNA before the invention is applied to the remaining DNA. In some embodiments, of the above, the duplex DNA is denatured in situ before addition of oligos.

In some embodiments, the location of modifications are also determined by using single molecule localization to determine the location of modifications such as 5 methyl C (5MC).

Some embodiments of the invention are designed to solve problems in digital molecular counting. One problem in counting molecules is that of obtaining high precision, reproducible data. Due to the stochastic nature of molecular interactions an end-point digital counting assay may miss certain events that are not present at the time the end-point measurement is made or it may count spurious events (e.g., non-specific binding or partial matches). For this reason a digital counting assay where the molecule being counted is detected by transient binding probes that bind multiple times (or repetitively) is more suitable. The multiple binding events give confidence that something real is being detected and can determined what is being detected or some characteristic of what is being detected (e.g., a partial match).

Thus, In some embodiments, the invention comprises a method of counting the number (or determining the copy number) of a type of molecule (e.g., DNA fragment containing a specific sequence) in a sample comprising:

a) Adding one or more probe species under conditions that the probe(s) can bind(s) transiently to the molecule;

b) Continuously monitoring individual binding events on the molecule on a detector and recording for a period of time;

c) Analyzing data from step b to filter out non-authenticate interactions and determine the number of authenticate interactions and thereby determine the copy number of the molecule;

and d) Optionally the molecule is immobilized on a surface or matrix before step a.

In some embodiments, the enumeration of a type of molecule is a result of an emergent property of the transient binding interactions. One probe binding event or an end-point determination of binding is not sufficient to determine an authentic value for the number of the type of molecule; an authentic determination emerges from (is an emergent property of) the analysis of multiple binding events, which can separate the wheat from the chaff (authentic events from non-authentic events).

In some embodiments, the invention comprises a method of counting interactions between one or more probes and a molecule comprising:

a) Adding one or more probe of a given specificity under conditions that the probe(s) can bind(s) transiently to the molecule;

b) Continuously monitoring individual binding events on the molecule on a detector and recording for a period of time;

c) Analyzing data from step b to determine the number of interactions that occurred during the period of time;

d) Optionally adding one or more probes of a different specificity and repeating steps b-c; and e) Optionally the molecule is immobilized on a surface or matrix before step a. In some such embodiments, in step c the interactions are classified by the duration of each interaction and the number of events that fall into each classification are recorded. This embodiment can be useful, for example, in a case where the degree of match between a sequence and different probes, is being measured. This embodiment can be adapted for the previous embodiment to differentiate authentic events from non-authentic events.

A number of criteria can be established to decide what constitutes an authentic event and what constitutes a non-authentic event, e.g., binding duration cut-off is one criteria to separate an authentic event from a non-authentic one.

In certain single molecule localization methods such as PAINT, which tackle a crowded field containing a high density of molecules that need to be measured, the localization accuracy is dependent on: (1) The number of photons collected (the extent of localization is inversely proportional to the number of photons, so a high number of photons is needed to obtain localization to a sub-nanometer or low nanometer level); (2) Low duty cycle, i.e. the time that each binding event lasts is short, which because the binding events are stochastic statistically means that only a fractional and hence individually resolvable signals are emitted at any given time.

In some alternative embodiments, where the field of molecules is not crowded or high-density or where the sites along an elongated or stretched polymer are sparse, a low duty cycle is not needed. The signal or the detectable photon emission can be long-lived, and the duration that are detected determines the extent to which localization can be done using single molecule localization algorithm. A long exposure time can be used in order to gather more photons. In such an embodiment it is useful to use pulsed or stroboscopic illumination to minimize photobleaching of probes. Also the signal from dyes can often be recovered by excitation with lower wavelength light. So the detection comprises:

1) Illumination with wavelength 1;
2) Detection of signal;
3) Illumination with wavelength 2; and
4) Repeat 1-3 until sufficient photons collected for localization required.

When this is applied to sequencing to determine the location of say, a 5mer probes along the length of a polynucleotide, the sequence bit can be localized to a few nanometers and the locations of each of the repertoire of probes can be use to put together the sequence of the polynucleotide, which is an emergent property of the locations of the repertoire of binding events. This embodiment, which does not require transient binding, is nonetheless novel because the signals are localized to nanometric or sub-nanometric dimensions.

In some embodiments, the polynucleotides are disposed in a flow channel containing a medium that can undergo a liquid to gel transition, such that after the polynucleotides are well dispersed and individually isolated, the sol-gel transition can be induced which fixes the polynucleotides in their location. The probes of this invention can then be applied to the polynucleotides trapped in the gel phase. As the polynucleotides will be dispersed in 3D (albeit aligned in one orientation), imaging methods such as light-sheet microscopy can be used to image 2-D slices.

In some embodiments, the solution has two phases, a liquid phase and a solid (or gel) phase. The polynucleotide are initially elongated and distributed in the liquid phase and then fixed by changing phase to the solid/gel phase (e.g., by heating, or in the case of polyacrylamide by adding a co-factor or with time). In some cases the polynucleotide can be elongated in the solid/gel phase. The sequencing chemistry of the invention is then applied to the static polynucleotides isolated in 3 dimensions in the solid phase. The detection of the sequencing reactions is then done by confocal, multi-photon, light sheet microscopy, spinning disc confocal microscopy etc. This embodiment is particularly relevant when substantially all the molecules in a sample need to be sequenced (not just those that can be captured on a surface). Polynucleotides is processed in a medium comprising poly(N-isoproylacrylamide); heating leads to a phase transition creating a hydrogel (Eriksen et al Biomicrofluidics 5:31101-311014 2011) which fixes the polynucleotides in 3D space but allows the exchange of reagents through the hydrogel.

In some embodiments, the polymer is capture at one end and then straightened or stretched due to the forces on the polymer due to the flow of liquid medium in which the polymer is disposed. The liquid/sol phase is transitioned to a gel phase, so that the molecules become static.

In some methods when the polymer is disposed or comes to be disposed in a gel, the relatively fixed or static position of the features (e.g., sequence buts or amino acids) along the length of the polymer, allows the location of labels along the length of the polymers to be determined by single molecule localization methods.

These embodiments thus comprises:
I) Aligning polynucleotides in a single orientation in a gel or matrix;
II) Flowing fluorescent oligos of a given specificity through the gel or matrix so that the oligos are able to make transient interactions with the polynucleotide;
III) Flowing fluorescent oligos of a different specificity through the gel or matrix so that the oligos are able to make transient interactions with the polynucleotide;
IV) Repeating step III; and
V) Determining the sequence of the target polynucleotide using information about the binding location of oligos of each specificity.

In some embodiments, sequence information is obtained by the transient binding of sequence-specific nucleic acid binding proteins, such as restriction enzymes, nicking endonucleases and methyltransferases. There is a large repertoire of such proteins commercially available, covering a large amount of the sequence space. A large number of sequence enzymes that recognize palindromic sequences are available, One feature of the three aforementioned proteins is that they recognize sequence in double-stranded DNA. These probes can be used to replace some oligonucleotides from a complete repertoire, for example some of those that would undergo self-self or hairpin interactions rendering them as relatively inefficient probes under the usual reaction conditions.

The transient binding of the antibody or binding protein can be effected by manipulation of reaction conditions such as salt concentration. In some embodiments, the salt concentration is raised to >100 mM to effect transient binding. In some embodiments, the salt concentration is raised to >200 mM. In some embodiments, the salt concentration is raised to >300 mM. In some embodiments, the transient binding is actively effected by exchanging buffer from low salt to high-salt. In some embodiments, the sequence or modification (e.g., Methylation) specific binding proteins are allowed to bind stably or transiently and their location is determined by single molecule localization of a label conjugated thereon or binding to the protein directly or via a tag.

In some embodiments, the reaction is reversed and the probes are immobilized and transient interactions with the molecule (target to be analyzed) in solution are determined.

In some embodiments of the invention the molecule is not immobilized on a surface or matrix but is freely diffusing in solution. The detection is carried out by fluorescence correlation spectroscopy (FCS). In some such embodiments, the molecule (e.g., is larger and) moves through the solution more slowly than the probes. Hence in each confocal spot many putative binding events of the probes with the molecule can be recorded before the molecule diffuses out of the confocal spot; these binding events will be cross-correlations. The binding cross-correlations can be distinguished from the non-binding cross-correlations by the time of residence of the probe in the confocal spot. In some embodiments, an encoded repertoire of oligos is provided and the identity of the binding oligo (which will statistically occur one at a time) is determined by decoding the fluorescent binding signals.

In some such embodiments, the method comprises:
I) Adding the polynucleotides into a solution;
II) Illuminating a confocal volume isolating a single polynucleotide;
III) Flowing or uncaging a fluorescent oligos of a given specificity so that the oligos are able to make transient interactions with the polynucleotide;
IV) Flowing or uncaging a fluorescent oligos of a different specificity so that the oligos are able to make transient interactions with the polynucleotide and their binding characteristics determined;
V) Repeating step IV; and
VI) Determining the sequence of the target polynucleotide using information about the duration and persistence of binding events detected for oligos of each specificity.

In some embodiments, the binding characteristics include whether a binding duration beyond a pre-determined threshold occurs.

In some embodiments, the polynucleotide remains in solution, its bulk allowing it to remain in relatively the same location or within a confocal volume and the oligos of the repertoire are passed through the volume one by one (or set by set) or preferably as an encoded repertoire all added at the same time. In some embodiments, the bulk of the polynucleotide allows it to be trapped at a fixed location by a physical trap, e.g., laser trapping, electrostatic trapping. In some embodiments, multiple polynucleotides can be individually trapped by multiple optical traps.

In some embodiments, the polynucleotide is confined within a container e.g., immiscible lipid vesicle. The container may allow exchange of probes but does not allow escape of the polynucleotide.

In some embodiment the confocal volume is a multi-photon volume.

In some embodiments, the polymer within solution is not stationary; the polymer is moved in a perpendicular direction to the direction of well isolated flowstreams (e.g., laminar flow streams) carrying different probes of the repertoire. The movement is electrophoretic (i.e. towards a positively biased electrode) acting on the polynucleotide which is of higher molecular weight than the oligos in the flow stream whose trajectory is not appreciably affected by the direction of movement of the polynucleotide.

In some embodiments, the polynucleotide is immobilized at only one end but is stretched out in a flow stream parallel to the surface (or a 2D plane of detection when immobilized to a optically trapped bead for example) and does not make long-lived interactions with the surface from locations along its length other than the one end. In some embodiments, the polynucleotide immobilized at one end is single stranded. The oligos of the repertoire are then exchanged in the fluidic volume. In some embodiments, the direction of flow of the oligos is the same as the direction of elongation of the polynucleotide. In some embodiments, detectable repeated transient binding of individual oligo molecules occur to complementary locations in the elongated polymer, even as the bulk of the oligos are in transit along the flow direction.

In some embodiments, the polynucleotide is stretched from its point of immobilization perpendicular to the flow direction. This can be effected by providing an electric field perpendicular to the flow direction. The flow is effected by pressure driven flow by applying from 1 millibar up to 1 bar of pressure and the electric field can be between 1 and 100 volts per centimetre, with the surface where the polynucleotide's end is immobilized, is made negative and another surface of the flow cell is made positive to which the polynucleotide is attracted.

In some such embodiments, the method comprises:

I. Attaching a polynucleotide to a surface by one end and elongating in one direction by a physical mechanism;

II. Flowing fluorescent oligos of a given specificity so that the oligos are able to make transient interactions with the polynucleotide;

III. Flowing fluorescent oligos of a different specificity so that the oligos are able to make transient interactions with the polynucleotide;

IV. Repeating step III; and

V. Determining the sequence of the target polynucleotide using information about the duration and persistence of binding events detected for oligos of each specificity In some embodiments, the physical mechanism is flow stretching, electrophoretic stretching, or stretching due to action on a bulky entity (e.g., bead) attached to one end of the polynucleotide. The bulky entity can then be subjected to laser trapping, electrostatic trapping (if it is charged), magnetic trapping (if it is paramagnetic).

Where the polynucleotides of the methods above, are genomic DNA, the method can further comprise, overlapping assembled polynucleotide sequences to assemble a chromosome.

In some embodiments, the invention concerns a method for delivering a biomacromolecule for analysis comprising:

1. Providing a protective entity comprising a biomacromolecule, said protective entity preserving the biomacromolecule close to its native state;

2. Placing the protective entity comprising the biomacromolecule in proximity of an analytical zone;

3. Releasing the biomacromolecule from the protective entity into the analytical zone; and 4. Analysing the biomacromolecule according to the methods described in this invention.

In some embodiments, probes are labeled according to just one defined nucleotide (e.g., NNNXNNN, where X is a defined or coded nucleotide). In some embodiments, the repertoire of NNNXNNN oligos comprise position X=A, C, G or T and position N is one of A, C, G and T. The central base in the oligos is differentially labelled according to its identity, A, C, G or T. In some embodiments, four libraries of NNNXNNN oligos (e.g., each library comprising set of oligonucleotides: NNNANNN, NNNTNNN, NNNGNNN and NNCNNN) are each differentially labelled and are used in a homogeneous reaction that requires no reagent exchange during the sequencing process.

It is very easy to detect nucleic acid sequences, using complementary nucleic acid sequences (e.g., oligo probes). The sequence (e.g., 5 base) that is bound by the oligonucleotide is referred herein as a sequence bit. In some assays, e.g., Fodor's gene-chip assays (e.g., as described in Chee et al Science 274:610-4. 1996), the probe is immobilized and the target is labeled and provided in solution. In many other assays the target is immobilized and the probe is labeled and provided in solution (e.g., via Southern Blot, as described in Southern EM, Journal of Molecular Biology, 98: 503-517 (1975)). In such assays, the probe hybridizes to the target nucleic acid sequence by Watson-Crick interactions, excess labeled probe is washed off and the remaining bound probe is detected. Hybridization requires correct binding to be stable enough to withstand washes and remain in place during detection. Methods have been proposed for sequencing immobilized polynucleotides solely by hybridization of a repertoire of oligonucleotides (e.g., as described in Drmanac et al Science, 260, 1649-1652, 1993) and this 'Sequencing by Hybridization' (SbH) approach has been demonstrated for the re-sequencing of a small genome (e.g., as described in Pihlak et al Nature, Biotechnlogy 26: 676-684 2008). Mir (WO2002074988, 2001), further proposed SbH of polynucleotides stretched on a surface. All of the aforesaid probing and sequencing methods are end-point assays and require the probe to form a long-lived interaction with the complementary polynucleotide target. Any nucleic acid interaction has an off-rate, but in the case of nucleic acid assays the off-rate is slow to the point that it has no significant effect on the assay. When the probe is bound stably, specific steps have to be taken involving stringent stripping protocols (including high temperature), to remove the probe before the next probe in the series can be hybridized. The harshness of the conditions can damage the DNA or remove the target DNA from the surface and from the inventor's experience, a substantial of amount probe remains stuck, effectively, permanently.

The present invention is a novel, counter-intuitive sequencing approach, which involves Watson-Crick interactions of a probe with a target sequence, which is short-lived. The chemical structure of the probe (e.g., sequence, 3D structure) is designed not to form long-lived stable interactions under the conditions used. Rather the probe is designed such that the majority of the probe molecules bind to the target and then unbind during the process of detection. This is different to hybridization where the majority of the probe is expected to stay bound during detection.

The inventive step comprises the fact that where hybridization based attempts at sequencing have involved stable long-lived binding, the present approach specifically requires short-lived unstable binding. Conditions have been found for unstable, transient repetitive binding of oligonucleotides as short as 5 interrogation bases, which is short enough to easily generate and run through an entire repertoire (1024 oligos).

While the invention has some similarities with SbH, it does not suffer from an intrinsic problem of SbH: Once one probe has bound, say a 5mer its footprint will cover a sequence of 5 bases and inhibit or obstruct other probes that will partially overlap with the 5 base footprint, from binding. Even where only one probe is used at a time, if a subsequence of the probe is tandemly repeated, the first binding oligo will prevent information to be obtained from adjacent positions. However, because the present invention involves transient binding, the first probe will come off, making the sequence accessible for binding by a second probe and the second would come off to allow binding of a third, and so on. Another advantage of the present approach is that the verity of each sequence bit, is verified by repetitive binding, whereas in SbH once something is bound it is stuck and it is difficult to determine if it is a result of specific or non-specific binding. In addition, the stable binding of mismatches causes a problem for SbH but in the case of the present invention mismatches can be differentiated from perfect match by duration of binding, frequency of long-duration binding etc. In some cases of mismatch for example 4 bases may form Watson-Crick base pair and the 5th does not form a base pair. In other cases, for example, 4 may form a Watson-Crick base pair and the 5th forms a non-Watson Crick base pair. In some cases (e.g., where a non-Watson-Crick bond forms) the non-perfect match which has some Watson-Crick base pairs and one or more non-Watson-Crick base-pairs may actually form a more stable interaction than the perfect match, and the average duration of binding is longer. Gathering empirical data about all such possibilities will improve the performance of the sequencing technology of this invention. Machine learning can be used to learn such behavior from a sub-set of experiments in order to predict the behavior of the full set.

The use of short oligonucleotides of the invention has the advantage that the search for a target sequence typically involves finding 3, 4, 5, or 6 matches, which can happen quite rapidly and the occurrence of the target sequence is quite frequent. In some embodiments, substantially all the matched and mismatch sites are bound transiently during the course of detection, while In some embodiments, only a fraction of sites are bound.

The polynucleotide sequencing of the present invention is an emergent property of the binding characteristics of a repertoire of oligos. SbH and hybridization assays in general, obtain information from the binding of perfect match according to Watson-Crick rules of a synthetic oligonucleotide to its targeted native polynucleotide and endeavor to remove binding that includes mismatches. Some embodiments of the present invention look at the repertoire of binding interactions (above a threshold binding duration) each oligonucleotide has had with the polynucleotide under analysis. In some embodiments, the sequencing does not only comprise stitching or reconstructing sequence from a perfect match but obtains the sequence by analyzing the binding proclivities of each oligo. The method is uniquely set up to measure the binding proclivities of each oligo species: the rate and duration of on-off binding is a function of the type and number of base-pairs the probe makes with the site it binds. In sum, the repetitive binding interactions of an oligo with a site where it forms full base-pairing or perfect match will tend to be different from those at locations where it forms a mismatch in which some of the bases in the probe do not pair with the target; binding to the mismatch site in most cases will tend to be shorter-lived than the perfect match site. Empirical data will be used to modify the expectation for certain outliers where the Watson-Crick mismatch binding is longer lived than the Watson-Crick match binding. The algorithm of the invention can take this into account.

In some embodiments of the invention, the detection step involves taking a number of image frames (e.g., movie or video), over which the binding-on and -off of the probe is recorded.

In some embodiments, the detection step involves detecting multiple binding-on and -off events to each complementary site. The multiple events is from the same probe molecule binding on or off, or being replaced by another molecule of the same specificity (i.e. it is specific to the same sequence or molecular structure), and this may occur multiple times. The binding on or off is not effected by altering conditions, both binding-on and binding-off occurs under the same conditions (salt concentration, temperature etc) and is due to the probe-target interaction being weak, such that the binding is transient.

In some embodiments of the invention sequencing is conducted by imaging multiple on-off binding events at multiple locations on a single target polynucleotide that is shorter, the same length or within an order of magnitude of the probe length. In such embodiments a longer target polynucleotide have been fragmented or a panel of fragments have been pre-selected and arrayed on a surface so that each polynucleotide molecule is individually resolvable. In these cases the frequency or duration of probe binding to a specific location is used to determine whether a probe corresponds to the target sequence. The frequency or duration of the probe binding can also determine whether a probe corresponds to all or part of the target sequence (with the remaining bases mismatched).

In some embodiments of the invention sequencing is conducted by imaging multiple on-off binding events at multiple locations on a single target polynucleotide that is longer than the probe. In some embodiments, the location of probe binding events over the single polynucleotide are determined. In some embodiments, the location of probe binding events over the single polynucleotide is determined by elongating the target polynucleotide, so that different locations along its length can be detected and resolved. In some embodiments, the elongation occurs on a surface. In some embodiments, the elongation occurs in a nanochannel. In some embodiments, the elongation occurs by hydrodynamic drag when one or both ends of the target are under tension. In some embodiments, the elongation occurs via electrophoretic forces, for example when one end of the target polynucleotide is tethered, anchored or trapped, and the other is dangling free in solution or gel.

In some embodiments, the on-off binding of the labeled probe requires, rejection or removal of signal from probes that have not bound. This can be done by using for example an evanescent field or waveguide for illumination or by utilizing a resonance energy transfer (RET, e.g., Fluorescence or Forster RET) or by utilizing photo activation (e.g., as described in Biophys J. 2015 Feb. 17; 108(4): 949-956).

In some embodiments, the probes are not labeled, but the interaction with the target is detected by a DNA stain such as an intercalating dye, which intercalates into the duplex as binding occurs or has occurred. One or more intercalating dyes may intercalate into the duplex. The fluorescence emitted by an intercalating dye once it is intercalated can be orders of magnitude greater than the fluorescence due to intercalating dye that is free in solution. For example the signal from an intercalating YOYO-1 dyes is about 100× greater than the signal from YOYO-1 dye free in solution.

This aspect of the invention was originally motivated by making the observation, that when a lightly stained (or after some degree of photobleaching) double stranded polynucleotide is imaged, individual signals along the polynucleotide can be observed likely corresponding to single intercalating dye molecules. To facilitate exchange of YOYO-1 dye in a duplex and to obtain a bright signal Redox-Oxidation system (ROX) comprising s and ascorbic acid can be provided in the binding buffer In some embodiments, the sequencing comprises subjecting the elongated polynucleotide to transient interactions from each of a complete sequence repertoire of probes provided one after the next (the solution carrying one probe sequence is removed, and the solution carrying the next probe solution is added). In some embodiments, the binding of each probe is carried out under conditions that would allow the probe to bind transiently. So for example, the binding would be conducted at 25° C. for one probe and 30° C. for the next. Also probes can be bound in sets, for example all probes that would bind transiently, in much the same way, can be gathered into sets and used together. In some such embodiments, each probe sequence of the set is differentially labeled or differentially encoded.

In some embodiments, or in some instances the multiple binding events to a location in the target are not from a single probe sequence, but are determined by analyzing the data from the repertoire, and taking into account events that occur from partially overlapping sequences. For example, the same (actually a sub-nanometically close) location is bound by probe ATTAAG and TTAAGC, which are 6mers that share a common 5 base sequence and each would validate the other, as well as extending the sequence one base on either side of the 5 base. In some cases the base on each side of the 5 base sequence is a mismatch (mismatches at the ends are typically expected to be tolerated more than mismatches that are internal) and only the 5 base sequence is that is present in both binding events us validated.

In some embodiments, the signal is detected by FRET from intercalating dye to a label on the probe or the target sequence. In some such embodiments, the probe is labeled at one of its ends with a Cy3B label. In some embodiments, after the target is immobilized the ends of all target molecules are labelled, for example by terminal transferase incorporating fluorescently labelled nucleotides that act as FRET partners.

In some embodiments, a complete sequence repertoire is not used, rather a tiling array of solution probes that cover a particular segment of sequence of interest. In some embodiments, a complete sequence repertoire is not used, rather a panel of probes is used so that multiple locations are interrogated by sequence specific transiently binding probes.

In some embodiments, the target polynucleotide has to be single stranded (e.g., mRNA) or has to be made single stranded in order for the invention to be implemented. In some embodiments, the target polynucleotide is double stranded and the transient binding is due to transient strand invasion of a probe. In some embodiments, the double stranded target contains nicks (e.g., natural or created by DNase1 treatment) and under conditions of reaction one strand transiently frays or peels away from the other, or natural base-pair breathing occurs, allowing the probe to transiently bind, before it is displaced by the native strand.

In some embodiments, the sequence is constructed by analyzing the transient data gathered for each of the probes.

In some embodiments, such data comprises coordinates of binding events on a 2-D surface, typically correlated with the path of the elongated polynucleotides.

The locations of the probe binding provides an order of binding of each of the probes, which can be compiled into a contiguous sequence.

In this specification and claims the term target polynucleotide is referred to both the case where there is only single strand and in the case where there are two double helical strands. Where double-stranded or single single stranded polynucleotide is solely intended, it is indicated in the text. When RNA is mentioned it is assumed it is single stranded.

In this specification and claims when binding or locations are recorded on a substrate it can be assumed that a substantial fraction of the binding has occurred on a nucleic acid on the substrate.

Extracting the Polynucleotide

In various embodiments, the method further comprises extracting the single target polynucleotide molecule from a cell, organelle, chromosome, virus, exosome or body material or fluid as a substantially intact target polynucleotide. In various embodiments, the target polynucleotide molecule is elongated/stretched. In various embodiments, the target polynucleotide molecule is immobilized on a surface. In various embodiments, the target polynucleotide molecule is disposed in a gel (e.g., compare to Shag et al Nature Protocols 7: 467-478 (2012)). In various embodiments, the target polynucleotide molecule is disposed in a micro- and/or nano-fluidic channel. In various embodiments, the target polynucleotide molecule is intact.

In various embodiments, the method further comprises sequencing the genome of a single cell. In various embodiments, the method further comprises releasing the polynucleotides from a single cell into a flow channel. In various embodiments, the walls of the flow channel comprise passivation that prevents polynucleotide sequestration. In various embodiments, the passivation comprises a lipid, polyethylene glycol (PEG), casein and or bovine serum albumin (BSA) coating.

In some embodiments, it is necessary to separate cells that are of interest from others that are not before extraction is conducted. There are several methods available for isolating circulating tumor cells or circulating fetal cells from blood, for example by using their surface markets for affinity capture. In some embodiments, it is necessary to separate microbial cells from human cells, where the interest is to detect and analyse polynucleotides from the microbial cells. Opsonins can be used to affinity capture a wide-range of microbes and separate them from mammalian cells, so that the microbial polynucleotides can be selectively sequenced. In addition differential lysis can be conducted. Here conditions are first used to lyse the mammalian cells. The microbial cells (especially mycobacterium) are hardy to the conditions used to lyse mammalian cells and hence remain intact and can be isolated by wash away the mammalian cell contents. Harsher conditions are then used to extract polynucleotides from the microbial cells and to selectively sequence them.

Sequencing

In general, the methods of the invention include:

a) providing a target nucleic acid;

b) conducting a transient binding reaction to obtain the locations of a first set of sequence bits on the target;

c) conducting a transient binding reaction to obtain the locations of a second set of sequence bits on the target; and d) conducting a transient binding reaction to obtain the locations a third set of sequence bits on the target and so on.

In some embodiments, multiple oligos are conjoined or are separated by a determinable distance.

In some embodiments, the targets from which sequence bits are obtained are aligned based on segments of sequence overlap between the targets, and a longer "in silico" contig and ultimately the sequence of the entire chromosome is generated.

In some embodiments of the invention the target polynucleotides are contacted with a gel. In some embodiments, the contacting a gel occurs, after elongating the target polynucleotide. In some embodiments, the contacting with a gel occurs, before elongating the target polynucleotide.

In some embodiments, sequences that commonly occur in the target polynucleotide are used. This can be one or more of several sequences that occur ultra-frequently in the genome. In this case a fingerprint of a genome, rather than the full sequence of the genome can be easily obtained.

In some embodiments, the invention increases the density of sequence information that can be obtained by super-resolving closely packed polynucleotides as well as sequence bits along the polynucleotides.

In one embodiment the method comprises the steps:
1) Extracting long lengths of genomic DNA and performing no modification or processing of the DNA;
2) Stretching or elongating the genomic DNA molecules on a surface;
3) Providing a flow cell (either the stretching has occurred in a flow cell or a flow cell is constructed atop the surface) so that solutions can flow over the DNA stretched on the surface;
4) Denaturing the DNA;
5) Adding transiently binding probes;
6) Detecting which probe binds at each location, e.g., using laser Total Internal Reflection (TIR) illumination, a focus detection/hold mechanism, a CCD camera an appropriate objective, relay lenses and mirrors;
7) Translating the stage on which the flow cell is mounted is with respect to the CCD camera so that genomic molecules or parts of molecules rendered at different locations (outside the field of view of the CCD at its first position) can be sequenced; and
8) Repeating steps 5-7 if necessary; and
9) Data Processing, comprising:
   a) processing images;
   b) making sequence calls;
   c) tying sequence calls to spatial locations;
   d) determining which sequence call locations fit a line;
   e) using the obtained information to assemble sequencing reads to provide a super-contiguous read;
   f) using the assembled reads to assemble a genome; and
   g) providing the sequence read and/or assembled genome to the user, preferably via a graphical interface on a computer or smartphone type device.

In the case where genomic DNA can be extracted from multiple cells many copies of the molecule are displayed on the surface; the results from the same homologs are collected and a consensus read is obtained; homologous molecules are separated, according to haplotype or parental chromosome specificity.

In some embodiments, the transient binding is recorded as a means of detection but is not used for improving the localization. In some cases the molecules are arrayed sparsely, and increased localization is not needed. However, the robustness against photobleaching and the ability to filter out non-specific background (permanently stuck signals can be processed out) makes the approach compelling.

In some embodiments, the probe remains bound to the target but has a tail or flap to which transiently binding labels bind on and off. In some embodiments, the tail is composed of a non-Watson-Crick base pairing nucleic acid analogues.

Single Base Interrogation

In some embodiments, probes are labeled according to just one defined nucleotide.

In some embodiments, the oligonucleotides are split into species in which different nucleotides, ACGT are defined and each oligos corresponding to each different nucleotide are differently labeled and optionally added to the sequencing reaction together In some embodiments, the oligos are not differentially labeled, but each base type is added separately, after washes have cleared out the previous nucleotide.

In some embodiments, in order to detect binding events over a relatively short time scale (e.g., one or more minutes) correspondingly higher concentrations of the oligos where only 1 or a few bases are defined are needed to deal with the higher complexity of the oligo library. Where 10 nM of an oligo where 5 bases are defined would be sufficient, 256× higher concentration of the oligo where only one base is defined, is needed. This corresponds to 2.56 uM of oligonucleotide (In some embodiments, a lower concentration would be sufficient due to mismatches etc), which would lead to a level of background fluorescence that would make it hard to detect the binding event on the polynucleotide target on the surface, even when an exponentially decaying evanescent field of illumination from the surface is used. As the background fluorescence is substantially due to light scattering, In some embodiments, it can be time-gated out. In some embodiments, a mechanism is employed where the high concentration of oligos in solution are not fluorescent but are fluorogenic, are quenched or are not directly excited, but only emit light when subject to resonance energy transfer from an entity attached to the surface or the target polynucleotide itself. In some embodiments, a dye which intercalates into the formed duplex is excited and transfers energy to the fluorescent label on the oligo when it binds. In some embodiments, where each of the defined oligo libraries is added one at time, no label is attached to the oligo and only nucleic acid stain or intercalating dye from solution is used to label the binding event.

In some embodiments, where only one base is defined in the oligonucleotide and the rest of the positions are degenerate, only 4 or fewer reagent exchange cycles are needed, for the 4 possible defined bases, A, C, G, or T. In some embodiments, each of the bases is coded by a distinct label, and where there is a means to detect all 4 labels simultaneously, no reagent exchange is necessary. When such a homogeneous or one-pot sequencing reaction is carried out, the instrument is very simple, essentially a microscope, where no reagent exchange is required. For example, just a drop of the oligo mix (mixture of oligonucleotide probe species) in appropriate buffer is added onto a cover glass on which the target polynucleotide is located and then binding events are observed for a period long enough to cover the whole sequence with one or more binding events. This homogeneous reaction is run for several hours, and is sealed against evaporation. If a high enough volume is used, the depletion of reagents that may occur near the surface can be overcome by facilitating reagent exchange by diffusion from the bulk of the solution (e.g., this can be enhanced by turbulent flow or chaotic mixing). Alternatively, reagent exchange is carried out, not for the purpose of adding a different oligo mix, but just to replace depleted reagent.

In some such embodiments, the target polynucleotides are elongated or stretched so that the location of the binding events, and hence location of nucleotides along the length of the polynucleotides can be determined. In some such embodiments, the polynucleotides are single stranded so that there is no ambiguity as to which strand the oligo binds; this is helpful because this single-nucleotide interrogation approach does not have the luxury of constructing tiling paths to deconvolve which strand of a denatured double helical polynucleotide an individual binding event occurs upon. There are several instances where the single-nucleotide interrogation approach can be applied to single strands. Firstly, RNA are natively single stranded in most cases. In other cases double stranded nucleic acid can be made single stranded and in further cases one of the strands of the double helix is copied to make a single strand, such as when the nucleic acid is made circular and is iteratively copied via rolling circle amplification.

In some such embodiments, there is a strong need to circumvent drift, because each binding event only provides a single base of information, tiling paths formed by overlapping bits of sequence cannot be extracted from the complete data-set which would facilitate placement of the nucleotide in the sequence. In order to get the precision required an extremely stable system in terms of vibrations and thermal drift is used. One such stable system is the IX2 Nosepiece Stage that can be used with Olympus's IX81 inverted laser TIRF microscope. In some embodiments, as an addition or alternative, a drift correction mechanism is used and a highly effective means for drift correction is to use fiduciary markers such as DNA Origami and do multiple rounds of processing to iteratively drift correct the data to produce an accurate, high precision super-resolution image. The DNA Origami is designed by those with skill in the art to have multiple binding sites for fluorescent labels at very well ordered and precisely located positions within the structure. For example a DNA Origami of the type described in Dai et al (Nature Nanotechnology 2016, 11:798-807), which is hereby incorporated by reference, can be used, comprising for example a 12 or 16 point grid. The Origami is labeled by a DNA PAINT mechanism where the single stranded docking sites protrude from the top surface of the grid and are transiently bound by a fluorescently labeled imager. Binding sites is provided on the grid to imagers labeled with the four distinct labels that are used to specifically label the four single-nucleotide defined oligo libraries. In some embodiments, the imager binding to the Origami grid is designed to have an orthogonal binding system than the Watson-Crick binding system of the sequencing reactions. Such an orthogonal system is an expanded alphabet nucleic acid base-pair system, for example using the Artificially Expanded Genetic Information System (AEGIS) phosphoramidite reagents available from Firebird Biomolecular Sciences LLC (firebirdbio.com). This system would provide Z:P and S:B base pairs which are orthogonal to the Watson Crick A:T and G:C base pairs used in the sequencing system of this invention.

In some embodiments, oligos, for example those in which 3mers are defined are allowed to bind at low temperature or high salt, this allows a large number of sites to bind some of which may not be resolvable. In some embodiments, to pinpoint the location of binding, the fluorescent labels are allowed to bleach, such that the precise location of each can be determined by single molecule localization. See e.g., Neely et al Nucleic Acids Res. 2014 April; 42(7): e50 and also U.S. patent application Ser. No. 13/701,628, filed on Dec. 3, 2012, which is incorporated herein by reference. In this non-transient binding approach it is possible that the binding of one oligo may obstruct the binding of overlapping oligos. To combat this multiple cycles are used. The first set of bound oligos are melted off by temperature and/or chemical denaturation and then binding is initiated again, allowing the possibility that locations blocked in the first cycle are able to bind in the second cycle and so on. This is optionally repeated for more cycles, allowing more previously blocked sites to bind. Similarly, in some embodiments, binding is detected by Stochastic Optical Reconstruction Microscopy (STORM; e.g., as described in U.S. Pat. Nos. 7,776,613 and 10,073,035, which are hereby incorporated by reference), switching on only some of the fluorophore signals at any one time. In some embodiments, this is repeated multiple times to maximally cover the sequence.

The speed of binding can be increased by increasing oligo concentration, increasing binding temperature, and/or changing the identity and concentration of salt and volume excluding agents. In some embodiments, volume excluding agents are selected from the group consisting of hydroxypropyl methyl cellulose (HPMC), hydroxyethyl methyl cellulose (HEMC), hydroxybutyl methyl cellulose, hydroxypropyl cellulose, methycellulose, and hydroxyl methylcellulose, PEG-800 at a concentration in the range from about 0.002% to about 15% w/w. In addition, divalent cation such as $MgCl_2$ at 100-600 mM concentration have an acceleration effect on the binding rate.

In some embodiments, an additional means to increase the speed of binding is by to taking the measurements in the presence of a flow. Thus in a flow cell volume of up to 50 ul a flow rate of 1 µl per minute is capable of increasing the binding rate. In some embodiments, the flow is turbulent. In some embodiments, the turbulent flow is induced by the presence of rods or bumps emanating from the surface, a herringbone pattern on the top surface of the flow cell or the presence of beads or microstructures in solution which cause the flow to be turbulent. In addition to increasing the speed of binding optimizing the flow process also increases the effectiveness of reagent exchange to ensure residual oligos from a previous cycle remain minimal. In some embodiments, during the process of exchange from one oligo species to the next one or more washes with clean buffer are needed and time is needed during the wash for oligo probes to diffuse away from the surface and reach an equilibrium concentration. In some embodiments, the time is one minute, in other embodiments the time is 10 minutes. In some embodiments, 10-100 volumes of buffer are passed through the flow cell to ensure the removal of residual oligos. In some embodiments, the time is reduced because the movements of the probes out of the TIRF range is facilitated, e.g., by applying an electric field that moves the −ver charged oligos to a positively biased electrode. One or more of the various process can be combined, time, turbulent flow, volume of buffer exchanged and electric field. In some embodiments, a degree of residual oligo is tolerated; as the identity of the previous oligos are known the assembly algorithm can take into account their presence in trace amounts.

In some embodiments, no degenerate positions are used and the desired stability of the oligonucleotide is obtained by appropriately manipulating conditions (e.g., low temperature, high salt) or using an oligo chemistry that in itself stable enough (e.g., gamma PNA etc) or conjugates such as spermine or stillbene are added to a terminus to increase stability of the short oligonucleotide.

In some embodiments, hybridization can be improved by using universal bases such as nitroindole or deoxyinosine at the degenerate rather than using a library of oligonucleotides comprising all possible sequences in the non-defined position. These universal bases can be specified at positions along the sequence in oligos purchased from various vendors. In some embodiments, some positions are occupied by a library of nucleotides and others are occupied by universal bases. Because the universal bases reduce the complexity of the mixture, a lower concentration of oligo probes can be employed.

Because in the one base coding the complexity of oligos that is used is high the concentration of oligo library that is used needs to be increased, so instead of 10 nM concentration, 1 uM or higher concentration needs to used and because of the large background this creates, in some embodiments, a FRET mechanism is used such as from an intercalating dye, an intercalation labeling schemes (without FRET) or the oligos are labelled with fluorogenic labels that fluoresce once hybridization occurs.

In some embodiments, with 2 defined bases, all 64 possible oligos are added at the same time and are differentially labeled. In some embodiments, 16 differential labels are available and so the library of 64 is split into 4 libraries of 16. So with just four cycles, the sequencing is concluded. In other embodiments, 4 labels are used, allowing four oligos to be added together, requiring 16 cycles to be conducted. They hybridization of 3 mers can be conducted in 4×SSC or buffers comprising, 2.4M TMACl or 3.5M TMACl, LiTCA, GUCN which can serve to better discriminate mismatches and/or equalize the effect of base composition.

Increasing Temporal Resolution.

The transient binding process can be sped up by tuning various biochemical parameters, such as salt concentration. There are a number of cameras with high frame rates that can be used to match the speed of binding, often the field of view is restricted to obtain a faster readout from a subset of pixels. One alternative approach is to use a galvanometer mirror to temporally distribute consecutive signals to different regions of a single sensor or to separate sensors, the latter allows one to utilize the full field of view of a sensor but increases overall temporal resolution when the distributed signals are compiled. The ability to reject during image processing instances of multiple signals within a diffraction limited spot, allows the process to be run faster as it can cope with high probe binding speeds.

Circumventing DNA Photo-Damage

In some embodiments, it is expedient to have a fluorescent moiety attached to an oligonucleotide via a protein to reduce the effects of photodamage on the nucleic acid being sequenced. In some embodiments, the effect of the protein moiety is to provide a protection to the oligo and the target sequence from various adverse effects of the fluorescent labels. Some of these adverse effects, such as oxidative damage can be overcome by including additives in the reaction solution such as reducing agents or redox systems. However other deleterious mechanisms such as electron transfer or tunnelling may not be prevented by the additives. In some embodiments, a reducing agent or redox system is physically linked to the oligo. In some embodiments, the protein is streptavidin. Fluorescently labelled versions of streptavidin are available e.g., streptavidin-phycoerythrin, including streptavidin-phycoerythrin conjugated to another dye to effect a wavelength shift by Fret for example. The streptavidin is then also bound to one or more biotinylated oligonucleotides by the well known biotin-streptavidin interaction. Various closely related proteins, avidin, neutravidin can also be used. The streptavidin have multiple dyes attached. Other suitable proteins include Ubiquitin and SNAP-tag protein. Other molecules than proteins can also be used, if they can be empirically found to provide a shield around the fluorescent dye to prevent damage.

Thus In some embodiments, the sequencing reagent comprises: a transient binding nucleotide/oligonucleotide attached to a first position on a protein; a dye component comprising at least one fluorescent dye moiety attached to a second position on the protein.

Single-Cell Resolved Sequencing

In various embodiments, the method further comprises sequencing the genome of a single cell. In some embodiments, the single cells are free from attachment from other cells. In some embodiments, the single cells are attached to other cells in clusters or in tissue. In some embodiments, such cells are disaggregated into individual non-attached cells.

In some embodiments, the invention comprises a method for sequencing a polynucleotide, the method comprising the steps of:
 i) introducing one or more cells into a flow cell;
 ii) treating said cells to cause polynucleotide to be released;
 iii) elongating released polynucleotide in the flow cell; and
 iv) conducting a sequencing reaction using said elongated polynucleotide as template/sequencing target.

In some embodiments, the invention comprises a method for sequencing a polynucleotide, the method comprising the steps of:
 i) introducing one or more cells into a micro-container;
 ii) treating said cells to cause polynucleotides to be released;
 iii) releasing contents of container into a flow cell;
 iv) elongating polynucleotide; and
 v) conducting a sequencing reaction using said elongated polynucleotide as template.

In some embodiments, a method is provided for sequencing a polynucleotide, the method comprising the steps of:
 i) exposing cells to a flow cell, the flow cell comprising an inlet and an outlet;
 ii) extracting a polynucleotide from a said cell;
 iii) attaching said polynucleotide to a surface of said flow cell, such that at least a portion of said polynucleotide is individually resolvable;
 iv) exposing oligos to said polynucleotide;
 v) identifying location of binding of oligos on said polynucleotide In some embodiments, the cell are disaggregated before they are fluidically transferred (e.g., by using a pipette) to the inlet of the structure (e.g., flow cell, or microwell) in which the polynucleotides are elongated. Disaggregation can be done by pipetting the cells, by applying proteases, sonication or physical agitation. In some embodiments, the cell are disaggregated after they are fluidically transferred into the structure where the polynucleotides are elongated.

In some embodiments, the single cell is isolated and the polynucleotide is released from single cell, such that all the polynucleotides originating from the same cell remain disposed close to one another and at a location that is distinct from the locations where the contents of other cells are disposed. In some embodiments, the trap structures as described in Lab Chip, 2006, 6, 1445-1449 are used.

In some embodiments, the single cell is trapped and the contents are released and then elongated. In some embodiments, the single cell is burst into an individual channel and each individual cell is reacted with a unique tag sequence via transposase mediated integration, before the polynucleotides are combined and sequenced in the same mixture. The transposase complex can be transfected into cells or is in a droplet merged into a droplet containing the cells.

In some embodiments, the aggregates are small clusters of cells and In some embodiments, the entire cluster is tagged with the same sequencing tag. In some embodiments, the cells are not aggregating and is free floating cells such as circulating tumor cells (CTCs) or circulating fetal cells.

In single cell sequencing there is a problem of cytosine-to-thymine single nucleotide variants caused by spontaneous cytosine deamination after cell lysis. This is overcome by pretreating samples with uracil N-glycosylase (UNG) prior to sequencing. (e.g., as described in Mol Diagn Ther. 2014 October; 18(5): 587-593.)

Cell-Specific Indexing of Polynucleotides

In various embodiments the method further applies to sequencing polynucleotides from a plurality of cells (or nuclei) where each polynucleotide retains information of its cell of origin.

In certain embodiments transposon mediated insertion occurs inside the cell, and each insertion comprises a unique ID sequence tag as a label for the cell of origin. In other embodiments the transposon mediated insertion occurs inside a container in which a single cell has been isolated, such containers comprising, agarose beads, oil-water droplets etc. The unique tag indicates that all the polynucleotides bearing the tag must originate from the same cell. All of the genomic DNA and or RNA can then be extracted, allowed to mix and be elongated. Then when SbS (or any other sequencing method) is originated from the PBS or promoter, the first sequence it obtains is from the cell identifying sequence, followed by the sequence of the polynucleotide. It is preferable to keep the cell identifying tag short. For 10,000 cells (e.g., from a tumor microbiopsy), 65,000 unique sequences can be provided by an identifier sequence of 8 nucleotides in length and around a million unique sequences from an identifier sequence of 10 nucleotides in length.

This same indexing principle can be applied to samples other than cells (e.g., from different individuals) when the aim is to mix the samples, sequence them together, but to recover the sequence information pertaining to each individual sample.

Thus, in some embodiments, the method comprises:

1) Isolating the contents of a cell;
2) Performing transposon mediated insertion of a unique sequence tag for the cell into the polynucleotides of the cell;
3) Immobilizing the polynucleotides of the cell; and
4) Carrying out the sequencing methods of this invention which encompasses reading the sequence of the tag and the sequence of the polynucleotide.

In some embodiments, the polynucleotide is RNA and a cDNA copy is sequenced. In such embodiments, addition of the tag can comprise cDNA synthesis with a primer containing the tag sequence.

In some embodiments, in order to keep the amount of sequence to be kept short, so that more of the sequence read can be devoted to sequencing the polynucleotide sequence itself, the tag sequence is distributed over a number of sites. Here multiple short identifier sequences, say three, are introduced into each cell or container. Then the origin of the polynucleotide is determined from the bits of the tag that are distributed along the polynucleotide. So in this case the bit of the tag read from one location may not be sufficient to determine the cell of origin, but multiple tag bits are sufficient to make the determination.

Sequencing by Multiple Methods

In some embodiments, following sequencing by transient binding, sequencing by a second method can be initiated on the same molecules. For example, longer more stable oligonucleotides can be bound to initiate sequencing by synthesis.

Target Polynucleotides

The term polynucleotide refers to DNA, RNA and variants or mimics thereof, and can be used synonymously with nucleic acid. A single target polynucleotide is one nucleic acid chain. The nucleic acid chain is double stranded or single stranded. The polymer can comprise the complete length of a natural polynucleotide such as long non-coding (lnc) RNA, mRNA, chromosome, mitochondrial DNA or it is a polynucleotide fragment of at least 200 bases in length, but preferably at least several thousands of nucleotides in length and more preferable, in the case of genomic DNA several 100s of kilobases to several megabases in length.

The invention, in various aspects and embodiments includes: obtaining long lengths of polynucleotide e.g., by preserving substantially native lengths of the polynucleotides during extraction from a biological milieu; disposing the polynucleotide in a linear state such that locations along its length can be traced with little or no ambiguity, ideally the polynucleotide is straightened, stretched or elongated; before or after disposition of the target polynucleotide in a linear state.

In various embodiments, the single target polynucleotide is a chromosome. In various embodiments, the single target polynucleotide is about 102, 103, 104, 105, 106, 107, 108 or 109 bases in length. The wheat chromosome 3b is 995 Million bases in length, whilst the largest human is chromosome 1 at 249 million bases. In various embodiments, the single target polynucleotide is single stranded. In various embodiments, the single target polynucleotide is double stranded.

The single target nucleotide is preferably a native polynucleotide. The single target nucleotide can be double stranded, such as genomic DNA. The single target polynucleotide can be single stranded such as mRNA. The single double stranded target polynucleotide can be denatured, such that each of the strands of the duplex is available for binding by an oligo. The single polynucleotide is damaged and is repaired. In various embodiments, the single target polynucleotide is the entire DNA length of a chromosome. The entire DNA length of a chromosome can remain inside the cell without extraction. The sequencing can be conducted inside the cell where the chromosomal DNA follows a convoluted path during interphase. The stable binding of oligos in situ has been demonstrated: B. Beliveau, A et al Nature Communications 6 7147 (2015). Such in situ binding oligos and their nanometric localization in 3D space can enable the sequence and territorial arrangement of a chromosomal molecule in the cell to be determined. The present invention differs in that the binding of the oligos is not stable—it is transient and enables ultra-fine resolution of chromosome territories. Similarly the location and quantity of RNA (e.g., microRNA, mRNA, lncRNA) can be determined by their binding pattern to the binding oligos.

Getting to the Limits of Sensitivity

Once the molecules are released from the cell substantially all the molecules are available for sequencing. Firstly, where relevant, areas are passivized to prevent molecules form sticking. Then substantially all the molecules are captured in one of two ways. For the first the molecules continue to flow in channels, being captured stochastically over the length of the channel, which is long enough that substantially all the molecules are eventually captured. For this the channel can be a meandering channel which allows an extremely long length to be packed into a small space. Second, all the molecules that are released from one or more cells, can be allowed to flow and segregate, enough to be individually resolvable in 3D space. Then the solution is jellified, i.e. is a solid-gel transition, so that the molecules become immobile in 3D space. Then the molecules can be subjected to the sequencing methods of this invention in which the 3-D space can be interrogated by a 3D sectioning method such as light sheet microscopy or spinning disc microscopy and 3D single molecule localization.

Capturing Polynucleotides on a Surface

In some embodiments, the target polynucleotide is attached to a surface via hydrophobic interactions with the termini. In some embodiments, the contacting of the polynucleotide with the surface occurs under stringency conditions where the termini are frayed allowing the hydrophobic single stands to be exposed.

In some embodiments, rather than using a flow cell to create stretching via the receding meniscus or perform flow stretching, the cover glass is dipped into a trough carrying the polynucleotides which are combed upon withdrawal of cover glass from the solution.

In some embodiments, an electrical field can be used to attract the negatively charged polynucleotides (so that a greater proportional of the sample can be sampled) and in some instances the oligo probes to the surface Fixing Polynucleotides on a Surface Immobilizing at one end and flow, allows wiggle, stretch and contraction etc, and due to fluctuations (it contracts and expands) in the degree of stretching along the length of the polymer, the x-y coordinates cannot be guaranteed for the a particular position in the target between one cycle and the next.

In some embodiments, the realization that in order to get reproducible, high precision and accurate localization it is desirous that the relative positions of multiple locations along the polymer are not subject to fluctuation. In such cases the elongated molecule should be immobilized or fixed to the surface by multiple points of contact along its length.

Therefore In some embodiments, the polymer is contacted to the surface by multiple interactions (as is done in the molecular combing technique (Michalet et al, Science 1999)). Then it is known that relative locations are fixed under the conditions of use. Given, there is some outliers that partly come off the surface and re-attach, although we have not seen such occurrences.

Therefore In some embodiments, in which long polymers are analyzed the long polymer forms multiple interactions with the surface or a matrix.

In some aspects the invention includes a method for detecting rare variants comprising interrogating each base on a single molecule multiple times. Each transient binding events interrogates one or more bases and each base is interrogated by multiple binding events. Moreover In some embodiments, each base is interrogated by multiple oligonucleotides whose sequences overlap, e.g., as a tiling series.

Polynucleotide Elongation

In various embodiments, the method further comprises extracting the single target polynucleotide molecule from a cell, organelle, chromosome, virus, exosome or body fluid as an intact target polynucleotide. The target polynucleotides often take up native folded states. For example genomic DNA is highly condensed in chromosomes, RNA forms secondary structures. In various embodiments of the invention steps are taken to unfold the polynucleotide. In various embodiments, the target polynucleotide molecule is rendered in a linear state so that its backbone can be traced. In various embodiments, the target polynucleotide molecule is elongated. Such elongation may render it equal to, longer or shorter than its crystallographic length (0.34 nm separation from one base to the next). In some embodiments, the polynucleotide is stretched beyond the crystallographic length.

In various embodiments the target polynucleotide is disposed in a gel or matrix. In various embodiments the target polynucleotide is extracted into a gel or matrix. In various embodiments the target polynucleotide is extracted inside a microfluidic flow cell or channel.

In various embodiments, the target polynucleotide molecule is immobilized on a surface. The polynucleotides can be disposed parallel to a planar surface or perpendicular to a surface. In the case they are parallel to a planar surface, their lengths can be imaged across an adjacent series of pixels in a 2-D array detector such as a CMOS or CCD camera. In the case they are perpendicular to the surface, their lengths can be imaged via Light Sheet Microscopy or Scanning Disc Confocal Microscopy or its variants.

In some embodiments, the polynucleotide is stretched via molecular combing (e.g., as described by Michalet et al, Science 277: 1518 (1997) and Deen et al, ACS Nano 9: 809-816 (2015)). This can enable the stretching and unidirectional aligning of millions and billions of molecules in parallel. In some embodiments, the molecular combing is done by translating a front of fluid/liquid over a surface. In some embodiments, the molecular combing is done in channels using methods or modified versions of methods described in Petit et al. Nano Letters 3:1141-1146 (2003).

The shape of the air/water interface determines the orientation of the elongated polynucleotides. In some embodiments, the polynucleotide is elongated perpendicular to the air water interface. In some embodiments, the target polynucleotide is attached to a surface without modification of one or both of its termini. In some embodiments, where the ends are captured by hydrophobic interactions, the stretching with a receding meniscus makes parts of the duplex denature and make further hydrophobic interactions with the surface.

In some embodiments, the polynucleotide is stretched via molecular threading (e.g., as described in Payne et al, PLoS ONE 8(7): e69058 (2013)). In some embodiments, the molecular threading is done after the target is made single stranded (e.g., by chemical denaturants, temperature or enzymes). In some embodiments, the polynucleotide is tethered at one end and then stretched in fluid flow (e.g., as described by Greene et al, Methods in Enzymology, 327: 293-315),In some embodiments, the polynucleotide is tethered at one end and then stretched by an electric field (e.g., as described by Giese et al Nature Biotechnology 26: 317-325 (2008)).

In various embodiments, the target polynucleotide molecule is disposed in a gel. In various embodiments, the target polynucleotide molecule is disposed in a micro-fluidic channel. In various embodiments the target polynucleotide is attached to a surface at one end and extended in a flow stream.

In some embodiments, the extension is due to electrophoresis. In some embodiments, the extension is due nanoconfinement. In some embodiments, the extension is due to hydrodynamic drag. In some embodiments, the polynucleotide is stretched in a crossflow nanoslit (e.g., as described by Marie et al. Proc Natl Acad Sci USA. 110:4893-8 (2013).

In some embodiments, rather than inserting polynucleotide into nanochannels via a micro- or nanofluidic flow cell, polynucleotides are inserted into open-top channels by constructing the channel in such a way that the surface on which the walls of the channel are formed, is electrically biased (e.g., see Asanov A N, Wilson W W, Oldham P B. Anal Chem. 1998 Mar. 15; 70(6):1156-6). A positive bias is applied to the surface, so that the negatively charged polynucleotide is attracted into the nanochannel. The ridges of the channel walls do not comprise a bias and so the polynucleotide is less likely to deposit there and can be made with or coated with a material which has non-fouling characteristics, and is passivated with Lipid, BSA, Caesin, PEG etc. In some embodiments, the polynucleotide which is attracted into the nanochannel is nanoconfined in the channel and is thereby elongated. In some embodiments, after nanoconfinement the polynucleotide becomes deposited on the biased surface, or on a coating or matrix atop the surface. The surface may comprise Indium Tin Oxide (ITO).

In some embodiments, the polynucleotides are not all well aligned in the same orientation or they are not straight, rather take up a curvilinear path over 2D or 3D space; although the same kind of information can be obtained as with straight, well aligned molecules, the image processing task is harder and in the case of molecules taking up different orientations, there is increased likelihood that they will overlap and lead to errors. This however, is a necessary evil when sequencing is conducted on polynucleotides in situ inside a cell.

In various embodiments, the method further comprises releasing the polynucleotides from a single or multiple chromosome, exosome, nuclei or cell into a flow channel.

In various embodiments, the walls of the flow channel comprise passivation that prevents polynucleotide sequestration. In various embodiments, the passivation comprises casein, PEG, lipid or bovine serum albumin (BSA) coating.

The terms elongated, extended, stretched, linearized, straightened can be used interchangeably and generally mean that the multiple binding sites are separated by a physical distance more or less correlated with the number of nucleotides they are apart. Some imprecision in the extent to which the physical distance matches the number of bases can be tolerated. In cases where the elongation or stretching is not uniform along the whole of the polynucleotide length, the physical distance is not correlated with the number of bases with the same ratio across the entire length of the polynucleotide. This may occur to a negligible extent and can be effectively ignored or handled by algorithms. Where this occurs to an appreciable extent, other measures are required. For example in some segments of the polynucleotide, the stretching is 90% of the crystallographic length, while in other regions it may diverge by around 50%. One way to handle it is via the assembly algorithm that puts together the contiguous sequence. At one extreme the algorithm, does not require distance data, only the order of the reads. Another way to handle it is by using an intercalating dye such as JOJO-1 or YOYO-1 to stain the length of the polynucleotide, then when the polynucleotide is less stretched in certain segments, more dye signal will be seen over the segment of the polynucleotide compared to a segment where it is more stretched. The integrated dye signal can be used as part of an equation to calculate distances between origins.

In various embodiments, the target polynucleotide molecule is intact. When the target is native genomic DNA it can be made single stranded before the oligonucleotides are bound. This can be done by first elongating or stretching the polynucleotide add then adding a denaturation solution (e.g., 0.5M or 1M NaOH) to separate the two strands. The oligos can be modified, so that they can form higher stability duplexes. The oligos isar a free 3' end from which extension can occur to increase stability. In some embodiments, the oligos may target specific ultra-frequent target sites in the genome (e.g., as described in Liu et al BMC Genomics 9: 509 2008).

The oligos may comprise a library, made using custom microarray synthesis. The microarray made library can comprise oligos targeting specific sites in the genome such as all exons or panels for a particular diseases such as a cancer panel. The microarray made library can comprise oligos that systematically bind to locations a certain distance apart across the polynucleotide. For example a library comprising one million oligos will bind around every 3000 bases. A library comprising ten million oligos can be designed to bind around every 300 bases and a library comprising 30 million oligos can be designed to bind every 100 bases. The sequence of the oligos can be designed computationally based on a reference genome sequence. If for example the oligos are designed to bind every 1000 bases, but after one or a few rounds of nucleotide incorporation it becomes apparent that the distances diverge, it is an indication that structural variation compared to the reference is occurring. A set of oligos can first be validated by using them to originate sequencing on polynucleotides from the reference itself and oligos that fail to bind to the right locations can be omitted from future libraries.

Detection of Closely Spaced Signals Along a Polynucleotide

Several detection methods, such as scanning probe microscopy (including High Speed AFM) and electron microscopy are capable of resolving nanometric distances when the polynucleotide molecule is elongated in the plane of detection. Furthermore super-resolution optical methods such as STED, stochastic optical reconstruction microscopy (STORM), Super-resolution optical fluctuation imaging (SOFI)), Single Molecule Localization Microscopy (SMLM) are capable of resolving such distances. Although encompassing these methods the present invention particularly takes advantage of a SMLM approach most similar to Points Accumulation in Nanoscale Topography (PAINT).

The present invention goes beyond simply localizing a single binding position to a short DNA target. A novel aspect of the invention is localizing multiple binding positions of a single oligo species along the length of a polynucleotide. Another novel aspect of the invention is localizing the binding of multiple oligonucleotide species on a polynucleotide. Another novel aspect of the invention is determining the distance between binding position of a single oligonucleotide species or of multiple oligonucleotide species. Another novel aspect of the invention is determining the nanometric locations of multiple binding positions along a polynucleotide. Another novel aspect of the invention is assigning probe binding events to particular polynucleotides present in an array of polynucleotides. Another novel aspect of the invention is determining the nanometric locations of multiple binding positions of multiple types of chemical entities (e.g., sequence binding probes, epigenomic mark binding probes) along a polynucleotide. Another novel aspect of the invention comprises nanometrically localizing epigenomic binding probe to a polynucleotide. Another aspect of the invention is increasing accuracy in detecting a sequence by repetitive interrogation of the sequence on a single polynucleotide. Another novel aspect of the invention is determining the sequence of a polynucleotide by determining the locations of a complete repertoire of oligonucleotides.

Another novel aspect of the invention is determining the sequence of a targeted segment of a polynucleotide by determining the locations of a tiling array of oligonucleotides.

Ordered Array

The polynucleotides can be rendered on the surface in an ordered manner, so that the molecules are maximally packed within a given surface area and that they do not overlap. This can be done by making a patterned surface, for example an ordered arrangement of hydrophobic patches at such locations to which the ends of a polynucleotide (e.g., 1 Mbp in length) binds where the next patch is just beyond the end of the polynucleotide. Alternatively, a spatially addressable array of oligonucleotides can be used to capture polynucleotides. The polynucleotides is single stranded and have a common sequence tract such as a polyA tail (e.g., mRNA). The polynucleotides is double strands with sticky ends generated by a restriction enzyme. For example rare cutting restriction enzyme, e.g., Pmme1 or NOT 1 can be used to generate long fragments, each containing a common end sequence.

An ordered array can also be created by using nanofluidics. In one case, an array of nanotrenches or nanogrooves (e.g., 100 nm wide, 150 nm deep), textured on the surface serve to order the long polynucleotides, where the residence one polynucleotide excludes the entry of another. In another case, a nanopit array, where segments of long polynucleotides are in the pits and long segments are in between pits. An ordered array can also be made.

Sequencing by Transient Probe Binding and Assembly

In some embodiments of the invention, sequencing reads are not obtained per se. In the case of sequencing by transient probe binding, the read is the complement of the oligo which hybridized to a specific location on the polynucleotide. At the first level an assembly is done from sequence information gathered by binding of oligos. Thus some embodiments of the invention comprise:

(i) Stretching the polynucleotide(s)

(ii) Denaturing the polynucleotide(s) (e.g., removing secondary structure if the target is RNA, or separating the double helix when the target is double stranded DNA, such as genomic DNA);

(iii) Adding short oligo probes that bind to the target with unstable interactions; and (iv) Determining a location of binding of each short oligo probes.

In some embodiments, each oligo sequence is added one at a time. In some embodiments, the oligo bears a tag from which its identity can be decoded, e.g., a sequence tag to which an orthogonal set of oligos can be bound or on which determines its identity. In some embodiments, more than one oligo is added at a time. In some embodiments, as many oligos as can be decoded are added. For example if 16 distinct codes are available, 16 oligo sequences each bearing one of the codes are added simultaneously. In some embodiments, substantially more oligos are added and distinguished by using optical barcodes such as DNA origami (e.g., as descried in Nat Chem. 10:832-9, 2012). In some embodiments, a complete set of oligos, e.g., every 5-mer or 6-mer (optionally supplemented with degenerate or universal positions) are used.

At a second level an assembly is done of whole chromosomes by overlap of the polynucleotides assembled at the first level. Where there is sufficient length of overlap haplotype phased assemblies can be conducted.

Transient Probe Binding Effected Through Competition

It must be understood that the binding of the oligo probes is a dynamic process and a probe that is bound is constantly breathing (at a rate determined by various factors including temperature and salt concentration), hence there is an opportunity for displacement of one strand with another. For example, in one embodiment probe complements are used which creates a continuous competition between annealing to the stretched target DNA on the surface, with the complement in solution. In another embodiment the probe has three parts: the first part is complementary to the target; the second part is partially complementary to the target and partially complementary to an oligo in solution; the third part is complementary to the oligo in solution.

In some embodiments, Toehold probes (e.g., as described in Nature Methods 10: 865 (2013)) are used comprising partial double strand that are competitively destabilized when bound to a mismatching target (e.g., as described in Nature Chemistry 5, 782-789 (2013)).

This method can ensure the accuracy of sequencing by transient probe binding. The method comprises:

(i) Stretching a polynucleotide;

(ii) Where the polynucleotide is not single stranded, making it substantially single-stranded (e.g., through denaturing);

(iii) Applying a repertoire of toehold probe sets to the target polynucleotide;

(iv) Determining a location of binding of one oligo from the toehold probe set for each toehold probe set in the repertoire; and (v) Reconstructing the sequence based on the localization data for all the toehold probes in the repertoire.

In some embodiments, the toe-hold probes are used to ensure correct hybridization. In some embodiments, toehold probes are used to facilitate the off reaction.

Assembling Short Range Sequence and Conjoining to Make Long Range Sequence

In some embodiments, the localization accuracy or precision is not sufficient to stitch sequence bits together. A sub-set of probes is found to bind within a specific locality but strictly from the localization data their order is hard to determine with confidence. In some cases the resolution is diffraction limited. In some embodiments, the short-range sequence within the locality or diffraction-limited spot can be assembled by sequence overlap of the probes that locate within the locality or spot. The short-range sequence is thus assembled for example, by using information about how the individual sequence of the sub-set of oligos overlap. Short range sequences constructed in this way can then be stitched together, based on their order on the polynucleotide, into a long-range sequence. The long-range-sequence is thus obtained by Conjoining the Short-Range Sequence Obtained from Adjacent or Overlapping Spots.

Homopolymers and Short Tandem Repeats

There is a problem of homopolymers, when the length is greater than length of oligo it is hard to enumerate the number of bases e.g., a 10 base homopolymer. Also short tandem repeats can be hard to enumerate. This can be tackled in a number of ways, for example any one of the following:

1. Increase the localization accuracy so that the precise range over which a repeat extends can be determined.

2. The kinetics of binding to a region will be different when there are multiple tandem copies (of any repeat sequence) or even when there is a partial copy, the number of copies can be estimated by the increase in binding rate;

the off rate will also be affected as an olio that has bound one site may move to another adjacent site without having to go through 3-D space.

3. Also the number of bases between two strands in a duplex should match and when they are not consistent it suggest an inaccuracy.

4. For homopolymers, as well the 5-mer repertoire, longer homopolymer oligos can be added at the appropriate Tm, e.g., 6As, 7As, 8As etc.

5. Take the reference genome into account.

6. Provide a likelihood of the homopolymer or repeat being a certain length.

Polynucleotide Identification

The identity of a polynucleotide can be determined by the pattern of probe binding along its length. The identity might be the identity of a RNA species, an RNA isoform. It may also be the location in a reference the polynucleotide corresponds to.

Localization of Epigenomic Modifications

Methylation analysis can be carried out orthogonally to the sequencing. In some embodiments, this is done before sequencing. Anti-methyl C antibodies or methyl binding proteins (Methyl binding domain (MBD) protein family comprise MeCP2, MBD1, MBD2 and MBD4) or peptides (based on MBD1) can be bound to the polynucleotides, their location detected via labels before they are removed (e.g., by adding high salt buffer, chaotrophic reagents, SDS, protease, urea and/or Heparin). Preferably the reagents bind transiently, due to use of a transient binding buffer that promotes on-off binding or the reagents are engineered to bind transiently.

A similar approach be taken for other polynucleotide modifications such as hydroxymethylation or sites of DNA damage, for which antibodies are available or can be raised. After the locations of the modifications have been detected and the modification binding reagents are removed the sequencing can commence. In some embodiments, the anti-methyl and anti-hydroxymethyl antibodies etc are added after the target polynucleotide is denatured to be single stranded. The method is highly sensitive and is capable of detecting a single modification on a long polynucleotide.

There are no reference epigenomes, for DNA modifications such as methylations. In order to be useful, the methylation map of an unknown polynucleotide needs to be linked to the nucleic acid sequence or a sequence-based map. Thus the epi-mapping methods of this invention can be correlated to sequence bits obtained by oligo binding, in order to provide context to the epigenomic map. In addition to sequence reads, other means of obtaining sequence information can be coupled with an epigenomic map. This includes, nicking endonuclease-based maps, oligo-binding based maps and Denaturation and Denaturation-Renaturation maps. In some embodiments, transient binding of one or more oligos can be used to map the polynucleotides. In addition to functional modifications to the genome, the same approach can be applied to other features that map on to the genome, such as sites of DNA damage and protein (e.g., transcription factor) or ligand binding.

In the present invention either the base sequencing or the epigenomic sequencing can be done first. In some embodiments, both can be done at the same time. For example antibodies against specific epi-modification can be differentially coded from the oligos and conditions are used, such as low salt, that makes binding of both types of probes transitory.

In some embodiments, antibodies can be used on chromosomes or chromatin to not only detect modifications on DNA but also modifications on histones, such as histone acetylation and methylation. The location of these modifications can be determined by the transient binding of the antibodies to locations on the chromosome or chromatin. In some embodiments, the Antibodies are labeled with oligo tags and do not bind transiently but can be fixed permanently or semi-permanently to their binding site. In this case the locations can be detected by using transient binding of complementary oligos to the ones that tag the antibody.

Treating Samples for Locational Preservation of Reads

In some embodiments, after the polynucleotide is elongated a gel overlay is applied. After elongation and denaturation on the surface the polynucleotide (double stranded or denatured) can be covered with a gel layer. Alternatively the polynucleotide is elongated whilst is already in a gel environment. In some embodiments, after the polynucleotide is elongated it is cast in a gel. For example when the polynucleotide is attached to a surface at one end and stretched in flow stream or by electrophoretic current, the surrounding medium can become cast into a gel. This can occur by including acrylamide, ammonium persulfate and TEMED in the flowstream which when set becomes polyacrylamide. Alternatively gel that responds to heat can be applied. In some embodiments, the end of the polynucleotide can be modified with acrydite which polymerizes with the acrylamide. An electric field can then be applied which elongates the polynucleotide towards the positive electrode, given the negative backbone of native polynucleotides.

In some embodiments, the sample is cross-linked to the matrix of its environment; this is the cellular milieu. For example when the sequencing is conducted in situ in a cell, the polynucleotide is cross-linked to the cellular matrix using a heterobifunctional cross linker. This was done when sequencing is applied directly inside cells using a technique such as FISSEQ (e.g., as described in Lee et al. Science 343:1360-3 (2014)).

In some embodiments, a panel of probes is used, to enable targeted sequencing. Because only a subset of polynucleotides from the complex sample (e.g., whole genome or transcriptome) need to be analyzed when targeted sequencing is done, the polynucleotides can disposed on the surface or matrix at a higher density than usual. So even when there are several polynucleotides elongated within a diffraction limited space, when a signal is detected, there is high probability that it is from only one of the targeted loci. This then allows the imaging required for targeted sequencing to be concomitant with the fraction of the sample that is targeted. For example if the <5% of the genome which comprises exons is targeted, then the density of polynucleotides can be 20× greater and thus the imaging time can be 10× shorter than if the whole genome was to be analyzed.

In some embodiments, the parts of the genome that are targeted are specific genetic loci. In other embodiments the parts of the genome that are targeted are a panel of loci, for example genes linked to cancer, or genes within a chromosomal interval identified by a Genome-wide Association study. The targeted loci can also be the dark matter of the genome, heterochromatic regions of the genome which are typically repetitive, as well the complex genetic loci that are in the vicinity of the repetitive regions. Such regions included the telomeres, the centromeres, and the short arms of the acrocentric chromosomes, as well as other low complexity regions of the genome. Traditional sequencing methods cannot address the repetitive parts of the genome, but when the nanometric precision is high the methods of this invention can comprehensively address these regions.

The advantage of the present invention is that it enables long reads to be obtained without actually carrying out costly, and time consuming individual long reads, by stitching together contiguous or overlapping sequence information obtained by the binding of short oligos instead. A plurality of short, 3, 4, 5 or 6 base bits of sequence information are simultaneously obtained along the length of a single polynucleotide molecule, and hence they are all connected, and when the polynucleotide has been saturated with on-off binding oligos their nanometric position, resolution and order reveal the sequence of the whole molecule. The sequencing of a polynucleotide takes less time than current methods as multiple bits of sequence information are being obtained simultaneously rather than a single long read being obtained by a SbS reaction from one location in the molecule to another (e.g., PacBio sequencing).

Another major advantage of the invention is that it enables structural variation of all types to be detected, small or large, including balanced copy number variation and inversions, which are challenging for microarray based technologies, the current dominant approach and at a resolution and scale that can't be approached by microarray, cytogenetic or other current sequencing methods.

Moreover, the method allows sequencing through repetitive regions of the genome. For conventional sequencing the problem with reads through such parts of the genome is that firstly, such regions are not well represented in reference genomes and technologies such as Illumina, Ion Torrent, Helicos/SeqLL, and Complete Genomics typically deal with large genomes by making alignments to a reference, not by de novo assembly. Secondly, when the reads do not span the whole of the repetitive region, it is hard to assemble the region through shorter reads across the region. This is because it can be hard to determine which of multiple alignments that are possible between the repetitive regions on one molecule with the repetitive region on another molecule are correct. A false alignment can lead to shortening or lengthening of the repeat region in the assembly. In the sequencing methods of the invention, when there is complete or near complete coverage of a single molecule by multiple reads either taken simultaneously or one set after the other, an assembly can be constructed that spans the whole of the repetitive region (when the polynucleotide itself spans the whole of the repetitive region). The methods of this invention can be applied to polynucleotides that are long enough to span repetitive regions. Polynucleotides between 1 and 10 Mb are enough to span most of the repetitive regions in the genome. The methods of the invention can be applied to complete chromosomal lengths of polynucleotides from a eukaryote genome as shown in Freitag et al. and attempted in (e.g., as described in Rasmussen, et al Lab on a Chip, 11: 1431-3 (2011) so it is possible to span all or most of the possible repetitive lengths in the genome.

Preserving Polynucleotide In Situ Territorial Information

In some embodiments, the sequencing methods of this invention are applied in situ inside the cell. In the case of RNA and genomic DNA after it has been denatured, sequencing can be initiated. In the case of mRNA, sequencing can be initiated optionally after denaturing secondary structure. In some embodiments, the sequencing is done on slices of the cell, obtained for example by a Microtome.

Carrying out the sequencing methods of this invention inside a cell allows one to not only sequence the genomic DNA but also to establish the location of the genomic DNA in the cell. Moreover, when applied to tissues it enables the distribution of somatic variant in the cells of a tissue to be analyzed as well as differences in chromosome organization. This is very important, because different parts of the genome interact with each other inside the cell. For example enhancers contact genic regions through loops and in situ genome analysis enables such interactions to be seen. Also, the organization of the genome or individual chromosome inside the cell can be visualized or determined. In addition the process can be conducted on a population of cells grown in a dish (e.g., Fibroblasts or neurons) or on tissue sections. In the case of cells or tissues that are substantially three-dimensional, sequencing can be done on slices of the cells or tissues. In some embodiments, the chromatin DNA inside cells is subject to denaturation (using 0.5M NaOH for example), the transient binding interactions of the invention are then conducted. RNA can be removed by adding RNAses. In some embodiments, the transient binding interactions are detected from intercalating dye binding into the duplex formed by unlabelled probe binding. In some embodiments, the probe is labeled and binding is detected via FRET between dye that intercalates into the duplex and the label on the probe.

Identity and Spatial Positions of Binding Probes

One aspect of the invention is to store the identity and spatial position of probes transiently bound to each of the plurality of sequence fragments. The position of binding of a probe along a polynucleotide is determined by a location sensitive aspect of the detector. If a 2-D detector such as CCD is used, the location is determined by the x-y coordinates of the pixels the image is projected on to. A number of computational filters are used to remove spurious binding of labels from what is a true detection event. A label must be correlated with a line that traces through several origins to show the path followed by the polynucleotide; when the path is straight the position that passes the filter falls on the straight line.

The identity of a probe that binds to a biopolymer can be determined in one of two ways. If the a plurality of probes differently labeled and used together in one reaction volume, then the identity of the oligo is determined by detecting a code labels is detected at the particular location along the polynucleotide. This can be done either by firing four different laser, one for each label, using four different emission filters, one for each label or using a combination of different lasers and emission filters. In this case an image is taken for one wavelength, can be mapped to polynucleotide, then the next and so on. An alternative to serially detecting the four labels is to simultaneously detecting the four labels. This can be done by using a prism to split the emission light to distinct locations on a 2-D detector. This can also be done by using dichroic mirrors and emission filters to split the emission wavelengths into four channels, one for each of the four labels. Finally, the emission wavelengths can be split between any number of channels, and the intensity of each signal is detected in each channel to give a label specific-signature. In some embodiments, a signature spanning the channels for each fluorophore is first obtained and then the signature is used to identify the label and hence the sequence from the recorded data.

Sequencing Tags

In some embodiments, segments of DNA are tagged in situ (i.e. along the length of genomic DNA or within a cell) and the location and identity of the tags are determined using transient binding methods of this invention. The tags can be sequence tags and can be designed in a way that only a small pool of transiently binding oligos can be used to determine their identity. In some embodiments, once the location and identity of the tags have been determined, the polynucleotide can be extracted from the cell or released from the surface, while the sequence tags remain attached to polynucleotide fragments. The polynucleotides+sequence tag can be optionally amplified and sequenced using any sequencing method, e.g., high-throughput Illumina sequencing. From the output of the sequencing the sequence of the tag can be used to localize particular segments of sequences to specific locations in the genome.

Dye Photophysics

Detection of single fluorescent dyes is susceptible to the idiosyncrasies of each specific dye type. Certain dyes have photophysical characteristics such as dark states, fast photobleaching, and low quantum yield that rule them out as candidate dyes. Also the chemical characteristics of the dyes, their structure and whether they carry a charge also affects how well they can be incorporated and the extent to which they non-specifically bind. The choice of dye depends on avoidance of poor photophysical and chemical issues as well as how well they can be excited and detected in a chosen instrument set-up and how well they can be discriminated from the other three dyes. In some embodiments of the invention, other characteristics such as FRET or quenching efficiencies are also important. Fortunately, there are several dye manufacturers and a large list of dyes to choose from. Four dyes that can work well are Atto 488, Cy3b, Atto 655 and Cy7 or Alexa 594. Another four good single molecule dyes that can be used in the invention are shown in Sobhy et al [Rev. Sci. Instrum. 82, 113702 (2011), where a 405 nm, 488 nm, 532 nm and 640 nm laser can be used to excite, Atto 425, Atto 488, Cy3, and Atto647N respectively. Each of the labels indicates a different base identity. Certain dyes need a pulse of light of a different wavelength from their peak excitation wavelength to release them from trapped photophysical states. A number of redox systems are known that minimize the photophysical including: Trolox, Beta-mercaptanol; glucose, glucose oxidase and catalase; protocatechuic acid and protocatechuate-3,4-dioxygenase; methylviologen and ascorbic acid. (see Ha and Tinnefeld, Annu Rev Phys Chem. 2012; 63: 595-617). As an alternative to continuous illumination, In some embodiments, the sample is subject to pulsed or stroboscopic illumination; this reduces photobleaching.

Imaging

The images of the polynucleotides are projected onto the array of a 2-D Detector (e.g., Charge-couple device (CCD) camera), from which they are digitized and stored in memory. The images stored in memory are then subjected to image analysis algorithms. These algorithms can distinguish signal from background, monitor changes in signal characteristics, and perform other signal processing functions. The memory and signal processing is performed off-line on a computer, or in specialized digital signal processing (DSP) circuits controlled by a microprocessor or Field Programmable Gate Arrays (FPGA).

Image Processing

When a fluorescent label has been transiently bound to the elongated polynucleotide, it can be detected by taking an image with a 2D array detector. The next task is to extract the sequencing data from the images taken. Efforts are made to align the stretched molecules along one axis of the 2-D array detector (e.g., CCD or CMOS sensor) either along the pixel rows or columns of the 2D array detector.

In the case where Time-delayed Integration (TDI) imaging or a line scanner is used, where a continuous image strip is obtained (e.g., as described in Hesse et al. Anal Chem. 2004 Oct. 1; 76(19):5960-4.), one embodiment of the invention comprises, matching the direction of the image translation (or stage translation) with the linear direction of elongation of the polynucleotides. This is so that a contiguous image of very long polynucleotides, 100s of microns, several mms or several tens of mms in length can be obtained, and extra computational resources do not need to be devoted to stitching images which can also lead to errors at the image interface.

In some embodiments, the system of the invention includes a method for obtaining rapid and accurate long-range images of polymers comprising:

i) Stretching the polymers in one direction;
ii) Using a 2-D detector equipped with time-delay integration (TDI);
iii) translating the sample in relation to the detector in the direction of DNA stretching; and
iv) reading the lines in the direction of translation where the long polymer molecules are analyzed from single long image swathes/strips (without the need for stitching separate frames).

In some such embodiments, the translation speed is a fraction of the read-out speed. This allows multiple signal events to be captured from each position by the sensor elements before the next position on the surface is imaged by the sensor. Therefore, multiple binding events can be detected, where a certain number of consecutive pixels capture temporal events around a location before the position is shifted enough to be capturing events from an adjacent location.

In other cases the ultra-long polynucleotide is folded into a meandering pattern, through its confinement in a meandering nanochannel (see Frietag et al) and then imaged within the frame of a single CCD or CMOS.

Where the direction of elongation does not correspond to an axis of the 2-D array detector, a first image processing step is done to transform the image so that the lines are aligned along an axis in the image. In some embodiments of the invention, where the polynucleotides are aligned straight in a single orientation, the location of the polynucleotides can be traced by looking at pixels that are activated along a linear axis. Not every pixel needs to be activated, just a sufficient number to be able to trace the polynucleotide over background/non-specific binding to the surface. Signals that do not fall along the axis are ignored. In some embodiments, the backbone of the polynucleotide is labeled. For example binding of fluorescent dye such as Sybr Gold can be used to trace the polynucleotide. Instead of a traditional DNA stain, conjugated cationic polymers can be used.

Fluorescence Lifetime and Background Scatter Rejection

The different binding probes (including those that bind transiently) can be coded with luminescent entities (e.g., dyes) with different fluorescent lifetimes. The fluorescence lifetime of a molecule is the average time the molecule spends in the excited state before returning to the ground state by emission of a fluorescence photon Pulsed laser excitation can then be used to excite the dyes and a time correlated singe photon detector (or other detector capable of high resolution time correlated detection) is used to detect the fluorescence lifetime profiles of each dye. The detector is am intensified CCD (IMCCD). It can also be an array of point detectors that can bin the arrival times of photons. In addition the detection time of emission can be gated so that the early (picosecond range) fluorescence due to light scattering can be gated out so that the fluorescence emitted by the dye is detected above background.

The methods of the invention can be conducted with or without an evanescent field and with relatively high concentrations of oligos, but background fluorescence due to scattering is removed by rejecting the early time window of fluorescence. So using pulsed excitation and time gated or time correlated detection one can kill two birds with one stone: one can code the sequencing interrogation reagents (nucleotides, oligos) with labels that are differentiated by their different fluorescence lifetimes and one can reject the background fluorescence due to scattering.

The background fluorescence due to the dyes (not scattering) in solution still remains, but this can be reduced by using an evanescent wave for excitation, a zero mode waveguide and/or a RET mechanism. Or the reagents can be quenched (e.g., Molecular beacons etc).

An example setup includes a wide-field Fluorescence Lifetime Imaging Microscope (FLIM) system with the illumination of the sample using a 405 nm pulsed laser diode and collect the shifted fluorescence signal with an ICCD camera. A 4 Picos intensified CCD camera (Stanford computer optics) with a shortest gating time of 200 ps can be used. A beam-splitter is used within the microscope to separate the laser pulse from the fluorescence signal. This beam-splitter reflects the excitation wavelength of 405 nm and transmits the fluorescence signal of the sample which is shifted to longer wavelengths. The wide field FLIM setup needs additionally a trigger synchronization of the pulsed laser diode and the intensified CCD camera. The excitation source of time-resolved measurements is either pulsed or modulated which enables the measurement of fluorescence emission and kinetics. Time domain fluorescence measurement methods are generally more easily understood because they generate a true representation of the fluorescence decay curve. Typically time domain systems consist of a pulsed light source providing excitation coupled with a fast response detector. The lifetime results can be improved by increasing the number of time gates and development of the fitting algorithm to account for multi-exponential decay fitting. The time-correlated detection be combined with single molecule localization.

Fluidics

The invention can be carried out in fluidic device (flow cell or wells). A means to deliver and exchange reagents can take various forms. Syringe pumps or pressure-driven systems, acoustic driven systems can be used to move reagents where they are stored to the location where the sequencing is done and then removed as waste. Where multiple probes need to be delivered (e.g., each of 1024 oligos), one means for storing a large number of oligos and delivering them to the sequencing system which can be used to execute the method of the invention is described by Pihalk et al. Anal. Chem. 2005, 77, 64-71. Another approach that can be used is described by Linder et al Anal. Chem. 2005, 77, 64-71). One simple way of delivering a large number of different probes or probe sets is to load them into a capillary each separated by an air gap. Wash solutions can also be interspersed. Then the loop is run at an appropriate speed (e.g., by pull from a syringe pump) so that each probe and wash solution contacts the surface for a period sufficient to undertake the imaging required for the invention.

Sequence Quality: Minimizing Sequencing Error and Coverage Bias

All sequencing technologies are subject to some level of error, and different sequencing platforms are susceptible to different kinds of error. According to Schirmer et al. (Nucl. Acids Res. 2015; nar.gku1341)I, Illumina MiSeq raw error rates are 2%. This includes errors introduced by library prep, cluster amplification, pre-phasing (errors in early incorporations), and phasing (error in the later incorporations). This can be reduced by trimming and overlapping reads to build a consensus.

In embodiments of the present invention no PCR is conducted, so there is no coverage bias introduced due to PCR and there are no errors due to polymerase misincorporation during PCR. In Illumina, ABI SOLID, Ion Torrent, Intelligent Biosystems and Complete Genomics sequencing, amplification errors can be introduced during library preparation and during clonal amplification (e.g., DNA nanoball, polony or cluster generation).

The usual means for overcoming error in next generation sequencing is to carry out the sequencing on multiple copies of the unamplified genome in order to obtain reads of the same segment of the genome from multiple separate (non-amplicon) copies of the genome. The sequence is then assigned from a consensus of the many molecules. If two sequences are predominant, it may indicate heterozygosity. This is not an option when sequencing is done on a single cell. It is also problematic when the tissue or cell from which the multiple copies are obtained is not homogeneous. For example within a tumor there can be multiple clonal populations intermixed and somatic mutations is present. The genomes are also altered in immune cells and direct single cell sequencing is needed. The methods of the invention are applied to such cases on a single polynucleotide basis.

In some applications it is important to detect the somatic mutations that have occurred in a population of cells. In this case it is better not to rely on being able to prune out error by obtaining consensus reads from many molecules, as it might be difficult to differentiate error from true rare mutations. Another problem with this is that the different copies is paralogous, in that they are from different duplicons of a segment of the genome (segmental duplications), but which may contain small differences.

When sequencing is being done according to the method of this invention raw error can be diminished by fortifying the sequence call by multiple probe binding events.

When sequencing on single molecules via detecting the incorporation of nucleotides, labeled with a single dye molecule as is done in Helicos and PacBio sequencing, errors can be introduced due to the dye not being detected. This can be because the dye has photobleached, the cumulative signal detected is weak due to dye blinking, the dye emits too weakly or the dye enters into a long dark photophysical state. This can be overcome in the present invention in a number of ways. The first is to label the dye with robust individual dyes that have favorable photophysical properties (e.g., Cy3B). Another is to provide buffer conditions and additives that reduce photobleaching and dark photophysical states (e.g., beta mercaptoethanol, Trolox, Vitamin C and its derivatives, redox systems). Another is to minimize exposure to light (e.g., having more sensitive detectors requiring shorter exposures or providing stroboscopic illumination). The second is to label with nanoparticles such as Quantum dots (e.g., Qdot 655), Fluorospheres, Plasmon Resonant Particles, light scattering particles etc. instead of single dyes. Another is to have many dyes per nucleotide rather than a single dye. In this case the multiple dyes is organized in a way that minimizes their self-quenching (e.g., using rigid nanostructures, DNA origami that spaces them far enough apart) or a linear spacing via rigid linker. Genovoxx were able to incorporate nucleotides containing many fluorophores, Mir (WO2005040425) have been able incorporate nucleotides to which nanoparticles have been attached.

However the most means to reduce errors due to dye Photophysics that is most pertinent to this invention is to take advantage of the transient binding as described in this invention. Here the readout during the imaging step is obtained as an aggregate of many on/off interactions of different label-bearing probes so even if one label is photobleached or is in a dark state, the labels on other binding probes that land on the molecule may not be photobleached or in a dark state.

The detection error rate is further reduced (and signal longevity increased) in the presence of one or more compound(s) selected from urea, ascorbic acid or salt thereof, and isoascorbic acid or salt thereof, beta-mercaptoethanol (BME), DTT, a redox system, Trolox in the solution.

Read Aggregation by Array Capture

In another embodiment capture reagents targeting specific polynucleotides or specific segments of polynucleotides that are disposed on a surface or in a matrix are used to capture the target polynucleotides. In some embodiments, the capture probes are designed to target certain generic sequences present on all polynucleotides in a sample. For example, an oligo (dT) capture reagent would target all RNA. In some embodiments, a common oligo sequence is grafted on to the target polynucleotides, so that they can be captured. Different capture reagents can be used to capture different polynucleotides, and the different capture reagents can be disposed in a spatially addressable ordered array such as a microarray. Once the polynucleotides are captured they can be elongated by fluid flow or electrophoretic flow.

Making Sense-Antisense Single-Strands for Sequencing

In some embodiments, a hairpin is ligated onto an end of a double stranded target and one of the other ends is immobilized on a surface via only one of the strands. The polynucleotide is then denatured and elongated/stretched from the point of attachment. The polynucleotide is then fixed in the elongated state.

This provides a way to ensure that the target is single stranded. Further the reads obtained from the end-on-end sense and antisense strands provide complementary reads, which is an internal validation of the verity of the sequencing obtained. Such sense-antisense strands can also be made by doing cDNA synthesis on RNA using AMV reverse transcriptase which naturally makes a hairpin to synthesize a second strand. In some embodiments, the primer for reverse transcription is modified with a moiety that allows attachment to the surface.

Single Strand Assembly

In some embodiments, of this invention the sample comprises a single-stranded polynucleotide without a native complementary strand in close proximity. Here, when the binding locations for each of the oligos of the repertoire along the polynucleotide is compiled the sequence can be reconstructed by aggregating all the sequence bits according to their location and stitching them together. In fact a complete repertoire would provide tiling series of sequence bits. In the real world, the pattern can be complicated by mismatch and non-specific binding on the polynucleotide; however the mismatch can be distinguished by their temporal binding pattern and hence can be considered as a secondary layer of sequence information. In this case, when a binding signal, due to its temporal binding characteristics is adjudged to be a mismatch the sequence bit can be bioinformatically trimmed to remove putative mismatching bases and the remaining sequence bit can be added to the sequence reconstruction. As mismatches are most likely to occur at the end of hybridizing oligos, according to the temporal binding characteristics one or more bases can be trimmed from the end. As to which base is trimmed can be informed by information from other oligos tiling over the same sequence space.

Simultaneous Duplex Consensus Assembly

In some embodiments, of this invention both strands of a double helix are present in close proximity and it is not possible to distinguish which strand the oligo has bound to from the transient signals that are detected. However when the binding locations for each of the oligos of the repertoire along the polynucleotide is compiled, it may look like two oligo sequences bind to the same location. These oligos should be complementary in sequence. In order to determine whether a single binding event is to one or the other strand, the data in totality is then considered: two tiling series of oligos cover the locality in question, with each tile being an incremental shift in localization along the length of the polynucleotide in one direction or the other; which of two tiling series the signal belongs to will be assigned based on which series the oligo sequence generating the signal overlaps with; this is illustrated in FIG. 28. In some embodiments, the sequence is then reconstructed by first using location of binding and sequence overlap to construct each of the two tiling series. Then the two tiling series are aligned as reverse complements and the base assignment at each location is accepted only if the two strands are perfect reverse complements at each of those locations (this providing duplex consensus sequence). Any mismatch is flagged as being an ambiguous base call where one of the two possibilities needs to be corroborated by additional layers of information, such as that from independent mismatch binding events. In some embodiments, once the duplex consensus has been obtained a conventional (multi-molecule) consensus is determined by comparing data from other polynucleotides that cover the same region of the genome (when DNA from multiple cells are available), taking care not to mix individual haplotypes. Alternatively, In some embodiments, individual strand consensus is obtained before the duplex consensus of the individual strand consensus is obtained. In such embodiments of the invention the sequence of each of the strands of the duplex is obtained simultaneously, without additional sample preparation steps such differentially tagging the two strand of a duplex with molecular barcodes, as is currently available for Next Generation Sequencing (NGS) [J. Salk, et al. "Detection of ultra-rare mutations by next-generation sequencing". Proc. Natl. Acad. Sci., vol. 109 no. 36. 2012]. Also, this simultaneous both strand (sense and antisense) sequence acquisition compares favorably with 2D or 1D2 consensus sequencing that is available for nanopores which requires sequence to be obtained for one strand of the duplex before the sequence of the second strand is obtained. Duplex consensus sequencing can provide accuracy in the $10^6$ range i.e. one error in a million bases (compared to the $10^2$-$10^3$ raw accuracy of other NGS approaches) and in the case of the present invention the duplex consensus is an intrinsic part of sequence acquisition without additional sample preparation steps. This makes the method highly compatible with the need to resolve rare variants that arise if one is trying to detect circulating DNA for early cancer detection or trying to detect DNA from low frequency sub-clones in a tumor cell population.

Integrating Reads from Multiple Polynucleotides

Preferably the contiguous sequence is obtained via de novo assembly. However, the reference sequence can also be used to facilitate assembly. This allows a de novo assembly to be constructed but it is harder resolve individual haplotypes of very long distances, enough locations need to be encountered along the molecule that are informative about the haplotype. When complete genomes sequencing requires a synthesis of information from multiple molecules spanning the same segment of the genome (ideally molecules that are derived from the same parental chromosome), algorithms are need to process the information obtained from multiple molecules. One algorithm is of the kind that aligns molecules based on sequences that are common between multiple molecules, and fills in the gap in each molecule by imputing from co-aligned molecules where the region is covered. So a gap in one molecule is covered by read in another (co-aligned molecule). Further, shotgun assembly methods such as that developed by Eugene Myers can be adapted to carry out the assembly, with the additional advantage that a multitude of reads are pre-assembled (e.g., it is already known the location of reads with respect to each other, the length of gaps between reads is known). Other algorithmic approaches, such as the SUTTA described by Mishra et al (Bioinformatics, Oxford Journals, (2011) 27 (2): 153-160), can also be adapted for assembly of the data. In various embodiments, a reference genome can be used to facilitate assembly, either of the long-range genome structure or the short-range polynucleotide sequence or both. The reads can be partially de-novo assembled and then aligned to the reference and then the reference-assisted assemblies can be de-novo assembled further. Various reference assemblies (e.g., from different ethnic groups) can be used to provide some guidance for a genome assembly, however, information obtained from actual molecules (especially if it is corroborated by two or more molecules) is weighted greater than any information from references. The prior art does not show that a contiguous sequence can be reconstructed by aligning locational sequence obtained from a plurality of individually examined single polynucleotide molecules.

Sequencing without a Reference

In various embodiments, the sequence is determined without using another copy of the target polynucleotide molecule or reference sequence for the target polynucleotide molecule. In this case the most of the reads (e.g., 90%) will have coalesced and the gap between reads of those reads that have not coalesced will be known. The gap distance will be known because the linear length of the polynucleotide will be traceable and the gap distance can be determined by counting the number of pixels between reads, and using knowledge of the length of DNA each pixel spans.

Haplotype Resolved Sequencing

Genomic sequence would have much greater utility if haplotype information (the association of alleles along a single DNA molecule derived from a single parental chromosome) could be obtained over a long range.

In various aspects and embodiments, the methods can be used for sequencing haplotypes. Sequencing haplotypes can include the steps of sequencing a first target polynucleotide spanning a haplotypic of a diploid genome using a method according to the invention; sequencing a second target polynucleotide spanning the haplotypic branch of the diploid genome using a method according to the invention, where the first and second target polynucleotides are from different copies of a homologous chromosome; and comparing the sequence of the first and second target polynucleotides, thereby determining the haplotypes on the first and second target polynucleotides.

Determining Haplotype Diversity and Frequency in a Cell Population

In many existing methods where the aim is to look at the heterogeneity of genomes in a population of cells, single cell analysis is used which is technically demanding. However, a remarkable feature of the present invention is that the heterogeneity of genomes in a population can be analyzed without the need to keep the content of single cells together because if molecules are long enough one can determine the different chromosomes, long chromosomes segments or haplotypes that are present in the population of cells. Although this does not indicate which two haplotypes are present in a cell together, it does report on the diversity of genomic structural types (or haplotypes) and their frequency and which aberrant structural variants are present. This embodiment comprises the steps:

1. Extracting genomic DNA from two or more cells;
2. Elongating the DNA and carrying out a sequencing method of this invention;
3. Analyzing the data to determine which DNA strands are homologs;
4. Determining the different haplotypes among the homologs; and
5. Determining the frequency of the different haplotypes.

Synergizing with Other Sequencing Technologies

In some embodiments, the methods of this invention stop short of being a complete genome sequencing and are used to provide a scaffold for short read sequencing such as that from Illumina. In this case it is advantageous to conduct Illumina library prep by excluding the PCR amplification step to obtain a more even coverage of the genome. One advantage of some of these embodiments that fold coverage of sequencing required can be halved from about 40× to 20× for example. In some embodiments, this is due to the addition of sequencing done by the methods of the invention and the locational information that methods provide.

Sequencing Panels

In some embodiments, it is desirous to sequence a subset of the genome corresponding to specific genes or loci. In this case, the genomic DNA is made single stranded and sequence-specific oligos are transiently annealed over the regions of interest. One advantage of targeting the sequencing in this way, is that even if the whole of the genome is stretched onto the surface, only the targeted regions light up. So imaging time can be shortened by going directly to the light detectable target regions. Furthermore, the genome can be arrayed on the surface at a much higher density than normal, because only a small sub-fraction of the molecules need to be detected. As an example, the BRCA1 region of the human genome can be sequenced by annealing a plurality of oligonucleotides complementary to BRCA1 sequences. Other parts of the genome remain undetected.

Cell-Free Nucleic Acids

Some of the most accessible DNA or RNA for diagnostics is found extraneous of cells in body fluids or stool. DNA circulating in blood is used for pre-natal testing for trisomy 21 and other chromosomal and genomic disorders. It is also a means to detect tumor derived DNA and other DNA or RNA that is markers for certain pathological conditions. However the molecules are typically in the ~200 bp length range in blood and shorter in urine. The copy number of a genomic region is determined by comparison to the number of reads that align to the reference compared to other parts of the genome.

In some case it is useful to determine in a sequence-specific manner if the nucleic acid is methylated. For example one way of differentiating fetal from maternal DNA is the former is methylated in loci of interest; this can be useful for Non-Invasive Prenatal Testing (NIPT).

The present invention can be applied to the enumeration or analysis of cell free nucleic acids sequences by two approaches. The first involves immobilizing the short nucleic acid before or after denaturation. The transiently binding reagents can be used to interrogate the nucleic acid in order to determine the identity of the nucleic acid, its copy number, whether mutations or certain SNP alleles are present, and whether the sequence detected is methylated or bears other modifications (biomarkers).

This involves:

1) Isolating cell free nucleic acids from body fluids e.g., blood;

2) Immobilizing the isolated cell free nucleic acids on a substrate; and

3) Performing sequencing by probe binding to the immobilized cell free nucleic acids.

The second involves, first concatenating the small fragments, so that the concatamer can be stretched out. This comprises:

4) Isolating cell free DNA from blood;

5) Concatenating DNA; and

6) Performing sequencing by probe binding on the concatenated DNA.

In some embodiments, concatenation is done by polishing the ends of the DNA and performing blunt end-ligation. Alternatively, the blood or the cell free DNA can be split into two aliquots and one aliquot is tailed with poly A (using Terminal Transferase) and the other aliquot is tailed by a poly T.

The resulting concatamers are then subjected to sequencing. The resulting "super" sequence read is then compared to reference to extract individual reads. The individual reads are computationally extracted and then processed in the same manner as other short reads.

Nucleic acids are also found in stool, a medium that contains a high number of exonucleases which can degrade nucleic acids; high amounts of chelators (e.g., EDTA) of divalent cations, which are needed by exonucleases to function, can be employed to keep the DNA sufficiently intact and sequenced according to the methods of the invention. Another way that DNA is shed from cells is via encapsulation in exosomes. Exosomes can be isolated by ultracentrifugation or by using spin columns (Qiagen), and the DNA or RNA contained therein can be collected and sequenced according to the methods of the invention.

In some embodiments, the binding of one, but usually at least two, preferably several oligonucleotides, to a nucleic acid is sufficient to determine its identity or what part of the genome the nucleic acid comes from or originates from. Hence, incomplete sequencing before a full repertoire is tested, may provide the requisite information. In some embodiments, the ratio of different chromosomes or genomic regions is determined by counting the number of nucleic acid molecules identified according to their genomic origination. In some embodiments, this allows information about the fetal fraction of the sample to be determined. In some embodiments, along with determination of the identity or origin of a nucleic acid molecule the occurrence of a single nucleotide variant or indel is determined by analyzing the binding of the one or more oligos.

The longer the oligonucleotide is bound the fewer the oligonucleotide is needed to determine the identity or origin of a nucleic acid molecule. In this regard, specific genes or loci can be detected by providing a panel of oligonucleotide probe sequences, such probes is oligo lengths greater than 10 nucleotides or multiple specific short oligonucleotides <10 nt in length. Hence, a panel of cancer related probes is applied to nucleic acids molecules extracted from blood, to identify cancer related genes and then further oligonucleotides binding can be used to identify single nucleotide variants or indels. The advantages of the approaches described in this invention for this include the multiple binding events and, in some embodiments, the probing of both strands, to give greater confidence in calling a variant.

RNA Sequencing

The lengths of RNA are typically shorter than genomic DNA but it is challenging to sequence RNA from one end to the other using current technologies. Nevertheless, because of alternative splicing it is vitally important to obtain determine the full sequence composition of the mRNA. In some embodiments of the invention mRNA can be captured by binding of its polyA tail by immobilized oligo d(T), its secondary structure removed by stretching force and denaturation conditions so that it can be elongated on the surface. This then allows binding reagents (which is exon-specific) to be transiently bound. Because of the short length of RNA it is beneficial to employ the single molecule localization methods described in this invention to resolve and differentiate exons. In some embodiments, just a few binding events scattered across the RNA is sufficient to determine the order and identity of exons in the mRNA for a particular mRNA isoform.

Preserving the Integrity of a Biomacromolecule Prior to Analysis

It is recurring challenge in biology to observe biomolecules in their native state. All too often, the process of retrieving information of a biomolecule in its native state leads to disruption of some aspects of the native state.

In the case of the genome, it is a challenge to analyze the information content of the genome in its native chromosomal state. The DNA in human chromosome can range in length from 50 million bases to 250 million but today's shotgun sequencing technologies can only read lengths of a few hundred bases. This is despite it becoming increasingly appreciated that the location and copy number of a DNA sequence has important implications for phenotype.

Much of the disruption occurs in the process of extracting the biomolecule from cells and tissues and the subsequent handling of the biomolecule before it can be analysed. In the case of DNA, aspects of its handling that lead to its loss of integrity includes pipetting, vortexing, freeze-thawing and excessive heating. Mechanical stress can be minimized (e.g., as described in ChemBioChem, 11:340-343 (2010). In addition high concentrations of divalent cations, EDTA, EGTA or Gallic Acid (and its analogues and derivatives) inhibit degradation by nucleases. In some embodiments, a 2:1 ratio of sample to divalent cation weight is sufficient to inhibit nucleases even in samples such as stool, where there are extreme levels of nucleases.

The problem an alternative aspect of the invention seeks to address is how to preserve the native integrity of a biomacromolecule prior to analysis, in particular how to preserve genomic DNA in its native or somewhat closer to its native long lengths. This is relevant both for sequencing using the methods of this invention or for using other methods. It is particularly relevant to nanopore sequencing.

In some embodiments, the invention concerns a method for delivering a biomacromolecule for analysis comprising:

1) Providing a protective entity comprising a biomacromolecule, said protective entity preserving the biomacromolecule close to its native state;

2) Placing the protective entity comprising the biomacromolecule in proximity of an analytical zone; and 3) Releasing the biomacromolecule from the protective entity into the analytical zone.

In some embodiments, the invention concerns a method for preparing a biomacromolecule for analysis comprising:

1) Providing a protective entity comprising a biomacromolecule, said protective entity preserving the biomacromolecule close to its native state;

2) Placing the protective entity comprising the biomacromolecule in proximity of an analytical zone;

3) Releasing the biomacromolecule from the protective entity; and

4) Passing the biomacromolecule into the analytical zone.

In some embodiments, the invention concerns a method for preparing a biomacromolecule for analysis comprising:

1) Providing a protective entity comprising a biomacromolecule, said protective entity preserving the biomacromolecule close to its native state;

2) Placing the protective entity comprising the biomacromolecule in proximity of an analytical zone; and 3) Releasing the biomacromolecule from the protective entity into the analytical zone.

In a further embodiment the invention concerns a method for analyzing a biomacromolecule comprising:

1) Providing a protective entity comprising a biomacromolecule, said protective entity preserving the biomacromolecule close to its native state;

2) Placing the protective entity comprising the biomacromolecule in proximity of an analytical zone;

3) Releasing the biomacromolecule from the protective entity;

4) Passing the biomacromolecule into the analytical zone; and

5) Detecting at least one feature of the biomacromolecule in the analytical zone.

In some embodiments, the invention concerns a method for delivering genomic DNA for analysis comprising:

1) Providing a protective entity comprising genomic DNA, said protective entity preserving the genomic DNA close to its native length 2) Placing the protective entity comprising the genomic DNA in proximity of an analytical zone 3) Releasing the genomic DNA from the protective entity 4) Passing the genomic DNA into the analytical zone In a further embodiments the invention comprises:

1) Providing an agarose gel comprising genomic DNA, said agarose gel preserving a substantial fraction of the genomic DNA to greater than 200 Kb in length;

2) Placing the agarose comprising the genomic DNA in proximity of a surface where the DNA is to be analyzed;

3) Releasing the genomic DNA from the agarose onto the surface; and

4) Elongating the DNA in one orientation.

In some embodiments, the invention concerns a method for preparing a biomacromolecule for analysis where rare target molecules are to be detected, comprising:

1) Extracting biomacromolecules in a vessel that contains an environment that minimizes mechanical stress and/or contains a high concentration of divalent cations/Gallic Acid and in an area of the vessel that is passivated (e.g., via a lipid layer) to minimize sequestration of macromolecules;

2) Immobilizing the extracted biomacromolecules on a surface within the vessel; and 3) Analyzing/sequencing the extracted and immobilized biomacromolecules according to the methods of this invention.

In some embodiments, the genomic DNA length is >50 Kb, 100 Kb, 200 Kb, 400 Kb, 800 Kb. In some embodiments, a certain fraction of the DNA is greater than approximately 1 Mb in length. In some embodiments, some molecules of DNA are greater than 5 Mb in length. In some embodiments, the target molecules of DNA are close to a substantial length of a chromosome. In some embodiments, the whole length of a chromosome, telomere to telomere is preserved and analyzed.

In some embodiments, the agarose gel is in the form of an agarose bead. In some embodiments, the DNA is encapsulated in a droplet. In some embodiments, the DNA substantially remains as chromatin. In some embodiments, the DNA remains as a chromosome. In some embodiments, the chromosome is a chromosome at the metaphase stage of the cell cycle. In some embodiments, the chromosome is a chromosome at the anaphase stage of the cell cycle.

In some embodiments, the sample comprises substantially the entire DNA content of a single cell. In some embodiments, the sample comprises substantially the entire RNA content of a single cell. In some embodiments, the sample comprises substantially the entire protein/polypeptide/peptide content of a single cell. In some embodiments, the sample comprises substantially the entire DNA and RNA content of a single cell. In some embodiments, the sample comprises substantially the entire DNA, RNA, Protein content of a single cell.

In some embodiments, the sample comprises substantially the entire cytoplasmic content of a single cell. In some embodiments, the sample comprises substantially the entire nuclear content of a single cell. In some embodiments, the sample comprises the entire cytoplasmic content of RNA and the entire nuclear content of DNA. In some embodiments, the sample comprises substantially the entire membrane content of protein.

In some aspects the method comprises:

1. A method for delivering a biomacromolecule to an analytical zone:

a. Providing a protective entity comprising a biomacromolecule, said protective entity preserving the biomacromolecule close to its native state;

b. Placing the protective entity comprising the biomacromolecule in proximity of an analytical zone;

c. Releasing the biomacromolecule from the protective entity;

d. Passing the biomacromolecule into the analytical zone; and e. Being able to detect at least one feature of the biomacromolecule in the analytical zone.

2. A method according to 1 where the protective entity is juxtaposed with the analytical zone.

3. A method according to 1 where the protective entity comprises the natural environ of the biomacromolecule.

4. A method according to 3 where the protective entity comprises chromosome, chromatid or chromatin.

5. A method according to 3 where the protective entity comprises a cell, nuclei, organelle, vesicle, exosome, capsid.

6. A method according to 1 where the protective entity comprises a condensed, folded or other rendering of the biomacromolecule in a compact structure.

7. A method according to 1 where the protective entity is a droplet, bead or gel.

8. A method according to 5 where the protective entity is a gel bead, gel plug, gel slab, gel capillary or other gel formation.

9. A method according to 8 where the gel is agarose.

10. A method according to previous aspects 1-9 where the biomacromolecule is encased within or wrapped with the protective entity prior to step 1 of aspect 1.

11. A method according to 8 where the biomacromolecule is released from the protective entity via application of an electrical field.

11a. A method where the biomacromolecule is released into a microfluidic structure.

11b. A method according to 11 a where the microfluidic structure is passivated.

11c. A method according to 11b where the passivation is via lipid coating.

12. A method according to 1 where the analytical zone is a nanopore, nanogap or other nano-scale detection station/reading head.

12b. A method according to 12 where nanopores sequencing is done on individual polynucleotides after they are released close to the analytical zone.

13. A method according to 1 where the analytical zone is a surface.

14. A method according to 12 where the surface comprises agents that can bind to one or more sites on the biomacromolecule.

15. A method according to 1 where the analytical zone is a nanochannel, nanogroove, nanopit or nanoslit.

16. A method according to 1 where the biomacromolecule is released into a structure that is in fluidic contact with the analytical zone.

17. A method according to 15 where the biomacromolecule is passed through a microfluidic channel before it reaches the analytical zone.

18. A method according to 1 where the biomacromolecule is released via electrophoresis, or electrosmosis.

19. A method according to 1 where the rate of passing into the analytical zone is controlled by molecule ratchet, molecular motor, hydrodynamic drag, electrical field, optical tweezers, magnetic tweezers.

20. A method according to 1 where the biomacromolecule is released by an agent that disrupts the protective entity.

21. A method according to 20 where the disruptive agent is a enzyme, detergent, acid solution or alkali solution.

22. A method according to 21 where the enzyme is a protease.

23. A method according to 20 where the disruptive agent comprises sonication, electrical charge switch, temperature change, heat shock, cold shock, defrosting etc.

24. A method according to 1 where protection is from shear forces.

25. A method according to 1 where protection is from nucleases, proteases.

26. A method according to claim 1 where step e comprises detecting two or more features at two or more locations on the biomacromolecule.

27. A method according to 1 where method where the biomacromolecule is a polymer.

28. A method according to claim 27 where the preservation of close to the native state comprises preservation of the polymer in substantially long lengths.

29. A method according to 28 where the polymer is a DNA polymer and the length is preserved over 40 Kb, 100 Kb, 200 Kb, 500 Kb, 1 Mb, 5 Mb, 50 Mb, 250 Mb.

30. A method according to 1 where the biomacromolecule is released by flow of reagent perpendicular (crossflow) to the direction of movement of the biomacromolecule.

31. A method according to 30 where the crossflow comprises RNAse, protease, alkali, detergent.

32. A method according to 1 the biomacromolecule traverses an array of pillars or posts subsequent to its release and before its entry into the analytical zone.

33. A method according to 1 to where the protective entity comprises paraffin.

34. A method according to 33 where the protected entity comprises a formalin fixed paraffin embedded biomacromolecule.

35. A method according to 1 where the biomacromolecule is exposed to a solution that preserves its integrity and repairs damage.

36. A method according to 35 where the biomacromolecule is DNA and the solution contains repair enzymes (e.g. PCR repair mix by NEB).

35. A method according to aspects 1-36 where release of the biomacromolecule is the process of extracting the biomacromolecule from its natural encasing (for example, the extraction of DNA from a cell).

36. A method according to 1 where the steps are carried out without use of micro-pipetting, vortexing and/or centrifugation once the biomacromolecule is released from the protective entity.

Alternative Embodiments

In one alternative embodiment, the probes bind stably but their transience is controlled by an external trigger that switches the environment to off mode. Such a trigger is heat, pH, electric field or reagent exchange which cause the probes to unbind. Then the environment is switched back to on mode, allowing probes to bind again. In some embodiments, when the binding does not saturate all sites in the first round of binding, the second round may take up other sites than the first. These cycles can be carried out multiple times at a controllable rate.

Alternative Super-Resolution and Single Molecule Localization Methods

In alternative embodiments the probe is bound relatively stably, but there are a number of approaches for resolving optical signals that are closer than the diffraction limit. Firstly, where the optical characteristic of an emitting label such as quantum dot or a dye are known, it is possible to use the point spread function of the entity to resolve two closely spaced signals along the polynucleotide. This is easier to do when two closely spaced signals are emissions at different wavelength. Secondly, it is possible to resolve the signals by allowing them to photobleach, a stochastic process (J Biomed Opt. 2012 December; 17(12):126008). Thirdly, there are a number of hardware approaches that have been described and are commercially available; these include scanning optical microscopy, 4Pi, STED, and SIM. In the case of STED, specific compatible sets of fluorophores must be used. A number of molecular approaches have also been described, based on closely spaced signals being temporally separated and this includes STORM (Sub-diffraction-limit imaging by stochastic optical reconstruction microscopy (STORM) M. J. Rust, M. Bates, X. Zhuang Nature Methods 3: 793-795 (2006); in this case specific sets of compatible fluorophores must be used.

A single molecule localization method, DNA PAINT (Jungmann et al Nano Lett. 2010, 10: 4756) can also be used in various embodiments of this invention. In the case of DNA PAINT, each binding probe is labeled with an oligo tag to which a complementary oligo anti-tag transiently binds. Each of the binding probes is associated with binding partner pairs of different sequence complements. In order to be differentiated the anti-tag associated with each of the binding probes is distinguishable from the other. The element that makes them distinguishable can be a different wavelength emitting label (e.g., Atto 488, Cy3B, Alexa 594 and Atto 655/647N), labels with different lifetime or it can be that the different anti-tags are designed to have different on/off binding kinetics.

DNA PAINT can be used to precisely assign coordinates of localization of the signals. Localization is easier to determine when the fluorophore emitting the signal remains close to the site of incorporation, therefore the length and degree of flexibility of the linker or bridge joining the wavelength emitting moiety (e.g., fluorophore) to the base must be constrained, e.g., in some embodiments, a short length and a stiff linker are used.

Another alternative means to obtain a super-resolution image is by expansion (e.g., as described by Chen, Tillberg, and Boyden Science 30 Jan. 2015: Vol. 347 no. 6221 pp. 543-548). Here the elongated polynucleotide is rendered in a gel which is then expanded thereby stretching out the biological material. Specific labels associated with the polynucleotide are covalently anchored to the swellable polymer network. Upon swelling even if the polynucleotide is broken (or no longer has a contiguous polyphosphate backbone), the order of fragments is retained and the invention can still be practiced.

Such super-resolution approach does not require transient binding. Hence, the probe binding of each cycle can be done by dipping the surface (e.g., cover glass) into different troughs carrying different oligos or oligo sets of the repertoire.

Benefits of Transient Binding

The transient binding approach method has the advantage that the photobleaching of fluorophores that bind is not of concern because they are always replaced by fresh fluorophores. Therefore the choice of fluorophore, the provision of antifade, redox system is not that important and a simpler optical system can be constructed, e.g., without an f-stop to prevent illumination of molecules that are not in the field of view of the camera, because illumination only bleaches labels that transiently come into the evanescent wave and these bleached labels are continuously replaced by molecules from the bulk solution.

The advantage of the on-off binding is simply that it avoids the dark state or photobleaching problem of probes labeled with single dye molecules. If a particular probe molecule is bleached or in a dark state the binding event of that probe will not be detected. Nevertheless, the targeted position is likely to be detected by the next binding event to that location.

In some embodiments, the advantage of the on-off binding is so that multiple measurements can be made to increase confidence in the detection. For example, in some cases due to the typical stochastic nature of molecular processes a probe may bind to an incorrect location, but such an outlier can be discarded, and only those binding events that can be corroborated by multiple detected interactions are accepted as valid detection events for the purpose of sequence determination.

In some embodiments of the invention the advantage of the transient binding approach is very important for how the sequence along the elongated polynucleotide is determined. This advantage is the fact that transient binding means that not all of the probe locations that should bind are bound at the same time. This allows one to detect binding events at sites that are closer than the diffraction limit of light. For example if the sequence AAGCTT is repeated after 60 bases, the approximate 20 nm distance (when the target is elongated and straightened to Watson-Crick distances=0.34 nm) would not normally be distinguishable by optical imaging. However, if the probes to the two sites bind at different times during imaging, they can be individually detected. This allows one to carry out super-resolution imaging of the binding events by a method known as Points Accumulation of Nanoscale Topograpy (PAINT). Algorithms (e.g ThunderSTORM) can be used which allow nanometric or sub-nanometric localization of the signals. With this one can determine the precise location and hence the precise order of binding of probes. Nanometric precision is particularly important for resolving repeats and determining their number.

An advantage of the approach over the droplet based partitioning and barcoding approach developed by 10× Inc. is that the genome structure and haplotype information can be obtained by direct visualization of molecules not by inference or by computational reconstruction. A unique advantage of the method is that when conducted efficiently the genome from a single cell can be sequenced and haplotypes therein resolved. Even when the method is not efficient, much fewer copies of the genome are needed for de novo reconstruction of the genome, than needed by approaches that require partitioning and barcoding of molecules. Also, much fewer processing steps are needed as well as less overall reagent use. Furthermore, because the method can work on genomic DNA without amplification, it does not suffer from amplification bias and error and epigenomic marks are preserved and can be detected orthogonally to the acquisition of sequence. Alkylation of carbon-5 (C5) yields several cytosine variants in mammals: C5-methylcytosine (5-mC), C5-hydroxymethylcytosine (5-hmC), C5-formylcytosine, and C5-carboxylcytosine. Eukaryotic and prokaryotic organisms also methylate adenine to N6-methyladenine (6-mA). In prokaryotes, N4-methylcytosine is also prevalent. Antibodies are available or can be raised against each of these modifications. Affimers, Nanobodies or Aptamers that target the modifications are particularly relevant due to the possibility of a smaller footprint. In addition other, naturally occurring DNA binding proteins, e.g., methyl proteins (MBD1, MBD2 etc) can be used.

Accordingly, in various aspects and embodiments, the invention provides methods of sequencing a single, elongated target polynucleotide molecule with the inclusion of epigenomic information.

In various aspects and embodiments, the methods can be used for phased sequencing where haplotypes are resolved and may include the steps of sequencing a first target polynucleotide spanning a haplotypic branch of a diploid genome using the method of the preceding paragraph; sequencing a second target polynucleotide spanning the haplotypic branch of the diploid genome using the method of the preceding paragraph, where the first and second target polynucleotides are from different homologous chromosomes; thereby determining the haplotypes (linked alleles) on the first and second target polynucleotides.

The advantage of the present invention is that it enables long reads to be obtained without actually carrying out costly, and time consuming individual long reads, by stitching together contiguous or overlapping sequence information obtained by the binding of short oligos instead. A plurality of short, 3, 4, 5 or 6 base bits of sequence information are simultaneously obtained along the length of a single polynucleotide molecule, and hence they are all connected, and when the polynucleotide has been saturated with on-off binding oligos their nanometric position, resolution and order reveal the sequence of the whole molecule. The sequencing of a polynucleotide takes less time than current methods as multiple bits of sequence information are being obtained simultaneously rather than a single long read being obtained by a SbS reaction from one location in the molecule to another (e.g., PacBio sequencing).

Another major advantage of the invention is that it enables structural variation of all types to be detected, small or large, including balanced copy number variation and inversions, which are challenging for microarray based technologies, the current dominant approach and at a resolution and scale that can't be approached by microarray, cytogenetic or other current sequencing methods.

Moreover, the method allows sequencing through repetitive regions of the genome. For conventional sequencing the problem with reads through such parts of the genome is that firstly, such regions are not well represented in reference genomes and technologies such as Illumina, Ion Torrent, Helicos/SeqLL, and Complete Genomics typically deal with large genomes by making alignments to a reference, not by de novo assembly. Secondly, when the reads do not span the whole of the repetitive region, it is hard to assemble the region through shorter reads across the region. This is because it can be hard to determine which of multiple alignments that are possible between the repetitive regions on one molecule with the repetitive region on another molecule are correct. A false alignment can lead to shortening or lengthening of the repeat region in the assembly. In the sequencing methods of the invention, when there is complete or near complete coverage of a single molecule by multiple reads either taken simultaneously or one set after the other, an assembly can be constructed that spans the whole of the repetitive region (when the polynucleotide itself spans the whole of the repetitive region). The methods of this invention can be applied to polynucleotides that are long enough to span repetitive regions. Polynucleotides between 1 and 10 Mb are enough to span most of the repetitive regions in the genome.

Impact on Various Sequencing Metrics

Impact on Speed—The approach is simple, with no lengthy sample processing steps or cycle times. There are no enzymatic steps, only hybridization, which there are multiple means to speed up.

Impact on Cost—The approach is extremely low cost, the only reagents needed are extremely small amounts of oligos e.g., 0.5-3 nM of oligo probe.

Impact on read-length—The read-length is potentially as long as a molecule of

DNA of any length (including whole chromosomes)

Impact on Accuracy—There is potential for the proposed technology to be the highest accuracy sequencing technology. Apart from a few outliers short oligos are exquisitely specific, as a mismatch of just one base leads to a large drop in stability. Given the right binding conditions the perfect match can be discriminated from mismatches of one or more bases in the majority of instances; this ability can be enhanced by repetitive interrogation of each sequence site. Moreover, the method can utilize mismatch information in the determination of sequence. Furthermore, the simultaneous sequence acquisition from both strands of a duplex increases accuracy. The accuracy level of the technology will be sufficient to detect rare mutations.

Impact on Sensitivity—As the method is a single molecule technology it has the potential to be exquisitely sensitive. As there are no inefficient preparative steps such as ligation, molecules will not be lost. As extraction can be integrated close to the site of sequencing, molecules are not lost by sticking to containers and the internal walls of the microfluidic device itself can be passivated to prevent sequestration of molecules. Also substantially all the molecules that are released from a cell can be accessed within the flow channel. Moreover the method has the potential to obtain a full contiguous read from just one molecule. This is relevant to sequencing from a single cell, where the method will allow unprecedented coverage and low allelic dropout.

Sequencing Applications and Uses

In some embodiments, the invention comprises uses of sequence information that is obtained from a single elongated polynucleotide directly, where the context of the sequence reads obtained within a long polynucleotide (from ~100 Kb to a whole chromosome) are preserved. The context information can just comprise the information that the short read originates from a particular polynucleotide. The context can also extend to knowing the precise or approximate location of the sequencing read within the polynucleotide.

Moreover, even longer-range information than the length of an individual polynucleotide (if it is of sub-chromosomal length) can be obtained when the polynucleotide is part of a plurality of polynucleotides, of similar or different lengths that stem from the same chromosome (or other type of complete polynucleotide, e.g., an RNA transcript). In some embodiments, sequence reads from each of the polynucleotides in the plurality are obtained independently of reads from other polynucleotides that comprise the plurality of polynucleotides. In this case, the sequencing data obtained from the plurality of polynucleotides is used to reconstruct or assemble the polynucleotide into the native polynucleotide sequence from which the polynucleotides originally emanated. This can be the case when sequencing is done on genomic DNA extracted from many cells of a given type, and it is expected that DNA from many of the same chromosome homologs are present. For example, in cell extraction from one million cells, (e.g., a lymphoblastoid cell line from a CEPH panel, e.g., NA12878) one million chromosome homologs derived from the mother and one million chromosome homologs derived from the father would be expected in the extracted DNA.

In other embodiments the context of the short reads is preserved by sequencing an isolated long (~50-200 Kb) single polynucleotide. In some embodiments, the context of the short reads are preserved by sequencing along an elongated polynucleotide. In some embodiments, many copies of single polynucleotide that cover the same segment (with or without haplotype resolution), are used as targets to obtain a plurality of sequence reads per target, and the sequence reads are used to reconstruct a longer range sequence of the polynucleotide segment than can be represented by one of the single polynucleotides. Hence a de novo assembly of a genome, or large parts of the genome can be reconstructed. In order to make a haplotype resolved de novo assembly, when a sufficient fraction of a polynucleotide is covered with sequencing reads, it is possible to differentiate overlapping segments as belonging to a segment from one homologous chromosome or another (e.g., based on SNPs or structural variants found therein). The methods of the invention can be used to determine or resolve the following features that can be found in a genome that are difficult to obtain by current sequencing technologies.

Inversions

The orientation of a series of sequence reads along the polynucleotide will report on whether an inversion event has occurred. One or more reads in the opposite orientation to other reads compared to the reference, indicates an inversion.

Translocations

The presence of one or more reads that is not expected in the context of other reads in its vicinity indicates a rearrangement or translocation compared to reference. The location of the read in the reference indicates which part of the genome have shifted to another. In some cases the read in its new location is a duplication rather than a translocation.

Copy Number Variations

The absence or repetition of specific reads indicates that a deletion or amplification, respectively has occurred. The methods of this invention can particularly be applied in cases where there are multiple and/or complex rearrangements in a polynucleotide. Because the methods of the invention are based on analysing single polynucleotides, the structural variants described above can be resolved down to a rare occurrence in small numbers of cells for example, just 1% of cells from a population.

Duplicons

Segmental duplications or duplicons are persistent in the genome and seed a lot of the structural variation in individual genomes including somatic mutations. The segmental duplicons, may exist in distal parts of the genome. In current next generation sequencing, it is difficult to determine which segmental duplicon a read arises from. In some embodiments, of the present invention, because reads are obtained over long molecules (e.g., 0.1-10 Megabase length range), it is usually possible to determine the genomic context of a duplicon simply by using the reads to determine which segments of the genome are flanking the particular segment of the genome corresponding to the duplicon.

Repetitive Regions

The repeated occurrence of a read or related read carrying paralogous variation can be observed by the methods of the invention (after data analysis), as multiple or very similar reads occurring at multiple locations in the genome. These multiple locations is packed close together, as in satellite DNA or they is dispersed across the genome such as pseudogenes. The methods of the inventions can be applied to the Short Tandem Repeats (STRS), Variable number of Tandem Repeats (VNTR), trinucleotide repeats etc.

Finding Breakpoints

Breakpoints of structural variants can be pinpointed by the methods of the invention. Not only does the invention show at a gross level, which two parts of the genome have fused, but the precise individual read at which the breakpoint has occurred can be seen. Not only does the read comprise a chimera of the two fused regions, all the sequences on one side of the breakpoint will correspond to one of the fused segments and the other side is the other of the fused segments. This gives high confidence in determining a breakpoint. Even in cases where the structure is complex around breakpoint, the methods of the invention can resolve the structure. In some embodiments, the precise chromosomal breakpoint information is used in understanding of a disease mechanism, is used in detecting the occurrence of a specific translocation and is used diagnosing a disease.

Haplotypes

In some embodiments, the resolution of haplotypes enables improved genetic studies to be conducted. In other embodiments the resolution of haplotypes enables better tissue typing to be conducted. In some embodiments, the resolution of haplotypes or the detection of a particular haplotype enables a diagnosis to be made.

Compared to other inferential or partition and tagging haplotyping/phasing approaches, the present invention is not based on computer reconstruction of a probable haplotype. The visual nature of the information obtained by the invention, actually physically or visually shows a particular haplotype.

Hence, reads and assemblies that are obtained from the embodiments of this invention can be classed as being haplotype-specific. The only case where haplotype-specific information is not necessarily easily obtained over a long range is when assembly is intermittent; the location of the reads is provided nonetheless. Even here, if multiple polynucleotides cover the same segment of the genome the haplotype can be determined computationally.

Identification of Organisms

One embodiment of the invention is to identify the different individual organisms present in a mixed sample such as metagenomic sample, based on the sequence, epi- and structural information provided by the invention. As sequencing methods of this invention can sequence a substantial fraction of a genome from just one copy of the genome, it can sequence a diverse metagenomic mixture of organisms. Furthermore just the map of a single molecule obtained from one or a few bases of information is sufficient to identify a microorganism.

Cell Line Identification and Validation

In some embodiments, the genomic DNA is extracted from cells in culture, stretched out and methylation and/or sequence information is extracted from the stretched molecules using the methods of the invention. This information can be used to validate the identity of the cell line and to determine its molecular phenotype and to monitor changes in its epigenome through the course of passaging or as experiments are preformed (e.g., perturbation of growth conditions).

Disease Detection

In some embodiment the invention comprises use of the methods of the invention for the early detection of cancer, diagnosis of cancer, classification of cancer, analysing the cell heterogeneity within cancer, staging the cancer, monitoring development of cancer, deciding whether to apply drug treatment, which drug or combination of drugs to use, monitoring the effect of treatment, monitoring of relapse, prognosticating outcomes. In each of these cases, either a specific "biomarker" or set of biomarkers is looked for, which comprise a particular sequence, epi- or structural variant or, just the occurrence of structural variation in general above a certain threshold level is detected. This aspect comprises:

1. Obtaining sample biomaterial from a human patient or an individual that is being screened (e.g., being screened for early signs of cancer);
2. Performing sequencing and/or epi-analysis according to the methods of the invention;
3. Looking for sequence, epi- and/or structural variation in the data, compared to a reference or compared to other body tissue from the individual/patient;
4. Assessing the amount and/or type of variation and optionally providing a score; and
5. Optionally making a clinical decision based on 4.

The same five steps can be applied to other disease cases than cancer and can be applied to animals other than humans, such as livestock, dogs and cats. The sequence data can include RNA and DNA data. In some embodiments, only sequence, only structural or only methylation or other modification information is used to make the clinical decision.

In some embodiments, step 5 can comprise deciding which fertilized egg to choose in pre-implantation diagnosis or screening. In some embodiments, FFPE curls are obtained, DNA is extracted and immobilized and the transient binding of binding agents is conducted.

Genotype to Phenotype Correlations

In some embodiments, the methods of this invention are used to make genotype to phenotype correlations by
1. Obtaining sample biomaterial (e.g., RNA or DNA) from individuals in a population, cohort or family;
2. Performing sequencing and/or epi-analysis according to the methods of the invention;
3. Looking for sequence, epi-marks and/or structural variants in the data and comparing them between cases and controls for a specific disease, phenotype or trait whilst optionally taking ethnicities, stratification of phenotypes and misclassification of phenotype into account; and
4. Determining which sequence, epi- and/or structural motifs or markers variants correlate with phenotype.

Further, the phenotype correlated sequence, epi- and/or structural variants can be selected as candidate biomarkers for the phenotype. Optionally, further studies are done to fine tune or validate the candidate biomarkers.

Detailed Description of Experimental Methods

Various aspects, embodiments, and features of the invention are presented and described in further detail below. However, the foregoing and following descriptions are illustrative and explanatory only and are not restrictive of the invention, as claimed.

In some embodiments, the methods of this invention comprise various wash steps in between the main functional elements of the process, the need for wash steps at various points will be recognized by the skilled artisan. In general the wash buffer can comprise, Phosphate Buffered Saline, 2×SSC, TE, TEN, HEPES and is supplemented with small amounts of Tween 20, Triton X, Sarkosyl, and/or SDS etc. Typically 2-3 washes can be inserted in between functional steps. For example, in some cases wash steps will be performed when one oligo is exchanged for another.

It should be understood that in most cases what is described for a particular oligo length can also be the case for other oligo lengths. It should also be understood that where terms such as identifying, analyzing, measuring are used they are not mental acts but rather acts run on instrumentation, such instrumentation comprising a detector and automated fluidics used in combination with a computer algorithm.

Extracting and Elongating Megabase Range Genomic DNA on a Surface

A number of methods exist for extracting and stretching High Molecular weight (HMW) or long length DNA. See e.g., Allemand et al Biophysical Journal 73:2064-2070 1997; Michalet et al Science 277:1518-1523 (1999)). In some embodiments, methods adapted from Kaykov et al (Scientific Reports 6:19636 2016) can be used to extract and elongate DNA with average lengths in the mega-base range. In such embodiments, genomic DNA is extracted from cells (1×104 to 105 per block) in agarose blocks (e.g., using Biorad or Genomic Vision protocol or as described by Kaykov et al) using Proteinase K for 1 hour, the washing step includes 100 mM NaCl, the agarose block is melted and digested in a trough using Beta-Agarase (NEB, USA) for an extended period (e.g., 16 hrs) at 42° C. without mixing and then brought to room temperature. DNA is combed in a buffer containing 50 mM MES 100 mM of NaCl at pH 6. A device that can pull a substrate (e.g., coverslip) out of a trough (e.g., as described by Kaykov et al) is used to generate smooth, low friction z movement with minimal vibration. A combing speed of 900?m/second is used to uniformly stretched DNA molecules with minimum breaking. Around 50% of the molecules are longer than 1 Mb with an average of 2 Mb in length and 5% over 4 MB.

Several other methods for stretching on a surface can be used (e.g., as described in ACS Nano. 2015 Jan. 27; 9(1): 809-16). Alternatively, elongation on a surface can be conducted in a flow cell including using the approach described by Petit and Carbeck (Nano. Lett. 3: 1141-1146 (2003)), which shows that for combing in a 20-100 uM channel a rate of fluid withdrawal of 4-5 μm/s yields a flat air-water interface which provides well aligned unidirectional polynucleotides. In addition to fluidic approaches, polynucleotides can be stretched by using an electric field (e.g., as described in Giess et al. Nature Biotechnology 26, 317-325 (2008). Several approaches are available for elongating polynucleotides when they are not attached to a surface (e.g., as described in Frietag et al Biomicrofluidics. 9(4):044114 (2015); and Marie et al. Proc Natl Acad Sci USA. 110: 4893-8 (2013)).

As an alternative to using DNA in a gel plug, chromosomes suitable for loading onto the chip can be prepared by the poly amine method as described by Cram et al. (L. S. Cram, C. S. Bell and J. J. Fawcett, Methods Cell Sci., 2002, 24, 27-35) and pipetted directly into the device. The proteins binding to DNA in a chromosome can be digested using a protease to release substantially naked DNA.

Preserving the Integrity of a Biomacromolecule Prior to Analysis

Much of the disruption occurs in the process of extracting the biomolecule from cells and tissues and the subsequent handling of the biomolecule before it can be analysed. In the case of DNA, aspects of its handling that lead to its loss of integrity includes pipetting, vortexing, freeze-thawing and excessive heating. Mechanical stress can be minimized (ChemBioChem, 11:340-343 (2010). In addition high concentrations of divalent cations, EDTA, EGTA or Gallic Acid (and its analogues and derivatives) inhibit degradation by nucleases. In some embodiments, a 2:1 ratio of sample to divalent cation weight is sufficient to inhibit nucleases even in samples such as stool, where there are extreme levels of nucleases.

Extracting and Isolating Nucleic Acids from a Single Cell

A number of different approaches area available for extracting biopolymers from single cells or nuclei which can be used for extracting biopolymers for the purpose of this invention. A number of suitable methods are reviewed in Kim et al. Integr Biol 2009 vol. 1 (10) pp. 574-86. Cells can be treated with KCL to remove cell membranes. Cells can be burst by adding a hypotonic solution. A variety of different chemical and physical lysis methods can be implemented as known in the art and previously tested in microfluidics.

Traps for single cells can be designed in microfluidic structures that hold the cells while the nucleic acid content is released. It includes using the device designs of WO/2012/ 056192, WO/2012/055415 * * * but instead of extracting DNA and stretching in nanochannels, in the present invention the cover-glass or foil that is used to seal the micro/ nanofluidic structures is coated with polyvinyl silane (or similarly disposed) to enable molecular combing, by movement of fluids as described by Petit et al. Nano Letters 3:1141-1146 (2003). The gentle conditions inside the fluidic chip enables the extracted DNA to be preserved in long lengths.

In some embodiments, the methods of the invention includes adaptation of the methods described in Strijp et al. Sci Rep. 7:11030 (2017). Prior to stretching, the nuclear and extra-nuclear constituents of a single cell are separately extracted by providing at least one cell to the feeding channel of a microfluidic device, capturing the at least one cell in the at least one trapping structure, lysing the cell captured in the at least one trapping structure without affecting integrity of the cell's nucleus by supplying a first lysis buffer to the cell; releasing the extra-nuclear constituents of the cell into a flow cell where the released RNA is immobilized; lysing the cell's nucleus by supplying a second lysis buffer to the nucleus; releasing the constituents of the cell's nucleus (e.g., genomic DNA) into a flow cell were it is immobilized. The extra- and intra-cellular components are immobilized at different locations of the same flow cell or in different flow cells within the device.

Adapters for Capture

In addition to capturing/immobilizing non-end-modified polynucleotides, In some embodiments, (especially those where short DNA is analyzed) the ends of DNA are adapted for interaction with capture molecules on a surface/matrix. This includes tailing using terminal transferase, e.g., tailing with poly A and binding to oligo d(T) capture probes on the surface or matrix. The olio d(T) capture probes is between 20 and 50 nt in length. It also includes using ligation or tagmentation to introduce adaptors for Illumina sequencing, onto the polynucleotide and capturing with complementary sequences on the surface or matrix. This enables users to use the well-established Illumina protocols to prepare the samples, which are then captured and sequenced by the methods of this invention. Preferably, polynucleotides are captured before amplification, which has the tendency to introduce error and bias.

In some embodiments, short (~<300 nt) such as cell-free DNA or microRNA or relatively short (<10,000 nt) polynucleotides such as mRNA are immobilized randomly on a surface, by capturing a modified or non-modified end using an appropriate capture molecule. Native mRNA carrying poly A tail can be captured on lawn of oligo d(T) probes on a surface. The sequencing is then carried out "vertically" from the surface. In some embodiments, short or relatively short polynucleotides make multiple interactions with the surface and sequencing is carried out "horizontally"; this allows splicing isoformic organization to be resolved, for example in some isoforms the location of exons that is repeated or shuffled can be delineated.

In some embodiments, the polynucleotides are captured on an ordered array of capture probes. The ordered array is a spatially addressable array. The ordered array may take the form of a molecular nanostructured array such as can be formed using the DNA Origami (Rothemund, Science) approach. The ordered array may take the form of a 2D molecular lattice such as can be formed by the self-assembly of DNA (Woo and Rothemund, Nature Communications, 5: 4889). The ordered array enables efficient sub-diffraction packing of molecules allowing higher density of molecules (high density array) per field of view; the single molecule localization methods of the invention allow the molecules within the high density array (e.g., 40 nm point to point distance) to be resolved.

Polynucleotide Repair

A polynucleotide can become damaged during extraction, storage or preparation. Nicks and adducts can form in a native double stranded genomic DNA molecule. This is especially the case for when the sample polynucleotides are from FFPE material. A DNA repair solution is introduced before or after DNA is immobilized. This can be done after DNA extraction in a gel plug. Such repair solution may contain DNA endonuclease, kinases and other DNA modifying enzymes. Such repair solution may comprise polymerases and ligases. Such repair solution is the pre-PCR kit form New England Biolabs. The following references are hereby incorporated in their entirety: Karimi-Busheri et al. Nucleic Acids Res. 1998 Oct. 1; 26(19):4395-400; and Kunkel et al. (1981) Proc. Natl Acad Sci. USA, 78, 6734-6738.

Staining the Polynucleotide

Optionally, for some embodiments, to trace out the backbone of a polynucleotide DNA stains and other polynucleotide binding reagents can be used. Intercalating dyes, major groove binders, labeled non-specific DNA binding proteins cationic conjugated polymers can be bound to the DNA. Intercalating dyes can be used at various nucleobase to dye ratios. Use of multiple intercalating dye donors at a dye to base pair ratio of about 1:5-10 leads to the labeling of DNA with dye molecules (e.g., Sybr Green 1, Sytox Green, YOYO-1) sufficient to serve as donors for nucleotide additions along the growing DNA strand. Some DNA binding reagents are able to substantially cover the polynucleotide. These DNA stains can also act as FRET Partners in homogeneous or real-time sequencing. Once an intercalating dye such a YOYO-1 is added it is helpful to keep the DNA in the dark and to add reagents such as BME to prevent DNA nicking. In some embodiments, the polynucleotide is not pre-stained but the stain is added during the binding process to denatured DNA. When the polynucleotide-oligo duplex forms, dye can intercalate and fluorescence is detected at that point, without label on the probe. In some embodiments, there is label on the probe, a FRET partner and there is a FRET interaction between the label and the intercalator dye.

In some embodiments, the binding probes can be excited via FRET donor such as an intercalator dye, which intercalates when the duplex between the binding probes form. It is possible to obtain resolution of a few nanometers (e.g., as described in Chemphyschem. 2014 Aug. 25; 15(12):2431-5).

Sequencing Along Elongated DNA Using Single Molecule Localization

The transient binding concept can be extended to various types of binding probes, as long as they are able to transiently bind under reaction conditions. Binding probes can be labelled with different flavors of labels, e.g., fluorophores with different wavelength emission.

In some embodiments, fluorescently modified DNA oligos are purchased from Biosynthesis. Streptavidin is purchased from Invitrogen (Catalog number: S-888). Bovine serum albumin (BSA), and BSA-biotin is obtained from Sigma Aldrich (Catalog Number: A8549). Glass slides and coverslips are purchased from VWR. Three buffers are used for sample preparation and imaging: Buffer A (10 mM Tris-HCl, 100 mM NaCl, 0.05% Tween-20, pH 7.5), buffer B (5 mM Tris-HCl, 10 mM MgCl2, 1 mM EDTA, 0.05% Tween-20, pH 8), and buffer C (1×Phosphate Buffered Saline, 500 mM NaCl, pH 8).

In some embodiments, fluorescence imaging is carried out on an inverted Nikon Eclipse Ti microscope (Nikon Instruments) with the Perfect Focus System, applying an objective-type TIRF configuration using a Nikon TIRF illuminator with an oil-immersion objective (CFI Apo TIRF 100×, NA 1.49, Oil). For 2D imaging an additional 1.5 magnification is used to obtain a final magnification of ?150-fold, corresponding to a pixel size of 107 nm. Three lasers are used for excitation: 488 nm (200 mW, Coherent Sapphire), 561 nm (200 mW, Coherent Sapphire) and 647 nm (300 mW, MBP Communications). The laser beam is passed through cleanup filters (ZT488/10, ZET561/10, and ZET640/20, Chroma Technology) and coupled into the microscope objective using a multi-band beam splitter (ZT488rdc/ZT561rdc/ZT640rdc, Chroma Technology). Fluorescence light is spectrally filtered with emission filters (ET525/50m, ET600/50m, and ET700/75m, Chroma Technology) and imaged on an EMCCD camera (iXon X3 DU-897, Andor Technologies).

In some embodiments, for sample preparation, a coverslip (No. 1.5, 18×18 mm2, ?0.17 mm thick) and a glass slide (3×1 inch2, 1 mm thick) are sandwiched together by two strips of double-sided tape to form a flow chamber with inner volume of ~20 μL. First, 20 μL of biotin-labeled bovine albumin (1 mg/ml, dissolved in buffer A) is flown into the chamber and incubated for 2 min. The chamber is then washed using 40 μL of buffer A. 20 μL of streptavidin (0.5 mg/ml, dissolved in buffer A) is then flown through the chamber and allowed to bind for 2 min. After washing with 40 μL of buffer A and subsequently with 40 μL of buffer B, 20 μL of biotin-labeled DNA oligo template and primer (~300 pM monomer concentration) and DNA origami drift markers (~100 pM) in buffer B are finally flown into the chamber and incubated for 5 min.

Ideally the temperature and oligo sequence is chosen so that a salt concentration suitable for the incorporation can be implemented. The CCD readout bandwidth is set to 1 MHz at 16 bit and 5.1 pre-amp gain. Imaging is performed using TIR illumination with an excitation intensity of 294 W/cm2 at 561 nm.

Faster CMOS cameras are becoming available that will enable faster imaging, for example the Andor Zyla Plus allows up to 398 fps over 512×1024 with just a USB 3.0 connection, and faster over regions of interest (ROI) or a CameraLink connection. Therefore, operating with shorter docking/imager strands or at a higher temperature or lower salt concentration it is possible to gather enough information for the required resolution in short time periods; for this the laser power is preferably high, e.g., 500 mW; Camera Quantum Yield is preferably high, e.g., ~80% and the dye brightness is preferably high. With this the acquisition time required can be reduced to a few seconds. But this can give a resolution gain of >10fold over diffraction limit methods.

In one embodiment of the invention a novel method of imaging is implemented, using time-delayed integration with a CCD or CMOS camera, where the sample stage is translated in synchrony with the camera read-out so that the temporal resolution is spread over many pixels. This speeds up the image acquisition as there is no delay in moving from one location on the surface to another. What results is an imaging strip, where say the first 1000 pixels in a column represent 10 seconds of imaging of one location and the next 1000 pixels represent imaging of 10 seconds of the next location. The method described in Appl Opt. 54:8632-6 (2015) can also be adapted.

When light scattering nanoparticles (e.g., gold nanoparticles) or semiconductor nanocrystals are used there is a substantial further step-up in speed, because of the brighter, near non-exhaustive optical response of these particles. Again, the camera frame rate and imager on/off rate need to be tailored to get maximum speed enhancement when using such nanoparticle labels.

An of the transient binding approach is there is little effect of photobleaching or dark states, and sophisticated field stops or Powell lenses are not needed to limit illumination. In addition, the effects of non-specific binding to the surface are mitigated by such non-persistence of probe binding to non-specific sites is not persistent and once one imager has occupied a non-specific (i.e. not on the target docking) binding site it can get bleached but remains in place blocking further binding to that location. Typically, the majority of the non-specific binding sites, which prevent resolution of the imager binding to the target polynucleotide, are occupied and bleached within the early phase of imaging, leaving the on/off binding to of the imager to the polynucleotide site to be easily observed thereafter. Hence in one embodiment, high laser power is used to bleach probes that initially take up on-specific binding sites, optionally images are not taken during this phase, and then the laser power is optionally reduced and imaging is started to capture the on-off binding to the polynucleotide. After the initial non-specific binding, further non-specific binding is less frequent (because probes which have bleached can remain stuck to the non-specific binding sites) and can be computationally filtered out by applying a threshold, for example to be considered as specific binding to the docking site, the binding to the same location must be persistent, i.e. should occur at the same site at least 5 times or more preferably at least 10 times. Typically around 20 specific binding events to the docking site are detected.

Another means to filter out binding that is non-specific for our purpose, is that the signals must correlate with the linear strand stretched on the surface which can be done by staining the linear strand or by tracing a line through other persistent binding sites. Signals that do not fall along a line, whether they are persistent or not can be discarded. Similarly, when a supramolecular lattice is used binding events that do not correlate with the structure of the lattice can be discarded.

Isolating Single Cells on a Surface and Extracting Both DNA and RNA

Surfaces with positive charges such as poly(L)lysine (PLL) (e.g., as available from Microsurfaces Inc. or coated in house) are known to be able to bind to cell membranes. A height of flow channel of low height (<30 micron) will be used so that there is increased chance for the cells to collide with the surface; this can be enhanced by using a herringbone pattern in the flow cell ceiling, which will introduce turbulent flow. The cell attachment does not need to be efficient as cells need to seed at low density onto the surface, to ensure that there is sufficient space between cells to keep the RNA and DNA extracted from each individual cell to remain spatially separated. The cells are burst using proteinase treatment so that both the cell and nuclear membrane are disrupted, so that the cellular contents spew out in the medium and are captured at the surface in the vicinity of the isolated cell. For genomic DNA there is precedence for this approach from the well-established cytogenetics technique Fiber FISH. Once immobilized the DNA and RNA can be stretched. Stretching buffer will be flowed unidirectionally across the coverglass surface which leads the DNA and RNA polynucleotides to stretch out and align in the direction of fluid flow. With temperature, composition of the stretching buffer and the physical force of the flow most of the RNA secondary/tertiary structure can be removed so that RNA is available for binding to antibodies. Once the RNA is stretched, in a denatured form it is possible to switch from denaturation buffer to binding buffer.

Alternatively, the RNA is extracted and immobilized first by disrupting the cell membrane and inducing flow in one direction. The nuclear membrane is disrupted next by using proteinase and flow is induced in the opposite direction. In some embodiments, the DNA is fragmented before or after release, by using rare-cutting restriction enzymes for example (e.g., NOT1, PMME1). This fragmentation aids in disentangling DNA and allows individual strands to be isolated and combed. It is ensured that the system I set-up so that the immobilized cells are far enough apart that the RNA and DNA extracted from each cell do not co-mingle. This can be aided by inducing a liquid to gel transition before, after or during bursting of the cell.

Stretching RNA

The stretching of nucleic acids on a charged surface is affected by the solution cationic concentration. At low salt concentrations, RNA which is single stranded and bears negative charges along its backbone is likely to bind to the surface randomly along its length.

One approach to this is to initially promote its globular form by using high salt, in such case the ends, particularly the poly A tail is more accessible to interaction. Once it has been bound in the globular form, a different buffer can be applied into the flow cell, which as a denaturing buffer. Alternatively, we have the option to pre-coat the PLL with oligo d(T) to capture the poly A tails of the mRNA Multiple groups have demonstrated binding of mRNA to a surface using oligo(dT) binding to the polyadenylated 3' of a mRNA (e.g., Ozsolak F, et al.) [4]. The homopolymer nature the poly A tail means that it is a region that should be relatively free from secondary structure which may otherwise obstruct capture. As poly A tails are relatively long (250-3000 nt) in higher eukaryotes long oligo d(T) capture probes can be designed so that hybridization can be done at a relatively high stringency (temperature, salt conditions) sufficient to melt a significant fraction of intramolecular base pairing in the RNA. The oligo d(T) will be tested with modifications that increase the stability of binding, and can be tested with a crosslinking modification, to fix the RNA to the capture probe after binding. After binding, transitioning the rest of the RNA structure from a globular to a linear state can be done by using denaturing conditions which are not sufficient to abrogate the capture but can disrupt intramolecular base-pairing in the RNA and by fluid flow or electrophoretic forces.

Sequencing Instrumentation and Device

The sequencing methods of this invention have common instrumentation requirements. Basically the instrument must be capable of imaging and exchanging reagents. The imaging requirement includes, one or more from the group: objective lens, relay lens, beam-splitter, mirror, filters and a camera or point detector. The camera includes a CCD or array CMOS detector. The point detector includes a Photo-multiplier Tube (PMT) or Avalanche Photodiode (APD). In some case high speed camera is used. Other optional aspects depending on the format of the method, an illumination source (e.g., lamp, LED or laser) and a means for coupling illumination on to the substrate, e.g., prism, grating, sol-gel, lens, translatable stage or translatable objective, moving the sample in relation to the imager, sample mixing/agitation, temperature control and electrical.

For the single molecule implementations of the invention the illumination is preferably via the creation of an evanescent wave, via e.g., Prism-based Total Internal Reflection, Objective-based Total Internal Reflection, Grating-based waveguide, hydrogel based waveguide or an evanescent waveguide created by bringing laser light into the edge of the substrate at a suitable angle; the waveguide may include a core layer and a first cladding layer. The illumination may alternatively comprise highly inclined and laminated optical (HILO) illumination or a light sheet. In some single molecule instruments, the effects of light scatter are mitigated by using synchronization of pulsed illumination and time-gated detection; here light scattering is gated out. In some embodiments, dark field illumination is used. In some instruments are set up for fluorescence lifetime measurements.

In some embodiments, the instrument also contains means for extraction of the polynucleotide from cells, nuclei, organelles, chromosome etc.

A suitable instrument for most embodiments of the invention is the Genome Analyzer IIx from Illumina; this instruments comprises Prism-based TIR, a 20× Dry Objective, a light scrambler, a 532 nm and 660 nm laser, an Infra-red laser based focusing system, an emission filter wheel, a Photometrix CoolSnap CCD camera, temperature control and a syringe pump-based system for reagent exchange. Modification of this instrument with a alternative camera combination can enable better single molecule sequencing. For example the sensor preferably has low electron noise, <2 e. Also the sensor have a large number of pixels. The syringe-pump based reagent exchange system can also be replaced by one based on pressure-driven flow. The system can be used with a compatible Illumina flow cell or with a custom-flow cell adapted to fit the actual or modified plumbing of the instrument.

Alternatively, a motorized Nikon Ti-E microscope coupled with a laser bed (lasers dependent on choice of labels) or the laser system and light scrambler from the genome analyzer can be used, a EM CCD camera (e.g., Hamamatsu ImageEM) or a scientific CMOS (e.g., Hamamatsu Orca FLASH) and optionally temperature control. In some embodiments, a consumer rather than scientific sensor is used. This has the potential to reduce the cost of sequencing dramatically. This is coupled with a pressure driven or syringe pump system and a specifically designed flow cell. The flow cell can be fabricated in glass or plastic, each having advantages and disadvantages. Cyclic Olefin Copolymer (COC), e.g., TOPAS, other plastics, or PDMS or in silicon or glass using microfabrication methods. Injection molding of Thermoplastics provides a low-cost router to industrial scale manufacture. In some optical configurations the thermoplastic needs to have good optical properties with minimal intrinsic fluorescence. Polymers excluding containing aromatic or conjugated systems should ideally be excluded since they are expected to have a significant intrinsic fluorescence. Zeonor 1060R, Topas 5013, PMMA-VSUVT (U.S. Pat. No. 8,057,852 B2) have been reported to have reasonable optical properties in the green and red wavelength range (e.g., for Cy3 and Cy5), with Zeonar 1060R the most favourable. Methods for covalently bonding probes to some of such surfaces are available. Methods for bonding of thermoplastics have been reported (e.g., Microfluidics and Nanofluidics, 19(4), 913-922). In some embodiments, the glass cover glass onto which the biopolymers are attached is bonded to a thermoplastic fluidic architecture. Although glass has excellent optical properties as well as several other advantages it has been hard to produce complex microfluidic devices at low cost although there are options available now (Scientific Reports 5: 13276 (2015)).

Alternatively, a manually operated flow cell can be used atop the microscope. This can be easily constructed by making a flow cell using a double-sided sticky sheet, laser cut to have channels of the appropriate dimensions and sandwiched between a coverslip and a glass slide.

From one reagent exchange cycle to another the flow cell can remain on the instrument/microscope, to registration from frames to frame. A motorized stage with linear encoders can be used to ensure when the stage is translated during imaging of a large area, the same locations are correctly revisited; Fiduciary markers can be used to ensure correct registration. Alternatively, the flow cell is removed from the instrument/microscope after each imaging round, and the incorporation reaction is done elsewhere, e.g., on a thermocycler with a flat block before it is returned to the microscope for the next round of imaging (the term imaging is used to include 2-D array or 2D scanning detectors). In this case, it is vital to have fiduciary markings such as etchings in the flow cell or surface immobilized beads within the flow cell that can be optically detected. If the polynucleotide backbone is stained (for example by YOYO-1) their fixed position distributed locations can be used to align images from one frame to the next.

In one embodiment, the illumination mechanism described in U.S. Pat. No. 7,175,811 or Ramachandran et al (Scientific Reports 3:2133) using laser or LED illumination can be coupled with an optional temperature control mechanism and reagent exchange system to carry out the methods of this invention. In some embodiments, a smartphone based imaging set up (ACS Nano 7:9147) can be coupled with an optional temperature control module and a reagent exchange system; principally the camera on the phone is used, but other aspects such as illumination and vibration capabilities of the iPhone can also be used.

Rather than using the various microscope-like components of an optical sequencing system like the GAIIx, a more integrated, monolithic device can be constructed for sequencing. Here the polynucleotide is attached and optionally elongated directly on the sensor array or on a substrate that is adjacent to the sensor array. Direct detection on a sensor array has been demonstrated for DNA hybridization to an array (Lamture et al Nucleic Acid Research 22:2121-2125 (1994)). The sensor can be time gated to reduce background fluorescence due to Rayleigh scattering which is short lived compared to the emissions from fluorescent dyes.

In one embodiment, the sensor is a CMOS detector. In some embodiments, multiple colors are detected (US20090194799). In some embodiments, the detector is a Foveon detector (e.g., U.S. Pat. No. 6,727,521). The sensor array can be an array of triple-junction diodes (U.S. Pat. No. 9,105,537). In some embodiments, the different labels on oligos or other binding reagents are coded by wavelength of emission. In some embodiments, the different labels are coded by fluorescence lifetime. In some embodiments, the different labels are coded by fluorescence polarization. In some embodiments, the different labels are coded by a combination of wavelength, fluorescence lifetime.

It is advantageous to use a single wavelength as a light source and not have to use filters, both for the simplicity of the set-up and because there is inevitably some loss of light when filters are used. In some embodiments, the different labels are coded by repetitive on-off hybridization kinetics; different binding probes with different association-dissociation constants are used. In some embodiments, the probes are coded by fluorescence intensity. The probes can be fluorescent intensity coded by having different number of non-self quenching fluors attached. The individual fluorophores typically need to be well separated in order not to quench and a rigid linker or a DNA nanostructure where they are held in place at a suitable distance is a good way to achieve this. One alternative embodiment for coding by fluorescence intensity is to use dye variants that have similar emission spectra but their quantum yield or other measureable optical character differs, for example Cy3B (558/572) is substantially brighter (Quantum yield 0.67) than Cy3 (550/570) (Quantum yield 0.15) but have similar absorption/emission spectra. A 532 nm laser can be used to excite both dyes. Other dyes that can be used include Cy3.5 (591/604) which while has an up shifted excitation and emission spectra, will nonetheless be excited by the 532 nm laser but even though both have similar quantum yields, because Cy3.5 is being excited by a sub-optimal wavelength will appear less bright in the bandpass filter designed to select emission from cy3. Atto 532 (532/553) has a quantum yield of 0.9 and would be expected to be bright as the 532 nm laser hits it at its sweet spot. Despite these expectations, the dyes to be used must be empirically tested to properly measure their performance; if dyes from the aforementioned set cannot be distinguished other dyes can be tested. Another approach to obtaining multiple codes using a single excitation wavelength is to measure the emission lifetimes of the dyes. For this a set comprising Alexa Fluor 546, Cy3B, Alexa Fluor 555 and Alexa Fluor 555 can be used as well as many other combinations. In some embodiments, the repertoire of codes can be expanded by using FRET pairs and also by measuring the polarization of emitted light. Hence, with wavelength, lifetime, polarization and my combinations of FRET pairs one can make a large repertoire of distinguishable labels. Another means for increasing the number of labels is by coding with multiple colors.

Current optical sequencing methods require an image processing step in which the sequence signals are extracted from the images. This usually involves extracting the relevant signals from each frame of the image. In one embodiment, an alternative is to capture signals from all pixels, vertically through all cycles and use an algorithm to compute the sequence. One advantage of this approach is that when the trajectory of signals is viewed vertically through the cycles, it is easy to filter out non-specific or background signals, they do not usually occur at the same location through the cycles, whereas the real incorporations do. It is also easy to determine which signals belong to a particular elongated molecule as they can be traced by a straight line through a series of pixels.

Lipid Passivation

For the creation of lipid bilayers (LBLs) on the surface of nanofluidic channels we used zwitterionic POPC (1-palmitoyl-2-oleoyl-sn-glycero-3-phosphocholine) lipids with 1% Lissamine™ rhodamine B 1,2-dihexadecanoyl-sn-glycero-3-phosphoethanolamine, triethylammonium salt (rhodamine-DHPE) lipids added to enable observation of the LBL formation with fluorescence microscopy. Prior to each coating procedure, lipid vesicles of approximately 70 nm diameter were created by extrusion (see ESI). The extruded vesicle solution was flushed through one of the microchannels of the fluidic system. Subsequently, the lipid vesicles settle down on the surface, rupture and form patches of LBL that connect within a few minutes to a continuous LBL, coating the entire microchannel. The LBL is subsequently allowed to spread spontaneously into the nanochannels while the flow of lipid vesicles is sustained in the coated microchannel to ensure a steady supply of vesicles. During the coating process a counter flow (~80 μm/s) through the nanochannels is imposed into the coated microchannel to avoid any debris or vesicles in the nanochannels. An alternative slightly quicker method was also tested involving flushing lipid vesicles from the LBL-coated microchannel through the nanochannels results in deposition and rupture of lipid vesicles inside the nanochannels. However, with this method care needs to be taken to prevent vesicles and other residues from getting deposited and potentially blocking the nanochannels.

Epi-Marking Reagents and Labelling Methods

Genomic or epigenetic modifications (Epi-Marks) on polynucleotides can be detected using the methods of the invention. The focus in this specification is on binding to methyl groups on genomic DNA, which in humans occurs in the form of 5-Methyl Cytosine and usually in the context of the CpG motif. However, the same principles can be applied other modifications such a hydroxyl methyl C as well as DNA damage of various kinds. Modifications on RNA can be similarly marked. Synthetic DNA and RNA and RNA models such as the trRNAa that contain different number of modifications of one or more types (a range of modifications are available to oligonucleotide synthesis) can be obtained from commercial vendors (e.g., IDT, Trilink). For DNA, affinity binding of antibodies against genomic methyl C (available from Diagenode and others), methyl binding protein 1 (MBD1) and a peptide fragment of MBD1 (both from Abcam) can be tested and optimized. For RNA antibodies such as those against methyladenosine (m6A) (available from Abcam) and m7G-cap (as a control) (available from SySy.com) can be tested and optimized. The efficiency of binding to DNA or RNA containing these modifications can be measured with two metrics. Firstly, the binding of affinity reagents to modified and unmodified versions of the oligonucleotide sequences as well as against both DNA and RNA versions can be tested for example using spotting and binding on filter paper. The efficiency of binding and specificity of each antibody against synthetic oligonucleotides that either contain the target modifications, contain a non-target modification or contain no modification can be established. For the anti-methyl antibodies it is preferable to denature the genomic DNA in situ.

Mitigating Effects of Local Depletion and Laminar Flow

Local depletion of probes can be addressed by ensuring there is efficient mixing or agitation of the probe solution. This can be done by using acoustic waves, by including particles in solution that produce turbulence and/or by structuring the flow cell (e.g., herringbone pattern on one or more surfaces) to produce turbulent flows. In addition, because of laminar flow in flow cells, there is typically little mixing and the solution close to the surfaces may mix very little with the bulk solution. This creates a problem in removing reagents/binding probes that are close to the surface and to bring fresh reagents/probes to the surfaces. The above turbulence creating approaches can be implemented to combat this, and/or extensive fluid flow/exchange over the surface can be conducted. One approach is that after the target molecules have been arrayed, non-fluorescent beads or spheres are attached to the surface, which give the surface landscape rough texture, to create the eddies and currents needed to more effectively mix and/or exchange fluids close to the surface.

High Speed Imaging

Single-molecule localization microscopy (SMLM) methods rely on high photon counts. High photon counts improve the precision with which the centroid of the fluorophore-generated of Gaussian pattern can be determined, but the need for high photon counts is also associated with long image acquisitions and dependence upon bright and photostable fluorophores. The speed of the process can be increased by coupling high frame detection with an increased concentration of probes. However, high concentrations of labeled probes can cause high background fluorescence which can obscure detection of the signals on the surface. This can be combatted by using a DNA stain or intercalating dye to label the duplex that is formed on the surface. The dyes does not intercalate when the target is single stranded nor does it intercalate with the single stranded probe but it does intercalate when a duplex is formed between them. In some embodiments, the probe is unlabeled and the signal that is detected is due to the intercalating dye only. In some embodiments, the probe is labeled with a label that acts as a FRET partner to the intercalating dye or DNA stain. The intercalating dye can be the donor and can couple with acceptors of different wavelengths, hence allowing the probe to be encoded with multiple fluorophores.

Additional Examples

Detecting the Location of Epi-Marks on the Polynucleotide

Optionally before (or sometimes after or during) the oligo binding process, transient binding of epigenomic binding reagents is carried out. Depending on which binding reagent is used, binding is done before or after denaturation. In some embodiments, anti-methyl C antibodies binding is done on denatured DNA whereas for methyl binding proteins, binding is done on double stranded DNA before any denaturation step.

Step 1—Transient Binding of Methyl-Binding Reagents.

After denaturation, the flow cell is flushed with PBS-washes and a Cy3B labelled anti-methyl antibody 3D3 clone (Diagenode) is added in a transitory protein binding reagent and the binding is imaged.

Alternatively, before denaturation, the flow cell is flushed with Phosphate Buffered Saline and Cy3B-labeled MBD1 is added and imaged in transitory protein binding reagent. Imaging is conducted as described above for transient oligo binding.

The transient binding buffer is an elution buffer at 2.8 pH. A typical elution buffer comprising 50 mM HEPES (pH7.9), 0.1 M NaCl, 1.5 mM MgCl2, 0.05% TritonX-10. Transient interactions can also be carried out in 0.2% SDS and 0.1% Tween-20 7 min at RT. Furthermore, transient protein interactions with DNA can be carried out in 0.1 M glycine.HCl, pH 2.5-3; this buffer effectively dissociates most protein or antibody binding interactions without permanently affecting protein structure. However, some antibodies and proteins are damaged by low pH, so eluted protein fractions are best neutralized immediately by addition of 1/10th volume of alkaline buffer such as 1 M Tris.HCl, pH 8.5 or PBS buffer.

In some embodiments, PBS is used for binding and stable, not transitory binding is detected and locations recorded.

Step 2—Stripping Away Methyl-Binding Reagents

Typically, the epi-analysis is done before sequencing, therefore optionally the methyl-binding reagents are flushed out before the polynucleotide before sequencing commences. This can be done by flowing through multiple cycles of PBS/PBST and/or high salt or elution buffer and SDS and then checking by imaging that removal has occurred. If it is evident that more than a negligible amount of binding reagent remains, harsher treatments such as the chaotrophic salt, GuCL can be flowed through to remove the remaining reagents.

Step 3—Data Correlation

After sequencing and epi-genomics data has been obtained correlations are made betwen the location of the sequencing binding locations and epi-binding location is correlated to provide the sequence context of the methylation or omic information.

Preparation of RNA

Poly A RNA is hybridized to oligo dT attached (0.1-1 uM) to the surface. The oligo dT comprises one or more psoralen residues, which allows the RNA to be crosslinked to the oligo dT. Then as the RNA is fixed in place the RNA is stretched using fluid flow, a receding meniscus or electrophoretically in a denaturing solution which helps open up ny secondary structure. Once the RNA is stretched or elongated, the oligo binding approaches of this invention are applied.

Preparation of Long ssDNA Using Rolling Circle Amplification

Double stranded DNA targets are circularized and then rolling circle amplification is carried out to produce tandem single strand copies of one of the duplex strands. The dsDNA is polished by using T4 DNA polymerase 1 (Roche) and dNTPs (Promega); T4 Polynucletide Kinase phosphorylates the 5' hydroxyl group. Stem-loops (dT:dA stem of 8-200 bases loop comprises GGTTTTTCGCCCTTT-CACGTTGGA (SEQ ID NO: 11) are then ligated to both ends of the polished DNA using T4 DNA ligase. The priming can occur from a nick or from a primer that binds within the stem-loop.

Rolling circle amplification can also be done on a circular single stranded target using a primer, e.g., 1 µL of 1 nM M13mp18 template (NEB) can be amplified in the protocol below. The protocol can also be applied th the double strandd DNA wi the stem loops attached at both ends. In this case, 10 µL of 10× reaction buffer (10×phi29 DNA Polymerase Buffer (B7020, Enzymatics, 500 mMTris-HCl, 100 mM (NH4)2SO4, 40 mM DTT, 100 mM MgCl2, pH 7.5), 2.5 µL of 100 nM primer (TCCAACGT-CAAAGGGCGAAAAACC, (SEQ ID NO: 12) IDT) and 1.6 µL of dNTP mix (Enzymatics N2050L) is brought to a volume of 48 µL in water. The mixture is incubated at 95° C. for 1 min, then 60° C. for 1 min, then brought to 4° C. The mixture is put on ice, and 2 µL of phi29 DNA polymerase (10 U/µL, Enzymatics P7020-LC-L) is added. The whole mixture is then incubated at 30° C. for 4 hr, then brought to 4° C. diluted in 450 µL of 1×PBS (pH 7.4). The recovered solution is then diluted 100× in PBS. Before sequencing, the stored solution is added to a surface containing a complementary sequence, (GGTTTTTCGCCCTTTGACGTTGGA (SEQ ID NO: 13), IDT) to the rolling circle amplicon such that the amplicon becomes immobilized via multiple interactions along its length.

Alternatively, double stranded DNA with a single strand overhang is attached to a vinylsilane surface via hydrophobic interaction between the exposed bases in the overhang and the surface, in MES buffer pH 5.5. The buffer is then exchanged for a denaturing buffer (0.5M-1M NaOH) and a number of washes are done so that the non-immobilized strand can be flushed away. The cover glass is then exposed to MES again and the DNA is elongated by a receding meniscus. Similarly, an end of DNA can be modified, e.g., a homopolymer tail can be added by terminal transferase (NEB) and the DNA can then be captured on a complementary homopolymer oligonucleotide. The non captured strand of the double stranded DNA can then be melted off using heat and/or chemical denaturation or by using a motor protein such as a helicase (e.g., He1308) that separates the strands. For this the homopolymers tail can be several tens to hundreds of nucleotides and the capture probe can be similarly long. Alternatively, a crosslinking reagent is provided to hold the tailed strand in place while the other strand is denatured off. The tailed DNA can also be ligated at the other end with a stem-loop in order to link the two strands of the double helix, so that when the DNA is captured, both strands of the DNA can be sequenced; in this case the transient binding buffer is configured to weaken the base pairs of the duplex (to prevent its reformation and thus obstructing binding of oligos) compared to the interaction with the transiently binding oligo, which comprises LNA residues.

Binding of NNNXNNN Oligonucleotide Species to Nucleic Acid

In the case of sequencing using NNNXNNN (where N is a degenerate position and X is a specified position), each of four oligonucleotide libraries 5' NNNANNN 3', 5' NNNCNNN 3', 5' NNNGNNN 3' and 5' NNNANNN3' are differentially labeled with Atto488, Atto 542, Alexa 594, and Atto 655 respectively and combined into a 15 ul droplet comprising 2.4-3.5M TMACl or 4×SSC and 0.01-0.1% Tween 20, each at a concentration of 100 nM to 1 uM, and applied to the surface on which the nucleic acid molecules have been elongated or stretched. The coverglass is sealed to a glass slide by using epoxy, cow gum or nail varnish. The coverglass is placed onto the microscope IX2 Nosepiece stageon an Olympus 1X81 inverted microscope, 4 combined laser lines (Agilent), 488 nm, 532 nm, 590 and 640 nm are used to simultaneously illuminate the sample through a quad-band TIRF filter cube (Chroma) and a 1.45NA Olympus TIRF Objective lens. Optionally a fiber optic scrambler (Point Source) is used to homogenize the beams. Laser powers are adjusted for each wavelength between 40 and 150 mW to give equivalent signal brightness. TIRF angles are also adjusted to give best contrast images for each of the illumination channels. The emissions are either split onto the four quadrants of a Quad-view device (Photometrics) before being projected onto a 95B Scientific CMOS camera (Photometrics). Alternatively the emission wavelengths four the four dyes are split onto multiple cameras using a series of dichroic and reflective mirrors. The camera settings are adjusted together with the laser power to obtain roughly equivalent signal strengths for each dye; however as the binding information that is gathered is digital the signals from the four dyes do not need to be exactly equivalent in brightness. The identity of each signal is determined by software by taking into account the emission profile of each of the dyes in the different emission channels of Quad-view quadrants or the multiple cameras. The emission profiles that are previously determined may then be used to determine the identity of the dyes.

Optionally, 1 nM YOYO-1 or similar intercalating dye is also added to the reaction mix and a high concentration, up to 1 uM of the oligos is used, coupled with high camera frame rate. Here only a single 488 nm laser is used to excite the four dyes via a FRET mechanism.

Optionally, 1 uM DNA origami grid, together with DNA PAINT imagers are also added as part of the 15 ul mix, as fiducial markers.

The imaging data is processed using a super-resolution image processing package, e.g., Thunderstorm which is a plug in to ImageJ/Fiji or Picasso (J. Schnitzbauer*, M. T. Strauss*, T. Schlichthaerle, F. Schueder, R. Jungmann Super-Resolution Microscopy with DNA-PAINT. Nature Protocols (2017). 12: 1198-1228 DOI: https://doi.org/10.1038/nprot.2017.024).

The super-resolution images are then processed to find the coordinates of binding positions along the nucleic acid strands and data from the different colors corresponding to the different defined nucleotides, are compiled to re-construct the sequence of each of the nucleic acid strands. More complete information about the image processing and sequence assembly is described in PCT and its offspring Drift To obtain the highest localization precision (e.g., a few nanometers or sub-nanometer) it is important to control vibrations and drift (e.g., caused by thermal fluctuations). To prevent drift an automated stage should not be used as there is often residual movements when the stage is stopped, which lead to several or tens of pixels in drift. Fiducial markers can be used for correcting drift. As well as fluorescently labeled latex particles, gold or silver particles, semiconductor nanocrystals, nanodiamonds are a particularly favourable nanoparticle label. They emit light with high Quantum efficiency (QE), have high photostability, long fluorescent lifetimes (17 ns) which can be used to time gate our light scattering/autofluorescence (1-2 ns) and can be small (e.g., 40 nm).

Drift can also be corrected computationally. The drift correction involves tracking the position of each marker through the duration of each movie, averaging the trajectory of all detected markers to globally correct drift in the image. Also Fiji/ThunderSTORM as well as MatLab have inherent drift correction algorithms which are reasonably effective and do not require fiduciary markers but rather correct drift by autocorrelation. The Nikon Ti microscopes have Perfect Focus and Olympus have Z drift compensation module (IX3-ZDC2). Also a low tech method for avoiding drift is to robustly attach the sample stage to the objective (e.g., Olympus nosepiece stage). Also if thermal environment is well controlled, drift can be made negligible and/or stabilizes after a few minutes.

DNA origami, 100 nm gold nanoparticles, (Sigma Aldrich; 10 nM in buffer C, added before imaging), 100 nM Tetrasppeck beads (Thermofisher) or nanodiamond can be used as drift and alignment markers. Off the shelf cameras such as Photometrics Prime 95B include particle tracking capability that can be used to keep the fiducial markers in focus.

In another case, drift of the focus position can be eliminated by a custom-built focus stabilization. A near-infrared laser (LP785-SF20, Thorlabs) was totally internally reflected from the glass-water interface of cover-slide and sample. The beam position is monitored on a CMOS camera (UI-3240CP-NIR-GL, Imaging Development Systems, Obersulm, Germany). A feedback control implemented in LabVIEW 2015 (National Instruments) maximized the cross-correlation of the images of the laser spot and a reference image, respectively. The axial sample position is adjusted every 200 ms accordingly (P737.2SL and E-709.SRG, Physikalische Instrumente). The sample and objective are temperature stabilized to 23° C. (H101-CRYO-BL stabilization unit, with H101-MINI sample chamber and OKO-MOC objective stabilization, Okolab, Ottaviano, Italy).

Systems for Minimizing Bleaching, Triplet States and Photo-Damage

The following reagents are effective depending on the dye used to label the oligonucleotide:

(a) pyranose oxidase, catalase, glucose; (b) protocatechuate-dioxygenase, 3,4-protocatechuic acid (c) Catalase, Glucose Oxidase, Sucrose or Glucose (A high stability commercial version of, FluMaXx (Hypermol) is available).

(d) methylene blue and Dithiotrol (DTT); (e) a reducing agent comprising, Beta mercaptoethanol, TCEP, or Dithiotrol (DTT); (f) a triplet state quencher/fluorescence promoting comprising Trolox, 1,3,5,7 cyclooctatetraene, and/or 4-nitrobenzylalchohol.

Pyranose oxidase, catalase, glucose (PO+C) as oxygen scavenger is particularly effective and is prepared as follows:

PO+C, is incubated for 1 hour prior to measurement with the PO+C oxygen scavenger system (1×PO, 1×C, 0.8% Glucose), with 1× Trolox added. Stock solutions: 100×PO solution consists of 26 mg of PO (P4234-250UN, Sigma-Aldrich Chemie GmbH, Taufkirchen, Germany), 684 µL of enzyme buffer; 100×C solution consists of 2 mg Catalase in 1 ml enzyme buffer. Both were centrifuge filtered (Ultrafree MC-GV, Merck KGaA, Darmstadt, Germany; 0.22 µm), flash frozen in liquid nitrogen and stored at ?80° C.; 100× Trolox solution consists of 100 mg of Trolox (Sigma-Aldrich 238813-1G), 430 µL of methanol and 345 µL of NaOH (1 M) in 3.2 mL of H2O, stored at ?20° C.);

The fluorescent label can induce photodamage on the target DNA, to minimize this In addition to adding one or more of the above additives, it is helpful to separate the fluorescent label from the target DNA. This is done in one or both of two ways. The first is to simply add a spacer between the oligonucleotide species and the fluorescent label. An 18-mer spacer can be added to the oligonucleotide probe and is effective when the label is Cy3B. The second way is to add a protein shield between the label and the oligonucleotides, such that when the oligonucleotides bind to the target polynucleotides/nucleic acids, the protein acts as a shield lessening the impact of oxidative processes on the nucleic acid on the substrate. A plethora of proteins can be used as shields, one example is streptavidin which can be linked to a biotinylated oligonucleotide species, and can be labelled with one or more fluorescent dyes.

Large Area Sensor

To get a large field of view for long molecules a camera with a large numberof pixels is coupled with a low magnification objective lens.Cameras containing Sony IMX253 sensor which comprises 12 million 3.5 micron pixels and low electron noise can be used. This sensor is coupled to a 10 GigE interface fro fast data transfer (allowing 80 frames per second in the HR1200 by Emergent Vision Technologies (Canada). This camera is coupled with a 20×0.75NA Nikon objective and is capable of imaging ~2 Megabase length of stretched DNA in one axis of the sensor.

Temperature Control and Reagent Exchange

Temperature control and reagent exchange is implemented using a system comprising a CherryTemp (France) fast switching and precise temperature control system and a perfusion chamber that is bonded onto the cover glass comprising the fixed elongated/stretched nucleic acid and multiple reagent inlets and one or more outlets that are connected to a pressure driven flow system (Elvesys, France). To deliver multiple reagents the Elvesys pressure generator pipes into a splitter that exerts pressure into the tubes of the reagents to be delivered, pushing the reagents into a valve that is then switched to deliver specific reagents via capillary tubing to the flow cell. A flow sensor is integrated into the flow line to measure flow rates between 0 and 80 ul/min and providing feedback to dial the pressure generator to the appropriate level for the flow rate needed, e.g., 10 ul/min.

The invention is most thoroughly understood in light of the teachings of the specification and the references cited within. The embodiments within the specification provide an illustration of embodiments of the invention and should not be construed to limit the scope of the invention. The skilled artisan readily recognizes that many other embodiments are encompassed by the invention. Those skilled in the art will recognize, or be able to ascertain, many equivalents to the specific embodiments of the invention described herein using no more than routine experimentation. Such equivalents are intended to be encompassed by the claims (below).

Additional Embodiments

1. A method for identifying the sequence of sub-units in a single polymer molecule comprising:
   i. immobilizing the polymer;
   ii. contacting the polymer with molecular probes which recognize sub-units of said polymer;
   iii. localizing the sites of binding of the molecular probes; and
   iv. determining the location of the subunits by determining the binding location of the molecular probes.

2. A method according to 1 comprising repeating steps (ii) and (iii) multiple times.

3. A method according to 2 comprising binding the probes of the same specificity multiple times.

4. A method according to 2 comprising binding probes of different specificities at each iteration of (ii).

5. A method according to 1 where the contacting the molecular probes comprises multiple transient binding events of the probe(s) with the polymer.

6. A method for sequencing nucleotide modifications and/or bases on a single target polynucleotide comprising:
   i. Immobilizing the polynucleotide on a surface or matrix;
   ii. Adding one or more probe species under conditions that the probes bind transiently to their binding sites, such transience allowing multiple probes to bind one after the other to each of the binding sites, and binding to the target site can be differentiated from binding to non-target sites (e.g., by difference in binding duration);
   iii. Continuously imaging (or taking multiple frames of) the polynucleotide on a 2D detector and recording the pixel coordinates of binding, so that a threshold number of binding events have been accumulated;
   iv. Removing the probes of ii;
   v. Repeating steps ii-iv each time with a different one or more probe species;
   vi. Compiling data from each iteration of step iii. using a single molecule localization algorithm to provide the nanometric or sub-nanometric location of each of the binding sites to which probes bind persistently (e.g., 10 or more binding events to the binding sites) and correlating the nanometrically localized site with the identity of the probe species (e.g., a specific oligonucleotide sequence or a specific antibody); and
   vii. Using vi to determining the order (sequence) of the binding species at each of the nanometric locations to compile the nucleotide modification and/or base sequence of the polynucleotide.

7. A method according to 1 and 6 comprising elongating as well as immobilizing.

8. A method according to 1 where the identity of the probes of each specificity are known or can de determined.

9. A method according to 1 and 6 where the binding probes are oligonucleotides.

10. A method according to 1 and 6 where the binding probes are antibodies, affybodies, affimers, nanobodies, aptamers or a nucleic acid binding proteins.

11. A method according to 6 where the probe species can be differentiated.

12. The method according to of 1 and 6 where the binding is detected via a spatially resolvable signal.

13. The method according to 12 where the spatially resolvable signal is due to one or more labels on the probes.

14. A method according to 13 where the identity of the probes are encoded.

15. A method according to 9 where the binding probes comprise a complete repertoire of recognition sequences, e.g., 64 3mers, 245 4mers, 1024 5mers or 4096 6mers, and optionally comprise additional degenerate or universal bases.

16. The method according to 6, where the single target polynucleotide is derived from, or is a chromosome or a portion thereof.

17. The method according to 6, where the single target polynucleotide is about $10^2$, $10^3$, $10^4$, $10^5$, $10^6$, $10^7$, $10^8$, $10^9$ bases in length.

18. The method of 6 further comprising extracting the single target polynucleotide molecule from a cell, organelle, chromosome, virus, exosome or body fluid/substance with minimal perturbation of the polynucleotide.

19. The method of 1 and 6, where the target polymer/polynucleotide molecule is immobilized on a surface.

20. The method of 1 and 6, where the target polymer/polynucleotide molecule is disposed in a gel or matrix.

21. The method of claims 1 and 6, where the target polymer/polynucleotide molecule is disposed in a micro- or nano-fluidic channel.

22. The method of claims 1 and 6, where the target polymer/polynucleotide molecule is substantially intact.

23. The method of claim 6, where the sequence is determined without using another copy of the target polynucleotide molecule or reference sequence for the target polynucleotide molecule.

24. A method of haplotype resolved sequencing of a diploid or polyploid genome comprising:
   i. sequencing a first target polynucleotide representing a first haplotype of a diploid/polyploid genome using the methods of 1 or 6
   ii. sequencing a second target polynucleotide representing a second haplotype of the diploid/polyploid genome using the methods of 1 or 6; and
   iii. for a polyploid genome, sequencing further target polynucleotides representing further haplotypes of the polyploid genome using the methods of claim 1 or 6; where the first and second and further target polynucleotides are from different homologous chromosomes (chromosome homologs); and thereby determining the first, second, and further haplotypes of the genome.

25. A method of obtaining a long-contiguous sequencing read comprising:
   i. Obtaining a first short read based on probe binding events;
   ii. Obtaining a second short read adjacent to the first read based on probe binding events;
   iii. Obtaining further short reads near to the first or second short read based on probe binding events; and
   iv. Stitching at least two short reads together to obtain a contiguous long read.

26. A method according to 25 where some of the reads for haplotype resolved sequencing are obtained from separate polynucleotides (e.g., from multiple cells) of each homolog.

27. A method according to 6 where the nanometric localization or order is facilitated by using one or more reference sequences to infer location.

28. A method according to previous claims where the target polynucleotides are contacted with a gel or matrix.

29. A method according to 1 and 10 where base sequencing is combined with analysis of epi-marks (e.g., methylation) by the labeling of epi-marks orthogonally to base sequence.

30. A method of determining the chemical structure of a polymer comprising elongating the polymer and binding a plurality of temporally resolvable labels to a plurality of sites along the elongated polymer, a plurality of which are not resolvable by diffraction limited optical imaging and determining their location with nanometric or sub-nanometric accuracy.

31. A method according to 6 where the transient binding comprises active unbinding.

32. A method according to 31 where the binding comprises stable binding.

33. A method according to 32 where the actively unbinding comprises disrupting the binding by means comprising, heat, change in pH, change in salt concentration, chemical or biochemical degradation of the probe.

34. A method according to 31 where the binding and active unbinding is conducted using temperature cycling in a homogenous reaction.

35. A method according to previous claims where the binding probes bind to discrete sequence bits (defined according to the specification).

36. A method according to previous claims where the binding probes are localized with nanometric accuracy and precision.

37. A method according to previous claims where the binding sites are localized with sub-nanometric accuracy and precision.

38. A method according to previous claims where two or more sequence bits, where two or more binding probes bind, are super-resolved with respect to each other.

39. A method according to 1-38 where the probes are labeled directly.

40. A method according to the 1-38 where the probes are labeled indirectly.

41. A method according to 40 where the indirectly labeled probe comprises a target binding domain and at least one labeling domain.

42. A method according to 41 where said target binding domain comprises at least three nucleotides and is capable of transiently binding to a target nucleic acid.

43. A method according to 41 where said labelling domain comprises a nucleic acid sequence capable of stably binding a complementary nucleic acid molecule that is labelled.

44. A method according to 41 in which the probe comprises a target binding domain and multiple labeling domains.

45. A method according to 44 where said multiple labeling domains each comprise a nucleic acid sequence capable of stably binding a complementary nucleic acid molecule that is labeled.

46. A method according to 44 where each binding domain comprises a distinct sequence.

47. A method according to 44 where the each distinct binding domain corresponds to one of the at least three nucleotides.

48. A method according to 47 where the identity of the one of the at least three nucleotides is determined by distinct labels.

49. A method according to 48 where at least 12 distinct labels are used or 11 distinct labels and one blank are used.

50. A method according to 41 and 44 where target binding domain comprises at least three nucleotides and one or more degenerate nucleotide positions.

51. A method according to 48 where the labels are distinct due to wavelength, lifetime, brightness, polarization of radiated, emitted or scattered light etc.

52. A method according to the previous embodiments, where the polynucleotides are tailed at an end and captured via a sequence complementary to the tail.

53. A method according to 52 where the sequence complementary to the tail are organized in an ordered array.

54. A method according to 52 where the ordered array comprises a supra-molecular grid (e.g., DNA Origami) comprising spatially ordered sequences complementary to the tail.

55. A method according to 52 where the polynucleotides are tailed using terminal transferase.

56. A method according to 52 where the target polynucleotides are short, cell-free or circulating nucleic acids.

57. A method according to 52 where the target polynucleotides are mRNA and are already naturally tailed at one end.

58. A method according to 52 where the target polynucleotides are RNA that are not already naturally tailed at one end.

59. A method according to previous embodiments, where the polymers/polynucleotides are denatured prior to probe binding.

60. A method according to previous embodiments where the single polymer/polynucleotide is stretched or elongated.

61. A method according to previous embodiments, where the single polymer/polynucleotide is immobilized on a surface.

62. A method according to previous embodiments where the single polymer/polynucleotide is immobilized in a gel or matrix.

63. A method of identifying and ordering chemical structures in a heterogeneous polymer comprising: Elongating the polymer and binding a plurality of probes that identify the chemical structures at a plurality of sites along the elongated polymer; A plurality of said sites are closer than would be resolvable by diffraction limited optical imaging but are resolved because their labeling is temporally separated; The location of binding of the probes that identify the chemical structure is determined with nanometric (sub-diffraction) precision and thereby the spatial order of chemical structures in a heterogeneous polymer is determined.

64. A method of sequencing polymers in which the sequence of a polymer is determined through an emergent property of the binding interactions of a repertoire of molecular probes to the polymer.

EXAMPLES

Example 1: Preparing Samples for Sequencing

Step 1: Extracting Long Lengths of Genomic DNA.

NA12878 or NA18507 cells (Coriell Biorepository) are grown in culture and harvested. Cells are mixed with low-melting temperature agarose heated to 60° C. The mixture is poured into a gel mold (e.g., purchased from Bio-Rad) and allowed to set into a gel plug, resulting in about $4 \times 10^7$ cells (this number is higher or lower depending on the desired density of the polynucleotides). The cells in the gel plug are lysed by bathing the plug in a solution containing Proteinase K. The gel plugs are gently washed in TE buffer (e.g., in a 15 mL falcon tube filled with wash buffer but leaving a small bubble to aid in the mixing, and placing on a tube rotator). The plug is placed in a trough with around 1.6 mL volume and DNA is extracted by using agarase enzyme to digest the DNA. 0.5M MES pH 5.5 solution is applied to the digested DNA. The FiberPrep kit (Genomic Vision, France) and associated protocols are used to carry out this step to give 300 Kb average length of the resulting DNA molecules. Alternatively, genomic DNA extracted from these cell lines is itself available from Corriel and is directly pipetted into the 0.5M MES pH 5.5 solution using a wide bore pipette (~10 uL in 1.2 mL to give <1 μM average spacing).

Step 2: Stretching Molecules on a Surface.

The final part of step 1 renders the extracted polynucleotides in a trough in a 0.5M MES pH 5.5 solution. The substrate cover glass, coated with vinylsilane (e.g., CombiSlips from Genomic Vision) is dipped into the trough and allowed to incubate for 1-10 minutes (depending on the density of target nucleic acids required). The cover glass is then slowly pulled out, using a mechanical puller, such as a syringe pump with a clip attached to grasp the cover glass (alternatively, the FiberComb system from Genomic Vision is used). The DNA on the coverglass is cross-linked to the surface using an energy of 10,000 micro Joules using a crosslinker (Stratagene, USA). If the process is carried out carefully, it results in High Molecular Weight (HMW) polynucleotides with an average length of 200-300 Kb elongated on the surface, with molecules greater than 1 Mb, or even around 10 Mb, in length present amongst the population of polynucleotides. With greater care and optimization, the average length is shifted to the megabase range (see Mega-base range combing section above).

As an alternative, as mentioned above, pre-extracted DNA (e.g., Human Male Genomic DNA from Novagen cat. No. 70572-3 or Promega) is used, and comprises a good proportion of genomic molecules of greater than 50 Kb. Here, a concentration of about 0.2-0.5 ng/μL, with dipping for about 5 minutes is sufficient to provide a density of molecules where a high fraction is individually resolved using diffraction limited imaging.

Step 3: Making a Flow Cell.

The coverslip is pressed onto a flow cell gasket fashioned from double-sided sticky 3M sheet that has already been attached to a glass slide. The gasket (with both sides of the protective layer on the double-sided sticky sheet on) is fashioned, using a laser cutter, to produce one or more flow channels. The length of the flow channel is longer than the length of the coverglass, so that when the coverglass is placed at the center of the flow channel, the portions of the channel one at each end that are not covered by the coverglass is used, respectively, as inlets and outlets for dispensing fluids into and out of the flow channel. Fluids pass above the elongated polynucleotides that are adhered on the vinylsilane surface. The fluids are flowed through the channel by using safety swab sticks (Johnsons, USA) at one end to create suction as fluid is pipetted in at the other end. The channel is pre-wetted with Phosphate Buffered Saline-Tween and Phosphate Buffered Saline (PBS-washes).

Step 4: Denaturation of Double Stranded DNA.

Before the next target nucleic acids can be added the previous target nucleic acids need to be efficiently washed away; this can be done by exchanging with buffer up to 4 times and optionally using denaturing agents such as DMSO or an alkali solution to remove persistent binding). The double-stranded target nucleic acid is denatured by flushing alkali (0.5M NaOH) through the flow cell and incubating for about 20-60 minutes at room temperature. This is followed by PBS/PB ST washes. Alternatively, incubation is also done with 1 M HCL for 1 hour followed by PBS/PB ST washes.

Step 5: Passivation.

Optionally, a blocking buffer such as BlockAid (Invitrogen, USA) is flowed in and incubated for ~5-15 minutes. This is followed by the PBS/PBST washes.

Example 2: Sequencing by Transient Binding of Oligonucleotides to a Denatured Polynucleotide Step 1: Adding Oligonucleotide Probe Species Under Transiently Binding Conditions.

The flow cell is pre-conditioned with PBST and optionally Buffer A (10 mM Tris-HCl, 100 mM NaCl, 0.05% Tween-20, pH 7.5). ~1-10 nM of each of the oligonucleotide probe species are applied to the elongated denatured target nucleic acids in Buffer B (5 mM Tris-HCl, 10 mM $MgCl_2$, 1 mM EDTA, 0.05% Tween-20, pH 8) or Buffer B+5 mM Tris-HCl, 10 mM $MgCl_2$, 1 mM EDTA, 0.05% Tween-20, pH 8, 1 mM PCA, 1 mM PCD, 1 mM Trolox).

The length of the oligonucleotide probe species typically ranges from 5 to 7 nucleotides and the reaction temperature depends on the Tm of the oligonucleotide probe species. One probe type that we have used is of the general formula 5'-Cy3-NXXXXXN-3' (X are specified bases, N are degenerate positions), with LNA nucleotides at positions 1, 2, 4, 6 and 7, DNA nucleotides at positions 3 and 5; probes were purchased from Sigma Proligo and as previously used by Pihlak et al. Binding of temperature was linked to the Tm of each oligonucleotide probe species sequence.

After washing with A+ and B+ solution transient binding of oligonucleotide probe species is carried out with between 0.5 and 100 nM of oligo (typically between 3 nm and 10 nm) in B+ solution at room temperature for an LNA DNA chimera oligonucleotide probe species 3004 NTgGcGN (where upper case letters are LNA and lowercase are DNA nucleotides). Different temperatures and/or salt conditions (as well as concentrations) are used for different oligonucleotide probe species sequences, according to their Tm and binding behavior. If a FRET mechanism is used for detection, a much higher concentration of oligo, up to 1 uM can be used. In some embodiments, the FRET is between an intercalating dye molecules (1 in 1000 to 1 in 10,000 diluted form neat depending on which intercalating dye is used from YOYO-1, Sytox Green, Sytox Orange, Sybr Gold etc; Life Technologies) which intercalate into the transiently formed duplexes and a label on the oligo. In some embodiments, intercalating dye is directly used as label, without FRET. In this case, the oligonucleotide probe species are not labeled. As well as being cheaper, unlabeled oligonucleotide probe species can be used at higher concentrations than labeled oligonucleotide probe species, because the background from intercalated dye upon duplex formation is 100-1000 brighter (e.g., depending on which intercalant is used) than un-intercalating dye.

Step 2: Imaging—Taking Multiple Frames.

The flow channel is placed on an inverted microscope (e.g., Nikon Ti-E) equipped with Perfect Focus, TIRF attachment, and TIRF Objective lasers and a Hamamatsu 512×512 Back-thinned EMCCD camera. The probes are added in Buffer B+ and optionally supplemented with imaging.

The probes binding to the polynucleotides disposed on the surface are illuminated by an evanescent wave generated by total internal reflection of 75-400 mW laser light (e.g., green light at 532 nm) conditioned via fiber optic scrambler (Point Source) at a TIRF angle of ~61.5° through a 1.49 NA 100× Nikon oil immersion objective on a Nikon Ti-E with TIRF attachment. The images are collected through the same lens with 1.5× further magnification and projected via the dichroic mirror and an emission filter to a Hamamatsu ImageEM camera. 5000-30,000 frames of 50-200 milliseconds are taken with an EM gain of 100-140 using Perfect Focus. In some embodiments, high laser power (e.g., 400 mW) is used in the early seconds to bleach out initial non-specific binding, which reduces the almost a blanket of signal from the surface to a lower density where individual binding events are resolved. Thereafter the laser power is optionally lowered.

FIGS. 22A-22E illustrate examples of illumination of oligonucleotide probespecies transiently binding to target nucleic acids. In these figures, the target nucleic acids are human DNA. Dark spots indicate regions of probe fluorescence, with darker spots indicating more regions that were bound more often by oligonucleotide probe species (e.g., more photons were collected). FIGS. 22A-22E are images from a time series (e.g., a video) captured during sequencing of one target nucleic acid. Points 2202, 2204, 2206, 2208 are indicated throughout the time series as examples of regions in the target nucleic acids that were bound with more or less intensity over time (e.g., as different sets of oligonucleotide probe species were exposed to the target nucleic acid).

Imaging buffer is added. The imaging buffer is supplemented or replaced by a buffer containing beta-mercaptoethanol, enzymatic redox system, and/or ascorbate and gallic acid in some embodiments. Fluorophores are detected along lines, indicating that oligonucleotide probe species binding has occurred. Optionally, if the flow cell is made with more than one channel, one of the channels is stained with YOYO-1 intercalating dye for checking the density of polynucleotides and quality of the polynucleotide elongation (e.g., using Intensilight or 488 nm laser illumination).

Step 3: Imaging—Moving to Other Locations (Optional Step).

The cover glass, which has been mounted onto the slide holder of the Nikon Ti-e (via attachment to glass slide as part of the flow cell,) is translated with respect to the objective lens (hence the CCD) so that separate locations are imaged. The imaging is done at a multiple of other locations so that oligonucleotide probespecies binding to target nucleic acids or parts of target nucleic acids rendered at different locations (outside the field of view of the CCD at its first position) is imaged. The image data from each location is stored in computer memory.

Step 4: Adding the Next Set of Oligos.

The next set of oligonucleotide probe species is added and steps 1-3 are repeated until the whole of the target nucleic acid has been sequenced.

Step 5: Determining the Location and Identity of Binding.

The location of each instance of optical activity is determined, recording the pixel locations whereupon the fluorescence from the bound labeled oligonucleotide probe species is projected. The identity of the bound oligonucleotide probe species is determined by determining which labeled oligonucleotides probe species have been bound (e.g., using wavelength selection by optical filters) the fluorophores, are detected across multiple filters and in this case the emission signature of each fluorophore across the filter set is used to determine the identity of the fluorophore and hence the oligonucleotide probe species. Optionally, if the flow cell is made with more than one channel, one of the channels is stained with YOYO-1 intercalating dye, for checking the density of target nucleic acids and quality of the target nucleic acid elongation (e.g., by using Intensilight or 488 nm laser illumination). One or more images or movies are taken, one for each of the fluorescence wavelengths used to label the oligonucleotide probe species.

Step 6: Data Processing.

When both strand of the duplex target nucleic acid remain attached to the surface, binding of oligonucleotide probe species occurs to their complementary locations on both strands of the double-strand target nucleic acid simultaneously. Then the total data-set is analyzed to find sets of oligonucleotide probe species that give closely localizing signals to a particular position on the target nucleic acid, their locations are confirmed by overlapping the oligonucleotide probe species sequences that correspond to a chosen point in the polynucleotide; this then reveals two overlapping tiling series of oligonucleotide probe species at each point. Which tiling series the next signal in the locality fits, indicates which strand it is binding to.

As the target nucleic acid strands remain fixed on the surface, the binding locations recorded for each oligonucleotide probe species can be overlaid using a software script running an algorithm. This results in the signals showing that the oligonucleotide probe species binding locations fall within the framework of two oligonucleotide probe species sequence tiling paths, a separate (but which should be complementary) path for each strand of the denatured duplex target nucleic acid. Each tiling path, if complete, spans the entire length of the strand. The tiled sequence for each strand is then compared to provide a double-strand (also known as 2D) consensus sequence. If there are gaps in one of the tiling paths, the sequence of the complementary tiling path is taken. In some embodiments, the sequence is compared with multiple copies of the same sequence or to the reference, to aid base assignment and to close gaps.

Example 3: Detecting the Location of Epi-Marks on the Polynucleotide

Optionally before (or sometimes after or during) the oligo binding process, transient binding of epigenomic binding reagents is carried out. Depending on which binding reagent is used, binding is done before or after denaturation. For anti-methyl C antibodies binding is done on denatured target nucleic acids whereas for methyl binding proteins, binding is done on double-stranded target nucleic acids before any denaturation step.

Step 1—Transient Binding of Methyl-Binding Reagents.

After denaturation, the flow cell is flushed with PBS-washes and a Cy3B labeled anti-methyl antibody 3D3 clone (Diagenode) is added in PBS.

Alternatively, before denaturation, the flow cell is flushed with PBS and Cy3B-labeled MBD1 is added.

Imaging is conducted as described above for transient oligonucleotide probe species binding.

Step 2: Stripping Away Methyl-Binding Reagents.

Typically, the epi-analysis is done before sequencing. Therefore, optionally the methyl-binding reagents are flushed out before the before sequencing of the target nucleic acid commences. This is done by flowing through multiple cycles of PB S/PB ST and/or a high salt buffer and SDS and then checking by imaging that removal has occurred. If it is evident that more than a negligible amount of binding reagent remains, harsher treatments such as the chaotrophic salt, GuCL is flowed through to remove the remaining reagents.

Step 3: Data Correlation.

After sequencing epi-genomics data has been obtained correlations are made between the location of the sequencing probe species binding locations and epi-binding location is correlated to provide the sequence context of the methylation.

Example 4: Fluorescence Collected from Transient Binding in Lambda Phage DNA

FIGS. 23A, 23B, and 23C illustrate examples of transient binding events. They collectively illustrate transient binding of Oligo I.D. Lin2621, Cy3 labeled 5' NAgCgGN 3' at 1.5 nM concentration in Buffer B+ at room temperature. The target nucleic acid is lambda phage genome that has been combed manually onto a vinylsilane surface (Genomic Vision) in MES pH 5.5 buffer+0.1 M NaCl. Laser 532 nm at 400 mW through Point Source Fiber Optic scrambler. The fluorescence has been collected with a TIRF attachment and multi-chroic, including a 532 nm excitation band, a TIRF Objective 100×, 1.49 NA, and with extra 1.5× magnification. No vibration isolation was implemented. The images were captured with Perfect Focus onto Hamamatsu ImageEM 512×512 with 100 EM Gain setting. 10000 frames were collected over 100 ms. The concentration of Cy3 in the oligonucleotide probe sets was about 250 nM-300 nM. FIG. 23A displays the fluorescence that was collected before cross-correlation drift correction in ThunderSTORM. FIG. 23B displays fluorescence that was collected after cross-correlation drift correction with scale bar. FIG. 23C displays fluorescence in a magnified region of FIG. 23B. FIG. 23C show long polynucleotide strands traced out by the persistent binding of the Lin2621 to multiple locations. From the image, it is clear that the target nucleic acid strands were immobilized and elongated on the imaging surface at distances closer than the diffraction limit of Cy3 emission.

Example 5: Fluorescence Collectedfrom Transient Binding in Synthetic DNA

FIG. 24 illustrates an example of fluorescence data collected from three different polynucleotide strands. Multiple probing and washing steps are shown on synthetic 3 kilobase denatured double-stranded DNA. Synthetic DNA was combed in MES pH 5.5 on a vinylsilane surface and denatured. A series of binding and washing steps were carried out, and a video was recorded and processed in ImageJ using ThunderSTORM. Three example strands (1, 2, 3) were excised from the super-resolution image for the following experimental series carried out with 10 nM oligo in Buffer B+ at ambient temperature: Oligonucleotide probe species 3004 binding, washing, oligo 2879 binding, washing, oligo 3006 binding, washing and oligonucleotide probe species 3004 binding (again). This shows that a binding map can be derived from transient binding, the binding pattern can be erased by washing, a different binding pattern is then obtained with a different oligonucleotide probe species on the same first and second strands of the synthetic DNA. The return to oligonucleotide probe species 3004 on the last of the series and its resemblance to the pattern when it is used as the first in the series points to the robustness of the process even without any attempt at optimization.

The experimentally determined binding locations correspond to the expected, with duplex strands 1 and 3 showing 3 of 4 possible perfect match binding sites, and duplex strand 2 showing all 4 binding locations and one prominent mismatch location. It is observed that the second probing with oligonucleotide probe species 3004 appears to show cleaner signals, perhaps due to less mismatch. This is consistent with the likelihood that the temperature is slightly raised due to heating from pro-longed exposure to laser light.

The oligo sequences used in this experiment are as follows (Capitalized bases are Locked Nucleic Acid (LNA)):
Oligonucleotide probe species 3004: 5' cy3 NTgGcGN
Oligonucleotide probe species 2879: 5' cy3 NGgCgAN
Oligonucleotide probe species 3006: 5' cy3 NTgGgCN:

The Sequence Listing (at bottom of document) for sequence of 3 kbp synthetic template is as follows:

(SEQ ID NO. 2)
AAAAAAAAACCGGCCCAGCTTTCTTCATTAGGTTATACATCTACCGCTCG

CCAGGGCGGCGACCTCGCGGGTTTTCGCTATTTATGAAAATTTTCCGGTT

TAAGGCGTTTCCGTTCTTCTTCGTCATAACTTAATGTTTTTATTTAAAAT

ACCCTCTGAAAAGATAGGATAGCACACGTGCTGAAAGCGAGGCTTTTTGG

CCTCTGTCGTTTCCTTTCTCTGTTTTTGTCCGTGGAATGAACAATGGAAG

TCAACAAAAGCAGCTGGCTGACATTTTCGGTGCGAGTATCCGTACCATT

CAGAACTGGCAGGAACAGGGAATGCCCGTTCTGCGAGGCGGTGGCAAGGG

TAATGAGGTGCTTTATGACTCTGCCGCCGTCATAAAATGGTATGCCGAAA

GGGATGCTGAAATTGAGAACGAAAAGCTGCGCCGGGAGGTTGAAGAACTG

CGGTTCTTATACATCTAATAGTGATTATCTACATACATTATGAATCTACA

TTTTAGGTAAAGATTAATTGAGTACCAGGTTTCAGATTTGCTTCAATAAA

TTCTGACTGTAGCTGCTGAAACGTTGCGGTTGAACTATATTTCCTTATAA

CTTTTACGAAAGAGTTTCTTTGAGTAATCACTTCACTCAAGTGCTTCCCT

GCCTCCAAACGATACCTGTTAGCAATATTTAATAGCTTGAAATGATGAAG

AGCTCTGTGTTTGTCTTCCTGCCTCCAGTTCGCCGGGCATTCAACATAAA

AACTGATAGCACCCGGAGTTCCGGAAACGAAATTTGCATATACCCATTGC

TCACGAAAAAAATGTCCTTGTCGATATAGGGATGAATCGCTTGGTGTAC

CTCATCTACTGCGAAAACTTGACCTTTCTCTCCCATATTGCAGTCGCGGC

ACGATGGAACTAAATTAATAGGCATCACCGAAAATTCAGGATAATGTGCA

ATAGGAAGAAAATGATCTATATTTTTTGTCTGTCCTATATCACCACAAAA

CCTGAAACTGGCGCGTGAGATGGGCGACCGTCATCGTAATATGTTCTAG

CGGGTTTGTTTTTATCTCGGAGATTATTTTCATAAAGCTTTTCTAATTTA

ACCTTTGTCAGGTTACCAACTACTAAGGTTGTAGGCTCAAGAGGGTGTGT

CCTGTCGTAGGTAAATAACTGACCTGTCGAGCTTAATATTCTATATTGTT

GTTCTTTCTGCAAAAAAGTGGGGAAGTGAGTAATGAAATTATTTCTAACA

TTTATCTGCATCATACCTTCCGAGCATTTATTAAGCATTTCGCTATAAGT

TCTCGCTGGAAGAGGTAGTTTTTTCATTGTACTTTACCTTCATCTCTGTT

CATTATCATCGCTTTTAAAACGGTTCGACCTTCTAATCCTATCTGACCAT

TATAATTTTTTAGAATGCGGCGTTTTCCGGAACTGGAAAACCGACATGTT

GATTTCCTGAAACGGGATATCATCAAAGCCATGAACAAAGCAGCCGCGCT

GGATGAACTGATACCGGGGTTGCTGAGTGAATATATCGAACAGTCAGGTT

AACAGGCTGCGGCATTTTGTCCGCGCCGGGCTTCGCTCACTGTTCAGGCC

GGAGCCACAGACCGCCGTTGAATGGGCGGATGCTAATTACTATCTCCCGA

AAGAATCCGCATACCAGGAAGGGCGCTGGGAAACACTGCCCTTTCAGCGG

GCCATCATGAATGCGATGGGCAGCGACTACATCCGTGAGGTGAATGTGGT

GAAGTCTGCCCGTGTCGGTTATTCCAAAATGCTGCTGGGTGTTTATGCCT

ACTTTATAGAGCATAAGCAGCGCAACACCCTTATCTGGTTGCCGACGGAT

GGTGATGCCGAGAACTTTATGAAAACCCACGTTGAGCCGACTATTCGTGA

-continued

```
TATTCCGTCGCTGCTGTTAATTGAGTTTATAGTGATTTTATGAATCTATT

TTGATGATATTATCTACATACGACTGGCGTGCCATGCTTGCCGGGATGTC

AAATTTAATAAGGTGATAGTAAATAAAACAATTGCATGTCCAGAGCTCAT

TCGAAGCAGATATTTCTGGATATTGTCATAAAACAATTTAGTGAATTTAT

CATCGTCCACTTGAATCTGTGGTTCATTACGTCTTAACTCTTCATATTTA

GAAATGAGGCTGATGAGTTCCATATTTGAAAAGTTTTCATCACTACTTAG

TTTTTTGATAGCTTCAAGCCAGAGTTGTCTTTTTCTATCTACTCTCATAC

AACCAATAAATGCTGAAATGAATTCTAAGCGGAGATCGCCTAGTGATTTT

AAACTATTGCTGGCAGCATTCTTGAGTCCAATATAAAAGTATTGTGTACC

TTTTGCTGGGTCAGGTTGTTCTTTAGGAGGAGTAAAAGGATCAAATGCAC

TAAACGAAACTGAAACAAGCGATCGAAAATATCCCTTTGGGATTCTTGAC

TCGATAAGTCTATTATTTTCAGAGAAAAAATATTCATTGTTTTCTGGGTT

GGTGATTGCACCAATCATTCCATTCAAAATTGTTGTTTTACCACACCCAT

TCCGCCCGATAAAAGCATGAATGTTCGTGCTGGGCATAGAATTAACCGTC

ACCTCAAAAGGTATAGTTAAATCACTGAATCCGGGAGCACTTTTTCTATT

AAATGAAAAGTGGAAATCTGACAATTCTGGCAAACCATTTAACACACGTG

CGAACTGTCCATGAATTTCTGAAAGAGTTACCCCTCTAAGTAATGAGGTG

TTAAGGACGCTTTCATTTTCAATGTCGGCTAATCGATTTGGCCATACTAC

TAAATCCTGAATAGCTTTAAGAAGGTTATGTTTAAAACCATCGCTTAATT

TGCTGAGATTAACATAGTAGTCAATGCTTTCACCTAAGGAAAAAAACATT

TCAGGGAGTTGACTGAATTTTTTATCTATTAATGAATAAGTGCTTGACCT

ATTTCTTCATTACGCCATTATACATCTAGCCCACCGCTGCCAAAAAAAAA
```

Example 6: Integrated Isolation of Single Cells, Extracting Nucleic Acids and Sequencing Step 1: Design and Fabricate Microfluidic Architecture Microchannels are designed to accommodate cells from a human cancer cell line with a typical diameter of 15 um, so the microfluidic network has minimal depths and widths of 33 um. The device comprises an inlet for cells and an inlet for buffer that merge into a single channel to feed the single-cell trap (illustrated in FIG. 17). At the intersection between the cell and buffer inlets, cells get aligned along the side wall of the feeding channel where one or more traps are located. Each trap is a simple constriction dimensioned to capture a cell from a human cancer cell line. The constriction for cell trapping has a trapezoidal cross section: It is 4.3 um wide at the bottom, 6 um at middle depth, and 8 um at the top with a depth of 33 um. Each cell trap connects the feeding channel to a bifurcation, one side of which is a waste channel (not shown in FIG. 17) and the other a channel comprising the flow-stretch section (for nucleic acid elongation and sequencing), one for each cell. The flow-stretch section consists of a 20 um (or up to 2 mm) wide, 450 um-long, 100 nm (or up to 2 um-deep) channel. In some embodiments, the flow-stretch channel is narrower to start and widens to the stated dimensions.

Step 2: Device Fabrication

The device is fabricated by replicating a nickel shim using injection molding of TOPAS 5013 (TOPAS). Briefly, a silicon master is produced by UV lithography and reactive ion etching. A 100-nm NiV seeding layer is deposited and nickel is electroplated to a final thickness of 330 um. The Si master is chemically etched away in KOH. Injection molding is performed using a melt temperature of 250° C., a mould temperature of 120° C., a maximum holding pressure of 1,500 bar for 2 s, and an injection rate varying between 20 cm3/s and 45 cm3/s. Finally, either coverglass (1.5) is bonded to the device or a 150 um TOPAS foil is used to seal the device by a combined UV and thermal treatment under a maximum pressure of 0.51 MPa. The surface roughness of the foil is reduced by pressing the foil at 140° C. and 5.1 MPa for 20 min between two flat nickel plates electroplated from silicon wafers before sealing the device. This ensures that the lid of the device is optically flat, allowing for high-NA optical microscopy. The device is mounted on an inverted fluorescence microscope (Nikon Ti-E) equipped with an oil TIRF objective (100×/NA 1.49), and an EMCCD camera Hamamatsu ImageEM 512). Fluids are driven through the device using a pressure controller (MFCS, Fluigent) at pressures in the 0 to 10 mbar range. The device is primed with ethanol, and then degassed, FACSFlow Sheath Fluid (BD Biosciences) is loaded in all microchannels except the microchannel connecting the flow-stretch device The selective loading is effectuated by putting a negative pressure or suction at the outlet of the waste channel, while putting a positive pressure at the outlet of the flow stretch channel, while maintaining a positive pressure at the inlet of feeding channel from where the solutions are introduced. A buffer suitable for single-molecule imaging and electrophoresis (0.5×TBE+0.5% v/v Triton-X100+1% v/v beta-mercaptoethanol, BME) is loaded in the channels of the flow-stretch device. This buffer prevents DNA sticking in the flow-stretch section and suppresses electroosmotic flow that can counteract the introduction of the extracted DNA when the height of the flow-stretch section is low.

Step 3: Cell Preparation

LS174T colorectal cancer cells are cultured in Dulbecco's modified Eagle's medium (DMEM; Gibco) with 10% fetal bovine serum (FBS; Autogen-Bioclear UK Ltd.) and 1% penicillin/streptomycin (Lonza) before freezing at a concentration of 1.7 106 cells per milliliter in 10% DMSO in FBS. After thawing, cell suspension is mixed 1:1 with FACSFlow buffer, centrifuged at 28.8×g (A-4-44, Eppendorf) for 5 min, and resuspended in FACSFlow buffer. Finally, the cells are stained with 1 uM Calcein AM (Invitrogen) and loaded in the chip at 0.35 $10^6$ cells per milliliter. About 5-10,000 cells are loaded and the first cell trapped in each trap is analyzed.

Step 4: Operation

Cells and buffer are introduced simultaneously, aligning the cells along the side wall of the microchannel where the trap is located. A single cell is captured and kept in the trap for a buffer flow through the trap up to 30 nL/min. The lysis buffer composed of 0.5×TBE+0.5% v/v Triton-X100+0.1 uM YOYO-1 (Invitrogen) is loaded in one of the inlets and injected at 10 nL/min through the trap for 10 min. Then, the solution is exchanged to a buffer without YOYO-1 in all wells to stop the staining. Next, the cell nucleus is exposed to blue excitation light at a dose of 1 $nW/(um)^2$ for up to 300 s, causing a partial photonicking of the DNA (see SI Appendix of www.pnas.org/cgi/doi/10.1073/pnas.1804194115). Then, the buffer is changed to a solution containing BME (0.5×TBE+0.5% v/v triton-X100+1% v/v BME), and the intensity of the fluorescence lamp is lowered to the minimum intensity that still allows fluorescence imaging. Next, the temperature is raised to 60° C., and a proteolysis solution (Proteinase K >200 μg $mL^{-1}$ (Qiagen), 0.5×TBE+0.5% v/v Triton-X100+1% v/v BME+200 g/mL) is introduced, pushing the lysate through the trap. DNA travels through to the adjacent flow stretch section, and an oil immersion objective is moved into place for single molecule imaging (100×, NA 1.49, with an additional 1.5× magnification giving a 120-nm pixel image size). DNA fragments are introduced from the microchannel to the flow-stretch device using electrophoresis by applying a voltage of 5 to 10 V across the flow-stretch section. When a DNA fragment has both ends in opposite microchannels, voltage is turned off. The 450 um portion of the molecule stretched at 100-150% corresponds to >1 Megabase lengths of the extracted genomic DNA from the single cell. In some embodiments, after proteolysis the DNA content is pushed through the device by substituting 0.5×TBE for a capture buffer; in such embodiments the flow stretch section dimensions are optionally larger, so that thousands of megabase fragments can concurrently be captured (by hydrophobic or electrostatic interactions) and stretched inside the channel. This is done either by using a pH buffer 8 (e.g., HEPES) and here the coverglass that is bonded is positively charged such as APTES or poly-lysine or a vinylsilane cover glass is bonded and 0.5M MES Buffer at pH 5.5-5.7 is used to flow in the DNA which is then combed by following the MES buffer with air. If the or foil comprises Zeonex, then molecular combing can be done with 0.6M MES buffer at pH 5.7.

Once double-stranded targetnucleic acid is immobilized, denaturation solution, 0.5M NaOH and or 6% DMSO is flowed through. Then the single cell sample is ready for the sequencing methods of this invention, where a complete set of oligonucleotide probe species is flowed through and oligonucleotide probe species binding is imaged.

In some embodiments, the cell lysis is two step, so that RNA does not contaminate and cause fluorescence within the flow stretch section. Here, the first lysis buffer (e.g., 0.5×TBE containing 0.5% (v/v) Triton X-100, to which the DNA intercalating YOYO-1 dye is added) is applied. This buffer lyses the cell membrane, releasing the cytosol contents into the trap outlets filled with 10-20 µl nuclease-free H2O, leaving the nucleus with the DNA in the trap (e.g., as described by van Strijp et al. Sci Rep. 7:11030 (2017). The cytosol content of each cell is removed after lysis and either shunted into the waste outlet or the device is designed to have a flow-stretch section for RNA that is separate from the flow stretch section for DNA. In some embodiments, RNA is sent to a separate flow stretch section, that has been coated with oligo dT, which captures polyA RNA. In some embodiments, the flow stretch section for RNA comprises nanowells or nanopits (Marie et al, Nanoscale DOI: 10.1039/c7nr06016e) 2017), in which the RNA is trapped and enzymatic reagents are used to add capture sequence, using for example polyA addition by terminal transferase. The nuclear lysis is performed with a second buffer (0.5×TBE containing 0.5% (v/v) Triton X-100 and Proteinase K) and the DNA is shunted to the flow-stretch section for DNA.

To minimize loss of the nucleic acids, the distance from the traps and flow stretch section is short, and the device walls are well passivated including by coating with lipids (e.g., as described by Persson et al, Nanoletters 12:2260-5 (2012)).

REFERENCES CITED AND ALTERNATIVE EMBODIMENTS

All references cited herein are incorporated herein by reference in their entirety and for all purposes to the same extent as if each individual publication or patent or patent application was specifically and individually indicated to be incorporated by reference in its entirety for all purposes.

All headings and sub-headings are used herein for convenience only and should not be construed as limiting the invention in any way.

The use of any and all examples, or exemplary language (e.g., "such as") provided herein, is intended merely to better illuminate the invention and does not pose a limitation on the scope unless otherwise claimed. No language in the specification should be construed as indicating any non-claimed element as essential to the practice of the invention.

It will also be understood that, although the terms first, second, etc. is used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject.

The terminology used in the present disclosure is for the purpose of describing particular embodiments only and is not intended to be limiting of the invention. As used in the description and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is construed to mean "when" or "upon" or "in response to determining" or "in response to detecting," depending on the context. Similarly, the phrase "if it is determined" or "if [a stated condition or event] is detected" is construed to mean "upon determining" or "in response to determining" or "upon detecting (the stated condition or event)" or "in response to detecting (the stated condition or event)," depending on the context.

The citation and incorporation of patent documents herein is done for convenience only and does not reflect any view of the validity, patentability, and/or enforceability of such patent documents.

The present invention can be implemented as a computer program product that comprises a computer program mechanism embedded in a non-transitory computer readable storage medium. For instance, the computer program product could contain the program modules shown in any combination of FIG. 1A. These program modules can be stored on a CD-ROM, DVD, magnetic disk storage product, USB key, or any other non-transitory computer readable data or program storage product.

The embodiments within the specification provide an illustration of embodiments of the invention and should not be construed to limit the scope of the invention. The skilled artisan will recognize that many other aspects and embodiments are encompassed by the methods of this invention. The embodiments of the invention and technical details provided below can be varied by the skilled artisan and can be tested and systematically optimized without undue experimentation or re-invention.

The invention is most thoroughly understood in light of the teachings of the specification and the references cited within. Many modifications and variations can be made without departing from its spirit and scope, as will be apparent to those skilled in the art. The specific embodiments described herein are offered by way of example, only. The embodiments were chosen and described in order to best explain the principles and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed:

1. A method of determining a sequence of at least a portion of a nucleic acid molecule, comprising:

fixing the nucleic acid molecule on a test substrate when the nucleic acid molecule is a single stranded molecule or denaturing the nucleic acid molecule to a single stranded molecule and fixing the single stranded nucleic acid molecule on the test substrate when the nucleic acid molecule is a double stranded molecule or fixing the nucleic acid molecule on the test substrate and denaturing the nucleic acid molecule on the test substrate to a single stranded molecule when the nucleic acid molecule is a double stranded molecule, thereby forming a fixed single stranded nucleic acid on the test substrate;

exposing the fixed single stranded nucleic acid to a respective oligonucleotide probe species in a set of oligonucleotide probe species, wherein each respective oligonucleotide probe species of the set of oligonucleotide probe species is capable of hybridizing to its complementary portion located at one or more locations on the fixed single stranded nucleic acid and has: (i) a unique respective predetermined sequence, (ii) a predetermined length, and (iii) a respective label selected from the group consisting of a dye, a fluorescent nanoparticle, a plasmon resonant particle, a light-scattering particle, a nanoparticle, and a fluorescence resonance energy transfer (FRET) partner which is capable of producing a fluorescent signal, wherein the exposing step occurs under conditions such that:

i) oligonucleotide probes of the respective oligonucleotide probe species of the set of oligonucleotide probe species repetitively transiently and reversibly bind to the one or more locations on the fixed single stranded nucleic acid on the test substrate, thereby forming a respective transient heteroduplex on each of the one or more locations on the fixed single stranded nucleic acid on the test substrate, and ii) respective instances of optical activity from the respective label are generated by repetitively transiently and reversibly binding the oligonucleotide probes of the respective oligonucleotide probe species of the set of oligonucleotide probe species to the one or more locations on the fixed single stranded nucleic acid on the test substrate and are detected at each of the one or more locations on the fixed single stranded nucleic acid on the test substrate;

determining which one or more portions on the fixed single stranded nucleic acid are complementary to the respective oligonucleotide probe species of the set of oligonucleotide probe species by measuring the respective instances of optical activity on each of the one or more locations on the fixed single stranded nucleic acid on the test substrate occurring during the exposing step using a two-dimensional imager capable of detecting the respective instances of optical activity generated from the respective label, thereby obtaining a first set of one or more positions on the fixed single stranded nucleic acid that are complementary to the respective oligonucleotide probe species of the set of oligonucleotide probe species;

washing the test substrate to remove the respective oligonucleotide probe species of the set of oligonucleotide probe species from the test substrate;

repeating the exposing step, measuring step, and washing step by exposing the fixed single stranded nucleic acid on the test substrate to the another respective oligonucleotide probe species in the set of oligonucleotide probe species, thereby obtaining a second set of one or more positions on the fixed single stranded nucleic acid that are complementary to the another respective oligonucleotide probe species in the set of oligonucleotide probe species; and determining the sequence of at least the portion of the nucleic acid based at least in part on the first set of one or more positions on the fixed single stranded nucleic acid that are complementary to the respective oligonucleotide probe species of the set of oligonucleotide probe species and the second set of one or more positions on the fixed single stranded nucleic acid that are complementary to the another respective oligonucleotide probe species of the set of oligonucleotide probe species.

2. The method according to claim 1, wherein the respective label on each oligonucleotide probe species of the set of oligonucleotide species is a distinct label that allows each respective probe oligonucleotide species of the set of oligonucleotide probe species to be distinguished from each other.

3. The method according to claim 1, wherein the respective instances of the optical activity is only located on the fixed single stranded nucleic acid on the test substrate.

4. The method according to claim 1, wherein the respective instances of the optical activity is a fluorescent signal generated from the respective label.

5. The method according to claim 1, wherein a drift of the fixed single stranded nucleic acid in relation to the two-dimensional imager is minimized by locking a substrate stage, which holds the substrate, to an objective lens.

6. The method according to claim 5, wherein the drift is corrected.

7. The method according to claim 1, wherein a plurality of fiduciary drift correction markers are provided on the test substrate to correct a drift of the fixed single stranded nucleic acid in relation to the two-dimensional imager.

8. The method according to claim 7, wherein the plurality of fiduciary drift correction markers comprise an origami grid.

9. The method according to claim 1, wherein more than one different respective oligonucleotide probe species in the set of oligonucleotide probe species is exposed to the fixed single stranded nucleic acid during the exposing step.

10. The method according to claim 1, wherein more than seventy percent of the respective instances of optical activity from the respective label are localized on the fixed single stranded nucleic acid on the test substrate with sub-diffraction precision.

11. The method according to claim 1, wherein the respective oligonucleotide species comprises a structure in a form: a probe nucleotide sequence complementary to its target nucleic acid-a spacer-a shield-the respective label, wherein the probe nucleotide sequence comprises degenerate bases and/or specific bases; the spacer comprises either a chemical linker or a nucleic acid sequence, said linker being bifunctional and able to link the probe nucleotide sequence to the shield and the respective label; the shield comprises a protein; and the respective label comprises a tag that acts as a docking site for the respective label.

12. The method according to claim 1, wherein an oxygen scavenging/fluorescence promoting molecular system is provided during the exposing step and said system comprises one or more of (a) pyranose oxidase, catalase, or glucose; (b) protocatechuate-dioxygenase and 3,4-protocatechuic acid; (c) catalase, glucose oxidase, sucrose or glucose; (d) methylene blue and Dithiotrol (DTT); (e) a reducing agent comprising Beta mercaptoethanol, TCEP, or Dithiotrol (DTT); and (f) a triplet state quencher/fluorescence promoter comprising Trolox, 1,3,5,7 cyclooctatetraene, and/or 4-nitrobenzylalchohol.

13. The method according to claim 1, wherein the nucleic acid molecule is a cell free nucleic acid molecule.

14. The method of claim 13, wherein the cell free nucleic acid molecule is isolated from a body fluid of a subject.

15. The method according to claim 1, wherein the test substrate has a vinyl silane or Zeonex surface and the fixing step comprises attachment of an end of the nucleic acid molecule to the surface by binding of the bases at one of the ends of the nucleic acid molecule to the surface of the test substrate in a presence of a buffer comprising 2-(N-morpholino)ethanesulfonic acid (MES) when the nucleic acid molecule is a single stranded molecule or a double stranded molecule.

16. The method according to claim 1, wherein the fixing step comprises modifying an end of the nucleic acid molecule using a terminal transferase in the presence of nucleotides when the nucleic acid molecule is a single stranded molecule or a double stranded molecule.

17. The method according to claim 1, the method further comprising determining whether the portion of the nucleic acid molecule has an epigenetic modification.

18. The method according to claim 1, wherein the fixed single stranded nucleic acid on the test substrate is exposed to a field of electromagnetic radiation during the exposing step.

19. The method according to claim 1, wherein the respective instances of optical activity comprise a fluorescence signal or a light scattering signal generated from the respective label.

20. The method according to claim 1, wherein the nucleic acid molecule in the fixing step is denatured to a single stranded molecule using sodium hydroxide, dimethyl sulfoxide, formamide, or urea when the nucleic acid molecule is a double stranded molecule.

21. The method according to claim 1, wherein the nucleic acid molecule in the fixing step is denatured to a single stranded molecule using heat when the nucleic acid molecule is a double stranded molecule.

22. The method according to claim 1, wherein the nucleic acid molecule in the fixing step is denatured to a single stranded molecule using a helicase when the nucleic acid molecule is a double stranded molecule.

23. The method of claim 1, wherein the test substrate is coated with biotin, streptavidin, a lipid layer, a hydrogel or a gel layer.

* * * * *

SEQUENCE LISTING

```
<160> NUMBER OF SEQ ID NOS: 13

<210> SEQ ID NO 1
<211> LENGTH: 16
<212> TYPE: DNA
<213> ORGANISM: Artificial Sequence
<220> FEATURE:
<223> OTHER INFORMATION: Synthetic

<400> SEQUENCE: 1 aaaacccegg ggtttt                                                       16

<210> SEQ ID NO 2
<211> LENGTH: 3000
<212> TYPE: DNA
<213> ORGANISM: Artificial Sequence
<220> FEATURE:
<223> OTHER INFORMATION: synthetic

<400> SEQUENCE: 2
aaaaaaaaac cggcccagct ttcttcatta ggttatacat ctaccgctcg ccagggcggc        60
gacctcgcgg gttttcgcta tttatgaaaa ttttccggtt taaggcgttt ccgttcttct       120
tcgtcataac ttaatgtttt tatttaaaat accctctgaa aagataggat agcacacgtg       180
ctgaaagcga ggcttttttgg cctctgtcgt ttcctttctc tgttttttgtc cgtggaatga    240 acaatggaag tcaacaaaaa gcagctggct gacattttcg gtgcgagtat ccgtaccatt      300
cagaactggc aggaacaggg aatgcccgtt ctgcgaggcg gtggcaaggg taatgaggtg     360
ctttatgact ctgccgccgt cataaaatgg tatgccgaaa gggatgctga aattgagaac     420
gaaaagctgc gccgggaggt tgaagaactg cggttcttat acatctaata gtgattatct   480
acatacatta tgaatctaca ttttaggtaa agattaattg agtaccaggt ttcagatttg    540
cttcaataaa ttctgactgt agctgctgaa acgttgcggt tgaactatat ttccttataa     600
cttttacgaa agagtttctt tgagtaatca cttcactcaa gtgcttccct gcctccaaac    660
gatacctgtt agcaatattt aatagcttga aatgatgaag agctctgtgt ttgtcttcct     720
gcctccagtt cgccgggcat tcaacataaa aactgatagc acccggagtt ccggaaacga    780
aatttgcata tacccattgc tcacgaaaaa aaatgtcctt gtcgatatag ggatgaatcg    840
cttggtgtac ctcatctact gcgaaaactt gacctttctc tcccatattg cagtcgcggc    900
acgatggaac taaattaata ggcatcaccg aaaattcagg ataatgtgca ataggaagaa    960
aatgatctat attttttgtc tgtcctatat caccacaaaa cctgaaactg gcgcgtgaga   1020
tggggcgacc gtcatcgtaa tatgttctag cgggtttgtt tttatctcgg agattatttt    1080
cataaagctt ttctaattta acctttgtca ggttaccaac tactaaggtt gtaggctcaa    1140
gagggtgtgt cctgtcgtag gtaaataact gacctgtcga gcttaatatt ctatattgtt   1200
gttctttctg caaaaaagtg gggaagtgag taatgaaatt atttctaaca tttatctgca   1260
tcataccttc cgagcattta ttaagcattt cgctataagt tctcgctgga agaggtagtt   1320
ttttcattgt actttacctt catctctgtt cattatcatc gcttttaaaa cggttcgacc   1380
ttctaatcct atctgaccat tataattttt tagaatgcgg cgttttccgg aactggaaaa   1440
```

```
ccgacatgtt gatttcctga aacgggatat catcaaagcc atgaacaaag cagccgcgct    1500
ggatgaactg ataccggggt tgctgagtga atatatcgaa cagtcaggtt aacaggctgc    1560
ggcattttgt ccgcgccggg cttcgctcac tgttcaggcc ggagccacag accgccgttg    1620
aatgggcgga tgctaattac tatctcccga aagaatccgc ataccaggaa gggcgctggg    1680
aaacactgcc ctttcagcgg gccatcatga atgcgatggg cagcgactac atccgtgagg    1740
tgaatgtggt gaagtctgcc cgtgtcggtt attccaaaat gctgctgggt gtttatgcct    1800
actttataga gcataagcag cgcaacaccc ttatctggtt gccgacggat ggtgatgccg    1860
agaactttat gaaaacccac gttgagccga ctattcgtga tattccgtcg ctgctgttaa    1920
ttgagtttat agtgatttta tgaatctatt ttgatgatat tatctacata cgactggcgt    1980
gccatgcttg ccgggatgtc aaatttaata aggtgatagt aaataaaaca attgcatgtc    2040
cagagctcat tcgaagcaga tatttctgga tattgtcata aaacaattta gtgaatttat    2100
catcgtccac ttgaatctgt ggttcattac gtcttaactc ttcatattta gaaatgaggc    2160
tgatgagttc catatttgaa aagttttcat cactacttag ttttttgata gcttcaagcc    2220
agagttgtct ttttctatct actctcatac aaccaataaa tgctgaaatg aattctaagc    2280
ggagatcgcc tagtgatttt aaactattgc tggcagcatt cttgagtcca atataaaagt    2340
attgtgtacc ttttgctggg tcaggttgtt ctttaggagg agtaaaagga tcaaatgcac    2400
taaacgaaac tgaaacaagc gatcgaaaat atcccttttgg gattcttgac tcgataagtc    2460
tattattttc agagaaaaaa tattcattgt tttctgggtt ggtgattgca ccaatcattc    2520
cattcaaaat tgttgtttta ccacacccat tccgcccgat aaaagcatga atgttcgtgc    2580
tgggcataga attaaccgtc acctcaaaag gtatagttaa atcactgaat ccgggagcac    2640
tttttctatt aaatgaaaag tggaaatctg acaattctgg caaaccattt aacacacgtg    2700
cgaactgtcc atgaatttct gaaagagtta cccctctaag taatgaggtg ttaaggacgc    2760
tttcattttc aatgtcggct aatcgatttg gccatactac taaatcctga atagctttaa    2820
gaaggttatg tttaaaacca tcgcttaatt tgctgagatt aacatagtag tcaatgcttt    2880
cacctaagga aaaaaacatt tcagggagtt gactgaatttt tttatctatt aatgaataag    2940
tgcttgacct atttcttcat tacgccatta tacatctagc ccaccgctgc caaaaaaaa     3000
```

<210> SEQ ID NO 3
<211> LENGTH: 68
<212> TYPE: DNA
<213> ORGANISM: Artificial Sequence
<220> FEATURE:
<223> OTHER INFORMATION: synthetic

<400> SEQUENCE: 3

```
accggttgta ctagaggatt cggatagcta aaatcgtaaa aatgcggatt ataatgtccc    60
cccctcag                                                             68
```

<210> SEQ ID NO 4
<211> LENGTH: 68
<212> TYPE: DNA
<213> ORGANISM: Artificial Sequence
<220> FEATURE:
<223> OTHER INFORMATION: synthetic

<400> SEQUENCE: 4

```
accggttgta ctagaggacc ccaatagctg gatgcgtaaa aatgcggatt ataatgtccc    60
cccctcag                                                             68
```

```
<210> SEQ ID NO 5
<211> LENGTH: 68
<212> TYPE: DNA
<213> ORGANISM: Artificial Sequence
<220> FEATURE:
<223> OTHER INFORMATION: synthetic

<400> SEQUENCE: 5
acaaattgta ctagaggatt cggatagcta aaatcgtaaa aatgcggatt ataatgtccc      60
cccctcag                                                              68

<210> SEQ ID NO 6
<211> LENGTH: 17
<212> TYPE: DNA
<213> ORGANISM: Artificial Sequence
<220> FEATURE:
<223> OTHER INFORMATION: synthetic

<400> SEQUENCE: 6
acggtgttgc cacagtt                                                    17

<210> SEQ ID NO 7
<211> LENGTH: 11
<212> TYPE: DNA
<213> ORGANISM: Artificial Sequence
<220> FEATURE:
<223> OTHER INFORMATION: synthetic

<400> SEQUENCE: 7
aacggtgtca t                                                          11

<210> SEQ ID NO 8
<211> LENGTH: 11
<212> TYPE: DNA
<213> ORGANISM: Artificial Sequence
<220> FEATURE:
<223> OTHER INFORMATION: synthetic

<400> SEQUENCE: 8
ttgccacagt a                                                          11

<210> SEQ ID NO 9
<211> LENGTH: 22
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1)..(5)
<223> OTHER INFORMATION: n is a, c, g, or t
<220> FEATURE:
<221> NAME/KEY: misc_feature
<222> LOCATION: (17)..(22)
<223> OTHER INFORMATION: n is a, c, g, or t

<400> SEQUENCE: 9
nnnnnttgcc acagtannnn nn                                              22

<210> SEQ ID NO 10
<211> LENGTH: 15
<212> TYPE: DNA
<213> ORGANISM: Artificial Sequence
<220> FEATURE:
<223> OTHER INFORMATION: Synthetic
```

```
<400> SEQUENCE: 10
aacagtatga cttttt                                                  15

<210> SEQ ID NO 11
<211> LENGTH: 24
<212> TYPE: DNA
<213> ORGANISM: Artificial Sequence
<220> FEATURE:
<223> OTHER INFORMATION: synthetic

<400> SEQUENCE: 11
ggtttttcgc cctttcacgt tgga                                         24

<210> SEQ ID NO 12
<211> LENGTH: 24
<212> TYPE: DNA
<213> ORGANISM: Artificial Sequence
<220> FEATURE:
<223> OTHER INFORMATION: synthetic

<400> SEQUENCE: 12
tccaacgtca aagggcgaaa aacc                                         24

<210> SEQ ID NO 13
<211> LENGTH: 24
<212> TYPE: DNA
<213> ORGANISM: Artificial Sequence
<220> FEATURE:
<223> OTHER INFORMATION: synthetic

<400> SEQUENCE: 13
ggtttttcgc cctttgacgt tgga                                         24
```